US009493531B2

(12) United States Patent
Lillard, Jr.

(10) Patent No.: US 9,493,531 B2
(45) Date of Patent: Nov. 15, 2016

(54) CHEMOKINE-IMMUNOGLOBULIN FUSION POLYPEPTIDES, COMPOSITIONS, METHOD OF MAKING AND USE THEREOF

(71) Applicant: JYANT TECHNOLOGIES, INC., Marietta, GA (US)

(72) Inventor: James W. Lillard, Jr., Smyrna, GA (US)

(73) Assignee: JYANT TECHNOLOGIES, INC., Marietta, GA (US)

( * ) Notice: Subject to any disclaimer, the term of this patent is extended or adjusted under 35 U.S.C. 154(b) by 0 days.

(21) Appl. No.: 14/978,684

(22) Filed: Dec. 22, 2015

(65) Prior Publication Data

US 2016/0115214 A1   Apr. 28, 2016

Related U.S. Application Data

(63) Continuation of application No. 14/612,884, filed on Feb. 3, 2015, now Pat. No. 9,249,204, which is a continuation-in-part of application No. 13/962,401, filed on Aug. 8, 2013, now Pat. No. 8,987,210, which is a continuation of application No. 13/962,110, filed on Aug. 8, 2013, now Pat. No. 8,796,422, which is a continuation-in-part of application No. 13/480,526, filed on May 25, 2012, now Pat. No. 8,541,564.

(60) Provisional application No. 61/492,260, filed on Jun. 1, 2011.

(51) Int. Cl.

| | |
|---|---|
| *A61K 38/00* | (2006.01) |
| *A61K 38/16* | (2006.01) |
| *A61K 39/00* | (2006.01) |
| *A61K 39/395* | (2006.01) |
| *C07K 16/00* | (2006.01) |
| *C07K 14/52* | (2006.01) |
| *C07K 16/18* | (2006.01) |

(52) U.S. Cl.
CPC ............. *C07K 14/521* (2013.01); *C07K 16/18* (2013.01); *A61K 38/00* (2013.01); *C07K 2319/30* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 5,766,897 A | 6/1998 | Braxton | |
| 7,279,460 B2 | 10/2007 | Wang et al. | |
| 7,740,833 B2 | 6/2010 | Proudfoot et al. | |
| 8,012,928 B2 | 9/2011 | Bluth | |
| 8,277,809 B2 | 10/2012 | Bugelski | |
| 2001/0053539 A1* | 12/2001 | Lauffer | C07K 14/505 435/69.7 |
| 2002/0058800 A1 | 5/2002 | Kingsbury | |
| 2002/0114806 A1* | 8/2002 | Pardo-Semo | C12Q 1/6883 424/146.1 |
| 2005/0053579 A1 | 3/2005 | Galipeau et al. | |
| 2007/0036750 A1 | 2/2007 | Chou et al. | |
| 2007/0116669 A1 | 5/2007 | Merzouk et al. | |
| 2009/0098101 A1 | 4/2009 | Raines et al. | |
| 2010/0166733 A1 | 7/2010 | Levin et al. | |
| 2010/0196406 A1 | 8/2010 | Karin et al. | |

FOREIGN PATENT DOCUMENTS

| | | |
|---|---|---|
| CN | 101443357 | 5/2009 |
| JP | 2009-504158 | 2/2009 |
| WO | 2005/037305 | 4/2005 |
| WO | 2007/021807 | 2/2007 |
| WO | 2007/148317 | 12/2007 |

OTHER PUBLICATIONS

Islam et al. 2013. J. Exp. Med 210:1889-1898.*
U.S. Appl. No. 13/480,526, filed May 25, 2012, Patented.
PCT/US12/39550, May 25, 2012, Expired.
U.S. Appl. No. 13/962,362, filed Aug. 8, 2013, Patented.
U.S. Appl. No. 13/962,110, filed Aug. 8, 2013, Patented.
U.S. Appl. No. 13/962,401, filed Aug. 8, 2013, Patented.
U.S. Appl. No. 14/612,884, filed Feb. 3, 2015, Pending.
Biragyn, A., et al., "Mediators of Innate Immunity That Target Immature, But Not Mature, Dendritic Cells Induce Antitumor Immunity When Genetically Fused with Nonimmunogenic Tumor Antigens", The Journal of Immunology, Dec. 1, 2001, vol. 167, No. 11, pp. 6644-6653.
Fagete, S., et al., "Specificity tuning of antibody fragments to neutralize two human chemokines with a single agent", MAbs, May-Jun. 2009, vol. 1, No. 3, pp. 288-296.
Van Heeke, G., et al. "Expression of Human Asparagine Synthetase in *Escherichia coli*," The Journal of Biological Chemistry, vol. 264, No. 10, Apr. 5, 1989, pp. 5503-5509.
Allen, S.J., et al. "Chemokine: Receptor Structure, Interactions, and Antagonism," Annu. Rev. Immunol., 2007, 25: 787-820.
File history of U.S. Appl. No. 13/480,526, filed on May 25, 2012.
File history of U.S. Appl. No. 13/962,110, filed on Aug. 8, 2013.
File history of U.S. Appl. No. 13/962,401, filed on Aug. 8, 2013.
Nextprot Beta, CCL25—C—C motif chemokine 25, 2011.
File history of U.S. Appl. No. 14/612,884, filed on Feb. 3, 2015.
The International Search Report and the Written Opinion of the International Searching Authority (Application No. PCT/US2012/039550, International Filing Date: May 25, 2012), mailed Dec. 18, 2012.
European Search Report issued in European Patent Application No. 12792144.3 mailed on Mar. 5, 2015.

* cited by examiner

*Primary Examiner* — Shulamith H Shafer
(74) *Attorney, Agent, or Firm* — Ping Wang; Andrews Kurth Kenyon LLP

(57) ABSTRACT

This application is directed to chemokine-immunoglobulin fusion polypeptides and chemokine-polymer conjugates. The fusion polypeptides and conjugates can be used for treating chemokine receptor-mediated disorders and modulating inflammation, inflammatory cell motility, cancer cell motility, or cancer cell survival.

11 Claims, 70 Drawing Sheets

FIG.1A
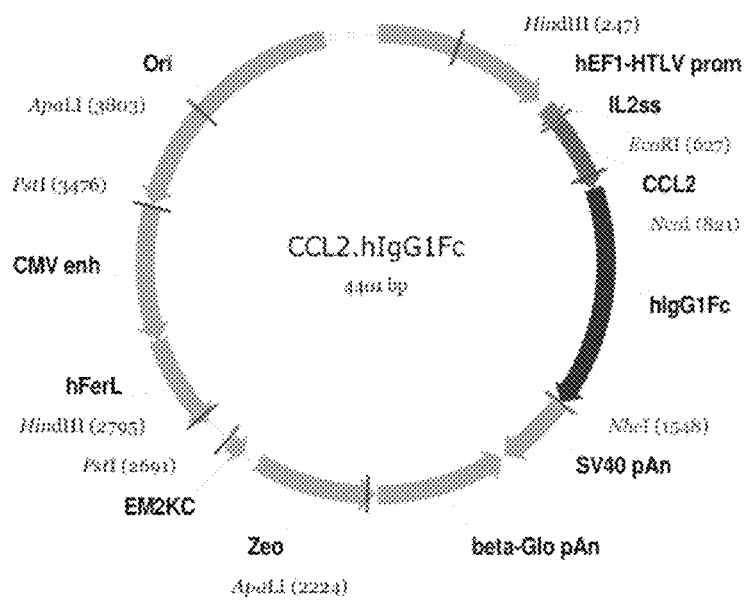
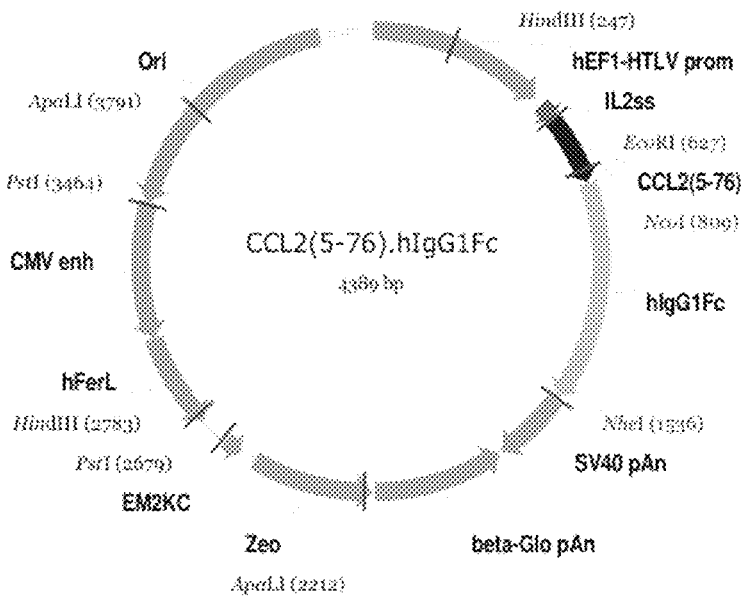
FIG.1B

FIG. 1C

IL2ss.CCL2.hIgG1Fc GAGless plasmid sequence

```
2401 ACCACCTGGT CCTGGACCGC GCTGATGAAC AGGGTCACGT CGTCCCGGAC CACACCGGCG AAGTCTCCT CCACGAAGTC CCGGGAGAAC CCGAGCCGGT
2501 CGGTCCAGAA CTCGACCGCT CCGCGCGACGT CGCGCGCGGGT GAGCACCGGA ACGGCACTGG TCAACTTGGC CATGATGGCT CCTCCTGTCA GGAGAGGAAA
                                                                                    AseI
                                                                                 --------
2601 GAGAAGAAGG TTAGTACAAT TGCTATAGTG AGTTGTATTA CCAATGATTA ATTGTCAAAC TAGGGCTGCA GGGTTCATAG
2701 TGCCCACTTT CCTGCACTGC CCCATCCCT GCCCACCCTT AGACAGTCAG TGACTTACCA AACTCACAGG AGGGAGAAGG CAGAAGCTTG
2801 AGACAGACCC GCGGGACCGC CGAACTCCGA GGGGACGTGG CTAGGGCGGC TTCTTTTATG GTGCGCCGGC CCTCGGAGGC AGGGCGCTCG GGCAGGCCTA
2901 GCGGCCAATC TGCGGTGGCA GGAGGCGGGG CCGAAGGCCG GGAAGGCCTT CATAGGAGTC CAGCCCCCC TCAGCCCCCC GCCCAAAGC AAGGGAAGT
3001 CACGCGCCTG TAGCGCCAGC GTGTTGTGAA ATGGGGGCTT GGGGGGGTTG GGGCCCTGAC TAGTCAAAAC AAACTCCCAT TGACTCAAT GGGGTGGAGA
3101 CTTGGAAATC CCCGTGAGTC AAACCGCTAT TGATGTACTG CCAGCCCCAT ATCATCATCG TAATAGCGAT GACTAATACG TAGATGTACT
3201 GCCAAGTAGG AAAGTCATGT ACTGGGACGA AAGGTCAGCG ATGCCAGGCG GGCCATTTAC GTCAATAGGG GGCCTACTTG GCATATGATA
3301 CACTTGATGT ACTGCCAAGT GGGTAAATAC TCCACCCATT GACGTCAATG GAAAGTCCCT ATTGGCGTTA CTATGGGAAC ATACGTCATT
3401 ATTGACGTCA ATGGGCGGGG GTCGTTGGGC GGCTCAGCCG CGCGGCCCATT TATGTAACGC CTGCAGGTTA ATTAAGAACA TGTCAGCAAA
3501 AGGCCAGCAA AAGGCCAGGA ACCGTAAAAA CTGGCGTTTT TCCATAGGCT CCGCCCCCCT GACGAGCATC ACAAAAATCG ACGCTCAAGT
3601 CAGAGGTGGC GAAACCCGAC AGGACTATAA AGATACCAGG CGTTTCCCCC TGGAAGCTCC CTCGTGCGCT CTCCTGTTCC GACCCTGCCG CTTACCGGAT
3701 ACCTGTCCGC CTTTCTCCCT TCGGGAAGCG TGGCGCTTTC TCATAGCTCA CGCTGTAGGT ATCTCAGTTC GGTGTAGGTC GTTCGCTCCA AGCTGGGCTG
3801 TGTGCACGAA CCCCCCGTTC AGCCCGACCG CTGCGCCTTA TCCGGTAACT ATCGTCTTGA GTCCAACCCG GTAAGACACG ACTTATCGCC ACTGGCAGCA
3901 GCCACTGGTA ACAGGATTAG CAGAGCGAGG TATGTAGGCG GTGCTACAGA GTTCTTGAAG TGGTGGCCTA ACTACGGCTA CACTAGAAGA ACAGTATTTG
4001 GTATCTGCGC TCTGCTGAAG CCAGTTACCT TCGGAAAAAG AGTTGGTAGC TCTTGATCGG GCAAACAAGC CACCGCTGGT AGCGGTGGTT TTTTTGTTTG
4101 CAAGCAGCAG ATTACGCGCA GAAAAAAAGG ATCTCAAGAA GATCCTTTGA TCTTTTCTAC GGGGTCTGAC GCTCAGTGGA ACGAAAACTC ACGTTAAGGG
4201 ATTTTGGTCA TGGCTAGTTA ATTAACATTT AAATCAGCGG CCGCAATAAA ATATCTTTAT TTTCATTACA TCTGTGTGTT GGTTTTTTGT GTGAATCGTA
4301 ACTAACATAC GCTCTCCATC AAAACAAAAC GAAACAAAAC AAACTAGCAA AATAGCAA AATAGCAA ANTAGCAA CCCCAGTGCA AGTGCAGGTG CCAAGAACATT TCTCTATCGA
4401 A (SEQ ID NO: 79)
```

IL2ss.CCL2(5-76).hIgG1Fc GAGless plasmid sequence

```
   1  GGATCTGCGA TGCCTCCGGT GCCCGTCAGT GGGCAGAGCG CACATGCCCC ACAGTCCCCG AGAAGTTGGG GGGAGGGGTC GGGAATTGAA CGGGTGCCTA
 101  GAGAAGTGTG CCCGGGGTAA ACTGGGAAAG TGATGTCGTG CAACTCGTCC GCCTTTTCC CGGGGGTTGG GGAGAACCGT CTTCACGCCG AGTAGTCGCC
 201  GTGAACCTTC TTTTTCGCAA CAGGTTTGCC GCCAGAACAC AGCTCAAGCT TCGAGGGCT CGCATCTCTC CCGCCGCCCT ACCTAAGGCC
 301  GCCATCCACG CCGGTTGAGT CGCGTTCTGC CGCCTCCCGC TCGTGGTGCC TCCTGAACTG CGCCGCCGT CTAGGTAAGT GGTCGAGACC
 401  GGGCCTTTGT CCGGCGCTCC CTTGGAGCCT ACCTAGACTC AGCCGGCTCT CCAAGGCTTG CCTGACCCTG CTTGCTCAAC TCTACGTCTT TGTTTCGTTT
                                        KasI
                                        NarI
                                        SfoI
                                        BbeI
                                                                                                  IL-2 secretion signal
                                                                                                  MetTyrArg MetGlnLeu LeuSerCysIle
 501  TCTGTTCTGC GCCGTTACAG ATCCAAGCTG TGACCGGCGC CTACCTGAGA TCACCCGCGA AGGAGGGCCA CCATGTACAG GATGCAACTC CTGTCTTGCA
                             EcoRI
                                        ~~~~ CCL2(5-76)
                                        AlaLeuSer LeuAlaLeu ValThrAsnSer IleAsnAla ProValThr CysCysTyrAsn PheThrAsn ArgLysIle SerValGlnArg LeuAlaSer
 601  TTGCACTAAG TCTTGCACTT GTCAACAGTT CGATCAATGC CCCAGTCACA TGCTGTTATA ACTTCACCAA TAGGAAGATC TCAGTGCAGA GGCTCGCGAG
      TyrArgArg IleThrSerSer LysCysPro LysGluAla ValIlePheLys ThrIleVal AlaLysGlu IleCysAlaAsp ProLysGlu LysTrpVal
 701  CTATAGAAGA ATCACCAGCA GCAAGTGTCC CAAAGAAGCT GTGATCTTCA AGACCATTGT GGCCAAGGAG ATCTGTGCTG ACCCAAAGGA GAAGTGGGTT
                                        human IgG1 Fc (constant region)
      GlnAspSerMet AspHisLeu ThrGlnThrPro LysThrAsp LysThrHis ThrCysProPro CysProAla ProGluLeu LeuGlyGlyPro
 801  CAGGATTCCA TGGACCACCT GGACCAAGCAA ACCCAAACTC CGAAGACTGA CAAAACTCAC ACATGCCCAC CGTGCCCAGC ACCTGAACTC CTGGGGGGAC
      SerValPhe LeuPhePro ProLysProLys AspThrLeu MetIleSer ArgThrProGlu ValThrCys ValValVal AspValSerHis GluAspPro
 901  CGTCAGTCTT CCTCTTCCCC CCAAAACCCA AGGACACCCT CATGATCTCC CGGACCCCTG AGGTCACATG CGTGGTGGTG GACGTGAGCC ACGAAGACCC
      GluValLys PheAsnTrpTyr ValAspGly ValGluVal HisAsnAlaLys ThrLysPro ArgGluGlu GlnTyrAsnSer ThrTyrArg ValValSer
1001  TGAGGTCAAG TTCAACTGGT ACGTGGACGG CGTGGAGGTG CATAATGCCA AGACAAAGCC GCGGGAGGAG CAGTACAACA GCACGTACCG TGTGGTCAGC
      ValLeuThrVal LeuHisGln AspTrpLeu AsnGlyLysGlu TyrLysCys LysValSer AsnLysAlaLeu ProAlaPro IleGluLys ThrIleSerLys
1101  GTCCTCACCG TCCTGCACCA GGACTGGCTG AATGGCAAGG AGTACAAGTG CAAGGTCTCC AACAAAGCCC TCCCAGCCCC CATCGAGAAA ACCATCTCCA
      AlaLysGly GlnProArg GluProGlnVal TyrThrLeu ProProSer ArgGluGluMet ThrLysAsn GlnValSer LeuThrCysLeu ValLysGly
1201  AAGCCAAAGG GCAGCCCCGA GAACCACAGG TGTACACCCT GCCCCCATCC CGGGAGGAGA TGACCAAGAA CCAGGTCAGC CTGACCTGCC TGGTCAAAGG
      PheTyrPro SerAspIleAla ValGluTrp GluSerAsn GlyGlnProGlu AsnAsnTyr LysThrThr ProProValLeu AspSerAsp GlySerPhe
1301  CTTCTATCCC AGCGACATCG CCGTGGAGTG GGAGAGCAAT GGGCAGCCGG AGAACAACTA CAAGACCACG CCTCCCGTGC TGGACTCCGA CGGCTCCTTC
      PheLeuTyrSer LysLeuThr ValAspLys SerArgTrpGln GlnGlyAsn ValPheSer CysSerValMet HisGluAla LeuHisAsn HisTyrThrGln
1401  TTCCTCTACA GCAAGCTCAC CGTGGACAAG AGCAGGTGGC AGCAGGGGAA CGTCTTCTCA TGCTCCGTGA TGCACGAGGC TCTGCACAAC CACTACACGC
                             BmtI
                             NheI
      LysSerLeu SerLeuSer ProGlyLys***  (SEQ ID NO: 53)
1501  AGAAGAGCCT CTCCCTGTCT CCGGGTAAAT GAGTGCTAGC TGGCCAGACA TGATAAGATA CATTGATGAG TTTGGACAAA CCACAACTAG AATGCAGTGA
1601  AAAAAATGCT TTATTTGTGA AATTTGTGAT GCTATTGCTT TATTTGTAAC CATTATAAAC TGCAATAAAC AAGTTAACAA CAACAATTGC ATTCATTTTA
                                                                                                AseI
1701  TGTTTCAGGT TCAGGGGGAG GTGTGGGAGG TTTTTTAAAG CAAGTAAAAC CTCTACAAAT GTGGTATGGA ATTAATTCTA AAATACAGCA TAGCAAAACT
1801  TTAACCTCCA AATCAAGCCT CTACTTGAAT CCTTTTCTGA GGGATGAATA AGGCATAGGC ATCAGGGGCT GTTGCCAATG TGCATTAGCT GTTTGCAGCC
1901  TCACCTTCTT TCATGGAGTT TAAGATATAG TGTATTTTCC CAAGGTTTGA ACTAGCTCTT CATTTCTTTA TGTTTAAAT GCACTGACCT CCCACATTCC
2001  CTTTTTAGTA AATAATTTTA AATACATCAT TGCAATGAAA ATAAATGTTT TTTATTAGGC AGAATCCAGA TGCTCAAGGC CCTTCATAAT
2101  ATCCCCCAGT TTAGTAGTTG GACTTAGGGA ACAAAGGAAC CTTTAATGACA AATTGGACAG CAACAAAAGCG AGTTCTAGC TTATCCTCCT TCCTCTCCT
2201  CTGCCACAAA GTGCACGCAG TTGCGGGCCG GGGAACTCC GGGTCGCGGA CGTCGCCCCACG GCTGCTCGCC GATCGGGTC ATGGCCGGGCC CGGAGCCGTC
```

```
2301 CCGGAAGTTC GTGGACACGA CCTCCGACCA CTCGGCGGTAC AGCTCGTCCA GGCCGCGCAC CCACACCCAG GCCAGGGTGT TGTCCGGCAC CACCTGGTCC
2401 TGGACCGCGC TGATGAACAG GGTCACGTCG TCCCGGACCA CACCGGCGAA GTCGTCCTCC ACGAAGTCCC GGGAAGTCCC GAGCCGGTCG GTCCAGAACT
2501 CGACCGCTCC GGCGACGTCG CGGCGGGTGA GCACCGGAAC GGCACTGGTC AACTTGGCCA TGATGGCTCC TCCTGTCAGG AGAGGAAAGA GAAGAAGGTT
                                                                    AseI
2601 AGTACAATTG CTATAGTGAG TTGTATTATA CTATGCAGAT ATACTATGCC AATGATTAAT TGTCAAACTA GGGCTGCAGG GTTCATAGTG CCACTTTTCC
2701 TGCACTGCCC CATCTCCTGC CCACCCTTTC CCAGGCATAG ACAGTCAGTG ACTTACCAAA CTCACAGGAG GAGCTTGAG ACAGACCCGC
2801 GGGACCGCCG AACTGCGAGG GGACGTGGCT AGGGCGGCTT CTTTTATGGT GCGCAGGCAC TCGGAGCGG GGCCGCTAGC GAGGCCTAGC GGCCAATCTG
2901 CGGTGGCAGG AGGCGGGGCC GAAGGCCGTG CCTGACCAAT CCGGAGCACA GCCCTGACTA AGCCCCCGC CCCAAAGCAA GGGGAAGTCA CGCGCCTGTA
3001 GCGCCAGCGT GTTGTGAAAT GGGGGCTTGG CCTGGGTTGG GCCCTGACTA GTCAAAACAA ACTCCCATTG AGTCAATGG GGTGGAGACT TGGAAATCCC
3101 CGTGAGTCAA ACCGCTATCC ACGCCCATTG ATGTACTGCC AAAACCGCAT CATCATGGTA ATAGCGATGA CTAATACGTA GATTACTGC CAAGTAGGAA
3201 AGTCCCATAA GGTCATGTAC TGGGCATAAT GCCAGGCGGG CCATTTACCG TCATTGACGT CAATAGGGG CGTACTTGGC ATATGATGTAC CTTGATGTAC
3301 TGCCAAGTGG GCAGTTTACC GTAAATACTC CACCATTGA CGTCAATGGA AAGTCCCTAT TGGCGTTACT ATGGGAACAT AGTCATTAT TGACGTCAAT
3401 GGGCGGGGGT CGTTGGGCGG TCAGCCAGGC GGGCCATTTA CCGTAAGTTA TGTAACGCCT GCAGGTTAAT TAAGAACATG TGAGCAAAAG GCCAGCAAAA
3501 GGCCAGGAAC CGTAAAAAGG CCGCGTTGCT GGCGTTTTTC CATAGGCTCC GCCCCCCCTGA CGAGCATCAC AAAATCGAC GCTCAAGTCA GAGGTGGCGA
3601 AACCCGACAG GACTATAAAG ATACCAGGCG TTTCCCCCCTG GAAGCTCCCT CGTGCGCTCT CCTGTTCCGA CCCTGCCGCT TACCGGATAC CTGTCCGCCT
3701 TTCTCCCTTC GGGAAGCGTG GCGCTTCTC ATAGCTCACG CTGTAGTAT GAAGCTCCCT CGTGCGCTCG TGTAGGTCGT TCGCTCCAAG CTGGGCTGTG TGCACGAACC CACTGGTAAC
3801 CCCCGTTCAG CCCGACCGCT GCGCCTTATC CGGTAACTAT CGTCTTGAGT CCAACCCGGT AAGACACGAC TTATCGCCAC TGGCAGCAGC CACTGGTAAC
3901 AGGATTAGCA GAGCGAGGTA TGTAGGCGGT GCTACAGAGT TCTTGAAGTG GTGGCCTACA CGGCTACAC TACGGCTACA CCGCTGGTAG AGTATTGGT ATCTGCGCTC
4001 TGCTGAAGCC AGTTACCTTC GGAAAAAGAG TTGGTAGCTC TTGATCCGGC AAACAAACCA CCGCTGGTAG CGGTGGTTTT TTTGTTTGCA AGCAGCAGAT
4101 TACGCGCAGA AAAAAAGGAT CTCAAGAAGA TCCTTTGATC TTTTCTACGG GGTCTGACGC TCAGTGGAAC GAAAACTCAC GTTAAGGGAT TTTGGTCATG
4201 GCTAGTTAAT TAACATTTAA ATCAGCGGCC GCAATAAAAT ATCTTTATT TCATTACATC TGTGTGTTGG TTTTTTGTGT GAATCGTAAC TAACATACGC
4301 TCTCCATCAA AACAAAACGA AACAAAACAA ACTAGCAAAA TAGGCTGTCC CCAGTGCAAG TGCAGGTGCC AGAACATTTC TCTATCGAA (SEQ ID NO: 80)
```

IL2ss.CCL2(5-76).hIgG1Fc sequence [Alanine substitutions for removal of GAG binding sites -- Lys & His]

```
   1   GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101   GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201   GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301   GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401   GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                         KasI
                                         NarI
                                         SfoI
                                         BbeI
                                        ~~~~~~~                               IL-2 secretion signal
                                                                              MetTyrArg MetGlnLeu LeuSerCysIle
 501   TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                                 EcoRI
                                ~~~~~~  CCL2(5-76
        AlaLeuSer LeuAlaLeu ValThrAsnSer IleAsnAla ProValThr CysCysTyrAsn PheThrAsn ArgLysIle SerValGlnArg LeuAlaSer
 601   TTGCACTAAG TCTTGCACTT GTCACCAATT CGATCAATGC CCCAGTCACC TGCTGTTATA ACTTCACCAA TAGGAAGATC TCAGTGCAGA GGCTCGCGAG
        TyrArgArg IleThrSerSer LysCysPro LysGluAla ValIlePheLys ThrIleVal AlaAlaGlu IleCysAlaAsp ProAlaGln AlaTrpVal
 701   CTATAGAAGA ATCACCAGCA GCAAGTGTCC CAAAGAAGCT GTGATCTTCA AGACCATTGT GGCCgcgGAG ATCTGTGCTG ACCCCgctCA GgccTGGGTT
                                                               human IgG1 Fc (constant region)
       GlnAspSerMet AspAlaLeu AspAlaGln ThrGlnThrPro AlaThrAsp LysThrHis ThrCysProPro CysProAla ProGluLeu LeuGlyGlyPro
 801   CAGGATTCCA TGGACgctCT GGACgccCAA ACCCAAACTC CGgcgACTGA CAAAACTCAC ACATGCCCAC CGTGCCCAGC ACCTGAACTC CTGGGGGGAC
        SerValPhe LeuPhePro ProLysProLys AspThrLeu MetIleSer ArgThrProGlu ValThrCys ValValVal AspValSerHis GluAspPro
 901   CGTCAGTCTT CCTCTTCCCC CCAAAACCCA AGGACACCCT CATGATCTCC CGGACCCCTG AGGTCACATG CGTGGTGGTG GACGTGAGCC ACGAAGACCC
        GluValLys PheAsnTrpTyr ValAspGly ValGluVal HisAsnAlaLys ThrLysPro ArgGluGlu GlnTyrAsnSer ThrTyrArg ValValSer
1001   TGAGGTCAAG TTCAACTGGT ACGTGGACGG CGTGGAGGTG CATAATGCCA AGACAAAGCC GCGGGAGGAG CAGTACAACA GCACGTACCG TGTGGTCAGC
       ValLeuThrVal LeuHisGln AspTrpLeu AsnGlyLysGlu TyrLysCys LysValSer AsnLysAlaLeu ProAlaPro IleGluLys ThrIleSerLys
1101   GTCCTCACCG TCCTGCACCA GGACTGGCTG AATGGCAAGG AGTACAAGTG CAAGGTCTCC AACAAAGCCC TCCCAGCCCC CATCGAGAAA ACCATCTCCA
        AlaLysGly GlnProArg GluProGlnVal TyrThrLeu ProProSer ArgGluGluMet ThrLysAsn GlnValSer LeuThrCysLeu ValLysGly
1201   AAGCCAAAGG GCAGCCCCGA GAACCACAGG TGTACACCCT GCCCCCATCC CGGGAGGAGA TGACCAAGAA CCAGGTCAGC CTGACCTGCC TGGTCAAAGG
        PheTyrPro SerAspIleAla ValGluTrp GluSerAsn GlyGlnProGlu AsnAsnTyr LysThrThr ProProValLeu AspSerAsp GlySerPhe
1301   CTTCTATCCC AGCGACATCG CCGTGGAGTG GGAGAGCAAT GGGCAGCCGG AGAACAACTA CAAGACCACG CCTCCCGTGC TGGACTCCGA CGGCTCCTTC
       PheLeuTyrSer LysLeuThr ValAspLys SerArgTrpGln GlnGlyAsn ValPheSer CysSerValMet HisGluAla LeuHisAsn HisTyrThrGln
1401   TTCCTCTACA GCAAGCTCAC CGTGGACAAG AGCAGGTGGC AGCAGGGGAA CGTCTTCTCA TGCTCCGTGA TGCACGAGGC TCTGCACAAC CACTACACGC
                                         BmtI
                                         NheI
        LysSerLeu SerLeuSer ProGlyLys***(SEQ ID NO: 54)
1501   AGAAGAGCCT CTCCCTGTCT CCGGGTAAAT GAGTGCTAGC TGGCCAGACA TGATAAGATA CATTGATGAG TTTGGACAAA CCACAACTAG AATGCAGTGA
1601   AAAAAATGCT TTATTTGTGA AATTTGTGAT GCTATTGCTT TATTTGTAAC CATTATAAGC TGCAATAAAC AAGTTAACAA CAACAATTGC ATTCATTTTA
                                                                              AseI
1701   TGTTTCAGGT TCAGGGGGAG GTGTGGGAGG TTTTTTAAAG CAAGTAAAAC CTCTACAAAT GTGGTATGGA ATTAATTCTA AAATACAGCA TAGCAAAACT
1801   TTAACCTCCA AATCAAGCCT CTACTTGAAT CCTTTTCTGA GGGATGAATA AGGCATAGGC ATCAGGGGCT GTTGCCAATG TGCATTAGCT GTTTGCAGCC
1901   TCACCTTCTT TCATGGAGTT TAAGATATAG TGTATTTTCC CAAGGTTTGA ACTAGCTCTT CATTTCTTTA TGTTTTAAAT GCACTGACCT CCCACATTCC
2001   CTTTTTAGTA AAATATTCAG AAATAATTTA AATACATCAT TGCAATGAAA ATAAATGTTT TTTATTAGGC AGAATCCAGA TGCTCAAGGC CCTTCATAAT
2101   ATCCCCCAGT TTAGTAGTTG GACTTAGGGA ACAAAGGAAC CTTTAATAGA AATTGGACAG CAAGAAAGCG AGCTTCTAGC TTATCCTCAG TCCTGCTCCT
2201   CTGCCACAAA GTGCACGCAG TTGCCGGCCG GGTCGCGCAG GGCGAACTCC CGCCCCCACG GCTGCTCGCC GATCTCGGTC ATGGCCGGCC CGGAGGCGTC
2301   CCGGAAGTTC GTGGACACGA CCTCCGACCA CTCGGCGTAC AGCTCGTCCA GGCCGCGCAC CCACACCCAG GCCAGGGTGT TGTCCGGCAC CACCTGGTCC
```

```
2401 TGGACCCGCGC TGATGAACAG GGTCACGTCG TCCCGGACCA CACCGGCGAA GTCGTCCTCC ACGAAGTCCC GGGAGAACCC GAGCCGGTCG GTCCAGAACT
2501 CGACCGCTCC GGCGACGTCG CGCCGGGTGA GCACCGGAAC GGCACTGGTC AACTTGGCCA TGATGGCTCC TCCTGTCAGG AGAGGAAAGA GAAGAAGGTT
                                                                        AseI
2601 AGTACAATTG CTATAGTGAG TTGTATTATA ATACTATGCC AATGATTAAT TGTCAAACTA GGGCTGCAGG GTTCATAGTG CCACTTTTCC
2701 TGCACTGCCC CATCTCCTGC CCACCCTTTC CCAGGCATAG ACAGTCAGTG ACTTACCAAA CTCACAGGAG GGAGAAGGCA GAAGCTTGAG ACAGACCCGC
2801 GGGACCGCCG AACTGCGAGG GGACGTGGCT AGGGCGGCTT CCTGACCAAT GCGCCGGCCC TCGGAGCTCT GGCGCTCGGG GAGGCCTAGC GGCCAATCTG
2901 CGGTGGCAGG AGGCGGGGCC GAAGCCCGTG CCTGACCACA TAGGAGTCTC AGCCCCCCGC CCCAAAGCAA GGGAAGTCA CGCGCCTGTA
3001 GCGCCAGCGT GTTGTGAAAT GGGGGCTTGG GCCCTGACTA GTCAAAACAA ACTCCCATTG ACGTCAATGG GGTGGAGACT TGGAAATCCC
3101 CGTGAGTCAA ACCGCTATCC ACGCCATTG ATGTACTGCC CATCATGGA ATAGCCATGA CTAATACGTA GATGTACTGC CAAGTAGGAA
3201 AGTCCCATAA GGTCATGTAC TGGGCATAAT GCCAGGCGGG CCATTTACCG TCATTGACGT CGTACTTGGC ATATGATGTA CTTGATGTAC
3301 TGCCAAGTGG GCAGTTTACC GTAAATACTC CACCCATTGA AGTCCCTAT TGGCGTTACT ACGTCATTAT TGACGTCAAT
3401 GGGCGGGGGT CGTTGGGCGG GTAACGCCAA TAGGGCCATTA GCAGGCGCCT ATGGAACATG TAAGACATG TGAGCAAAAG GCCAGCAAAA
3501 GGCCAGGAAC CGTAAAAAGG CCGCGTTGCT GGCGTTTTTC CCCCCTCC GCAGCATCAC AAAATCGAC GCTCAAGTCA GAGGTGGCGA
3601 AACCCGACAG GACTATAAAG ATACCAGGCG TTTCCCCCTG GAAGCTCCCT CGTGCGCTCT CCTGTTCCGA CCCTGCCGCT TACCGGATAC CTGTCCGCCT
3701 TTCTCCCTTC GGGAAGCGTG GCGCTTTCTC ATAGCTCACG CGTAACTCAC TCCAAGCCTG TGTAGGTGCT CTGCCAAG TGCAGAACC
3801 CCCCGTTCAG CCCGACCGCT GCGCCTTATC CGGTAACTAT CGTCTTGAGT CCAACCCGGT AAGACACGAC TTATCGCCAC TGCACGAGC CATCGGTAC
3901 AGGATTAGCA GAGCGAGGTA TGTAGGCGGT GCTACAGAGT TCTTGAAGTG GTGGCCTAAC TACGGCTACA CTAGAAGAAC AGTATTGT ATCTGCCCTC
4001 TGCTGAAGCC AGTTACCTTC GGAAAAAGAG TTGGTAGCTC TTGATCCGGC AAACAAACCA CCGCTGGTAG CGGTGGGTT TTTGTTTGCA AGCAGCAGAT
4101 TACGCGCAGA AAAAAGGAT CTCAAGAAGA TCCTTTGATC TTTTCTACGG GTCTGACGC TCAGTGGAAC GAAAACTCAC GTTAAGGGAT TTGGTCATG
4201 GCTAGTTAAT TAACATTTAA ATCAGCGGCC GCAATAAAAT ATCTTTATTT TCATTACATC TGTGTGTGG TTTTTTGTGT GAATCGTAAC TAACATACGC
4301 TCTCCATCAA AACAAAACGA AACAAACAA ACTAGCAAAA TAGGCTGTCC CCAGTGCAAG TGCAGGTGCC AGAACATTC TCTATCGAA (SEQ ID NO: 81)
```

IL2ss.CCL7.hIgG1Fc sequence

```
   1 GGATCTGCCA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101 GAGAAGGTGG CGCGGGGTAA ACTGGGAAAG TGATGTCGTG TACTGGCTCC GCCTTTTCC TGGGGGGGCT TGGAGGGGCGT CGAGGGTGGG GGAGAACCGT ATATAAGTGC AGTAGTCGCC
 201 GTGAACGTTC TTTTTCGCAA CGGGTTTGCC GCCAGAACAC AGTGAAGCT TGGAGGGGCT TCCTGAACTG CGCATTCTC CTTCACGCGC CGCCGGCCCT ACCTGAGGCC
 301 GCCATCCACG CCGGTTGAGT CGCGTTCTGC CGCGTTCCGC CTGTGCCGT CCAGCCTTTG CGTCCGCCGT CTAGGTAAGT TTAAAGCTCA GGTCGAGACC
 401 GGGCCTTTGT CCGGCGCTCC CTTGGAGCCT ACCTAGACTC AGCCGGCTCT CCAAGCCTCT CCAGACCCTG CTTGCTCAAC TCTACGTCTT TGTTTCGTTT
                                  KasI
                                  NarI
                                  SfoI
                                  BbeI
                                                                                                 IL-2 secretion signal
                                                                                        MetTyrArg MetGlnLeu LeuSerCysIle
 501 TCTGTTCTGC GCCGTTACAG ATCCAAGCTG TGACCGGCGC CTACCTGAGA TCAACCGGCGA AGGAGGGCCA CCATGTACAG GATGCAACTC CTGTCTTGCA
                           EcoRI            ~~~~~~ CCL7 (1-76)
     AlaLeuSer LeuAlaLeu ValThrAsnSer CysCysTyr ArgPheIle AsnLysLysIle ProLysGln ArgLeuGlu SerTyrArgArg ThrThrSer
 601 TTGCACTAAG TCTTGCACTT GTCACGAATT CGTGCTGTA CAGATTTATC AATAAGAAAA TCCCTAAGCA GAGGCTGGAG AGTTACAGAA GGACCACCAG
     SerHisCys ProArgGluAla VallIlePhe LysThrLys LeuAspLysGlu IleCysAla AspProThr GlnLysTrpVal GlnAspPhe MetLysHis
 701 TAGCCACTGT CCCCGGGAAG CTGTAATCTT CAAGACCAAA CTGGACAAAG AGATCTGTGC CAGACCCACA CAGAAGTGGG TCCAGGACTT TATGAAGCAC
                                                   human IgG1 Fc (constant region)
     LeuAspLysLys ThrGlnThr ProLysLeu AspLysThrHis ThrCysPro ProCysPro AlaProGluLeu LeuGlyGly ProSerVal PheLeuPhePro
 801 CTGGACAAGA AAACCCAAAC TCCAAAGCTT GACAAAACTC ACACATGCCC ACCGTGCCCA GCACCTGAAC TCCTGGGGGG ACCTCAGTC TTCCTCTTCC
     ProLysPro LysAspThr LeuMetIleSer ArgThrPro GluValThr CysValValVal AspValSer HisGluAsp ProGluValLys PheAsnTrp
 901 CCCCAAACC CAAGGACACC CTCATGATCT CCCGGACCC TGAGGTCACA TGCGTGGTGG TGGACGTGAG CCACGAAGAC CCTGAGGTCA AGTTCAACTG
     TyrValAsp GlyValGluVal HisAsnAla LysThrLys ProArgGluGlu GlnTyrAsn SerThrTyr ArgValValSer ValLeuThr ValLeuHis
1001 GTACGTGGAC GGCGTGGAGG TGCATAATGC CAAGACAAAG CCGCGGGAGG AGCAGTACAA CAGCACGTAC CGTGTGGTCA GCGTCCTCAC CGTCCTGCAC
     GlnAspTrpLeu AsnGlyLys GluTyrLys CysLysValSer AsnLysAla LeuProAla ProIleGluLys ThrIleSer LysAlaLys GlyGlnProArg
1101 CAGGACTGGC TGAATGGCAA GGAGTACAAG TGCAAGGTCT CCAACAAAGC CCTCCCAGCC CCCATCGAGA AAACCATCTC CAAGGCCAAA GGGCAGCCCC
     GluProGln ValTyrThr LeuProProSer ArgGluGlu MetThrLys AsnGlnValSer LeuThrCys LeuValLys GlyPheTyrPro SerAspIle
1201 GAGAACCACA GGTGTACACC CTGCCCCCAT CCCGGGAGGA GATGACCAAG AACCAGGTCA GCCTGACCTG CCTGGTCAAA GGCTTCTATC CCAGCGACAT
                                                                                                     AseI
     AlaValGlu TrpGluSerAsn GlyGlnPro GluAsnAsn TyrLysThrThr ProProVal LeuAspSer AspGlySerPhe PheLeuTyr SerLysLeu
1301 CGCCGTGGAG TGGGAGAGCA ATGGGCAGCC GGAGAACAAC TACAAGACCA CGCCTCCCGT GCTGGACTCC GACGGCTCCT TCTTCCTCTA CAGCAAGCTC
     ThrValAspLys SerArgTrp GlnGlnGly AsnValPheSer CysSerVal MetHisGlu AlaLeuHisAsn HisTyrThr GlnLysSer LeuSerLeuSer
1401 ACCGTGGACA AGAGCAGGTG GCAGCAGGGG AACGTCTTCT CATGCTCCGT GATGCACGAG GCTCTGCACA ACCACTACAC GCAGAAGAGC CTCTCCCTGT
     ProGlyLys ***(SEQ ID NO: 55)
1501 CTCCGGGTAA ATGAGTGCTA GCTGGCCAGA CATGATAAGA TACATTGATG AGTTTGGACA AACCACAACT AGAATGCAGT GAAAAAAATG CTTTATTTGT
1601 GAAATTTGTG ATGCTATTGC TTTATTTGTA ACCATTATAA GCTGCAATAA ACAAGTTAAC ACAAGTAATT GCATTCATTT TATGTTTCAG GTTCAGGGGG
1701 AGGTGTGGGA GGTTTTTTAA AGCAAGTAAA ACCTCTACAA ATGTGGTATG GAATTAATTC TAAAATACAG CATAGCAAAA CTTTAACCTC CAAATCAAGC
1801 CTCTACTTGA ATCCTTTTCT GAGGGATCAA TAAGGCATAG GCATCAGGGG GCATCAGGGG CGTGTTGCAG CTGTTGGAGG CCTTACCCTC TTTCATGGAG
1901 TTTAAGATAT AGTGTATTTT CCAAGGGTTT CAGCTAGCTC TTCATTTCTT TATGTTTTAA ATGCACTGAC CTCCCACATT CCCTTTTTAG TAAAATATTC
2001 AGAAATAATT TAAATACATC ATTGCAATGA AAATAAATGT TTTTTATTAG GCAGAATCCA GATGCTCAAG GCCCTTCATA ATATCCCCCA GTTTAGTAGT
2101 TGGACTTAGG GAACAAAGGA ACCTTTAATA GAAATTTGAC AGCAAGAAAG CGAGCTTCTA GCTTATCCTC AGTCCTGCTC CTTGCCACA AAGTGCACGC
2201 AGTTGCCGGC AGGGCGGGC CGGTCGTCGG AGGGCGAACT CCGATGCTCG CCGATCGTCG CCCTGCTCGG TCATGGCGGG CCCGGAGCGG TCGTCGACAC
2301 GACCCTCCGA CACTCGGCGT ACAGATCCTC CAGGCCCGGC ACAGCCCGTC CAGGCCGGGT CTTGTCCCGG ACCACCTGGT CCTGGACCCGC GCTGATGAAC
```

```
2401 AGGGTCACGT CGTCCCGGAC CACACCGGCG AAGTCGTCCT CCACGAAGTC CCGGGAGAAC CCGAGCCGGT CGGTCCAGAA CTCGACCGCT CCGGCGACGT
2501 CGCGCGCGGT GAGCACCGGA ACGGCACTGG TCAACTTGGC CATGATGGCT CCTCCTGTCA GGAGAGAAGG GAGAAGAAGG TTAGTACAAT TGCTATAGTG
                                              AseI
2601 AGTTGTATTA TACTATGCAG ATATACTATG CCAATGATTA ATTGTCAAAC TAGGGCTGCA GGGTTCATAG TGCCACTTTT CCTGCACTGC CCCATCTCCT
2701 GCCCACCCTT TCCCAGGCAT AGACAGTCAG TGACTTACCA AACTCACAGG AGGGAGAAGG CAGAAGCTTG AGACAGACCC GCGGGACCGC CGAACTGGGA
2801 GGGGACGTGG CTAGGGCGGC TTCTTTTATG GTGCGCCGGC CCTCGGAGGC CCTCGGAGGC GGGAGGCCTA GGGGCCAATC TGCGGTGGCA GGAGGCGGGG
2901 CCGAAGGCCG TGCCTGACCA ATCCGGAGCA CATAGGAGTC TCAGCCCCCC GCCCAAAGC CACGCGCCTG TAGCGGCAGC GTGTTGTGAA
3001 ATGGGGGCTT GGGGGGGTTG GGGCCCTGAC TAGTCAAAAC AAACTCCCAT TGACGTCAAT GGGGTGGAGA CTTGGAAATC CCCGTGAGTC AAACCGCTAT
3101 CCACGCCCAT TGATGTACTG CCAAAACCGC ATCATCATGG TAATAGCGAT GACTAGTACT TAGAGTAGG GCCAAGTAGG AAAGTCCCAT AAGGTCATGT
3201 ACTGGGCATA ATGCCAGGCG GGCCATTTAC GTCAATTGAC GTCAATAGGG GGCGTACTTG GCATATGATA CACTTGATGT ACTGCCAAGT GGGCAGTTTA
3301 CCGTAAATAC TCCACCCATT GACGTCAATG GAAAGTCCCT ATTGGCGTTA CTATGCGAAC ATACGTCATT ATTGACGTCA ATGGGCGGGG GTCGTTGGGC
3401 GGTCAGCCAG GCGGGCCATT TACCGTAAGT CTGCAGGTTA TATGTAACGC GACGAGCATC TGTGAGCAACA AGGCCAGCAA AAGGCCAGGA ACCGTAAAAA
3501 GGCCGCGTTG CTGGCGTTTT TCCATAGGCT CCGCCCCCCT CTCCTGTTCC GACCCTGCCG ACGCTCAAGT CAGAGGTGGC GAAACCGAC CTTTCTCCCT
3601 AGATACCAGG CGTTTCCCCC TGGAAGCTCC CTCGTGCGCT GTTCGCTCCA AGCTGGGCTG TGTGCACGAA ACCTGTCCGC CCCCCGTTC AGCCCGACCG
3701 TGGCGCTTTC TCATAGCTCA CGCTGTAGGT ATCTCAGTTC GGTGTAGGTC GTTCGCTCCA AGCTGGGCTG TGTGCACGAA ACCTGTCCGC CCCCCGTTC AGCCCGACCG
3801 CTGGCGCTTA TCCGGTAACT ATCGTCTTGA GTCCAACCCG GTAAGACACG ACTTATCGCC ACTGGCAGCA ACAGGATTAG CAGAGCGAGG
3901 TATGTAGGCG GTGCTACAGA GTTCTTGAAG TCTTGATCCG GCAAACAAAC CACCGCTGGT AGCGGTGGTT TTTTTGTTTG CAAGCAGCAG ATTACGCGCA GAAAAAAGG
4001 TCGGAAAAAG AGTTGGTAGC TCTTGATCCG GCAAACAAAC CACCGCTGGT AGCGGTGGTT TTTTTGTTTG CAAGCAGCAG ATTACGCGCA GAAAAAAGG
4101 ATCTCAAGAA GATCCTTTGA TCTTTTCTAC GGGGTCTGAC GCTCAGTGGA ACGAAAACTC ACGTTAAGGG ATTTTGGTCA TGCCTAGTTA ATTAACATTT
4201 AAATCAGCGG CCGCAATAAA ATATCTTTAT TTTCATTACA CCCCAGTGGTG GTTCATTAC CCCCAGTGGT AGTGCAGGTG CCGAACATT TCTCTATCGA TCTAACATGC GTCTCCCATC AAAACAAAAC
4301 GAAACAAAAC AAACTAGCAA                                                                                                 A (SEQ ID NO: 82)
```

IL2ss.CCL7(5-76).hIgG1Fc sequence

```
2301  CTCGGCGTAC  AGCTCGTCCA  GGCCGCGCAC  CCACACCCAG  GCCAGGGTGT  TGTCCGGCAC  CACCTGGTCC  TGGACCCGCG  TGATGAACAG  GGTCACGTCG
2401  TCCCGGACCA  CACCGGCGAA  GTCGTCCTCC  ACGAAGTCCC  GGGAGAACCC  GAGCCGGTCG  GTCCAGAACT  CGACCGCTCC  GGGCGACGTCG  CCGGCGGTGA
2501  GCACCGGAAC  GGCACTGGTC  AACTTGGCCA  TGATGGCTCC  TCCTGTCAGG  AGAGGAAAGA  GAAGAAGGTT  AGTACAATTG  CTATAGTGAG  TTGTATTATA
                   AseI
2601  CTATGCAGAT  ATACTATGCC  AATGATTAAT  TGTCAAACTA  GGGCTGCAGG  GTTCATAGTG  CCACTTTTCC  TGCACTGCCC  CATCTCCTGC  CCACCCTTTC
2701  CCAGGCATAG  ACAGTCAGTG  ACTTACCAAA  CTCACAGGAG  GGAGAAGGCA  GAAGCTTGAG  ACAGACCCGC  GGGACCCGCG  AACTGCGAGG  GGACGTGGCT
2801  AGGGCGGCTT  CTTTTATGGT  CGCCCGGCCC  TCGGAGGCAG  GGCGCTCGGG  GAGGCCTAGC  GCCAATCTG  CGGTGGCAGG  AGGCGGGGCC  GAAGGCCGTG
2901  CCTGACCAAT  CGGAGCACA  TAGGAGTCTC  AGCCCCCCGC  CCCAAAGCAA  GGGAAGTCA  CGGCCCTGTA  GCGCCAGCGT  GTTGTGAAAT  GGGGGCTTGG
3001  GGGGTTGGG  GCCCTGACTA  GTCAAAACAA  ACTCCCATTG  ACGTCAATGG  GGTGAAGTCA  TGGAAATCCC  CGTGAGTCAA  ACCGCTATCC  ACGCCCATTG
3101  ATGTACTGCC  AAAACCGCAT  CATCATGGTA  ATAGCGATGA  CTAATACGTA  GATGTACTGC  CAAGTAGGAA  AGTCCCATAA  GGTCATGTAC  TGGGCATAAT
3201  GCCAGGCGGG  CCATTACCG  TCATTGACGT  CAATAGGGGG  CGTACTTGC  ATATGATACA  CTTGATGTAC  TGCCAAGTGG  GCAGTTTACC  GTAAATACTC
3301  CACCCATTGA  CGTAATGGA  AAGTCCCTAT  ATGGGAACAT  ACGTCATTAT  TGACGTCAAT  GGGCGGGGT  CGTTGGGCGG  TCAGCCAGGC
3401  GGGCCATTTA  CCGTAAGTTA  TGTAACGCCT  GCAGGTTAAT  TAAGAACATG  TGAGCAAAAG  GCCAGCAAAA  GGCCAGGAAC  CGTAAAAAG  CCGCGTTGCT
3501  GGCGTTTTTC  CATAGGCTCC  GCCCCCCTGA  CGAGCATCAC  AAAAATCGAC  GCTCAAGTCA  GAGGTGGCGA  AACCCGACAG  GACTATAAAG  ATACCAGGCG
3601  TTTCCCCCTG  GAAGCTCCCT  CGTGCGCTCT  CCTGTTCCGA  CCCTGCCGCT  TACCGGATAC  CTGTCCGCCT  TTCTCCCTTC  GGGAAGCGTG  GCGCTTTCTC
3701  ATAGCTCACG  CTGTAGGTAT  CTCAGTTCGG  TGTAGGTCGT  TCGCTCCAAG  CTGGGCTGTG  TGCACGAACC  CCCCGTTCAG  CCCGACCGCT  GCGCCTTATC
3801  CGGTAACTAT  CGTCTTGAGT  CCAACCCGGT  AAGACACGAC  TTATCGCCAC  TGGCAGCAGC  CACTGGTAAC  AGGATTAGCA  GAGCGAGGTA  TGTAGGCGGT
3901  GCTACAGAGT  TCTTGAAGTG  GTGGCCTAAC  TACGGCTACA  CTAGAAGAAC  AGTATTTGGT  ATCTGCGCTC  TGCTGAAGCC  AGTTACCTTC  GGAAAAAGAG
4001  TTGGTAGCTC  TTGATCCGGC  AAACAAACCA  CCGCTGGTAG  CGGTGGTTTT  TTTGTTTGCA  AGCAGCAGAT  TACGCGCAGA  AAAAAAGGAT  CTCAAGAAGA
4101  TCCTTTGATC  TTTTCTACGG  GGTCTGACGC  TCAGTGGAAC  GAAAACTCAC  GTTAAGGGAT  TTTGGTCATG  AGATTATCAA  AAAGGATCTT  CACCTAGATC
4201  GCAATAAAAT  ATCTTTATTT  TCATTACATC  TGTGTGTTGG  TTTTTTGTGT  GAATCGTAAC  TAACATACGC  TCTCCATCAA  ATCAGCGGCC
4301  ACTAGCAAAA  TAGGCTGTCC  CCAGTGCAAG  TGCAGGTGCC  AGAACATTTC  TCTATCGAA  (SEQ ID NO:83)
```

IL2ss.CCL7(5-76).hIgG1Fc sequence
Alanine substitutions for removal of GAG binding sites – Lys & His

```
   1 GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101 GAGAAGGTGG CGCGGGGTAA ACTGGGAAAG TGATGTCGTG TTACTCGCTCC GCCTTTTCC CGAGGGGTGG GGAGAACCGT ATATAAGTGC AGTAGTCGCC
 201 GTGAACGTTC TTTTTCGCAA CGGGTTTGCC GCCAGAACAC AGTGAAGCT TGGAGGGCT CGCATCTCTC CGCATCGCGC CTTCACGCGC CCGCGCCCT ACCTGAGGCC
 301 GCCATCCACG CCGGTTGAGT CGGGTTCTGC CGGGTGTGCC CTGTGGTGCC TCCTGAACTG CGTCCGCCGT CGTCCGCCGT CTAGGTAAGT TTAAAGCTCA GGTCGAGACC
 401 GGGCCTTTGT CCGGCGCTCC CTTGGAGCCT ACCTAGACTC AGCCGGCTCT CCACGGCTTG CCTGACCCTG CCTGCTCAAC TCTACGTCTT TGTTTCGTTT

IL-2 secretion signal
                                                                                            MetTyrArg MetGlnLeu LeuSerCysIle
 501 TCTGTTCGC GCCGTTACAG ATCCAAGCTG TGACCGGCGC CTACCTGAGA TCAGGGCGA AGGAGGGCCA CCATGTACAG GATGCAACTC CTGTCTTGCA
                                                                                           ─────────────────
        AlaLeuSer LeuAlaLeu ValThrAsnSer PheIleAsn LysLysIle ProLysPro CysProAla ProGluLeu LeuGlyGlyPro ProLysPhe
 601 TTGCACTAAG TCTTTGCACTT GTCACGAATT CGTTTATCAA TAAGAAAATC CCTAAGCAGA GGCTGAGTGA CTACAGAAGG ACCACCAGTA GCCACTGTCC
                            EcoRI                                        ─── CCL7 (5-76)
        ArgGluAla ValIlePheAla ThrIleAsp AspSerAlaGlu IleCysAlaGlu AspAlaAsp ProThrGln AlaTrpVal GlnAspPheMet AlaAlaLeu AspAlaAla
 701 CGGGAAGCT GTAATCTTCG ccACCggGT GGACGGCGAG ATCTGTGCTG ACCCACACA GGCCTGGGTC CAGGACTTTA TGgcGGCCT GGACGCggct
         KasI
         NarI
         SfoI
         BbeI
                 human IgG1 Fc (constant region)
        ThrGlnThrPro AlaLeuAsp LysThrHis ThrCysProPro CysProCys ProAla ProGluLeu LeuGlyGlyPro SerValPhe LeuPhePro ProLysProLys
 801 ACCCAAACTC CAGCCCTTGA CAAAACTCAC ACATGCCCAC CGTGCCCAGC ACCTGAACTC CTGGGGGGAC CGTCAGTCTT CCTCTTCCCC CCAAAACCCA
        AspThrLeu MetIleSer ArgThrProGlu ValThrCys ValValVal AspValSerHis GluAspPro GluValLys PheAsnTrpTyr ValAspGly
 901 AGGACACCCT CATGATCTCC CGGACCCCTG AGGTCACATG CGTGGTGGTG GACGTGAGCC ACGAAGACCC TGAGGTCAAG TTCAACTGGT ACGTGGACGG
        ValGluVal HisAsnAlaLys ThrLysProArg GluGluGln TyrAsnSer ThrTyrArg ValValSer ValLeuThrVal LeuHisGln AspTrpLeu
1001 CGTGGAGGTG CATAATGCCA AGACAAAGCC GCGGGAGGAG CAGTACAACA GCACGTACCG TGTGGTCAGC GTCCTCACCG TCCTGCACCA GGACTGGCTG
        AsnGlyLysGlu TyrLysCys LysValSer AsnLysAlaLeu ProAlaPro IleGluLys ThrIleSerLys AlaLysGly GlnProArg GluProGlnVal
1101 AATGGCAAGG AGTACAAGTG CAAGGTCTCC AACAAAGCCC TCCCAGCCCC CATCGAGAAA ACCATCTCCA AAGCCAAAGG GCAGCCCCGA GAACCACAGG
        TyrThrLeu ProProSer ArgGluGluMet ThrLysAsn GlnValSer LeuThrCysLeu ValLysGly PheTyrPro SerAspIleAla ValGluTrp
1201 TGTACACCCT GCCCCCATCC CGGGAGGAGA TGACCAAGAA CCAGGTCAGC CTGACCTGCC TGGTCAAAGG CTTCTATCCC AGCGACATCG CCGTGGAGTG
        GluSerAsn GlyGlnProGlu ValAsnTyr LysThrThr ProProValLeu AspSerAsp GlySerPhe PheLeuTyrSer LysLeuThr ValAspLys
1301 GGAGAGCAAT GGGCAGCCGG AGAACAACTA CAAGACCACG CCTCCCGTGC TGGACTCCGA CGGCTCCTTC TTCCTCTACA GCAAGCTCAC CGTGGACAAG
        SerArgTrpGln GlnGlyAsn ValPheSer CysSerValMet HisGluAla LeuHisAsn HisTyrThrGln LysSerLeu ProGlyLys***
1401 AGCAGGTGGC AGCAGGGGAA CGTCTTCTCA TGCTCCGTGA TGCACGAGGC TCTGCACAAC CACTACACGC AGAAGAGCCT CTCCCTGTCT CCGGGTAAAT
                                                                                                       (SEQ ID NO: 57)
        Bmti
      ** NheI
1501 GAGTGCTAGC TGGCCAGACA TGATAAGATA CATTGATGAG TTTGGACAAA CCACAACTAG AATGCAGTGA AAAAAATGCT TTATTTGTGA AATTTGTGAT
1601 GCTATTGCTT TATTTGTAAC CATTATAAGC TGCAATAAAC AAGTTAACAA CAACAATTGC ATTCATTTTA TGTTTCAGGT TCAGGGGGAG GTGTGGGAGG
                                                                       AseI
1701 TTTTTTAAAG CAAGTAAAAC CCTACAAAT GTGGTATGGA ATTATTTCTA AAATACAGCA TAGCAAAACT TTAACCTCCA AATCAAGCCT CTACTTGAAT
1801 CCTTTTCTGA GGGATGAATA AGGCATAGGC ATCAGGGGCT GTTGCCAATG TGCATTAGCT CCCACATTCC GTTTCAGCC TCACCTTCTT TCATGGAGTT TAAGATATAG
1901 TGTATTTTCC CAAGGTTTGA ACTAGTCTTT CATTTCTTTA TGTTTTAAAT GGACTGACCT CCCTTCATAAT CTTTTTAGTA AAATATTCAG AAATAATTTA
2001 AATACATCAT TGCAATGAAA ATAAATGTTT TTTATTAGCC AGAATCCAGA TGCTCAAGGC CCCATCATAAT ATCCCCCAGT TTGTAGTTG GACTTAGGGA
2101 ACAAGGAAC CTTTAATAGA AATTGGACAG CAAGAAAGCG AGCTTCTAGC TTATCCTAG CTGCACGAA TGTCACGCAG TTGCCGCCCG
```

```
2201  GGTCGCGCAG GGCGAACTCC CGCCCCCACG GCTGCTCGCC GATCTCGGTC ATGGCCGGCC CGGAGGCGTC CCGGAAGTTC GTGGACACGA CCTCCGACCA
2301  CTCGGCGTAC AGCTCGTCCA GGCCGCGCAC GCCAGGGTGT GCCAGCCCAC TGTCCGGCAC CACCTGGTCC TGGACCGCGC TGATGAACAG GGTCACGTCG
2401  TCCCGGACCA CACCGGCGAA GTCGTCCTCC ACGAAGTCCC GGGAGAACCC GAGCCGGTCG GTCCAGAACT CCGGACGTCC GGCGACGTCG CGCGCGGTGA
2501  GCACCGGAAC GGCACTGGTC AACTTGGCCA TGATGGCTCC TCCTGTCAGG AGAGGAAAGA GAAGAAGGTT AGTACAATTG CTATAGTGAG TTGTATTATA
                                    AseI
2601  CTATGCAGAT ATACTATGCC AATGATTAAT TGTCAAACTA GGGCTGCAGG GTTCATAGTG CCACTTTTCC TGCACTGCCC CATCTCCTGC CCACCCTTTC
2701  CCAGGCATAG ACAGTCAGTG ACTTACCAAA CTCACAGGAG GGAGAAGGCA GAAGCTTGAG ACAGACCCGC GGACCGCCG AACTGCGAGG GGACGTGGCT
2801  AGGGCGGCTT CTTTTATGGT GCGCCGGCCG TCCGAGGCAG GGCGCTCGGG GAAGCCTAGC GGCCAATCTG CGGTGGCAGG AGGCGGGGCC GAAGGCCGTG
2901  CCTGACCAAT CCGGAGCACA TAGGAGTCTC AGCCCCCGC CCCAAAGCAA GGGGAAGTCA CGGCCTGTA GCGCCAGCGT GTTGTGAAAT GGGGGCTTGG
3001  GGGGGTTGGG GCCCTGACTA GTCAAAACAA ACTCCCATTG ACGTCAATGG GGTGGAGACT TGGAAATCCC CGTGAGTCAA ACCGCTATCC ACGCCCATTG
3101  ATGTACTGCG AAAACCGCAT CATCATGATGA CTAATACGTA ATAGCCATGA CAAGTAGGAA AGTCCCATAA GGTCATGTAC TGGGCATAAT
3201  GCCAGGCGGG TCATTTACCG CAATAGGGGG CGTACTTGGC ATATGATACA CTTGATGTAC TGCCAAGTGG GCAGTTTACC GTAAATACTC
3301  CACCCATTGA CGTCAATGGA AAGTCCCTAT ATGGGAACAT ACGTCATTAT GGGCGGGGT CGTTGGCGG TCAGCCAGGC
3401  GGGCCATTTA CCGTAAGTTA TGTAACGCCT GCAGGTTAAT TAAGAACATG TGAGCAAAAG GCCAGCAAAA CCGCGTTGCT
3501  GGCGTTTTTC CATAGGCTCC GCCCCCCTGA CGAGCATCAC GCTCAAGTCA GAGGTGGCGA AACCCGACAG GACTATAAAG ATACCAGGCG
3601  TTTCCCCCTG GAAGCTCCCT CGTGCGCTCT CCTGTTCCGA CCCTGCCGCT TACCGGATAC CTGTCCGCCT TCTCCCTTC GGAAGCGTG GCGCTTTCTC
3701  ATAGCTCACG CGTGTAGGTAT CTCAGTTCGG TGTAGGTCGT TCGCTCCAAG TGGGCGTGTG TGCACGAACC CCCGTTCAG CCCGACCGCT GCGCCTTATC
3801  CGGTAACTAT CGTCTTGAGT CCAACCCGGT AAGACACGAC TTATCGCCAC TGGCAGCAGC CACTGGTAAC AGGATTAGCA GAGCGAGGTA TGTAGGCGGT
3901  GCTACAGAGT TCTTGAAGTG GTGGCCTAAC CTAGAAGAAC ATCTGCGCTC TGCTGAAGCC AGTTACCTTC GGAAAAAGAG
4001  TTGGTAGCTC TTGATCCGGC AAACAAACCA CCGCTGGTAG CGGTGGTTTT TTTGTTTGCA AGCAGCAGAT TACGCGCAGA AAAAAAGGAT CTCAAGAAGA
4101  TCCTTTGATC TTTTCTACGG GGTCTGACGC TCAGTGGAAC GAAAACTCAC GTTAAGGGAT TTTGGTCATG GCTAGTTAAT TAACATTTAA ATCAGGCCC
4201  GCAATAAAAT ATCTTTATTT TCATTACATC TGTGTGTTGG TTTTTTGTGT GAATCGTAAC TAACATACGC TCTCCATCAA AACAAAACGA AACAAAACAA
4301  ACTAGCAAAA TAGGCTGTCC CCAGTGCAAG TGCAGGTGCC AGAACATTTC TCTATCGAA (SEQ ID NO: 84)
```

*FIG. 2E (CONT)*

FIG. 3A
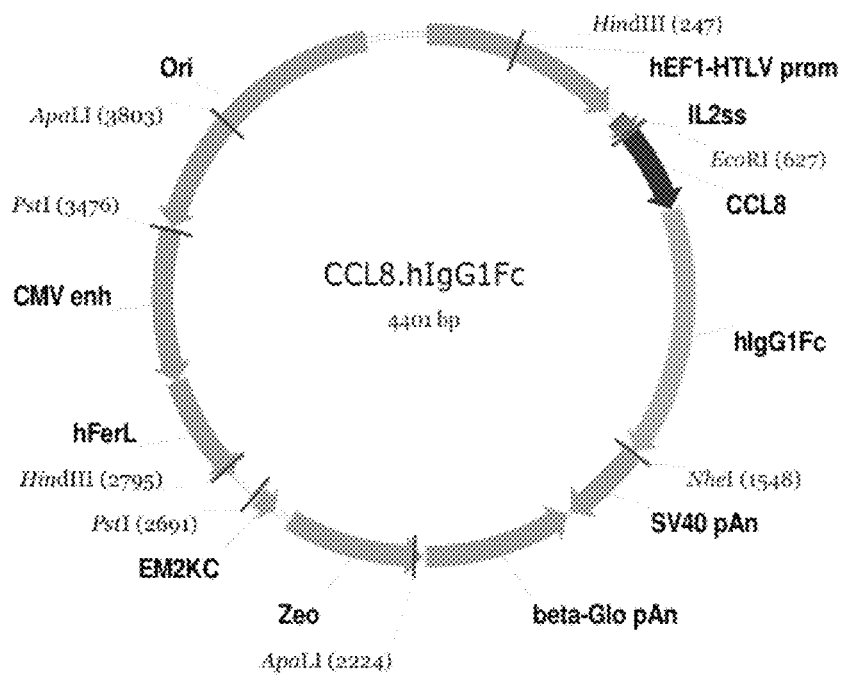
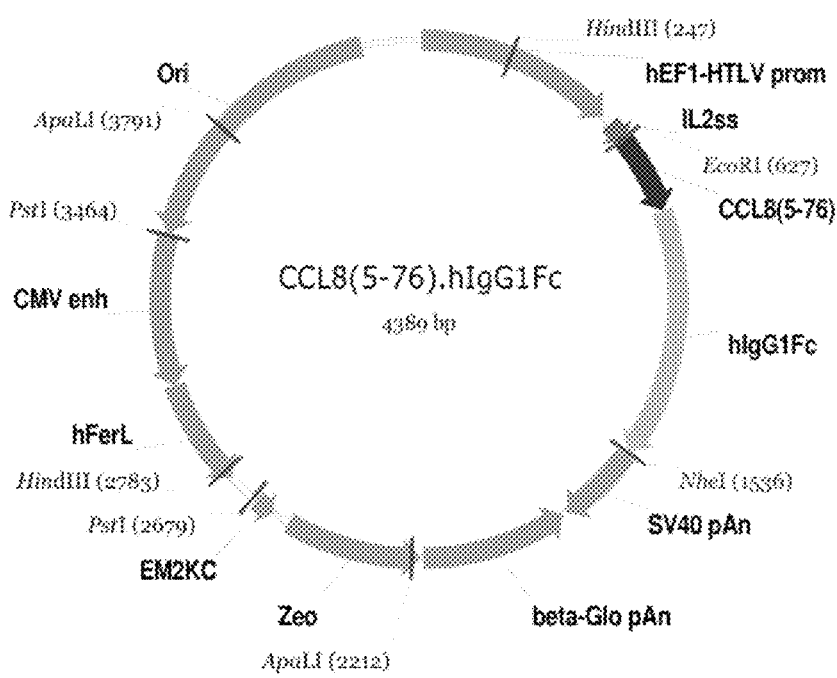
FIG. 3B

FIG. 3C

IL2ss.CCL8.hIgG1Fc sequence

```
   1 GGATCTGCGA TCGCTCCGGT GCCGTCAGT GGGCAGAGCG CACATCCCCG ACAGTCCCCG AGAAGTTGGG GGGAGGGGTC GGCAATTGAA CGGGGTGCCTA
 101 GAGAAGGTGG CCGGGGTAA ACTGGGAAAG TGATGTCGTG GCCAGAACAC AGCTGAAGCT GCCTTTTCC CGAGGGTGG GGAGAACCGT ATATAAGTGC AGTAGTCGCC
 201 GTGAACGTTC TTTTTCGCAA CGGGTTTGCC GCGTTCTGC CGCTCCCGC TCGAGGGGCT TCGATCTCT CGCATCACGC CTTCACGCGC CCGCGCCCT ACCTGAGGCC
 301 GCCATCCACG CCGGTTGAGT CGCGTTCTGC CGGTTCTGC AGCCGGCTCT TCCTGAACTG CGTCCGCCGT CTAGGTAAGT CTTGCTCAAC TTAAGCTCA GGTCGAGACC
 401 GGGCCTTTGT CCGGCGCTCC CTTGGAGCCT ACCTAGACTC AGCCGGCTCT                                                TCTACGTCTT TGTTTCGTTT

IL-2 secretion signal
                                                                                                       MetTyrArg MetGlnLeu LeuSerCysIle
 501 TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                          EcoRI
                                     --------- CCL8 (1-76)
                          AlaLeuSer LeuAlaLeu ValThrAsnSer GlnProAsp SerValSer IleProIleThr CysCysPhe AsnValIle AsnArgLysIle ProIleGln
 601 TGCACTAAG TCTTGCACTT GTCAGGATTC CGCACGTAA TTCAGTTTCC ATCCAATCA CCTGCTGCTT TAACGTGATC AATAGGAAAA TTCCTATCCA
                          ArgLeuGlu SerTyrThrArg IleThrAsn IleGlnCys ProLysGlu ValIlePhe ArgGlyLysPhe LysThrLys ArgValVal GluValThr CysValValVal AspValSer
 701 GAGGCTGGAG AGTACAGAA GAATCACCAA CATCCAAATGT CCCCAAGGAA CTGTGATCTT CAAGACCAAA CGGGAGCAAG AGTCTGTGC TGACCGTCAG human IgG1 Fc (constant region)
                          GluArgTrpVal ArgAspSer MetLysHis LeuAspAsn PheGlnAsn LeuLysPro AspLysThr HisThrCysPro ProCysPro AlaProGluLeu
 801 GAGAGATGGG TCAGGGATTC CATGAAGCAT CTGGACCAAA TATTTCAAAA TCTGAAGCCA GACAAAACTC ACACATGCCC ACCGTGCCCA GCACCTGAAC
                          LeuGlyGly ProSerVal PheLeuPhePro ProLysPro LysAspThr LeuMetIleSer ArgThrPro GluValThr CysValValVal AspValSer
 901 TCCTGGGGGG ACCGTCAGTC TTCCTCTTCC CCCCAAAACC CAAGGACACC CTCATGATCT CCCGGACCCC TGAGGTCACA TGCGTGGTGG TGGACGTGAG
                          HisGluAsp ProGluValLys PheAsnTrp TyrValAsp GlyValGluVal HisAsnAla LysThrLys ProArgGluGlu GlnTyrAsn SerThrTyr
1001 CCACGAGGAC CCTGAGGTCA AGTTCAACTG GTACGTGGAC GGCGTGGAGG TGCATAATGC CAAGACAAAG CCGCGGGAGG AGCAGTACAA CAGCACGTAC
                          ArgValValSer ValLeuThr ValLeuHis GlnAspTrpLeu AsnGlyLys GluTyrLys CysLysValSer AsnLysAla LeuProAla ProIleGluLys
1101 CGTGTGGTCA GCGTCCTCAC CGTCCTGCAC CAGGACTGGC TGAATGGCAA GGAGTACAAG TGCAAGGTCT CCAACAAAGC CCTCCCAGCC CCCATCGAGA
                          ThrIleSer LysAlaLys GlyGlnProArg GluProGln ValTyrThr LeuProProSer ArgGluGlu MetThrLys AsnGlnValSer LeuThrCys
1201 AAACCATCTC CAAAGCCAAA GGGCAGCCCC GAGAACCAA GGTGTACACC CTGCCCCCAT CCCGGGAGGA GATGACCAAG AACCAGGTCA GCCTGACCTG
                          LeuValLys GlyPheTyrPro SerAspIle AlaValGlu TrpGluSerAsn GlyGlnPro GluAsnAsn TyrLysThrThr ProProVal LeuAspSer
1301 CCTGGTCAAA GGCTTCTATC CCAGCGACAT CGCCGTGGAG TGGGAGAGCA ATGGGCAGCC GGAGAACAAC TACAAGACCA CGCCTCCCGT GCTGGACTCC
                          AspGlySerPhe PheLeuTyr SerLysLeu ThrValAspLys SerArgTrp GlnGlnGly AsnValPheSer CysSerVal MetHisGlu AlaLeuHisAsn
1401 GACGGCTCCT TCTTCCTCTA CAGCAAGCTC ACCGTGGACA AGAGCAGGTG GCAGCAGGGG AACGTCTTCT CATGCTCCGT GATGCACGAG GCTCTGCACA
                                                                                                       NheI
                                                                                                       AseI
                          HisTyrThr GlnLysLys LeuSerLeuSer ProGlyLys *** (SEQ ID NO: 58)
1501 ACCACTACAC GCAGAAGAGC CTCTCCCTGT CTCCGGGTAA ATGAGTGCTA GCTAGCCAGA CATGATAAGA TACATTGATG AGTTTGGACA AACCACAACT
1601 AGAATGCAGT GAAAAAAATG CTTTATTTGT GAAATTTGTG ATGCTATTGC TTTATTTGTA ACCATTATAA GCTGCAATAA ACAAGTTAAC AACACAATT
1701 GCATTCATTT TATGTTTCAG GTTCAGGGGG AGTGTGGGA CCTTACTTGA ATCCTTTTT AGCAAGTAAA ACCTCTACAA ATGTGGTATG GAATTAATTC TAAAATACAG
1801 CATAGCAAAA CTTTAACCTC CAATCAAGC TTTCATGGAG TTTAAGATAT AGTGTATTTT CCCAAGGTTT GAACTAGCTC TTCATTTCT TATGTTTTTAA ATGCATTAG
1901 CTGTTTGCAG CCTCACCTTC CCTTTTTAG TAAAATATTC AGAAATAATT TAAATACATC ATTGCAATGA AAATAAAATGT TTTTTATAG GCAGAATCCA GATGCTCAAG
2001 CTCCCACATT CCCCATT ANATCCCCCA GTTTAGTAGT TGGACTTAGG CAAGAAAGGA ACCTTTAATA GAAATTTGAC AGCAAGAAAG CGAGTCTTCA GCTTATCCTC
2101 GCCTTCATA ANATCCCCCA GTTTAGTAGT TGGACTTAGG CAAGAAAGGA ACCTTTAATA GAAATTTGAC AGCAAGAAAG CGAGTCTTGA TCATGGCGG
2201 AGTCCTGCTC CCTCACCCA AGTGCACGG AGTTCCGGG CGGGTGCCGC CACTCCGGAT ACAGCCGAAT CGGGTCCGGT ACAGCTCGTC CAGGCCCCGC TCATGGCGG
2301 CCCCGAGCGG TCCCGGAAGT GACCTCCGAC AGGGTCACGT CGTTCCCGAC CACCACGGCG AAGTCCTCCT CAGGCCCCGC AGGCCAGGGT GTTGTCCGGC CCGAGCCGT
2401 ACCACCTGGT CCTGACCCGC GCTGATGAAC GCTGAGAACGG
```

```
2501 CGGTCCAGAA CTCGACCGCT CCGGCGACGT CGCGCGCGGT GAGCACCGGA ACGGCACTGG TCAACTTGGC CATGATGGCT CCTCCTGTCA GGAGAGGAAA
                                                                            AseI
2601 GAGAAGAAGG TTAGTACAAT TGCTATAGTG AGTTGTATTA TACTATGCAG ATATACTATG CCAATGATTA ATTGTCAAAC TAGGGCTGCA GGGTTCATAG
2701 TGCCACTTTT CCTGCACTGC CCCATCTCCT GCCCACCCTT CTAGGGCGGG GGGGACGTGG AGACAGTCAG TGACTTACCA AACTCACAGG AGGGAGAAGG CAGAAGCTTG
2801 AGACAGACCC GCGGGACCGC CGAACTGCGA GGGGACGTGG CTAGGGCGGC TTCTTTTATG GTGCGCCGGC CCTCGGAGGC GTGCGCCTCG GGGAGGCCTA
2901 GCGCCAATC TGCGGTGGCA GGAGGCGGGG CCGAAGGCCC TGCCTGACCA ATCCGAGCA CATAGGAGTC TCAGCCCCCC GCCCAAAGC AAGGGGAAGT
3001 CACGCGCCTG TAGCGCCAGC GTGTTGTGAA ATGGGGGCTT GGGGGGGTTG GGGCCCTGAC TAGTCAAAAC AAACTCCCAT TGACGTCAAT GGGGTGAGA
3101 CTTGGAAATC CCCGTGAGTC AAACCGCTAT CCACGCCCAT TGATGTACTG CCAAAACCGC TAATCATCATGG TAATAGCGAT GACTAATACG TAGATGTACT
3201 GCCAAGTAGG AAAGTCCCAT AAGGTCATGT ACTGGGCATA ATGCCAGGCG TCCACCCATT GGCCATTTAC CGTCATTGAC GTCAATAGGG GGCGTACTTG GCATATGATA
3301 CACTTGATGT ACTGCCAAGT GGGCAGTTTA CCGTAAATAC TCCACCCATT GACGTCAATG GAAAGTCCCT ATTGGCGTTA CTATGGAAAC ATACGTCATT
3401 ATTGACGTCA ATGGGCGGGG GTCGTTGGGC GGTCAGCCAG GCGGGCCATT TACCGTAAGT TATGTAACGC CTGCAGGTTA ATTAAGAACA TGTGAGCAAA
3501 AGGCCAGCAA AAGGCCAGGA ACCGTAAAAA GGCCGCGTTG CTGGCGTTTT TCCATAGGCT CCGCCCCCCT GACGAGCATC ACAAAAATCG ACGCTCAAGT
3601 CAGAGGTGGC GAAACCCGAC AGGACTATAA AGATACCAGG CGTTTCCCCC CTGGAAGCTC CCTCGTGCGT CTCCTGTTCC GACCCTGCCG CTTACCGGAT
3701 ACCTGTCCGC CTTTCTCCCT TCGGGAAGCG TGGCGCTTTC TCATAGCTCA CGCTGTAGGT ATCTCAGTTC GGTGTAGGTC GTTCGCTCCA AGCTGGGCTG
3801 TGTGCACGAA CCCCCCGTTC AGCCCGACCG CTGCGCCTTA TCCGGTAACT ATCGTCTTGA GTCCAACCCG GTAAGACACG ACTTATCGCC ACTGGCAGCA
3901 GCCACTGGTA ACAGGATTAG CAGAGCGAGG TATGTAGGCG GTGCTACAGA GTTCTTGAAG TGGTGGCCTA GCAAACAAAC CACCGCTGGT AGCGGTGGTT TTTTTGTTTG
4001 GTATCTGCGC TCTGCTGAAG CCAGTTACCT TCGGAAAAAG AGTTGGTAGC TCTTGATCCG GCAAACAAAC CACCGCTGAC GCTCAGTGGA ACGAAAACTC ACGTTAAGGG
4101 CAAGCAGCAG ATTACGCGCA GAAAAAAAGG ATCTCAAGAA GATCCTTTGA TCTTTTCTAC GGGGTCTGAC TCTGTGTGTT TTTCATTACA AGCGGGTGTT ACGTTAAGGG
4201 ATTTTGGTCA TGGCTAGTTA ATTAACATTT AAATCAGCGG CCGCAATAAA ATATCTTTAT TTTCATTACA GAGAAAACTC ACGTTAAGGG
4301 ACTAACATAC GCTCTCCATC AAAACAAAAC GAAACAGCAA AACTAGCAA AATAGGCTGT CCCCAGTGCA AGTGCAGGTG CCAGAACATT TCTCTATCGA
4401 A (SEQ ID NO: 85)
```

IL2ss.CCL8(5-76).hIgG1Fc sequence

```
   1 GGATCTCCGA TGCTCCCGT  GCCCGTCAGT GGGCAGAGCG CACATCGCCC ACAGTCCCCG AGAAGTTCGG GGGAGGGGTC GGCAATTGAA CGGGTGCCTA
 101 GAGAAGTGG  CGCGGGGTAA ACTGGCGAAG TCATGTCGTG GCCAGAACAC GCCTTTTCC  TCGAGGGGCT CGAGGGTGG  GGAGAACCGT ATATAACTGC AGTAGTCGCC
 201 GTGAACGTTC TTTTTCCGAA CGGGTTTGCC GCCAGAACAC AGCTGAAGCT TCGAGGACTG CGTCCGCGT  CTTCACGCGC CCGCCGCCCT ACCTGAGGCC
 301 GCCATCCACG CCGGTTGAGT CCGCTTCCGC CGCCTCCCGC CGCTGTGTGC TCCTGAACTG CGTCCGCGT  CTAGGTAAGT TTAAAGCTCA GGTCGAGACC
 401 GGGCCTTTGT CCGGCGTTCC CTTGGAGCCT ACCTAGACTC AGCCGGCTCT CCAACGCTTTG CCTGACCCTG CTTGCTCAAC TCTACGTCTT TGTTTCGTTT

IL-2 secretion signal
                                                                                            MetTyrArg MetGlnLeu LeuSerCysIle
 501 TCTGTTCTGC GCCGTTACAG ATCCAAGCTG TGACCAAGCG CTACCTGAGA TCACCGGCGA AGGAGGGCCA CCATGTACAG GATGCAACTC CTGTCTTGCA
                           EcoRI
                                     ~~~~~ CCL8 (5-76)
     AlaLeuSer LeuAlaLeu ValThrAsnSer ValSerIle ProIleThr CysCysPheAsn LysProAsp ValIleAsn ArgLysIle ProIleGlnArg LeuGluSer
 601 TTGCACTAAG TCTTGCACTT GTCACGAATT CGGTTTCCAT TCCAATCACC TGCTGCTTTA ACGTGATCAA TAGGAAAATT CCTATCCAGA GGCTGGAGAG
     TyrThrArg IleThrAsnIle GlnCysPhe LysCysAla ValIlePheLys ThrLysArg GlyLysGlu ValCysAlaAsp ProLysGlu ArgTrpVal
 701 CTACACAAGA ATCACCAACA TCCAATGTCC CAAGGAAGCT GTGATCTTCA AGACCAAACG GGGCAAGGAG GTCTGTGCTG ACCCCAAGGA GAGATGGGTC
                                                                      human IgG1 Fc (constant region)
     ArgAspSerMet LysHisLeu AspGlnIle PheGlnLeuLys ProAspAsp LysThrHis ThrCysProPro CysProAla ProGluLeu LeuGlyGlyPro
 801 AGGGATTCCA TGAAGCATCT GGACCAAATA TTTCAAAATC TGAACCAGA  CAAAACTCAC ACATGCCCAC CGTGCCCAGC ACCTGAACTC CTGGGGGGAC
     SerValPhe LeuPhePro ProLysProLys AspThrLeu MetIleSer ArgThrProGlu ValThrCys ValValVal AspValSerHis GluAspPro
 901 CGTCAGTCTT CCTCTTCCCC CCAAAACCCA AGGACACCCT CATGATCTCC CGGACCCCTG AGGTCACATG CGTGGTGGTG GACGTGAGCC ACGAAGACCC
     GluValLys PheAsnTrpTyr ValGlnVal HisAsnAlaLys ThrLysPro ArgGluGlu GlnTyrAsnSer ThrTyrArg ValValSer
1001 TGAGGTCAAG TTCAACTGGT ACGTGGACGG CGTGGAGGTG CATAATGCCA AGACAAAGCC GCGGGAGGAG CAGTACAACA GCACGTACCG TGTGGTCAGC
     ValLeuThrVal LeuHisGln AspTrpLeu AsnGlyLysGlu TyrLysCys LysValSer AsnLysAlaLeu ProAlaPro IleGluLys ThrIleSerLys
1101 GTCCTCACCG TCCTGCACCA GGACTGGCTG AATGGCAAGG AGTACAAGTG CAAGGTCTCC AACAAAGCCC TCCCAGCCC  CATCGAGAAA ACCATCTCA
     AlaLysGly GlnProArg GluProGlnVal TyrThrLeu ProProSer ArgAspGluLeu ThrLysAsn GlnValSer LeuThrCysLeu ValLysGly
1201 AAGCCAAAGG GCAGCCCCGA GAACCACAGG TGTACACCCT GCCCCCATCC CGGGAGGAGA TGACCAAGAA CCAGGTCAGC CTGACCTGC  TGGTCAAAGG
     PheTyrPro SerAspIleAla ValGluTrp GluSerAsn GlyGlnProGlu AsnAsnTyr LysThrThr ProProValLeu AspSerAsp GlySerPhe
1301 CTTCTATCCC AGCGACATCG CCGTGGAGTG GGAGAGCAAT GGGCAGCCGG AGAACAACTA CAAGACCACG CCTCCCGTGC TGGACTCCGA CGGCTCCTTC
     PheLeuTyrSer LysLeuThr ValAspLys SerArgTrpGln GlnGlyAsn ValPheSer CysSerValMet HisGluAla LeuHisAsn HisTyrThrGln
1401 TTCCTCTACA GCAAGCTCAC CGTGGACAAG AGCAGGTGGC AGCAGGGGAA CGTCTTCTCA TGCTCCGTGA TGCACGAGGC TCTGCACAAC CACTACACGC LysSerLeu SerLeuSer ProGlyLys*** (SEQ ID NO. 59)
1501 AGAAGAGCCT CTCCCTGTCT CCGGGTAAAT GAGTCGTAGC TGGCCAGACA TGATAAGATA CATTGATGAG TTTGGACAAA CCACAACTAG AATGCAGTGA
1601 AAAAAATGCT TTATTTGTGA AATTTGTGAT GCTATTGCTT TATTTGTAAC CATTATAAGC TGCAATAAAC AAGTTAACAA CAACAATTGC ATTCATTTTA
                                                                                                         AseI
1701 TGTTTCAGGT TCAGGGGGAG GTGTGGGAGG TTTTTTAAAG CAAGTAAAAC TGGATATGA  GTGGTATGGA ATTAATTCTA AAATACAGCA TAGCAAAACT
1801 TTAACCTCCA AATCAAGCCT CTACTTGAAT GAGTCCTAGC GGGATGAATA AGGCATAGGC ATCAGGGGCT GTTGCCAATG TCCATTAGCT GTTTGCAGCC
1901 TCACCTTCTT TCATGGAGTT TAAGATATAG TGTTATTTCC CAAGGTTGA  ACTAAGTCTT CATTTCTTTA TGTTTTAAAT GACTTGACCT CCCACATTCC
2001 CTTTTTAGTA AATATATCAG AAATAATTTA TGCAATGAAA ATAAATGTTT TTTATTAGGC AGAATCCAGA TGCTCAAGGC CCTTCATAAT
2101 ATCCCCAGT  TTAGTAGGTTG GACTTAGGGA ACAAAGGAAC CTTTAATAGA AATTGGACAG AGCTTCTAGC CAAGAAAGCG TTATCCCTAG TCCTGCTCCT
2201 CTGACACAAA GTGCACGCAG TTGCGGGCCG GGTCGCGCAG GGCGAACTCC GGCCGCGCAC GCTGCTCGCC CCACACCCAG GATCTCGGTC ATGGCCGGCC CGGAGGCGTC
2301 CCGAAGTTC  GTGGACACGA CCTCCGACCA AGCTCGTCA  AGCTGCGTAC CTCCGGGCCG                                  TGTCCGGCAC CACCTGGTCC
```

```
2401  TGGACCGCGC TGATGAACAG GGTCACGTCG TCCCGGACCA CACCGGCGAA GTCGTCCTCC ACGAAGTCCC GGGAGAACCC GAGCCGGTCG GTCCAGAACT
2501  CGACCGCTCC GGCGACGTCG CGGCGGGTGA GCACCGGAAC GGCACTGGTC AACTTGGCCA TGATGGCTCC TCCTGTCAGG AGAGGAAGA  GAAGAGGTT
                                                                  AseI
2601  AGTACAATTG CTATAGTGAG TTGTATTATA CTATGCAGAT ATACTATGCC AATGATTAAT TGTCAAACTA GGGCTGCAGG GTTCATAGTG CCACTTTTCC
2701  TGCACTGCCC CATCTCCTGC CCACCCTTTC CCAGCATAG  ACAGTCAGTG ACTTACCAAA CTCACAGGAG GGAGAAGGCA GAAGCTTGAG ACAGACCCGC
2801  GGGACGCCCG AACTGCGAGG GGACGTGGCT CTTTTATGGT GCGCCGGCCC TCGGAGGCAG GGCGCTCGGG GAGGCCTAGC GGCCAATCTG
2901  CGGTGGCAGG AGGCGGGGCC GAAGGCCGTG CCTGACCAAT TAGGAGTCTC AGCCCCCGC  CCCAAAGCA  GGGAAGTCA  CGCGCCTGTA
3001  GCGCCAGCGT GTTGTGAAAT GGGGGCTTGG CCCCTGACTA GTCAAAACAA ACTCCCATTG ACGTCAATGG GGTGGAGACT TGGAAATCCC
3101  CGTGAGTCAA ACCGCTATCC ACGCCCATTG ATGTACTGCC AAAACCGCAT CATCATGGTA ATAGCGATGA CTAATACGTA GATGTACTGC CAAGTAGGAA
3201  AGTCCCATAA GGTCATGTAC TGGGCATAAT GCCAGGCGGG CCATTTACCG TCATTGACGT CGTACTTGGC ATATGATACA CTTGATGTAC
3301  TGCCAAGTGG GCAGTTTACC GTAAATACTC CACCCATTGA AAGTCCCTAT TGGCGTTACT ATGGGAACAT ACGTCATTAT TGACGTCAAT
3401  GGGCGGGGGT CGTTGGGCGG TCAGCCAGGC GGGCCATTTA CCGTAAGTTA TGTAACGCCT GCAGGTTAAT TAAGAACATG TGAGCAAAAG CCAGTAACAA
3501  GGCCAGGAAC CGTAAAAAGG CCGCGTTGCT GGCGTTTTTC CATAGGCTCC GCCCCCCTGA CGAGCATCAC CTGTTCCGA GCTCAAGTCA GAGGTGGCGA
3601  AACCCGACAG GACTATAAAG ATACCAGGCG TTTCCCCCTG GAAGCTCCCT CGTGCGCTCT CCTGTTCCGA CCCTGCCGCT TACCGGATAC CTGTCCGCCT
3701  TTCTCCCTTC GGGAAGCGTG GCGCTTTCTC ATAGCTCACG CTGTAGGTAT CTCAGTTCGG TGTAGGTCGT TCGCTCCAAG CTGGGCTGTG TGCACGAACC
3801  CCCCGTTCAG CCCGACCGCT GCGCCTTATC CGGTAACTAT CGTCTTGAGT CCAACCCGGT AAGACACGAC TTATCGCCAC TGGCAGCAGC CACTGGTAAC
3901  AGGATTAGCA GAGCGAGGTA TGTAGGCGGT GCTACAGAGT TCTTGAAGTG GTGGCCTACA CTAGAAGAAC CAGTATTTGGT ATCTGCGCTC
4001  TGCTGAAGCC AGTTACCTTC GGAAAAAGAG TTGGTAGCTC TTGATCCGGC AAACAAACCA CCGCTGGTAG CGGTGGTTTT TTTGTTTGCA AGCAGCAGAT
4101  TACGCGCAGA AAAAAGGAT CTCAAGAAGA TCCTTTGATC TTTTCTACGG GTCTGACGC GAAAACTCAC GTTAAGGGAT TTTGGTCATG
4201  GCTAGTTAAT TAACATTTAA ATCAGCGGCC GCAATAAAAT ATCTTTATTT TCATTACATC TGTGTGTTGG TTTTTTGTGT GAATCGTAAC TAACATACGC
4301  TCTCCATCAA AACAAAACGA AACAAAACAA ACTAGCAAAA TAGGCTGTCC CCAGTGCAAG TGCAGGTGCC AGAACATTTC TCTATCGAA       (SEQ ID NO: 86)
```

IL2ss.CCL8(5-76).hIgG1Fc sequence
[Alanine substitutions for GAG binding sites – Lys, Arg & His]

```
   1   GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101   GAGAAGGTGG CGCGGGGTAA ACTGGGAAAG TGATGTCGTG TACTGGCTCC GCCTTTTTCC CGAGGGTGGG GGAGAACCGT ATATAAGTGC AGTAGTCGCC
 201   GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301   GCCATCCACG CCGGTTGAGT CGCGTTCTGC CGCCTCCCGC CTGTGGTGCC TCCTGAACTG CGTCCGCCGT CTAGGTAAGT TTAAAGCTCA GGTCGAGACC
 401   GGGCCTTTGT CCGGCGCTCC CTTGGAGCCT ACCTAGACTC AGCCGGCTCT CCACGCTTTG CCTGACCCTG CTTGCTCAAC TCTACGTCTT TGTTTCGTTT
                                         KasI
                                         NarI
                                         SfoI
                                         BbeI
                                        ~~~~~~~~                                     IL-2 secretion signal
                                                                                     MetTyrArg MetGlnLeu LeuSerCysIle
 501   TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                             EcoRI
                             ~~~~~~~~ CCL8 (5-76)
        AlaLeuSer LeuAlaLeu ValThrAsnSer ValSerIle ProIleThr CysCysPheAsn ValIleAsn ArgLysIle ProIleGlnArg LeuGluSer
 601   TTGCACTAAG TCTTGCACTT GTCACGAATT CGGTTTCCAT TCCAATCACC TGCTGCTTTA ACGTGATCAA TAGGAAAATT CCTATCCAGA GGCTGGAGAG
        TyrThrArg IleThrAsnIle GlnCysPro LysGluAla ValIlePheLys ThrAlaAla GlyAlaGlu ValCysAlaAsp ProAlaGlu AlaTrpVal
 701   CTACACAAGA ATCACCAACA TCCAATGTCC CAAGGAAGCT GTGATCTTCA AGACCgccgc gGGCgctGAG GTCTGTGCTG ACCCCgccGA GgcgTGGGTC
                                                          human IgG1 Fc (constant region)
       AlaAspSerMet AlaAlaLeu AspGlnIle PheGlnAsnLeu AlaProAsp LysThrHis ThrCysProPro CysProAla ProGluLeu LeuGlyGlyPro
 801   gctGATTCCA TGgccgcgCT GGACCAAATA TTTCAAAATC TGgctCCAGA CAAAACTCAC ACATGCCCAC CGTGCCCAGC ACCTGAACTC CTGGGGGGAC
        SerValPhe LeuPhePro ProLysProLys AspThrLeu MetIleSer ArgThrProGlu ValThrCys ValValVal AspValSerHis GluAspPro
 901   CGTCAGTCTT CCTCTTCCCC CCAAAACCCA AGGACACCCT CATGATCTCC CGGACCCCTG AGGTCACATG CGTGGTGGTG GACGTGAGCC ACGAAGACCC
        GluValLys PheAsnTrpTyr ValAspGly ValGluVal HisAsnAlaLys ThrLysPro ArgGluGlu GlnTyrAsnSer ThrTyrArg ValValSer
1001   TGAGGTCAAG TTCAACTGGT ACGTGGACGG CGTGGAGGTG CATAATGCCA AGACAAAGCC GCGGGAGGAG CAGTACAACA GCACGTACCG TGTGGTCAGC
       ValLeuThrVal LeuHisGln AspTrpLeu AsnGlyLysGlu TyrLysCys LysValSer AsnLysAlaLeu ProAlaPro IleGluLys ThrIleSerLys
1101   GTCCTCACCG TCCTGCACCA GGACTGGCTG AATGGCAAGG AGTACAAGTG CAAGGTCTCC AACAAAGCCC TCCCAGCCCC CATCGAGAAA ACCATCTCCA
        AlaLysGly GlnProArg GluProGlnVal TyrThrLeu ProProSer ArgGluGluMet ThrLysAsn GlnValSer LeuThrCysLeu ValLysGly
1201   AAGCCAAAGG GCAGCCCCGA GAACCACAGG TGTACACCCT GCCCCCATCC CGGGAGGAGA TGACCAAGAA CCAGGTCAGC CTGACCTGCC TGGTCAAAGG
        PheTyrPro SerAspIleAla ValGluTrp GluSerAsn GlyGlnProGlu AsnAsnTyr LysThrThr ProProValLeu AspSerAsp GlySerPhe
1301   CTTCTATCCC AGCGACATCG CCGTGGAGTG GGAGAGCAAT GGGCAGCCGG AGAACAACTA CAAGACCACG CCTCCCGTGC TGGACTCCGA CGGCTCCTTC
       PheLeuTyrSer LysLeuThr ValAspLys SerArgTrpGln GlnGlyAsn ValPheSer CysSerValMet HisGluAla LeuHisAsn HisTyrThrGln
1401   TTCCTCTACA GCAAGCTCAC CGTGGACAAG AGCAGGTGGC AGCAGGGGAA CGTCTTCTCA TGCTCCGTGA TGCACGAGGC TCTGCACAAC CACTACACGC
                                         BmtI
                                         NheI
        LysSerLeu SerLeuSer ProGlyLys***(SEQ ID NO: 60)
1501   AGAAGAGCCT CTCCCTGTCT CCGGGTAAAT GAGTGCTAGC TGGCCAGACA TGATAAGATA CATTGATGAG TTTGGACAAA CCACAACTAG AATGCAGTGA
1601   AAAAAATGCT TTATTTGTGA AATTTGTGAT GCTATTGCTT TATTTGTAAC CATTATAAGC TGCAATAAAC AAGTTAACAA CAACAATTGC ATTCATTTTA
                                                                                     AseI
1701   TGTTTCAGGT TCAGGGGGAG GTGTGGGAGG TTTTTTAAAG CAAGTAAAAC CTCTACAAAT GTGGTATGGA ATTAATTCTA AAATACAGCA TAGCAAAACT
1801   TTAACCTCCA AATCAAGCCT CTACTTGAAT CCTTTTCTGA GGGATGAATA AGGCATAGGC ATCAGGGGCT GTTGCCAATG TGCATTAGCT GTTTGCAGCC
1901   TCACCTTCTT TCATGGAGTT TAAGATATAG TGTATTTTCC CAAGGTTTGA ACTAGCTCTT CATTTCTTTA TGTTTTAAAT GCACTGACCT CCCACATTCC
2001   CTTTTTAGTA AAATATTCAG AAATAATTTA AATACATCAT TGCAATGAAA ATAAATGTTT TTTATTAGGC AGAATCCAGA TGCTCAAGGC CCTTCATAAT
2101   ATCCCCCAGT TTAGTAGTTG GACTTAGGGA ACAAAGGAAC CTTTAATAGA AATTGGACAG CAAGAAAGCG AGCTTCTAGC TTATCCTCAG TCCTGCTCCT
2201   CTGCCACAAA GTGCACGCAG TTGCCGGCCG GGTCGCGCAG GGCGAACTCC CGCCCCCACG GCTGCTCGCC GATCTCGGTC ATGGCCGGCC CGGAGGCGTC
```

```
2301 CCGGAAGTTC GTGGACACGA CCTCCGACCA CTCGGCGTAC AGCTCGTCCA GGCCGCGCAC CCACACCCAG GCCAGGGTGT TGTCCGGCAC CACCTGTCCC
2401 TGGACCGCGC TGATGAACAG GGTCACGTCG TCCCGGACCA CACCGGCGAA GTCGTCCTCC ACGAAGTCCC GGGAGAACCC GAGCCGGTCG GTCCAGAACT
2501 CGACCGCTCC GGCGACGTCG CGGCGGGTGA GCACCGGAAC GGCACTGGTC AACTTGGCCA TGATGGCTCC TCCTGTCAGG AGAGGAAAGA GAAGAAGTT
```

Asel

```
2601 AGTACAATTG CTATAGTGAG TTGTATTATA CTATGCAGAT ATACTATGCC AATGATTAAT TGTCAAACTA GGGCTGCAGG GTTCATAGTG CCACTTTTCC
2701 TGCACTGCCC CATCTCCTGC CCACCCTTTC CCAGGCATAG ACAGTCAGTG ACTTACCAAA CTCACAGGAG GGAGAAGGCA GAAGCTTGAG ACAGACCCGC
2801 GGGCAGCCCG AACTGCGAGG GGACGTGGCT AGGGCGGCTT CTTTTATGGT GCCGCGGCCC TCCGAGGCAG GGCGCTCGGG GAGGCCTAGC GGCCAATCTG
2901 CGGTGGCAGG AGGCGGGGCC GAAGGCCGTG CCTGACCAAT CGGAGCACA TAGGAGTCTC AGCCCCCGC CCCAAAGCAA GGGGAAGTCA CGCGCCTGTA
3001 GCGCCAGCGT GTTGTGAAAT GGGGGCTTGG AGCCCCATTG GCCCTGACTA GTCAAAACAA ACTCCCATTG AGTGGAGACT TGGAAATCCC
3101 CGTGAGTCAA ACCGCTATCC ACGCCCATTG TGGGCATAAT GCCAGGCGGG AAAACCGCAT CATCATGGTA ATAGCCATGA CGTGGAGACT CAAGTAGGAA
3201 AGTCCCATAA GGTCATGTAC GCAGTTTACC GTAAATACTC CAGGGCATTGA AAGTCCCTAT TGGCGTTACT CGTACTTGGC ATATGATATA CTTGATGTAC
3301 TGCCAAGTGG CGTTGGGCGG TCAGCCAGGC GGGCCATTTA CCGTAAGTTA TGTAACGCCT GCAGGTTAAT ATGGGAACAT ACGTCATTAT TGACGTCAAT
3401 GGCGGGGGT CGTAAAAAGG CCGGCGTTGCT GGCGTTTTC CATAGCCTCG GAAGCTCTGA GCCCCCTGA CGAGCATCAC AAAAAATCGAC GCTCAAGTCA GCCAGCAAAA
3501 GGCCAGGAAC CGTAAAAAGG ATACCAGGCG TTTCCCCCTG GAAGCTCCCT CGTGCGCTCT CCTGTTCCGA CCCTGCCGCT TACCGGATAC GAGGTGGCGA
3601 AACCCGACAG GACTATAAAG ATACCAGGCG TTTCCCCCTG GAAGCTCCCT CGTGCGCTCT CCTGTTCCGA CCCTGCCGCT TACCGGATAC CTGTCCGCCT
3701 TTCTCCCTTC GGGAAGCGTG GCGCTTTCTC ATAGCTCACG CTGTAGGTAT CTCAGTTCGG TGTAGGTCGT TCGCTCCAAG CTGGGCTGTG TGCACGAACC
3801 CCCCGTTCAG CCCGACCGCT GCGCCTTATC CGGTAACTAT CGTCTTGAGT CCAACCCGGT AAGACACGAC TTATCGCCAC TGGCAGCAGC CACTGGTAAC
3901 AGGATTAGCA GAGCGAGGTA TGTAGGCGGT GCTACAGAGT TCTTGAAGTG GTGGCCTACA CTAGAAGAAC TACGGCTACA AGTATTTGGT ATCGCGCTC
4001 TGCTGAAGCC AGTTACCTTC GGAAAAAGAG TTGGTAGCTC TTGATCCGGC AAACAAACCA CCGCTGGTAG CGGTGGTTTT TTTGTTTGCA AGCAGCAGAT
4101 TACGCGCAGA AAAAAAGGAT CTCAAGAAGA TCCTTTGATC TTTTCTACGG GTCTGACGC TCAGTGGAAC GAAAACTCAC GTTAAGGGAT TTTGGTCATG
4201 GCTAGTTAAT TAACATTTAA ATCAGCGGCC GCAATAAAAT ATCTTTATTT TCATTACATC TGTGTGTTGG TTTTTGTGTGT GAATCGTAAC TAACATACGC
4301 TCTCCATCAA AACAAAACGA AACAAAACAA ACTAGCAAAA TAGGCTGTCC TGCAGGTGCC AGAACATTTC TCTATCGAA (SEQ ID NO:87)
```

IL2ss.CCL13.hIgG1Fc sequence

```
   1 GGATTGCGA TGCCTCCGGT GCCCTTCAGT GGGCAGAGCG CACATCGCCC ACAGTCCCCG AGAAGTTGGG GGAAGGGGTC GGCAATTGAA CGGGTGCCTA
 101 GAGAAGGTGG CGCGGGGTAA ACTGCGGAAA TGATGCTGG GCCAGAACAC TACTGGCTGG GCCTTTTCC GGAGAGTGGG GGAGAACCTG ATATAAGTGA
 201 GTGAACGTTC TTTTTCGCCAA CGGGTTTGCC GCCAGAACAC AGCTGAAGCT TCGAGGGGCT CGCATCTCTC CTTCACGCGC CCGGGCCCT ACCTGAGGCC
 301 GCCATCCACG CCCGTTCAGT CGCGTTCTGC CGCCTCCCGC CCTGAACCTG TCCTGAACTG CGTCCGCCGT CTAGGTAACT TTAAAGCTCA GGTCGAGACC
 401 GGGCCTTTGT CCGGCGCTCC CTTGGAGCTCT AGCCGGCTCT                                           CTTGCTCAAC TCTACGTCTT TGTTTCGTTT

SfoI
                                                             NarI
                                                             KasI
                                                             BbeI
                                                                                                                            IL-2 secretion signal
                                                                                                                            MetTyrArg MetGlnMet LeuSerCysIle
 501 TCTGTTCTGC GCCGTTACAG ATCCAAGCTG TGACCGGCGC CTACCTGAGA TCAACCGGGA AGGAGGGCCA CCATGTACAG GATGCAACTC CTGTCTTGCA
                                             EcoRI
                                                            ---------- CCL13 (1-75)

AlaLeuSer LeuAlaLeu ValThrAsnSer GlnProAsp AlaLeuAsn ValProSerThr CysCysPhe ThrPheSer SerLysLysIle SerLeuGln
 601 TTGCACTAAG TCTTGCACTT GTCACGAATT CCGAGCCAGA TGCACTCCAAC GTCCCATCTA CTTGCTGCTT CACATTAGC AGTAAGAAGA TCTCCTTGCA
       ArgLeuLys SerTyrValIle ThrThrSer ArgCysPro GlnLysPheArg ThrLysLeu GlyLysGluIle CysAlaAsp ProLysGlu
 701 GAGGCTGAAG AGCTATGTGA TCAACTGGTA CAGGTGTCCC CAGAAGGCTG TCATCTTCAG AACCAAACTG GGCAAGGAGA TCTGTGCTGA CCCAAAGGAG

LysTrpValGln AsnTyrMet LysHisLeu GlyArgLysAla HisThrHis LysThrAsp LysThrHisThr CysProPro CysProAla ProGluLeuLeu
 801 AAGTGGGTCC AGAATTATAT GAAACACCTG GGCCGGAAAG CTCACACCCT GAAGACTGAC AAAACTCACA CATGCCCACC GTGCCCAGCA CCTGAACTCC
       GlyGlyPro SerValPhe LeuPheProPro LysProLys AspThrLeu MetIleSerArg ThrProGlu ValThrCys ValValValAsp ValSerHis
 901 TGGGGGACC GTCAGTCTTC CTCTTCCCCC CAAACCCAA GGACACCCTC ATGATCTCCC GGACCCCTGA GGTCACATGC GTGGTGGTGG ACGTGAGCCA
       GluAspPro GluValLysPhe AsnTrpTyr ValAspGly ValGluValHis AsnAlaLys ThrLysPro ArgGluGluGln TyrAsnSer ThrTyrArg
1001 CGAAGACCCT GAGGTCAAGT TCAACTGGTA CGTGGACGGC GTGGAGGTGC ATAATGCCAA GACAAAGCCG CGGGAGGAGC AGTACAACAG CACGTACCGT
       ValValSerVal LeuHisGln AspTrpLeuAsn GlyLysGlu TyrLysCys LysValSerAsn LysAlaLeu ProAlaPro IleGluLysThr
1101 GTGGTCAGCG TCCTCACCGT CCTGCACCAG GACTGGCTGA ATGGCAAGGA GTACAAGTGC AAGGTCTCCA ACAAAGCCCT CCCAGCCCCC ATCGAGAAAA
       IleSerLys AlaLysGly GlnProArgGlu ProGlnVal TyrThrLeu ProProSerArg GluGluMet ThrLysAsn GlnValSerLeu ThrCysLeu
1201 CCATCTCCAA AGCCAAAGGG CAGCCCCGAG AACCACAGGT GTACACCCTG CCCCCATCCC GGGAGGAGAT GACCAAGAAC CAGGTCAGCC TGACCTGCCT
       ValLysGly PheTyrProSer AspIleAla ValGluTrp GluSerAsnGly GlnProGlu AsnAsnTyr LysThrThrPro ProValLeu AspSerAsp
1301 GGTCAAAGGC TTCTATCCCA GCGACATCGC CGTGGAGTGG GAGAGCAATG GGCAGCCGGA GAACAACTAC AAGACCACGC CTCCCGTGCT GGACTCCGAC
       GlySerPhePhe LeuTyrSer LysLeuThr ValAspLysSer ArgTrpGln GlnGlyAsn ValPheSerCys SerValMet HisGluAla LeuHisAsnHis
1401 GGCTCCTTCT TCCTCTACAG CAAGCTCACC GTGGACAAGA GCAGGTGGCA GCAGGGGAAC GTCTTCTCAT GCTCCGTGAT GCACGAGGCT CTGCACAACC
                                                                                                                                   AseI
       TyrThrGln LysSerLeu SerLeuSerPro GlyLys*** (SEQ ID NO:61)
1501 ACTACACGCA GAAGAGCCTC TCCCTGTCTC CGGGTAAATG AGTTGCTAGCT ATTTGTGATG CTATTGCTTT AGTTGCTAAC ATTGATCAGT TTGGACAAAC CACAACTAGA
1601 ATGTGGTGAA AAAAATGCTT TATTTGTGAA ATTTGTATG                                           ATTTGTGTT GCAATAACA AGTTAACAC AACAATTGCA
                                           BmtI
                                           NheI
1701 TTCATTTTAT GTTTCAGGTT CAGGGGAGG TGTGAGGAGT TTTTTAAAGC AAGTAAAAGC TCTACAAATG TGGTATGGAA TTAATTCTAA AATACAGCAT
1801 AGCAAAACTT TAACCTCCAA ATCAAGCCTC TCCCCTGAGC ACTTCGAG CTTTCTGAG GGATGAATAC GGCATAGGCA TCAGGGGCTG TTGCCAATGT GCATTAGCTG
1901 TTTTCAGCCT CACCTTCTTT CATGGAGTTT GTATTTCCC AAGGTTTGAA CTAGCTCTTC ATTTCTTTAT GTTTTAAATG CACTGACCTC
2001 CCACATTCCC TTTTTAGTAA AATATTCAGA ATACATCATT GCAATGAAAA TAAAATGTTT TTATTAGCCA GAATCCAGAT GCTCAAGGCC
2101 CTTCATAATA TCCCCCAGTT TAGTAGTTGG ACTTAGGGAA CAAAGAAACC TTTAATAGAA ATTGGACAGG AAGAAGGCA GTTCTAGCT TATCCTCAGT
2201 CCTGCTCCTC TGCCACAAAG TGCACCCACT TGCCGGCCCG GTCGGACCGG GCGAACTCCC GCCAACCCCC GCGCGCACC CTGCTCCCCG TGGCCCGCCC
2301 GGAGGCGTCC GGAAGTTCG GGACCGCGCT TCCGGACCAC CTCCGGAGG GTCGCGTACA ACCGGCCAC GCCGCCACC CACACCCAGG CCAGGGTGTT GTCCGGACCC
2401 ACCTGCTCCT GGACGTCCT GATGAACAGG GTCAACTGGG CCCGGACCAC TCGGACCTCGT CCCGGACCAA GCAGGGCAA TGGTCCTCCA CGAAGTCCC GGAGAACCCG AGCCGGTGCG
```

FIG. 4C (CONT)

```
2501  TCCAGAACTC GACCGCTCCG GCGACGTCGC GCGCGGTGAG CACCGGAACG GCACTGGTCA ACTTGGCCAT GATGGCTCCT CCTGTCAGGA GAGGAAAGAG
                                                                        AseI
2601  AAGAAGGTTA GTACAATTGC TATAGTGAGT TGTATTATAC CACCCTTTCC TGTATTATAC CAGGCATAGA CAGTCAGTGA ATGATTAATT GTCAAACTAG GGCTGCAGGG TTCATAGTGC
2701  CACTTTTCCT GCACTGCCCC ATCTCCTGCC GACTGGCTTC ACCCTTTCCT GACTGGCTA  TTTTATGGTG CTTACCAAAC CTCACAGGAGG TCACAGGAGG GAAGGCAG AAGCTTGAGA
2801  CAGACCCGCG GGACCCCCGA ACTGCGAGGG GACTGGCTA  GGGCGGCTTC TTTTATGGTG CGGAGCACAT AGGAGTCTCA CGGAGGCCCT CGGAGGCAGG GCGCTCGGGG AGGCCTAGCG
2901  GCCAATCTGC GGTGGCAGGA GGCGGGGCCG AAGGCCGTGC CTGACCAATC CGGAGCACAT CCCTGACTAG AAACAACAAA GCCCCCGCC  CCAAAGCAAG GGGAAGTCAC
3001  GCGCCTGTAG CGCCAGCGTG TTGTGAAATG GGGGCTTGGG TGTACTGCCA CCCTGACTAG TCAAAACAAA ATCATGGTAA CTCCCATTGA CGTCAATGGG GTGGAGACTT
3101  GGAAATCCCC GTGAGTCAAA CGCTATCCA  CGCCATTGGA TGTACTGCCA CCGGCGGGGC CATTTACCGT CATTGACGTC AATGGGGGC TAGCGATGAC TAATACGTAG ATGTACTGCC
3201  AAGTAGGAAA GTCCATAAAG GTCATGTACT GGGCATAATG TAAATACTCC ACCCATTGAC AGTCCCTATT GGCGTTACTA TGGGAACATA TATGATACAC
3301  TTGATGTACT GCCAAGTGGG CAGTTTACCG TAAATACTCC ACCCATTGAC AGTCCCTATT GGCGTTACTA TGGGAACATA CGTCATTATT
3401  GACGTCAATG GGCGGGGGTC GTTGGGCGGT CAGCCAGGCG GGCCATTTAC CGTAAGTTAT GTAACGCCTG CAGGTTAATT AAGAACATGT GAGCAAAAGG
3501  CCAGCAAAAG GCCAGGAACC GTAAAAAGGC CGCGTTGCTG GCGTTTTTCC ATAGGCTCCG CCCCCCTGAC GAGCATCACA AAAATCGACG CTCAAGTCAG
3601  AGGTGGCGAA ACCCGACAGG ACTATAAAGA TACCAGGCGT TTCCCCCTGG AAGCTCCCTC GTGCGCTCTC CTGTTCCGAC CCTGCCGCTT ACCGGATACC
3701  TGTCCGCCTT TCTCCCTTCG GGAAGCGTGG CGCTTTCTCA TAGCTCACGC TGTAGGTATC TCAGTTCGGT GTAGGTCGTT CGCTCCAAGC TGGGCTGTGT
3801  GCACGAACCC CCCGTTCAGC CCGACCGCTG CGCCTTATCC GGTAACTATC GTCTTGAGTC CAACCCGGTA AGACACGACT TATCGCCACT GGCAGCAGCC
3901  ACTGGTAACA GGATTAGCAG AGCGAGGTAT GTAGGCGGTG CTACAGAGTT CTTGAAGTGG TGGCCTAACT ACGGCTACAC TAGAAGAACA GTATTTGGTA
4001  TCTGCGCTCT GCTGAAGCCA GTTACCTTCG GAAAAAGAGT TGGTAGCTCT TGATCCGGCA AACAAACCAC CGCTGGTAGC GGTGGTTTTT TTGTTTGCAA
4101  GCAGCAGATT ACGCGCAGAA AAAAAGGATC TCAAGAAGAT CCTTTGATCT TTTCTACGGG GTCTGACGCT CAGTGGAACG AAAACTCACG TTAAGGGATT
4201  TTGGTCATGG CTAGTTAATT AACATTTAAA TCAGCGCCCG CAATAAAATA TCTTTATTTT CATTACATCT GTGTGTTGGT TTTTTGTGTG AATCGTAACT
4301  AACATACGCT CTCCATCAAA ACAAAACGAA ACAAAACAAA CTAGCAAAAT AGGCTGTCCC CAGTGCAAGT GCAGGTGCCA GAACATTTCT CTATCGAA
                                                                                                              (SEQ ID NO:88)
```

FIG.4D

```
2501  CCGCTCCGGC GACGTGCGCG GCGGTGAGCA CCGGAACCGG ACTGGTCAAC TTGGCCATGA TGGCTCCTCC TGTCAGGAGA GGAAAGAGAA GAAGGTTAGT
                                                                    AseI
2601  ACAATTGCTA TAGTGAGTTG TATTATACTA TGCAGATATA CTATGCCAAT GATTAATTGT CAAACTAGGG CTGCAGGGTT CATAGTGCCA CTTTTCCTGC
2701  ACTGCCCAT CTCCTGCCCA CCCTTTCCCA GGCATAGACA GTCAGTGACT TACCAAACTC ACAGGAGGGA GAAGGCAGAA GCTTGAGACA GACCCGCGGG
2801  ACCGCCGAAC TGCGAGGGGA CGTGGCTAGG GCAGGCTTCT TTATGGTGCG CCGGCCCTCG GAGGCAGGGC GCTCGGGGAG GCCTAGCGGC CAATCTGCGG
2901  TGGCAGGAGG CGGGGCCGAA GGCCCGTGCCT GACCACATAG GAGTCTCAGC AAAACAAACT CCCATTGACG AAAGCAAGGG GAAGTCACGC GCCTGTAGCG
3001  CCAGCGTGTT GTGAAATGGG GGCTTGGGGG CTGACTAGTC CATGGTAATA GCGATGACTA TCAATGGGGT GGAGACTTGG AAATCCCCGT
3101  GAGTCAAACC GCTATCCACG CCCATTGATG TACTGCCAAA ACCGCATCAT TTGACCGTCA CATGGTGGCGT ATACGTAGAT GTACTGCCAA GTAGGAAAGT
3201  CCCATAAGGT CATGTACTGC GCATAATGCC AGGCGGGCCA TTTACCGTCA CAATGGAAAG TCCCTATTGG CGTTACTATG ACTTGCACTT GATGTACTGC
3301  CAAGTGGGCA GTTTACCGTA TGGGCGGTCA GCCAGGCGGG CCATTTACCG TAAGTTATGT AACGCCTGCA GGTTAATTAA GAACATGTGA TCATTATTGA
3401  CGGGGTCGT AAAAAGGCCG CGTTGCTGGC GTTTTTCCAT AGGCTCCGGC CCCTGACGA GCATCACAAA AATCGACGCT CAAGTCAGAG GTGGCGAAAC
3501  CAGGAACCGT TATAAAGATA CCAGGCGTTT CCCCCCTGGAA GCTCCCTCGT GTTCCGACCC TGCCGCTTAC CGGATACCTG TCCGCCTTTC
3601  CCGACAGGAC AAGCGTGCGG CCTTTCTCATA GCTCACGCTG TAGGTATCTC AGTTCGGTGT AGGTCGTTCG CTCCAAGCTG GGCTGTGTGC ACGAACCCCC
3701  TCCCTTCGGG GACCCGTGCG CCTTATCCGG TAACTATCGT CTTGAGTCCA ACCCGGTAAG ACACGACTTA TCGCCACTGG CAGCAGCCAC TGGTAACAGG
3801  CGTTCAGCCC GGAGGTATGT AGGCGGTGCT ACAGAGTTCT TGAAGTGGTG GCCTAACTAC GGCTACACTA GAAGAACAGT ATTTGGTATC TGCGCTCTGC
3901  ATTAGCAGAG GAGCGGTGGT GAGCGGTGT ACAGAGTTCT TGAAGTGGTG GCCTAACTAC GGCTACACTA GAAGAACAGT ATTTGGTATC TGCGCTCTGC
4001  TGAAGCCAGT TACCTTCGGA AAAAGAGTTG GTAGCTCTTT ATCCGGCAAA CAAACCACCG CTGGTAGCGG TGGTTTTTTT GTTTGCAAGC AGCAGATTAC
4101  GCGCAGAAAA AAAGGATCTC AAGAAGATCC TTTGATCTTT TCTACGGGGT CTGACGCTCA GTGGAACGAA AACTCACGTT AAGGGATTTT GGTCATGGCT
4201  AGTTAATTAA CATTTAAATC AGCGGCCGCA ATAAAATATC TTTATTTTCA TTACATCTGT GTGTTGGTTT TTTGTGTGAA TCGTAACTAA CATACGCTCT
4301  CCATCAAAAC AAAACGAAAC AAAACAAACT AGCAAAATAG GCTGTCCCCA GTGCAAGTGC AGGTGCCAGA ACATTTCTCT ATCGAA (SEQ ID NO:89)
```

IL2ss.CCL13(5-75).hIgG1Fc sequence
[Alanine substitutions for removal of GAG binding sites – Lys & His]

```
   1 GGATCTCGCGA TCGCTCCGGT GCCCGTCAGT GGGCCAGAGCG CACAATGCCC ACAGTCCCCG AGAAGTGGG GGGAGGGGTC GGCAATTGAA CGGGTCCTA
 101 GAGGAGGTGG CCGCGGGTAA ACTGGGAAAG TGATGTCGTG GCCAGACACG GCCTTTTCC CGAGGGTCC GGAGGGTGGG GGAGAACCGT ATATAAGTGC ACTAGTCGCC
 201 GTGAACGTTC TTTTCGGCAA CGGGTTTCGC GCCAGAACAC AGCTGAAGCT TCGAGGGCC

```
2301 GAAGTTCGTG GACACGACCT CCGACCACTC GGGGTACAGC TCGTCCAGGC CGCGCACCCA CACCCAGGCC AGGGTGTTGT CCGGCACCAC CTGGTCCTGG
2401 ACCGCGCTGA TGAACAGGGT CACGTCGTCC CGGACCACAC CGGCGAAGTC GTCCTCCACG AAGTCCCGGG AGAACCCGAG CCGGTCGGTC CAGAACTCGA
2501 CCGCTCCGGC GACGTCGCGC GCGGTGAGCA CCGGAACGGC ACTGGTCAAC TTGGCCATGA TGGCTCCTCC TGTCAGGAGA GGAAAGAGAA GAAGGTTAGT
                                                    AseI
2601 ACAATTGCTA TAGTGAGTTG TATTATACTA TGCAGATATA CTATGCCAAT GATTAATTGT CAAACTAGGG CTGCAGGGTT CATAGTGCCA CTTTTCCTGC
2701 ACTGCCCCAT CTCCTGCCCA CCCTTTCCCA GGCATAGACA GTCAGTGACT TACCAAACTC ACAGGAGGGA GAAGGCAGAA GCTTGAGACA GACCCGCGGG
2801 ACCCCGAAAC TGCGAGGGGA CGTTGGCTAG GCGGCTTCTT TTATGGTGCG CCGGCCCTCG GAGGCAGGGC GCTCGGGGAG GCCTAGCGGC CAATCTGCGG
2901 TGGCAGGAGG CGGGGCCGAA GGCCCGTGCC TGACCAATCC GAGTGCTCAGC CCCCGCCCG AAAGCAAGGG GAAGTCACGC GCCTGTAGCG
3001 CCAGCGTGTT GTGAAATGGG GGCTTGGGGG CTGACTAGTC AAAACAAACT CCCATTGACG GGAGACTTGG AAATCCCCGT
3101 GAGTCAAACC GCTATCCACG CCCATTGATG TACTGCCAAA ACCGCATCAT CATGGTAATA GCGATGACTA ATACGTAGAT GTACTGCCAA GTAGGAAAGT
3201 CCCATAAGGT CATGTACTGG GTTTACCGTA AATACTCCAC AGGCGGGCCA TTTACCGTCA ACCCTATTGG TAGGGGCGT ACTTGGCATA TGATACACTT GATGTACTGC
3301 CAAGTGGGCA TGGGCGGTCA GCCAGGCGGG CCATTTACCG TAAGTTATGT AACGCCTGCA GGTTAATTAA CGTTACTATG GGAACATACG TCATTATTGA CGTCAATGGG
3401 CGGGGTCGT TGGCCCAGCC CGTTGCTGGC GTTTTTCCAT AGGCTCCGCC CCCCTGACGA GCATCACAAA GAACATGTGA GCAAAAGGCC AGCAAAAGGC
3501 CAGGAACCGT AAAAAGGCCG CCAGGCGTTT CCCCCTGGAA GCTCCCTCGT GCGCTCTCCT GTTCCGACCC TGCCGCTTAC CGGATACCTG TCCGCCTTTC
3601 CCGACAGGAC TATAAAGATA AGCGTGGCGC CTTTCTCATA GCTCACGCTG TAGGTATCTC AGTTCGGTGT CTCCAAGCTG GGCTGTGTGC ACGAACCCCC
3701 TCCCTTCGGG AAGCGTGGCG CTTTCTCATA GCTCACGCTG TAGGTATCTC AGTTCGGTGT CTCCAAGCTG GGCTGTGTGC ACGAACCCCC
3801 CGTTCAGCCC GACCGCTGCG CCTTATCCGG TAACTATCGT CTTGAGTCCA ACCCGGTAAG ACACGACTTA TCGCCACTGG CAGCAGCCAC TGGTAACAGG
3901 ATTAGCAGAG CGAGGTATGT AGGCGGTGCT ACAGAGTTCT TGAAGTGGTG GCCTAACTAC GGCTACACTA GAAGAACAGT ATTTGGTATC TGCGCTCTGC
4001 TGAAGCCAGT TACCTTCGGA AAAAGAGTTG GTAGCTCTTG ATCCGGCAAA CAAACCACCG CTGGTAGCGG TGGTTTTTT GTTTGCAAGC AGCAGATTAC
4101 GCGCAGAAAA AAAGGATCTC AAGAAGATCC TTTGATCTT TCTACGGGGT CTGACGCTCA GTGGAACGAA AACTCACCTT AAGGGATTTT GGTCATGCCT
4201 AGTTAATTAA CATTTAAATC AGCGGCCGCA ATAAAATATC TTTATTTTCA TTACATCTGT GTGTTGGTTT TTTGTGTGAA TCGTAACTAA CATACGCTCT
4301 CCATCAAAAA AAAACGAAAC AAAACAAAACT AGCAAAATAG GCTGTCCCCA GTGCAAGTGC AGGTGCCAGA ACATTTCTCT ATCGAA   (SEQ ID NO:90)
```

IL2ss.CCL25.hIgG1Fc sequence

```
   1 GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101 GAGAAGGTGG CGCGGGGTAA ACTGGGAAAG TGATGTCGTG TACTGGCTCC GCCTTTTTCC CGAGGCTGGG GGAGAACCGT CTTCACGCGC AGTAGTCGCC
 201 GTGAACGTTC TTTTTCGCAA CCGGTTTGCC GCCAGAACAC AGCTGAAGCT TCGAGGGGCG TCCTGAACTG CGTCCGCCGT CCCCGCGCT ACCTGAGGCC
 301 GCCATCCACG CGGGTTCGGT CGGGTTCTGC CGGCTTCCGC CTGGTGTCC TCCTGGTCGT CGTTCCGCCG CTTAGGTAAGT TTAAAGCTCA GGTGAGACC
 401 GGGCCTTTGT CCGGCGCTCC CTTGGAGCCT ACCTAGACTC AGCCGGCTCT CCAAGCTTG CCTGACCCTG CTTGCTCAAC TCTACGTCTT TGTTCGTTT
                                                           SfoI
                                                           NarI
                                                           KasI
                                                           EbeI                        IL-2 secretion signal
                                                                                        MetTyrArg MetGlnLeu LeuSerCysIle
 501 TCTGTTCTGC GCCGTTACAG ATCCAAGCTG TGACCGGCGC CTACCTGAGA AGGAGGGCCA CCATGTACAG GATGCAACTC CTGTCTTGCA
                                EcoRI                  ~~~~ CCL25 (1-127)
                                AlaLeuSer LeuAlaLeu ValThrAsnSer ThrGlnGly ValPheGlu AspCysCysLeu AlaTyrHis TyrProIle GlyTrpAlaVal LeuArgHis
 601 TTGCACTAAG TCTTGCACTT GTCACGAATT CGACCCAAGG TGTCTTTGAG CACTGCTGCC TGGCCTACCA CTACCCCATT GGCTGGGCTG TGCTCCGGCA
                                AlaTrpThr TyrArgIleGln GluValSer GlySerCys AsnLeuProAla AlaIlePhe TyrLeuPro LysArgHisArg LysValCys GlyAsnPro
 701 GCCTGGACT TACCGGATCC AGGAGGTGAG CGGAAGCTGC AATCTGCCTG CCATCTTCTA CCTGCCTAAG AGACACAGGA AAGTGTGTGG TGGAACCCC
                                LysSerArgGlu ValGlnArg AlaMetLys LeuLeuAspAla ArgAsnLys ValPheAla LysLeuArgHis ThrPheGln GlyProHisAla
 801 AAAAGCAGGG AGTGCAGAG AGCCATGAAG CTCCTGGATG CCCGAAATAA GGTTTTTGCA AAGCTCCGCC ACACACGGA GGCCTCATG
                                                                                                  human IgG1 Fc
                                                                                                  (constant region)
                                ValLysLys LeuSerSer GlyAsnSerLys LeuSerSer SerLysPhe SerAsnPro SerSerSer LysArgAsn ValSerAsplys ThrHisThr
 901 CTGTAAAGAA GTTGAGTTCT GGAAACTTCA AGTTATCATC GTCCAAGTTT AGCAACCCA TCAGCAGCAG CAAGAGGAAT GTCTCCGACA AAACTCACAC
                                CysProPro CysProAlaPro GluLeuLeu GlyGlyPro SerValPheLeu PheProPro LysProLys AspThrLeuMet IleSerArg ThrProGlu
1001 ATGCCACCG TGCCCAGCAC CTGAACTCCT GGGGGGACCG TCAGTCTTCC TCTTCCCCCC AAAACCCAAG GACACCCTCA TGATCTCCCG GACCCCTGAG
                                ValThrCysVal ValVal Asp ValSerHis GluAspProGlu ValLysPhe AsnTrpTyr ValAspGlyVal GluValHis AsnAlaLys ThrLysProArg
1101 GTCACATGCG TGGTGGTGGA CGTGAGCCAC GAAGACCCTG AGGTCAAGTT CAACTGGTAC GTGGACGGCG TGGAGGTGCA TAATGCCAAG ACAAAGCCGC
                                GluGluGln TyrAsnSer ThrTyrArgVal ValSerVal LeuHisGlnAsp TrpLeuAsn GlyLysGlu TyrLysCysLys ValSerAsn
1201 GGGAGGAGCA GTACAACAGC ACGTACCGTG TGGTCAGCGT CCTCACCGTC CTGCACCAGG ACTGGCTGAA TGGCAAGGAG TACAAGTGCA AGGTCTCCAA
                                LysAlaLeu ProAlaProIle GluLysThr IleSerLys AlaLysGlyGln ProArgGlu ProGlnVal TyrThrLeuPro ProSerArg GluGluMet
1301 CAAAGCCCTC CCAGCCCCA TCGAGAAAC CATCTCCAAA GCCAAAGGGC AGCCCCGAGA ACCACAGGTG TACACCCTGC CCCCATCCCG GGAGGAGATG
                                ThrLysAsnGln ValSerLeu ThrCysLeu ValLysGlyPhe TyrProSer AspIleAla ValGluTrpGlu SerAsnGly GlnProGlu AsnAsnTyrLys
1401 ACCAAGAACC AGGTCAGCCT GACCTGCCTG GTCAAAGGCT TCTATCCCAG CGACATCGCC GTGGAGTGGG AGAGCAATGG GCAGCCGGAG AACAACTACA
                                ThrThrPro ProValLeu AspSerAspGly SerPhePhe LeuTyrSer LysLeuThrVal AspLysSer ArgTrpGln GlnGlyAsnVal PheSerCys
1501 AGACCACGCC TCCCGTGCTG GACTCCGACG GCTCCTTCTT CCTCTACAGC AAGCTCACCG TGGACAAGAG CAGGTGGCAG CAGGGGAACG TCTTCTCATG
                                                                                                                              BmtI
                                                                                                                              NheI
                                SerValMet HisGluAlaLeu HisAsnHis TyrThrGln LysSerLeuSer LeuSerPro GlyLys*** (SEQ ID NO:64)
1601 CTCCGTGATG CACGAGGCTC TGCACAACCA CTACACCCAG AAGAGCCTCT CCCTGTCTCC GGGTAAATGA GTGCTAGCTG GCCAGACATG ATAAGATACA
1701 TTGATGAGTT TGGACAAACC AGCTATAGAA TGCAGTGAAA AAAATGCTTT ATTGTGAAA TTTGTGATGC TATTGCTTTA TTTGTAACCA TTATAAGCTG
1801 CAATAAACAA GTTAACAACA ACAATTGCAT TCATTTTATG TTTCAGGTTC AGGGGGAGGT GTGGGAGGTT TTTTAAAGCA AGTAAAACCT CTACAAATGT
     AseI
1901 GGTATGGAAT TAATTCTAAA ATACAGCATA GCAAAACTTT AACCTCCAAA TCAAGCCTCT ACTTGAATCC TTTTCTGAGG GATGAATAAG GCATAGGCAT
2001 CAGGGGCTGT TGCCAATGTG CATTAGCTGT TTGCAGCCTC ACCTTTTCTC ATGGAGTTTA AGATATAGTG TATTTCCCA AGTTTGAAC TAGTCTTTCA
```

```
2101 TTTCTTTATG TTTTAAATGC ACTGACCTCC CACATTCCCT TTTTAGTAAA ATATTCAGAA TACATCATTG CAATGAAAAT AAATGTTTTT
2201 TATTAGGCAG AATCCAGATG CTCAAGGCCC TTCATAATAT CCCCCAGTTT AGTAGTTGGA CTTAGGAAAC AAAGGAACCT TTAATAGAAA TTGGACAGCA
2301 AGAAAGCGAG CTTCTAGCTT ATCCTCAGTC CTGCTCCTCT GCCACAAAGT GCACGCAGTT GCCGGCCGGG TCGGCCAGGG CGAACTCCCG CCCCCACGGC
2401 TGCTCGCCGA TCTCGGTCAT GGCCGGCCCG GAGGCGTCCC GGAAGTTCGT GGACACGACC TCCGACCACT CGGCGTACAG CTCGTCCAGG CGTCCTCCAC
2501 ACACCAGGC CAGGGTGTTG TCCGGCACCA CCTGGTCCTG GACCGCGCTG ATGAACAGGG TCACGTCGTC CCGGACCACA CCGGCGAAGT CGTCCTCCAC
2601 GAAGTCCCGG GAGAACCCGA GCCGGTCGGT CCAGAACTCG CCAGAACTCG ACCGCTCCGG CGACGTGAGC CGCGGTGAGC ACCGGAACGG CACTGGTCAA CTTGCCATG
                                                                                                              AseI
2701 ATGGCTCCTC CTGTCAGGAG AGGAAAGAGA TACAATTGCT ATAGTGAGTT GTATTATACT ATGCAGATAT ACTATGCCAA TGATTAATTG
2801 TCAAACTAGG GCTGCAGGGT TCATAGTGCC ACTTTTCCTG CACTGCCCCA TCTCCTGCCC ACCCTTTCCC AGGCATAGAC AGTCAGTGAC TTACCAAACT
2901 CACAGGAGGG AGAAGGCAGA AGCTTGAGAC AGCCCGCGGA GACCGCCGAA CTGCGAGGGG ACGTGGCTAG GGCGGCTTCT TTTATGGTGC GCCGGCCCTC
3001 GGAGGCAGGG CGCTCGGGGA GGCCTAGCGG GTGGCAGGAG GCGGGCCGA AGGCCGTGCC TGACCAATCC GGAGCACATA GGAGTCTCAG
3101 CCCCCGCCC CAAAGCAAGG GGAAGTCACG CGCCTGTAGC GCCAGCGTGT TGTGAAATGG GGGCTTGGGC CCTGACTAGT CAAAACAAAC
3201 TCCCATTGAC GTCAATGGGG TGGAGACTTG TGAGTCCCCG GAAATCCCCG TGAGTCAAAC GCTCATCCAC GTACTGCCAA AACCGCATCA TCATGGTAAT
3301 AGCGATGACT AATACGTAGA TGTACTGCCA AGTAGGAAAG TCCCATAAGG TCATGTACTG CAGGCGGGCC ATTTACCGTC ATTGACGTCA
3401 ATAGGGGCG TACTTGGCAT ATGATACACT TGATGTACTG AGTTTACCGT AAATACTCCA CCATTGACG TCAATGAAAA GTCCCTATTG
3501 GCGTTACTAT GGGAACATAC GTCATTATTG AGTCAATGG GCGGGGGTCG TTGGGCGGTC AGCCAGGCGG GCCATTTACC GTAAGTTATG TAACGCCTGC
3601 AGTTAATTA AGAACATGTG AGCAAAAGGC CCAGCAAACCG CCAGGAACCG TAAAAAGGCC GCGTTGCTGG CGTTTTTCCA TAGGCTCCGC CCCCCTGACG
3701 AGCATCACAA AAATCGACGC TCAAGTCAGA GGTGGCGAAA CCCGACAGGA CTATAAAGAT ACCAGGCGTT TCCCCCCTGGA AGCTCCCTCG TGCGCTCTCC
3801 TGTTCCGACC CTGCCGCTTA CCGGATACCT GTCCGCCTTT CTCCCTTCCG GAAGCGTGGC GCTTTCTCAT AGCTCACGCT GTAGGTATCT CAGTTCGGTG
3901 TAGGTCGTTC GCTCCAAGCT GGGCTGTGTG CACGAACCCC CCGTTCAGCC CGACCGCTGC GCCTTATCCG GTAACTATCG TCTTGAGTCC AACCGGTAA
4001 GACACGACTT ATCGCCACTG GCAGCAGCCA CTGGTAACAG GATTAGCAGA GCGAGGTATG TTACCTTCGG AAAAAGAGTT TGGTAGCTCT TGATCCGGCAA ACAAACCACC
4101 CGGCTACACT AGAAGAACAG TATTTGGTAT CTGCGCTCTG CTGAAGCCAG CGGCCAGAAA AAAGGATCT CAAGAAGATC CTTTGATCTT TTCTACGGGG TCTGACGCTC
4201 AGTGGAACGA AAACTCACGT TAAGGGATTT TGGTCATGAG ATTATCAAAA AGGATCTTCA CCTAGATCCT TTTAAATTAA AAATGAAGTT TTAAATCAAT CTAAAGTATA
4301 TATGAGTAAA CTTGGTCTGA CAGTTACCAA TGCTTAATCA GTGAGGCACC TATCTCAGCG ATCTGTCTAT TTCGTTCATC CATAGTTGCC TGACTCCCCG TCGTGTAGAT
4401 AACTACGATA CGGGAGGGCT TACCATCTGG CCCCAGTGCT GCAATGATAC CGCGAGACCC ACGCTCACCG GCTCCAGATT TATCAGCAAT AAACCAGCCA GCCGGAAGGG
4501 CCGAGCGCAG AAGTGGTCCT GCAACTTTAT CCGCCTCCAT CCAGTCTATT AATTGTTGCC GGGAAGCTAG AGTAAGTAGT TCGCCAGTTA ATAGTTTGCG CAACGTTGTT
(SEQ ID NO: 91)
```

IL2ss.CCL25(4-127).hIgG1Fc sequence

```
2201 GAATCCAGAT GCTCAAGGCC CTTCATAATA TCCCCCAGTT TAGTAGTTGG ACTTAGGGAA CAAAGGAACC TTTTAATAGAA ATTGGACAGC AAGAAAGCGA
2301 GCTTCTAGCT TATCCTCAGT CCTGCTCCTC GGAAGTTCC TGCCGGCCAGT TGCACGCAGT TGCCGGCCGG TGCCGACCAGG GTCGCGCAGG GCCCCCACGG CTGCTGCCG
2401 ATCTCGGTCA TGGCGGCCC GGAAGTTCG TGGACACGAC CTCCGACCAC GTCACGTCGT CCCGGACCAC GCTCGTCCAG GCCGGCTACA CACACCCAGG
2501 CCAGGGTGTT GTCCGGCACC ACCTGGTCCT GGACCGCGCT GATGAACAGG GTCACGTCGT CCCGGACCAC ACCGGCGAAG TCGTCCTCCA CGAAGTCCCG
2601 GGAGAACCCG AGCCGGTCGG TCCAGAACTC GACCGGCTCG GCGACGTCGC GCGCGGTGAG CACCGGAACG GCACTGGTCA ACTTGGCCAT GATGGCTCCT

AseI
2701 CCTGTCAGGA GAGGAAAGAG AAGAAGGTTA GTACAATTGC TATAGTGAGT TGTATTATAC CAAAGGAACC TATGCAGATA ATGATTAATT GTCAAACTAG
2801 GGCTGCAGGG TTCATAGTGC CACTTTTCCT GCACTGCCCC ATCTCCTGCC CACCCTTTCC CAGGCATAGA CAGGTCAGTGA CTTACCAAAC TCACAGGAGG
2901 GAGAAGGCAG AAGCTTGAGA CAGACCCCGG GGACCGCCCA ACTGCGAGGG AAGGCCGTGC CCCGGACCAC GGGCGGCTTC CGCCGGGCCT CGGAGGCAGG
3001 GCGCTCGGGG AGGCCTAGCG GCCAATCTGC GGTGGGCAGGA GGCGGGGCCG TTGTGAAATG GGGGCTTGGG CTGACCAATC AGGAGTCTCA GCCCCGCGCC
3101 CCAAAGCAAG GGGAAGTCAC GCCAGCGTAG CGCCTATCCA CCGCTATCCA TGTACTGCCA CCCTGACTAG TCAAAACAAA CTCCATTGA
3201 CGTCAATGGG GTGGAGACTT GGAAATCCCC GTGAGTCAAA CGGCTATACT AAACCGCATC CAGGCGGGC CATTTACCGT ATCATGGTAA TAGGATGAC
3301 TAATACGTAG ATGTACTGCC AAGTAGGAAA GTCCCATAGA GCTTATGTACT CCGCCATTGA CCAGGCGGGC CATTTACCGT CATTGACGTC AATAGGGGC
3401 GTACTTGGCA TATGATACAC TTGATGTACT GCCAAGTGGG CAGTTTACCG TAAATACTCC ACCCATTGAC GTCAATGGAA AGTCCCTATT GGCGTTACTA
3501 TGGGAACATA CGTCATTATT GACGTCAATG GGCGGGGCGT GTTGGGCGGT CAGCCAGGCG CGTAAGTTAT GTAACGCCTG CAGTTAATT
3601 AAGAACATGT GAGCAAAAGG CCAGCAAACC GCCAGGAACC GTAAAAAGGC CGCGTTGCTG GCGTTTTTCC CCCCCTGAC AAGCTCCCTC GTGCGCTCTC CTGTTCCGAC
3701 AAAATCGACG CTCAAGTCAG AGGTGGCGAA ACTATAAAGA TACCAGGCGT TTCCCCCTGG AAGCTCCCTC GTGCGCTCTC CTGTTCCGAC
3801 CCTGCCGCTT ACCGGATACC TGTCCGGCCTT TCTCCCTTCG GAAGCGTGG GCTTTCTCA TAGCTCACGC TGTAGGTATC TCAGTTCGGT GTAGGTCGTT
3901 CGCTCCAAGC TGGGCTGTGT GCACGAACCC CCGTTCAGC CCGACCGCTG CGCCTTATCC GGTAACTATC GTCTTGAGTC CAACCCGGTA AGACACGACT
4001 TATCGCCACT GGCAGCAGCC ACTGGTAACA GGATTAGCAG AGCGAGGTAT GTAGGCGGTG CTACAGAGTT CTTGAAGTGG TGGCCTAACT ACGGCTACAC
4101 TGAAGAACA GTATTGGTA TCTGCGCTCT GCTGAAGCCA GTTACCTTCG GAAAAAGAGT TGGTAGCTCT TGATCCGGCA AACAAACCAC CGCTGGTAGC
4201 GGTGGTTTTT TTGTTTGCAA GCAGCAGATT ACGCGCAGAA AAAAAGGATC CTTTGATCT CAATAAAATA GTCTGACGCT CAGTGGAACG
4301 AAAACTCACG TTAAGGGATT TTGGTCATGA CTAGTTAAT AACATTTAAA TCAGCGGCCG CAATAAAAATA TCTTTATTTT CATTACATCT GTGTGTTGGT
4401 TTTTTGTGTG AATCGTAACT AACATACGCT CTCCATCAAA ACAAAACGAA CTAGCAAAAT AGGCTGTCCC CAGTGCAAGT GCAGGTGCCA
4501 GAACATTTCT CTATCGAA    (SEQ ID NO:92)
```

IL2ss.CCL25(4-127).hIgG1Fc sequence
[Alanine substitutions for GAG binding sites – Lys, Arg & His]

```
   1  GGATCTGCGA TCGCTCCGGT GCCCTCAGT GGGCAGAGCG CACATCGCCC ACAGTCCCCG AGAAGTTGGG GGGAGGGGTC GGCAATGAA CGGGTGCCTA
 101  GAGAAGGTGG CCGGGGTAA ACTGGGAAAG TGATTCGTTC GCCAGAACAC AGCTGAAGCT GCCTTTTTCC CGAGGGTCCC CGAGGGTGGG GGAGAACCGT ATATAAGTGC AGTAGTCGCC
 201  GTGAACGTTC TTTTTCGCAA CGGGTTTGCC GCCAGAACAC AGTGAAGCT TCGAGGGGCT CGCATCTCTC CTTCACGCGC CCGCCGCCT ACCTGAGGCC
 301  GCCATCCACG CCGGTTGAGT CCGTTGAGTC CGGTCCCGGC TCCTGAACTG CCTCCGAGCT TCCTGACTG CTAGGTAAGT TTAAAGCTCA GGTCGAGGCC
 401  GGGCCTTTGT CCGGCGCTCC CTTGGAGCCT AGCCGGCTCT AGCCGGCTCT CCACGCTTTG CCTGACCCTG CTTGCTCAAC TCTACGTCTT TGTTTCGTTT

501  TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                                                                                                  MetTyrArg MetGlnLeu LeuSerCysIle
                                                                                                  IL-2 secretion signal
                      EcoRI              SfoI
                                         NarI
                                         KasI
                                         BbeI
                                                  CCL25 (4-127)

601  AlaLeuSer AlaAlaLeu ValThrAsnSer ValPheGlu AspCysCys LeuAlaPhe TyrProIle GlyTrpAla ValLeuArgHis AlaTrpThr
      TTGCACTAAG TCTTGCACTT GTCACGAATT CGGTCTTTGA GGACTGCTGC CTGGCCTTAC ACTACCCCAT TGGGTGGGCT GTGCTCCGGC ACGCCTGGAC
 701  TyrArgIle GlnGluValSer GlySerCys AsnLeuPro AlaAlaIlePhe TyrLeuPro LysProLys AlaAlaAla AlaAlaValCys GlyAsnPro AlaSerAla
      TTACCGGATC CAGGAGGTGA GCGGAGCTG CAATCTGCCT GCTGCCATAT TCTACCTCCC CAAAACCCAA GCCGCCGCT GCCGCAGCCGCC TGTGGAACCC CGAATAGCGCC
 801  GluValGlnAla AlaMetAla LeuLeuAsp ValPheAla AlaLeuAla AlaAsnThrGln ThrPheGln GlyProAla AlaValAlaAla
      GAGGTGCAGG CTGCCATGGC CCTCCTGGAT GTGTTTGCA GCTGCTAATG CCGTTTTGC AGCACTCAG ACCAAACGC AGACCTTCCA AGGCCTAgcc GCTGTAgcca 901  LeuSerSer GlyAsnSer AlaLeuSerSer SerAlaPhe SerAsnPro IleSerSerPro AlaAlaAsn ValSerAsp LysThrHisThr CysProPro
      GCTGAGTG TGAAAACTCC GGCTTATCAT CGTCCGGCTT TAGCAATCCC ATCAGCAGCA GCGGCTGGCAA TCTCTCCGAC AAAACTCACA CATGCCCACC
1001  CysProAla ProGluLeuLeu GlyGlyPro SerValPhe LeuPheProPro LysProLys AspThrLeu MetIleSerArg ThrProGlu ValThrCys
      GTGCCAGCA CCTGAACTCC TGGGGGGAC GTCAGTCTTC CTCTTCCCCC CAAAACCCAA GGACACCCTC ATGATCTCCC GGACCCCTGA GGTCACATGC
1101  ValValValAsp ValSerHis GluAspPro GluValLysPhe AsnTrpTyr ValAspGly ValGluValHis AsnAlaLys ThrLysPro ArgGluGluGln
      GTGGTGGTGG ACGTGAGCCA CGAAGACCCT GAGGTCAAGT TCAACTGGTA CGTGGACGGC GTGGAGGTGC ATAATGCCAA GACAAAGCCG CGGGAGGAGC
1201  TyrAsnSer ThrTyrArg ValValSerVal LeuThrVal LeuHisGln AspTrpLeuAsn GlyLysGlu TyrLysCys LysValSerAsn LysAlaLeu.
      ACTACAACAG CACGTACCGT GTGGTCAGCG TCCTCACCGT CCTGCACCAG GACTGGCTGA ATGGCAAGGA GTACAAGTGC AAGGTCTCCA ACAAAGCCCT
1301  ProAlaPro IleGluLysThr IleSerLysAla LysGlyGln ProArgGluPro GlnValTyr ThrLeuProProSerArg GluGluMet ThrLysAsn
      CCCAGCCCCC ATCGAGAAAA CCATCTCCAA AGCCAAAGGG CAGCCCCGAG AACCACAGGT GTACACCCTG CCCCCATCCC GGGAGGAGAT GACCAAGAAC
1401  GlnValSerLeu ThrCysLeu ValLysGly PheTyrProSer AspIleAla ValGluTrp GluSerAsnGly GlnProGlu AsnAsnTyr LysThrThrPro
      CAGGTCAGCC TGACCTGCCT GGTCAAAGGC TTCTATCCCA GCGACATCGC CGTGGAGTGG GAGAGCAATG GGCAGCCGGA GAACAACTAC AAGACCACGC
1501  ProValLeu AspSerAsp GlySerPhePhe LeuTyrSer LysLeuThr ValAspLysSer ArgTrpGln GlnGlyAsn ValPheSerCys SerValMet.
      CTCCCGTGCT GGACTCCGAC GGCTCCTTCT TCCTCTACAG CAAGCTCACC GTGGACAAGA GCAGGTGGCA GCAGGGGAAC GTCTTCTCAT GCTCCGTGAT
                                      BmtI
                                      NheI
1601  HisGluAla LeuHisAsnHis TyrThrGln LysSerLeu SerLeuSerPro GlyLys*** (SEQ ID NO:66)
      GCATGAGGCT CTGCACAACC ACTACACGCA GAAGAGCCTC TCCCTGTCTC CGGGTAAATG AGTAGCTAGT GGCCAGACAT GATAAGATAC ATTCATGAGT
1701  TTGACAAAAC CACAACTAGA ATGCAGTGAA AAAAATGCTT TATTTGTGAA ATTTGTGAAT CTATTGCTTT ATTTGTAACC ATTATAAGCT ATTATAAGCT GCAATAAACA
                                                                                                                            AseI
1801  AGTTAACAAC AACAATTGCA TTCATTTTAT GTTTCAGGTT CAGGGGAGG TGTGGGAGGT TTTTTAAAGC AAGTAAAACC TCTACAAATG TGGTATGGAA
      AseI
1901  TTAATTCTAA AATACAGCAT AGCAAAACTT TAACCTCCAA ATCAAGCCCT CATGAGTTTT AAGAATAGT GTATTTCCCC AAGGTTTGAA GGATGAATAA TCAGGGGCTG TCAGCTTCTG ATTCTTTAT
2001  TTGCCAATGT GCATTAGCTG TTTGCAGCCT CACCTTCTTT CACCGAGTTT
```

```
2101 GTTTAAAATG CACTGACCTC CCACAATCCC TTTTTAGTAA AATAATTCAGA AATAATTTAA ATACATCATT GCAATGAAAA TAAATGTTTT TTATTAGGCA
2201 GAATCCAGAT GCTCAAGGCC CTTCATAATA TCCCCCAGTT TAGTAGTTGG ACTTAGGAAA CAAAGGAACC TTTAATAGAA ATTGGACAGC AAGAAAGCGA
2301 GCTTCTAGCT TATCCTCAGT CCTGCTCCTC TGCCACAAAG TGCACGCAGT TGCCGGCCGG GTCCGGCCGG GCGAACTCCC GCCCCACCCC CTGCTCGCCG
2401 ATCTCGGTCA TGGCCGGCCC GGAGGCGTCC CGGAAGTTCG TGGACACGAC CTCCGACCAC TCCGCGTCAG GTCGTCGTCC GCCGCGCACC CACACCCAGG
2501 CCAGGGTGTT GTCCGGCACC ACCTGGTCCT GGACCGCGCT GATGAACAGG GTCACGTCGT CCCGACCAC ACCGGCGAAG TCGTCCTCCA CGAAGTCCCG
2601 GGAGAACCCG AGCCGGTCGG TCCAGAACTC GACCGCTCCG GCGACGTCGG GCGCGGTGAG GCCGGAACG CACCGGAACG GCACTGGTCA ACTTGGCCAT GATGGCTCCT
                                                                                                    AseI
2701 CCTGTCAGGA GAGGAAAGAG AAGAAGGTTA GTACAATTGC TATAGTGAGT TGTATTATAC TATGCAGATA TACTATGCCA ATGATTAATT GTCAAACTAG
2801 GGCTGCAGGG TTCATAGTGC CACTTTTCCT GCACTGCCCC ATCTCCTGCC CACCCTTTCC CAGGCATAGA CAGTCAGTGA CTTACCAAAC TCACAGGAGG
2901 GAGAAGGCAG AAGTTGAGA CAGACCCGCG GGTGGCAGGA ACTGCGAGGG ACTGGGCTTA GGGCGGCTTC TTTTATGGTG CGCCGGCCCT CGGAGGCAGG
3001 GCGCTCGGGG AGGCTAGCG GCCAATCTGC GGTGGCAGGA GGGGGGCCCG AAGGCCGTGC CTGACCAATC AGGAGTCTCA GCCCCCCGCC
3101 CCAAGCAAG GGGAAGTCAC GCGCCTGTAG CGCCAGCGTG TTGTGAAATG GGGGCTTGGG CCCTGACTAG TCAAAACAAA CTCCCATTGA
3201 CGTCAATGGG GTGGAGACTT GGAAATCCCC GTGAGTCAAA CCGCTATCCA GTTACTGCCA AAACCGCATC ATCATGGTAA TAGCGATGAC
3301 TAATACGTAG ATGTACTGCC AAGTAGGAAA GTCCATAGA CCGCATAATG CAGGGCCGGC CATTTACCGT CATTGACGTC AATAGGGGGC
3401 GTACTTGGCA TATGATGTAC TTTGATGTACT CAGTTTACCG GGGCGCGT TAAATACTCC ACCCATTGAA GTCAATGAAA AGTCCCTATT GGCGTTACTA
3501 TGGGAACATA CGTCATTATT GACGTCAATG GGCGGGGGTC GTTGGGCGGT CAGCCAGGCG GGCCATTTAC CGTAAGTTAT GTAACGCCTG CAGGTTAATT
3601 AAGAACATGT GAGCAAAAGG CCAGCAAAAG GCCAGGAACC GTAAAAAGGC CGCGTTGCTG GCGTTTTTCC ATAGGCTCCG CCCCCCCTGAC GAGCATCACA
3701 AAAATCGACG CTCAAGTCAG AGGTGGCGAA ACCCGACAGG ACTATAAAGA TACCAGGCGT TTCCCCCTGG AAGCTCCCTC GTGCGCTCTC CTGTTCCGAC
3801 CCTGCCGCTT ACCGGATACC TGTCCGCCTT TCTCCCTTCG GGAAGCGTGG CGCTTTCTCA TAGCTCACGC TGTAGGTATC TCAGTTCGGT GTAGGTCGTT
3901 CGCTCCAAGC TGGGCTGTGT GCACGAACCC CCCGTTCAGC CCGACCGCTG CGCCTTATCC GGTAACTATC GTCTTGAGTC CAACCCGGTA AGACACGACT
4001 TATCGCCACT GGCAGCAGCC ACTGGTAACA GGATTAGCAG AGCGAGGTAT GTAGGCGGTG CTACAGAGTT CTTGAAGTGG TGGCCTAACT ACGGCTACAC
4101 TAGAAGAACA GTATTTGGTA TCTGCGCTCT GCTGAAGCCA GTTACCTTCG GAAAAAGAGT TGGTAGCTCT TGATCGGCA TGATCGGGCA CGCTGGTAGC
4201 GGTGGTTTTT TTGTTTGCAA GCAGCAGATT ACGCGCAGAA AAAAAGGATC TCAAGAAGAT CCTTTGATCT TTTCTACGGG GTCTGACGCT CAGTGGAACG
4301 AAAACTCACG TTAAGGGATT TGGTCATGAG CTAGTTAATT AACATTTAATI TCAGCGCCG CAATAAAATA TCTTTATTTT CATTACATCT GTGTGTTGGT
4401 TTTTTGTGTG AATCGTAACT CTCCATCAAA ACAAAACGAA CTAGCAAAAT CTAGCAAAAT AGGCTGTCCC CAGTGCAAGT GCAGTGCCA
4501 GAACATTTCT CTATCGAA (SEQ ID NO:93)
```

IL2ss.CXCL11.hIgG1Fc sequence

```
   1 GGATCGCCA TCGCTCCGGT GCCCGTCAGT GGGACAGAGCG CACATCGCCC ACAGTCCCCG AGAAGTTGGG GGGAGGGGTC GGCAATTGAA CGGGTGCCTA
 101 GAGAAGGTGG CCGGGGGTAA ACTGGGAAGA TGATGTCGTG GCCAGAACAC AGCTGAAGCT CTGAGGGCT TCGAGGGGGA CGAGGGTGCC ATATAAGTGC AGTAGTGCC
 201 GTGAAGCTTC TTTTTCGCAA CGGGTTTGCC GCCAGAACAC AGCTGAAGCT CTGTGGTGCC TCGAGGGGCT TCGAGGGGGA CGAGGGTGCC CTTCACGCGC ACCTGAGGCC
 301 GCCATCCACG CCGGTTCAGT CGCGTTCTGC CCGTTCTGC CGCTCCCGC CTGTGGTGCC TCCTGAACTC CGTCCGCCGT CTAGGTAAGT TTAAGCTCA GGTCGAGACC
 401 GGGCCTTGT CCGGCGTCC CTTGGAGCCT ACCTAGAGCT AGCCCGGCTCT AGCCGGCTCT CCACGGCTTTG CTTGACCCTG CTTGCTCAAC TCTACGTCTT TGTTTTCGTT

KasI
                                                                                   NarI
                                                                                   SfoI
                                                                                   BbeI
                                                                                                              IL-2 secretion signal
                                                                                                              MetTyrArg MetGlnLeu LeuSerCysIle
 501 TCTGTTCTGC GCCGTTACAG ATCCAAGCTG TGACCGGCGC CTACCTGAGA TCACCGGCGA AGGAGGGCCA CCATGTACAG GATGCAACTC CTGTCTTGCA
                                      EcoRI
                                             ..... CXCL11 (1-73)
     AlaLeuSer LeuAlaLeu ValThrAsnSer PheProMet PheLysArg GlyArgCysLeu CysIleGly ProGlyVal LysAlaValLys ValAlaAsp
 601 TTGCACTAAG TCTTGCACTT GTCACGAATT CCTTCCCCAT GTTCAAAAGA GGACGCTGTC TTGCATAGG CCCTGGGGTA AAAGCAGTGA AAGTGGCAGA
     IleGluLys AlaSerIleMet TyrProSer AsnAsnCys AspLysIleGlu ValIleIle ThrLeuLys GluAsnLysGly GlnArgCys LeuAsnPro
 701 TATTGAAAA GCCTCCATAA TGTACCCAAG TAACAACTGT GACAAAATAG AAGTGATTAT AACCCTGAAA GAAAATAAAG GACAACGATG CCTAAATCCC
                                                                                      human IgG1 Fc (constant region)
     LysSerLysGln AlaArgLeu IleIleLys LysValGluArg TyrAsnCAA AAAGTTGAAA LysAsnPhe AspLysThr HisThrCysPro AlaProGlu LeuLeuGlyGly
 801 AAATCCAAGC AAGCAAAGCT TATAATCAAA AAAGTTGAAA GAAAGAATTT TGACAAAACT CACACATGCC CACCGTGCCC AGCACCTGAA CTCCTGGGGG
     ProSerVal PheLeuPhe ProProLysPro LysAspThr LeuMetIle SerArgThrPro GluValThr CysValVal ValAspValSer HisGluAsp
 901 GACCGTCAGT CTTCCTCTTC CCCCCAAAAC CCAAGGACAC CCTCATGATC TCCCGGACCC CTGAGGTCAC ATGCGTGGTG GTGGACGTGA GCCACGAAGA
     ProGluVal LysPheAsnTrp TyrValAsp GlyValGlu ValHisAsnAla LysThrLys ProArgGlu GluGlnTyrAsn SerThrTyr ArgValVal
1001 CCCTGAGGTC AAGTTCAACT GGTACGTGGA CGGCGTGGAG GTGCATAATG CCAAGACAAA GCCGCGGGAG GAGCAGTACA ACAGCACGTA CCGTGTGTC
     SerValLeuThr ValLeuHis GlnAspTrp LeuAsnGlyLys GluTyrLys CysLysVal SerAsnLysAla LeuProAla ProIleGlu LysThrIleSer
1101 AGCGTCCTCA CCGTCCTGCA CCAGGACTGG CTGAATGGCA AGGAGTACAA GTGCAAGGTC TCCAACAAAG CCCTCCCAGC CCCCATCGAG AAAACCATCT
     LysAlaLys GlyGlnProArg GluProGln ValTyrThr LeuProPro SerArgGluGlu MetThrLys AsnGlnVal SerLeuThrCys LeuValLys
1201 CCAAAGCCAA AGGGCAGCCC CGAGAACCAC AGGTGTACAC CCTGCCCCA AGCGGGAGG AGATGACCAA GAACCAGGTC AGCCTGACCT GCCTGGTCAA
     GlyPheTyr ProSerAspIle AlaValGlu TrpGluSer AsnGlyGlnPro GluAsnAsn TyrLysThr ThrProProVal LeuAspSer AspGlySer
1301 AGGCTTCTAT CCCAGCGACA TCGCCGTGGA GTGGGAGAGC AATGGGCAGC CGGAGAACAA CTACAAGACC ACGCCTCCCG TGCTGGACTC CGACGGCTCC
     PhePheLeuTyr SerLysLeu ThrValAsp LysSerArgTrp GlnGlnGly AsnValPhe SerCysSerVal MetHisGlu AlaLeuHis AsnHisTyrThr
1401 TTCTTCCTCT ACAGCAAGCT CACCGTGGAC AAGAGCAGGT GGCAGCAGGG GAACGTCTTC TCATGCTCCG TGATGCATGA GGCTCTGCAC AACCACTACA GlnLysSer LeuSerLeu SerProGlyLys *** (SEQ ID NO:67)
1501 CGCAGAAGAG CCTCTCCCTG TCTCCGGGTA AATGAGTGCT AGCTGGCCAG ACATGATAAG ATACATTGAT GAGTTTGGAC AAACCACAAC TAGAATGCAG
1601 TGAAAAAAAT GCTTTATTTG TGAAATTTGT GATGCTATTG CTTTATTTGT AACCATTATA AGCTGCAATA AACAATTGTT TGTGTAA CAACAACAAT TGCATTCATT
                                                  NheI                                                     AseI
1701 TTATGTTTCA GGTTCAGGGG GAGGTGTGGG AGGTTTTTTA AAGCAAGTAA AACCTCTACA AATGTGGTAT GGAATTAATT CTAAAATACA GCATAGCAAA
1801 ACTTTAACCT CCAAATCAAG CCTCTACTTG AATTCCTTTC TGAGGGATGA ATAAGGCATA TCCCAAGGTT TGAACTAGCT CTTCATTTCT TTATGTTTCA GCTGTTTGCA
1901 GCCTCACCTT CTTTCATGGA GTTAAGATA TAGTGTATTT TCCCAAATCC CATTCCAATG AAAATAAATG AGAAATTGGA GCCAAGAAAA GCCGCTGCTC CCTCCACAT
2001 TCCCTTTTA GTAAATATT CAGAAAATAAT TTAAATACAT AGAAGTTTAAT AGAAATTTGGA GCCAAGAAAA GCCGCTGCTC AGTGACTCAA AGCCGCTTCAT
2101 AATATCCCCC AGTTAGTAG TTCGGACTTAG GGAACAAAGG AAAGCCGAAC TCCCGCCCGC ACGGGCTGCTC ACGGCTGCTC GTCATGCGCG CAGTCCTGCT
2201 CCTCTGCCAC AAAGTGCACG CAGTTGCGCG CCGGGTGCGG CAGGGCGGAC TCCCGGCGAAC ACGGCTGCTC CACCCACACC CCAGGCCAGGG GCCCGAGGGC
2301 GTCCCGGAAG TTCGTGGACA CGACCTCCGA TACAGCTCGT CCAGGCCGCG CACCCACACC TCCACGAAGT CAGAGGAGAA CCCGAGCCGG CACCACCTGG
2401 TCCTGGACCG CGCTGATTGAA CAGGGGTCACG TCGTCCCGGA CCAACAGGGC TCCAACGAAGT CCCAGGGAGT CCCGAGCCGG TCGGGTCCAGGA
```

```
2501 ACTCCACCGC TCCGGCGACG TCGCGCCGCG TGAGCACCGG AACGGCACTG GTCAACTTGG CCAATGATGC TCCTCCTGTC AGGAGAGGAA AGAGAAGAAG
                                                                    AseI
2601 GTTAGTACAA TTGCTATAGT GAGTTGTATT ATACTATGCA GATATACTAT GCCAATGATT AATTGTCAAA CTAGGGCTGC AGGGTTCATA GTGCCACTTT
2701 TCCTGCACTG CCCCATCTCC TGCCCACCCT TTCCCAGGCA TAGACAGTCA GTGACTTACC AAACTCACAG GAGGGAGAAG GCAGAAGCTT GAGACAGACC
2801 CGCGGGACCG CCGAACTGCG AGGGACGTG GCTAGGGCGG CTTCTTTTAT GGTGCGCCGG CCCTCGAGG CAGGGCCTC GGGAGGCCT AGCGGCAAT
2901 CTGCCGTGGC AGGAGGCGGG GCCGAAGGCC GTCGCTCACC AATCCGAGC ACATAGGAGT CTCAGCCCC CGCCCAAAG CAAGGGGAAG TCACGCGCCT
3001 GTAGCGCCAG CGTGTTGTGA AATGGGGGCT TGGGGGGGTT GGGGCCCTGA CAAACTCCCA TTGACGTCAA TGGGGTGGAG ACTTGGAAAT
3101 CCCCGTGAGT CAAACCGCTA TCCACGCCCA TTGATGTACT GCCAAAACCG CTAGTCATG CATCATCATG GTAATAGCGA TGACTAATAC TGCCAAGTAG
3201 GAAAGTCCCA TAAGGTCATG TACTGGGCAT AATGCCAGGC GGGCCATTTA GGGCCATTGA CGTCAATAGG CGTCAATAGG GGGCGTACTT ACACTTGATG
3301 TACTGCCAAG TGGGCAGTTT ACCGTAAATA CTCCACCCAT TGACGTCAAT GAAAGTCCC TATTGGCGTT ACTATGGGAA CATACGTCAT TATTGACGTC
3401 AATGGGCGGG GGTCGTTGGG CGGTCAGCCA GGCGGGCCAT TTACCGTAAG TTATGTAACG CCTGCAGGTT AATTAAGAAC ATGTGAGCAA AAGGCCAGCA
3501 AAAGGCCAGG AACGTAAAA AGGCCGCGT GCTGGCGTTT TTCCATAGGC TCCGCCCCC TGACGAGCAT CACAAAATC GACGCTCAAG TCAGAGGTGG
3601 CGAAACCCGA CAGGACTATA AAGATACCAG GCGTTTCCCC CTGGAAGCTC CCTCGTGCGC TCTCCTGTTC CGACCCTGCC GCTTACCGGA TACCTGTCCG
3701 CCTTTCTCCC TTCGGAAGC GTGCGCTTT CTCATAGCTC ACGCTGTAGG TATCTCAGTT CGGTGTAGG CGTTCGCTCC AAGCTGGGCT GTGTGCACGA
3801 ACCCCCGTT CAGCCCGACC GCTGCGCCTT ATCCGGTAAC TATCGTCTTG AGTCCAACCC GGTAAGACAC GACTTATCGC CACTGGCAGC AGCCACTGGT
3901 AACAGGATTA GCAGAGCGAG GTATGTAGGC GGTGCTACAG AGTTCTTGAA GTGGTGGCCT AACTACGGCT ACACTAGAAG AACAGTATTT GGTATCTGCG
4001 CTCTGCTGAA GCCAGTTACC TTCGGAAAAA GAGTTGGTAG CTCTTGATCC GGCAAACAAA CCACCGCTGG TAGCGGTGGT TTTTTTGTTT GCAAGCAGCA
4101 GATTACGCGC AGAAAAAAAG GATCTCAAGA AGATCCTTTG ATCTTTTCTA CGGGGTCTGA CGCTCAGTGG AACGAAAACT CACGTTAAGG GATTTTGGTC
4201 ATGCTAGTT AATTAACATT TAAATCAGCG GCCGCAATAA AATATCTTTA TTTTCATTAC ATCTGTGTGT TGGTTTTTTG TGTGAATCGT AACTAACATA
4301 CGCTCTCCAT CAAACAAAA CGAAACAAAA CAAACTAGCA AAATAGGCTG AAGTGCAGGT GCCAGAACAT TTCTCTATCG AA (SEQ ID NO:94)
```

IL2ss.CXCL11(4-73).hIgG1Fc sequence

```
   1 GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101 GAGAAGGTGG CGCGGGGTAA ACTCGGGAAAG TGATCTCGTG TACTGGCT\CC GCCTTTTCC CGAGGGTGGG GGAGAGTGC CGAGAGTGCC ACCTAGTGCC
 201 GTGAACGTTC TTTTTCGCAA CGGGTTTGCC GCCAGAACAC AGCTGAAGCT TCGAGGGGCT CGCATCTCTC CTTCACGCGC CCGCCGCCCT ACCTGAGGCC
 301 GCCATCCACG CCGGTTGAGT CCGCTTCTGC CGCCTCCGC TCCTGAACTG CGTCCGCCGF CTAGGTAAGT CTTGCCTAAG TTAAAGCTCA GGTCGAGACC
 401 GGGCCTTTGT CCGGCGCTCC CTTGGAGCCT ACCTAGAGCTC AGCCGGCTCT CCACGGCTTTG CCTGACCCTG AGAAAATAAA TCTGCCAAC TCTACGTCTT TGTTTGTTT
                                                KasI
                                                NarI
                                                SfoI
                                                BbeI
                                                                                                  IL-2 secretion signal
                                                                                                   MetTyrArg MetGlnLeu LeuSerCysIle
 501 TCTGTTCTGC GCCGTTACAG ATCCAAGCTG TGACCGGCGC CTACCTGAGA TCACCCGGCGA AGGAGGGCCA CCATGTACAG GATGCAACTC CTGTCTTGCA
                        EcoRI         ~~~~~~~ CXCL11 (4-73)
                                                                      AlaAlaLeu ValThrAsnSer PheLysArg GlyArgCys LeuCysIleGly ProGlyVal LysAlaVal LysValAlaAsp IleGluLys
 601 TTGCACTAAG TCTTGCACTT GTCACGAATT CGTTCAAAAG AGGACGCTGT CTTTGCATAG GCCCTGGGGT AAAAGCAGTG AAAGTGGCAG ATATTGAGAA
     AlaSerIle MetTyrProSer AsnAsnCys AspLysIle GluValIleIle ThrLeuLys GluAsnLys GlyGlnArgCys LeuAsnPro LysSerLys
 701 AGCCTCCATA ATGTACCCAA GTAACAACTG TGACAAAATA GAAGTGATTA TTACCCTGAA GGACAACGAT GCCTAAATCC CAAATGCAAG
                                                                       human IgG1 Fc (constant region)
     GlnAlaArgLeu IleIleLys LysValGlu ArgLysAsnPhe AspLysThr HisThrCys ProProCysPro AlaProGlu LeuLeuGly GlyProSerVal
 801 CAAGCAAGGC TTATAATCAA AAAAGTTGAA AGAAGAAATT TTGACAAAAC TCACACATGC CCACCCTGCA CCAGCACCTG ACTCCTGGGG GGACCGTCAG
     PheLeuPhe ProProLys ProLysAspThr LeuMetIle SerArgThr ProGluValThr CysValValVal ValAspVal SerHisGluAsp ProGluVal
 901 TCTTCCTCTT CCCCCCAAAA CCCAAGGACA CCCTCATGAT CTCCCGGACC CCTGAGGTCA CATGCGTGGT GTGGACGTG AGCCACGAAG ACCCTGAGGT
     LysPheAsn TrpTyrValAsp GlyValGlu ValHisAsn AlaLysThrLys ProArgGlu GluGlnTyr AsnSerThrTyr ArgValVal SerValLeu
1001 CAAGTTCAAC TGGTACGTGG ACGGCGTGGA AGTGCATAAT GCCAAGACAA AGCCGCGGGA GGAGCAGTAC AACAGCACGT ACCGTGTGGT CAGCGTCCTC
     ThrValLeuHis GlnAspTrp LeuAsnGly LysGluTyrLys CysLysVal SerAsnLys AlaLeuProAla GlyIleGlu LysThrIle SerLysAlaLys
1101 ACCGTCCTGC ACCAGGACTG GCTGAATGGC AAGGAGTACA AGTGCAAGGT CTCCAACAAA GCCCTCCCAG CCCCCATCGA GAAAACCATC TCCAAGCCA
     GlyGlnPro ArgGluPro GlnValTyrThr LeuProPro SerArgGlu GluMetThrLys AsnGlnVal SerLeuThr CysLeuValLys GlyPheTyr
1201 AGGGCAGCCC CGAGAACCA CAGGTGTACA CCCTGCCCCC ATCCCGGGAG GAGATGACCA AGAACCAGGT CAGCCTGACC TGCCTGGTCA AAGGCTTCTA
     ProSerAsp IleAlaValGlu TrpGluSer AsnGlyGln ProGluAsnAsn TyrLysThr ThrProPro ValLeuAspSer AspGlySer PheLeuTyr SerLys
1301 TCCCAGCGAC ATCGCGTGG AGTGGGAGAG CAATGGGCAG CCGGAGAACA ACTACAAGAC CACGCCTCCC GTGCTGGACT CCGACGGCTC CTTCTTCTCTC
     TyrSerLysLeu ThrValAsp LysSerArg TrpGlnGlnGly AsnValPhe SerCysSer ValMetHisGlu AlaLeuHis AsnHisTyr ThrGlnLysSer
1401 TACAGCAAGC TCACCGTGGA CAAGAGCAGG TGGCAGCAGG GGAACGTCTT CTCATGCTCC GTGATGCATGAA GGCCTTTGCA CAACCACTAC ACGCAGAAGA
                           BmtI
                           NheI
     LeuSerLeu SerProGly Lys*** (SEQ ID NO:68)
1501 GCCTCTCCCT GTCTCCGGGT AAATGAGTGC TAGCTGGCCA GACATGATAA GATACATTGA TGAGTTTGGA CAAACCACAA CTAGAATGCA GTGAAAAAAA
1601 TGCTTTATTT GTGAAATTTG TGATGCTATT GCTTTATTTG TAACCATTAT AAACAAGTTA AACAACACAACAA TTGCATTCAT TTTATGTTTC
1701 AGGTTCAGGG GGAGGTGTGG GAGGTTTTTT AAAGCAAGTA AAACTCCTAC AAATGTGTA TGGAATTAAT TCTAAAATAC AGCATAGCAA AACTTTAACC
1801 TCCAAATCAA GCCCTACTT GAATCCTTTT CTGAGGGATG TAGGGGAATG AATAAGGCAT AGGCATCAGG GGCTGTTTGCC AATGTGCATT AGTGTTTGC AGCCTCACCT
1901 TCTTTCATGG AGTTTAAGAT ATAGTGTATT TCATTGCAAT GAAAATAAAT GTTTTTATT AGGCAGAATC TTTATGTTT AAATGCACTG ACCTCCCACA TTCCCTTTT
2001 AGTAAAATAT TCAGAAATAA TTTAAATACA TCATTGCAAA GAAACTTTAA TAGAAATTGG ACAAGAAGAA ACGGAGCTTC CAGATGCTCA AGGCCCTTCA TAATATCCCC
2101 CAGTTTAGTA GTTGGACTTA GGGAACACAG CNCCGCCCC CAGGGCGAA CACGGCTGCT CGGCGATCTC GGTCATGGCC TAGCTTATCC TCAGTCCTGC TCCTCTGCCA
2201 CARAGTGCAC GCAGTTGCCG GCCAGGTCGC ACCACTCGGC GTACAGCTCG TCCAGGCCG GCACCACAC GGCGATTCTC GTGTTGTCCG GGCCGGAGG GTCCCGGAA
2301 GTTCGTGGAC ACGACCTCCG ACCACTCGGC CTCCAGGAGA TCCGGGAGA ACCGAGCCG GTCGGTCCAG ACCGAGCCGG TCCCGAGCCG GCACCACCTG GTCCTGGACC
2401 GCGCTGATGA ACAGGGTCAC GTCGTCCCGG ACCACACCGG CTCCCGGGAGA ACCGAGCCG GTCGGTCCAG AACTCGACCG
```

```
2501 CTCCGGCGAC GTCGCGCGCG GTGAGCACCG GAACGGCACT GGTCAACTTG GCCATGATGG CTCCTCCTGT CAGGAGAAGA AAGAGAAGAA GGTTAGTACA
                                                                AseI
2601 ATTGCTATAG TGAGTTGTAT TATACTATGC AGATATACTA TGCCAATGAT TAATTGTCAA ACTAGGGCTG CAGGGTTCAT AGTGCCACTT TTCCTGCACT
2701 GCCCCATCTC CTGCCCACCC TTTCCCAGGC ATAGACAGTC GCTTCTTTTA AGTGACTTAC CAAAACTCACA GGAGGGAGAA GGCAGAAGCT TGAGACAGAC CCGCGGGACC
2801 GCCGAACTGC GAGGGACGT GGCTAGGGCG CGTTCTTTA TGGTGCGCCG GCCCTCGGAG CACATAGGAG TCTCAGCCCC CCGAGGGGCT TAGCGCCAA TCTGCGGTGG
2901 CAGGAGGCGG GGCCGAAGGC CGTGCCTGAC CAATCCGGAG CACATAGGAG TCTCAGCCCC CCGAGGGGCT TAGCGCCAA TCTGCGGTGG
3001 GCGTGTTGTG AAATGGGGGC TTGGGCCCCT TGGGGCCCTG ACTAGTCAAA ACAAACTCCC ATTGACGTCA ATGGGGTGGA GACTTGGAAA TCCCCGTGAG
3101 TCAAACCGCT ATCCACGCCC ATTGATGTAC TGCCAAAACC GCATCATCAT GGTAATAGCG CGTAGATGTA CTGCCAAGTA GGAAAGTCCC
3201 ATAAGGTCAT GTACTGGGCA TAATGCCAGG ACTCCACCCA TTGACGTCCA ACCGTCATTG CTATTGGCGT TACTATGGGA TGGCATATGA TACACTTGAT GTACTGCCAA
3301 GTGGCAGTT TACCGTAAAT ACTCCACCCA TTGACGTCCA ACCGTCATTG CTATTGGCGT TACTATGGGA ACATACGTCA TTATTGACGT CAATGGCGG
3401 GGGTCGTTGG GCGGTCAGCC AGGCGGGCCA GTTATGTAAC GCCTGCAGT TAATTAAGAA CATGTGAGCA AAAGGCCAGC AAAAGGCCAG
3501 GAACCGTAAA AAGGCCGCGT TGCTGGCGTT TTTCCATAGG CTCCGCCCCC CTGACGAGCA TCACAAAAAT CGACGCTCAA GTCAGAGGTG GCGAAACCCG
3601 ACAGGACTAT AAAGATACCA GGCGTTTCCC CCTGGAAGCT CCCTCGTGCG CTCTCCTGTT CCGACCCTGC CGCTTACCGG ATACCTGTCC GCCTTTCTCC
3701 CTTCGGGAAG CGTGGCGCTT TCTCATAGCT CACGCTGTAG GTATCTCAGT TCGGTGTAGG TCGTTCGCTC CAAGCTGGGC TGTGTGCACG AACCCCCCGT
3801 TCAGCCCGAC CGCTGCGCCT TATCCGGTAA GAGTCCAACC CGGTAAGACA CGACTTATCG CCACTGGCAG CAGCCACTGG TAACAGGATT
3901 AGCAGAGCGA GGTATGTAGG CGGTGCTACA GAGTTCTTGA AGTGGTGGCC TAACTACGGC TACACTAGAA GAACAGTATT TGGTATCTGC GCTCTGCTGA
4001 AGCCAGTTAC CTTCGGAAAA AGAGTTGGTA GCTCTTGATC CGGCAAACAA ACCACCGCTG GTAGCGGTGG TTTTTTTGTT TGCAAGCAGC AGATTACGCG
4101 CAGAAAAAA GGATCTCAAG AAGATCCTTT GATCTTTTCT ACGGGGTCTG ACGCTCAGTG GAACGAAAAC TCACGTTAAG GGATTTTGGT CATGCTAGT
4201 TAATTAACAT TTAAATCAGC GGCCGCAATA ATTTTCATTA CATCTGTGTG TTGGTTTTT GTGTGAATCG TAACTAACAT ACGCCTCCA
4301 TCAAAACAAA ACGAAACAAA ACAAACTAGC AAAATAGGCT GTCCCCAGTG TGCCAGAACA TTTCTCTATC GAA (SEQ ID NO:95)
```

IL2ss.CXCL11(4-73).hIgG1Fc sequence [Alanine substitutions for removal of GAG binding sites – Lys & His]

```
   1 GGATCTGCGA TGCTCCGGT GCCGGTCAGT GGGCAGAGCG CACATCGCCC ACAGTCCCCG AGAAGTTGGG GGGAGGGGTC GGCAATTGAA CGGGTGCCTA
 101 GAGAAGGTGC CGCGGGTAA ACTCGGAAAG TGATGTCGTG GCCAGAACAC AGTCGAAGCT TCGAGGGGCT CGAGGTGGG GGAGAACCGT CTTCACCGCC AGTAGTCCCC
 201 GGTGAAGGTTC TTTTTCGCAA CGGGTTTGCC CGCCTCCCGC TCTGTGTGCC TCGAAGTCTG CCTGAACTG CGTCCGCCGT CTAGGTAAGT ATATTGACGC
 301 GCCATCCACG CCCGTTGAGT CGGTTCTGC CGCCTCCCGC TCTGTGTGCC AGCCGGCTCT CCAGCCTTTG CCTGACCCTG CTTGCCTCAAC TCTACGTCTT TGTTTCGTTT
 401 GGGCCTTTGT CCCGCGCTCC CTTGGAGCCT ACCTAGACTC A

```
2501 CTCCGGCGAC GTCGCGCGCG GTGAGCACCG GAACGGCACT GGTCAACTTG GCCATGATGG CTCCTCCTGT CAGGAGAGGA AAGAGAAGAA GGTTAGTACA
                                                                AseI
2601 ATTGCTATAG TGAGTTGTAT TATACTATGC AGATATACTA TGCCAATGAT TAATTGTCAA ACTAGGGCTG CAGGGTTCAT AGTGCCACTT TTCCTGCACT
2701 GCCCATCTC  CTGCCCACCC TTTCCCAGGC ATAGACAGTC AGTGACTTAC CAAACTCACA GGAGGGAGAA GGCAGAAGCT TGAGACAGAC CCGCGGGACC
2801 GCCGAACTGC GAGGGACGT  GGCTAGGGCG GCTTCTTTTA TGGTGCGCCG GCCCTCGGAG GCAGGGCGCT CGGGGAGGCC TAGCGGCCAA TCTGCGGTGG
2901 CAGGAGGCGG GGCCGAAGGC CGTGCCTGAC CAATCCGGAG CACATAGGAG TCTCAGCCGC CGCCCCAAA  GCAAGGGGAA GTCACGCGCC TGTAGCGCCA
3001 GCGTGTTGTG AAATGGGGGC TTGGGGGGGT TGGGGCCCTG ACTAGTCAAA ACAAACTCCC ATTGACGTCA ATGGGGTGGA GACTTGGAAA TCCCCGTGAG
3101 TCAAACCGCT ATCCACGCCC ATTGATGTAC TGCCAAAACC GCATCATCAT GGTAATAGCG ACGGTCAATA CGTAGATGTA CTGCCAAGTA GGAAAGTCCC
3201 ATAAGGTCAT GTACTGGGCA TAATGCCAGG CCGGTCATTG ACCGTCAATT ACGGTCAATG GGGCGTACTT TGGCATATGA TACACTTGAT GTACTGCCAA
3301 GTGGCAGTT  TACCGTAAAT ACTCCACCCA TTGACGTCAA TGGAAAGTCC CTATTGGCGT TACTATGGGA ACATACGTCA TTATTGACGT CAATGGGCGG
3401 GGGTCGTTGG GCGGTCAGCC AGGCGGGCCA TTTACCGTAA GCCTGCGTAA CATGTGAGCA AAAGGCCAGC AAAAGGCCAG
3501 GAACCGTAAA AAGGCCGCGT TGCTGGCGTT TTTCCATAGG CTCCGCCCCC CTGACGAGCA TCACAAAAAT CGACGCTCAA GTCAGAGGTG GCGAAACCCG
3601 ACAGGACTAT AAAGATACCA GGCGTTTCCC CCTGGAAGCT CCCTCGTGCG CTCTCCTGTT CCGACCCTGC CGCTTACCGG ATACCTGTCC GCCTTTCTCC
3701 CTTCGGGAAG CGTGGCGCTT TCTCATAGCT CACGCTGTAG GTATCTCAGT TCGGTGTAGG TCGTTCGCTC CAAGCTGGGC TGTGTGCACG AACCCCCCGT
3801 TCAGCCCGAC CGCTGCGCCT TATCCGGTAA CTATCGTCTT GAGTCCAACC CGGTAAGACA CGACTTATCG CCACTGGCAG CAGCCACTGG TAACAGGATT
3901 AGCAGAGCGA GGTATGTAGG CGGTGCTACA GAGTTCTTGA AGTGGTGGCC TAACTACGGC TACACTAGAA GAACAGTATT TGGTATCTGC GCTCTGCTGA
4001 AGCCAGTTAC CTTCGGAAAA AGAGTTGGTA GCTCTTGATC CGGCAAACAA ACCACCGCTG GTAGCGGTGG TTTTTTTGTT TGCAAGCAGC AGATTACGCG
4101 CAGAAAAAAA GGATCTCAAG AAGATCCTTT GATCTTTTCT ACGGGGTCTG ACGCTCAGTG GAACGAAAAC TCACGTTAAG GGATTTTGGT CATGGCTAGT
4201 TAATTAACAT TTAAATCAGC GGCCGCAATA ATTTTCATTA CATCTGTGTG TTGGTTTTTT GTGTGAATCG TAACTAACAT ACGCTCTCCA
4301 TCAAAACAAA ACGAAACAAA ACAAACTAGC AAAATAGGCT GTCCCCAGTG CAAGTGCAGG TGCCAGAACA TTTCTCTATC GAA (SEQ ID NO:96)
```

IL2ss.CXCL11.hIgG4Fc sequence

```
  1 GGATCTGCGA TCCCTCCCGT GCCCGTCAGT GGGCAGAGCC CACATCGCCC ACAGTCCCCG AGAAGTTGGG GGAGGGGTC GGCAATTGAA CGGGTGCCTA
101 GAGAAGGTGG CGGGGGGTAA ACTGGGAAAG TGATGTCGTG GCCAGAACAC AGTGGAAGCT CTTGGCTCC GCCTTTTTC CGAGGGTGG GGAGAACCGT ATATAAGTGC AGTAGTCGCC
201 GTGAACGTTC TTTTTCGCAA CGGGTTTGCC CGCGTTTGAG CGCCTCCGC CTTGGTGCC TCTTGAACTG CGTCCGCGT CTCACGCGC CTCACGCGC CTAGTAAGT TTAAGCTCA GGTCGAGACC
301 GCCATCCACG CCGGTTGAGT CGCGTTCTGC CTTGGAGCCT AGCCGGCTCC AGCCGGCTCC ACAGCTTTG CCTGACCCTG CTTGCTCAAC TCTACGTCTT TGTTTCGTTT
401 GGGCCTTTGT CCGGCGCTCC

501 TCTGTTCTGC GCCGTTACAG ATCCAAGCTG TGACCGGCGC CTACCTGAGA TCACCGGCGA AGGAGGGCCA CCATGTACAG GATGCAACTC CTGTGTTGCA
                                                                                IL-2 secretion signal
                                                                                MetTyrArg MetGlnLeu LeuSerCysIle
        EcoRI                   ------- CXCL11 (1-73)
        NarI
        SfoI
        KasI
        BbeI AlaLeuSer LeuAlaLeu ValThrAspArg PheProMet PheLysArg GlyArgCysLeu CysIleGly LysAlaVallys ValAlaAsp
601 TGCACTAAG TCTTGCACTT GTCACGGAATT CGTTCCCCAT GTTCAAAAGA GGACGCTTTC TGTTGCATAG CCCTGGGTA AAAGCAGTGA AAGTGGCAGA
        IleGluLys AlaSerIleMet TyrProSer AsnAsnCys AspLysIleGlu ValHisAsn AlaLysThrLys ThrGluLys GluAsnLysGly GlnArgCys LeuAsnPro
701 TATTGAGAAA GCCTCCATAA TGTACCCAAG TAACAACTGT GACAAGATTG AAGTGATTAT TACCCTGAAA GAAAATAAAG GACAACGATG CCTAAATCCC LysSerLysGln AlaArgLeu IleIleLys LysValGluArg LysAsnPhe ProSerCysPro ProProCys AlaProGlu PheLeuGly GlyProSerVal
801 AAATCGAAGC AAGCAAGGCT TATAATCAAG AAAGTTGAAA GAAAGAATTT TCCCCCATGC CCATCATGC CAGCACCTGA GTTCTGGGG GGACCATCAG
                                            human IgG4 Fc (constant region)
        PheLeuPhe ProProLys ProLysAspThr LeuMetIle SerArgThr ProGluValThr CysValVal ValAspVal SerGlnGluAsp ProGluVal
901 TCTTCCTGTT CCCCCCAAAA CCCAAGGACA CTCTCATGAT CTCCCGGACC CCTGAGGTCA CGTGCGTGGT GGTGGACGTG AGCCAGGAAG ACCCCGAGGT
        GlnPheAsn TrpTyrValAsp GlyValGlu ValHisAsn AlaLysThrLys ProArgGlu GluGlnPhe AsnSerThrTyr ArgValVal SerValLeu
1001 CCAGTTCAAC TGGTACGTGG ATGGCGTGGA GGTGCATAAT GCCAAGACAA AGCCGCGGGA GGAGCAGTTC AACAGCACGT ACCGTGTGGT CAGCGTCCTC
        ThrValLeuHis GlnAspTrp LeuAsnGly LysGluTyrLys CysLysVal SerAsnLys GlyLeuProSer SerIleGlu LysThrIle SerLysAlaLys
1101 ACCGTCCTGC ACCAGGACTG GCTGAACGGC AAGGAGTACA AGTGCAAGGT CTCCAACAAA GGCCTCCCGT CCTCCATCGA GAAAACCATC TCCAAAGCCA
        GlyGlnPro ArgGluPro GlnValTyrThr LeuProPro SerGlnGlu GluMetThrLys AsnGlnVal SerLeuThr CysLeuValLys GlyPheTyr
1201 AAGGGCAGCC CCGAGAGCCA CAGGTGTACA CCCTGCCCCC ATCCCAGGAG GAGATGACCA AGAACCAGGT CAGCCTGACC TGCCTGGTCA AAGGCTTCTA
        ProSerAsp IleAlaValGlu TrpGluSer AsnGlyGln ProGluAsnAsn TyrLysThr ThrProPro ValLeuAspSer AspGlySer PhePheLeu
1301 CCCCAGCGAC ATCGCCGTGG AGTGGGAGAG CAATGGGCAG CCGGAGAACA ACTACAAGAC CACGCCTCCC GTGCTGGACT CCGACGGCTC CTTCTTCCTC
        TyrSerArgLeu ThrValAsp LysSerArg TrpGlnGluGly AsnValPhe SerCysSer ValMetHisGlu AlaLeuHis AsnHisTyr ThrGlnLysSer
1401 TACAGCAGGC TAACCGTGGA CAAGAGCAGG TGGCAGGAGG GGAATGTCTT CTCATGCTCC GTGATGCATG AGGCTCTGCA CAACCACTAC ACACAGAAGA
        LeuSerLeu SerProGly Lys*** (SEQ ID NO:70)
1501 GCCTCTCCCT GTCTCCGGGT AAATGAGTGC TAGCTGGCCA GACATGATAA AAACCTCTAC AAATGTGGTA TGAGTTTGGA CAAACCACAA CTAGAATGCA GTGAAAAAAA
1601 TGCTTTATTT GTGAAATTTG TGAAGCTATT GCTTTATTTG TAACCATTAT AAGCTGCAAT AGGCATCAGG AACAAGTTA ACAACAAGAA TGCATTCAT TTTTATGTTTC
                                                                        AseI
1701 AGGTTCAGGG GGAGGTGTGG GAGGTTTTTT AAAGCAAGTA GAGGATCCT AAACCTCTAC AAATGTGGTA TGGAATTAAT TCTAAAATAC AGCATAGAC AACTTTAACC
1801 TCCAAATCAA GCCTCTACTT GAATCCTTT CCGAGGCATG TACTGGCCA TAATAAGCAT AGGCATCAGG GGCTGTTGCC TTTATGTTT AAATGCATT AGCTCCACCT
1901 TCTTTCATGG AGTTTAAGAT ATAGTGHATT TTCCCAAGGT GAAACTAGC TCTTCATTTC AGGCAGAATC AAATGCACTG ACCTCCACA TTCCCTTT
2001 AGTAAATAT TCAGAAATA TTTAAATACA TCATTGCAAT GTTTTTATT AGGAGAAT CAGATGCACA AGGCCTTCA TAATATCCCC
2101 CAGTTAGTA GTTGGACTTA GGGAACAAAG GAACCTTTAA TAGAAATGG ACAACAAGAA AGCGAGCTTC TAGCTTATCC TCAGTCCTGC TCCTCTGCCA
2201 CAAAGTGCAC GCAGTTGCCG GCCGGGTGCC GTACAGCTCG TCCAGGGCGA CACGGCTGCT CACGGCATCC GGTCATGGCC CCACCCGGAGG CGTCCCGGAA
2301 GATGCGTGGAG ACGACCTCGG ACCACCTCAC GTACAGCTCG TCCAGGGCAGG CCAGGCCAGG CCGTCAGC GTGTTCCG GCACCACCG GTCCGGAAGG
2401 GGCCTGATGA ACAGGGTCAC GTCTCCCCGG ACCACCCCGG CGAAGTGCTGC CTCCAGCCG CTCCAGGCGAGG AGGCTCTGCA CAACCACTAC GTCGGTCCAG AACTGACCG
```

```
2501 CTCCGGCGAC GTCGCGCGCG GTGAGCACCG GAACGGCACT GGTCAACTTG GCCATGATGG CTCCTCCTGT CAGGAGAGGA AAGAGAAGAA GGTTAGTACA
                                                                   AseI
2601 ATTGCTATAG TGAGTTGTAT TATACTATGC AGATATACTA TGCCAATGAT TAATTGTCAA ACTAGGGCTG CAGGGTTCAT AGTGCCACTT TTCCTGCACT
2701 GCCCATCTC CTGCCCACCC TTTCCCAGGC ATAGACAGTC AGTGACTTAC CAAACTTCACA GGAGGGAGAA GGCAGAAGCT TGAGACAGAC CCGCGGACC
2801 GCCGAACTGC GAGGGACGT GGCTAGGGCG GCTTCTTTTA TGGTGCGCG GCCCTCCGAG GCAGGGCGCT GCAGGAGGCC TAGCGGCCAA TCTGCGGTGG
2901 CAGGAGGCGG GGCCGAAGGC CGTGCCTGAC CAATCCGGAG CACATAGGAG TCTCAGCCCC CCGCCCCAAA GCAAGGGGAA GTCACGCGCC TGTAGCGCCA
3001 GCGTGTTGTG AAATGGGGGC TTGGGGGGGT TGGGCCCTG ACTAGTCAAA ACAAACTCCC ATTGACGTCA ATGGGGTGGA GACTTGAAA TCCCGTGAG
3101 TCAAACCGCT ATCCACGCCC ATTGATGTAC TGCCAAAACC GCATCATCAT GGTAATAGCG ATGACTAATA CGTAGATGTA CTGCCAAGTA GGAAAGTCCC
3201 ATAAGGTCAT GTACTGGGCA TAATGCCAGG CGGGCCATTT ACCGTCATTG ACGTCAATAG GGGGCGTACT TGGCATATGA TACACTTGAT GTACTGCCAA
3301 GTGGGCAGTT TACCGTAAAT ACTCCACCCA TTGACGTCAA TGGAAAGTCC CTATTGGCGT TACTATGGGA ACATACGTCA TTATTGACGT CAATGGGCGG
3401 GGGTCGTTGG GCGGTCAGCC AGGCGGGCCA TTTACCGTAA GTTATGTAAC GCCTGCAGGT TAATTAAGAA CATGTGAGCA AAAGGCCAGC AAAAGGCCAG
3501 GAACCGTAAA AAGGCCGCGT TGCTGGCGTT TTTCCATAGG CTCCGCCCCC CTGACGAGCA TCACAAAAAT CGACGCTCAA GTCAGAGGTG GCGAAACCCG
3601 ACAGGACTAT AAAGATACCA GGCGTTTCCC CCTGGAAGCT CCCTCGTGCG CTCTCCTGTT CCGACCCTGC CGCTTACCGG ATACCTGTCC GCCTTTCTCC
3701 CTTCGGGAAG CGTGGCGCTT TCTCATAGCT CACGCTGTAG GTATCTCAGT TCGGTGTAGG TCGTTCGCTC CAAGCTGGGC TGTGTGCACG AACCCCCCGT
3801 TCAGCCCGAC CGCTGCGCCT TATCCGGTAA CTATCGTCTT GAGTCCAACC CGGTAAGACA TCACTGGCAG CAGCCACTGG TAACAGGATT
3901 AGCAGAGCGA GGTATGTAGG CGGTGCTACA GAGTTCTTGA AGTGGTGGCC TAACTACGGC TACACTAGAA GAACAGTATT TGGTATCTGC GCTCTGCTGA
4001 AGCCAGTTAC CTTCGGAAAA AGAGTTGGTA GCTCTTGATC CGGCAAACAA ACCACCGCTG GTAGCGGTGG TTTTTTTGTT TGCAAGCAGC AGATTACGCG
4101 CAGAAAAAAA GGATCTCAAG AAGATCCTTT GATCTTTTCT ACGGGGTCTG GAACGAAAAC TCACGTTAAG GGATTTTGGT CATGGCTAGT
4201 TAATTAACAT TTAAATCAAG GCCCGCAATA AAATATCTTT ATTTTCATTA CATCTGTCTG TTGGTTTTTT GTGTGAATCG TAACTAACAT ACGCTCTCCA
4301 TCAAAACAAA ACGAAACAAA ACAAACTAGC AAAATAGGCT GTCCCCAGTG CAAGTGCAGG TGCCAGAACA TTTCTCTATC GAA (SEQ ID NO:97)
```

IL2ss.CXCL11(4-73).hIgG4Fc sequence

```
   1 GGATCTGCGA TCGCTCCGGT GCCCGTCAGT GGGCAGAGCG CACATCGCCC ACAGTCCCCG AGAAGTTGGG GGGAGGGGTC GGCAATTGAA CGGGTGCCTA
 101 GAGAAGGTGG CGCGGGGTAA ACTGGGAAAG TGATGTCGTG TACTCGGCTG GCTTTTTTCC GCTTTTTTCC CGAGGGTGGG GGAGAACCGT ATATAAGTGC AGTAGTCGCC
 201 GTGAACGTTC TTTTTCGCAA CGGGTTTGCC GCCAGAACAC AGCTGAAGCT TCGAGGGGCT TGCATCTCTC CGCATCCGCG CTTCACGCGC CCGCCGCCCT ACCTGAGGCC
 301 GCCATCCACG CCGGTTGAGT CGGTTCTGC ACCTAGAGCT CCTGAACTG CGTCCGCCGT CGTCGACCGC TTAGGTAAGT TTAAAGCTCA GGTCGAGACC
 401 GGGCCTTTGT CCGGCGCTCC CTTGGAGCCT AGCCGGCTCT CCAACGCTTG CCTGACCCTG AGAAAATAAA TCTGCTCAAC TCTACGTCTT TGTTTCGTTT

501 TCTGTTCTGC GCCGTTACAG ATCCAAGCTG TGACCGGCGC CTAACCTGAGA TCACCGGCGA AGGAGGGCCA CCATGTACAG GATGCAACTC CTGTCTTGCA
                                       EcoRI       ———CXCL11 (4-73)                        IL-2 secretion signal
                                                                                     MetTyrArg MetGlnLeu LeuSerCysIle
 601 TTGCACTAAG TCTTGCACTT GTCACGAATT CGTTCAAAAG AGGACGCTGT CTTTGCATAG GCCCTGGGGT AAAAGCAGTG AAGTGGCAG ATATTGAGAA
     AlaLeuSer LeuAlaLeu ValThrAsnSer PheLysArg GlyArgCys LeuCysIleGly ProGlyVal LysValAlaAsp IleGluLys
 701 AGCCTCCATA ATGTACCCAG GTAACAACTG TGACAAATA GAAGTGATTA TTACCCTGAA AGAAAATAAA GGACAACGAT GCCTAAATCC CAAATCCAAG
     AlaSerIle MetTyrProGly AsnAsnCys AspLysIle GluValIleIle ThrLeuLys GluAsnLys GlyGlnArgCys LeuAsnPro LysSerLys 801 CAAGCAAGGC TTATAATCAA AAAAGTTGAA AGAAAGAATT TCCCCATG CCCATCATGC CCAGCACCTG AGTTCCTGG GGGACACCA GTCTTCCTGT
     GlnAlaArgLeu IleIleLys LysValGlu ArgLysAsnPhe ProProCys ProAlaProGlu PheLeuGly GlyProSer ValPheLeuPhe
 901 TCCCCCCAAA ACCCAAGGAC ACTCTCATGA TCTCCCGGAC CCCTGAGGTC ACGTGCGTGG TGGTGGACGT CAGCCAGGAA GACCCCGAGG TCCAGTTCAA
     ProProLys ProLysAsp ThrLeuMetIle SerArgThr ProGluVal ThrCysValVal ValAspVal SerGlnGlu AspProGluVal GlnPheAsn
1001 CTGGTACGTG GATGGCGTG GAGTGCATAA TGCCAAGACA AAGCCGCGGG AGGAGCAGTT CAACAGCACG TACCGTGTGG TCAGCGTCCT CACCGTCCTG
     TrpTyrVal AspGlyValGlu ValHisAsn AlaLysThr LysProArgGlu GluGlnPhe AsnSerThr TyrArgValVal SerValLeu ThrValLeu
1101 CACCAGGACT GGCTGAACGG CAAGGAGTAC AAGTGCAAGG TCTCCAACAA AGGCCTCCCG TCCTCCATCG AGAAAACCAT CTCCAAGGCC AAAGGGCAGC
     HisGlnAspTrp LeuAsnGly LysGluTyr LysCysLysVal SerAsnLys GlyLeuPro SerSerIle GluLysThrIle SerLysAla LysGlyGlnPro
1201 CCCGAGAGCC ACAGGTGTAC ACCCTGCCCC CATCCCAGGA GGAGATGACC AAGAACCAGG TCAGCCTGAC CTGCCTGGTC AAAGGCTTCT ACCCCAGCGA
     ArgGluPro GlnValTyr ThrLeuProPro SerGlnGlu GluMetThr LysAsnGlnVal SerLeuThr CysLeuVal LysGlyPheTyr ProSerAsp
1301 CATCGCCGTG GAGTGGGAGA GCAATGGGCA GCCGGAGAAC AACTACAAGA CCACGCCTCC CGTGCTGGAC TCCGACGGCT CCTTCTTCCT CTACAGCAGG
     IleAlaVal GluTrpGluSer AsnGlyGln ProGluAsn AsnTyrLysThr ThrProPro ValLeuAsp SerAspGlySer PhePheLeu TyrSerArg
1401 CTAACCGTGG ACAAGAGCAG GTGGCAGGAG GGGAATGTCT TCTCATGCTC CGTGATGCAT GAGGCTCTG CACACAGAAG AGCCTCTCCC
     LeuThrValAsp LysSerArg TrpGlnGlu GlyAsnValPhe SerCysSer ValMetHis GluAlaLeuHis AsnHisTyr ThrGlnLys SerLeuSerLeu
                                                                                                        AseI
     SerProGly Lys***(SEQ ID NO:71)
1501 TGTCTCCGGG TAAATGAGTG CTAGCTGGCC AGATCATGATA AGATACATTG ATGAGTTTGG ACAAACCACA ACTAGAATGC AGTGAAAAAA ATGCTTTATT
1601 TGTGAAATTT GTGATGCTAT TGCTTTATTT GTAACCATTA TAAGCTGCAA TAAACAAGTT AACAACAACA ATTGCATTCA TTTTATGTTT CAGGTTCAGG 1701 GGGAGGTGTG GGAGGTTTTT TAAAGCAAGT TAAAGGATGGAT TCTGAGGGGA CAAATGTGT ATGGAATTAA TTCTAAAATA CAGCATAGCA AAACTTTAAC CTCCAATCA
1801 AGCCTCTACT TGAATCCTTT TGAATCCTTTG TCTGAGGGAT AATTAAGGCA TAGGGACTCAG CTCTTCAATT CTTTAATGTTTT TGCAGATATA CAGATCTACT TAGTGCTGT
1901 GAGTTAAGA TATAGTGTAT TTTCCCAAGG GGCGGAGTAG TTTGAACTAG GTCTTCATT TGTTTTTAT TAGGAGAAT CCAGATGCTC AAGGCCCTTC ATAATATCCC CCAGTTAGT
2001 TTCAGAAATA ATTTAAATAC ATCATTGCAA TGAAATAAA ATAAAATAAT GACAGAGAGTT GACACAAGAA AAGCGAGCTT CTAGCTTATC CTCAGTCCTG ACAAAGTCA
2101 AGTTGGACTT AGGGAACAAA GGAACCTTTA ATAGAAATTG ACTCCCGCGA CCGGCGGTGC TGGCGATCT CGGTCATGGC CTCAGCCGAG GGTCCGGAA AGTCGTGGA
2201 CGGAGTCTCC GGGGGTCC GCCGGGTCC GCCGGGCGA ACTCCGCCC
```

```
2301  CACGGACCTCC GACCACTCGG CGTACAGCTC GTCCAGGCCG CGCACCCACA CCCAGGCCAG GGTGTTGTCC GGCACCACCT GGTCCTGGAC CGCGCTGATG
2401  AACAGGGTCA CGTCCTCCCG GACCACACCG GCGAAGTCGT CCTCCACGAA GTCCCGGAGC AACCCGAGCC GGTCGGTTCA GAACTCGACC GCTCCCGCGA
2501  CGTCGCGCGC GGTGAGCACC GGAACGGCAC TGGTCAACTT GGCCATGATG GCTCCTCCTG TCAGGAGAGG AAAGAGAAGA AGGTTAGTAC AATTGCTATA
                                                           AseI
                                                           ~~~~~
2601  GTGAGTTGTA TTATACTATG CAGATATACT ATGCCAATGA TTAATTGTCA AACTAGGGCT GCAGGGTTCA TAGTGCCACT TTTCCTGCAC TGCCCCATCT
2701  CCTGCCCACC CTTTCCCAGG CATAGACAGT CAGTGACTTA CAAAACTCAC AGGAGGGAGA AGGCAGAAGC TTGAGACAGA CCCGCGGGAC CGCCGAACTG
2801  CGAGGGGACG TGGCTAGGGC GGCTTCTTTT ATGGTGCGCC GGCCCTCGGA GGCAGGGCGC TCGGGGAGGC CTAGCGGCTG CTGTAGCGCC GCAGGAGGCG
2901  GGGCCGAAGG CCGTGCCTGA CCAATCCGGA GCACATAGGA GTCTCAGCGC CCCGCCCCAA AGCAAGGGGA AGCCACGCGC AGTCACGCGC AGCGTGTTGT
3001  GAAATGGGGG CTTGGGCCCT TTGGGCCCTT CATTGACGTC AACAAACTCC CATTGACGTC AATGGGGTGG AGCAAGGGTG AGACTTGGAA GTCAAACCGC
3101  TATCCACGCC CATTGATGTA CTGCCAAAAC CGCATCATCA TGGTAATAGC GATGACTAAT ACGTAGATGT ATCCCCGTGA CATAAGGTCA
3201  TGTACTGGGC ATAATGCCAG GCGGGCCATT TACCGTCATT GACGTCAATA GGGGCGTAC TTGGCATATG ATACACTTGA TGTACTGCCA AGTGGCAGT
3301  TTACCGTAAA TACTCCACCC ATTGACCGTA AGTTATGTAA CGCCTGCAGG TTAATTAAGA ACATGTGAGC ATTATTGACG TCAATGGGCG GGAACCGTTG
3401  GGCGGTCAGC CAGGCGGGCC ATTTACCGTC GCTCCGCCCC CCTGACGAGC ATCACAAAAA TCGACGCTCA AAAAGGCCAG GACAGGACTA
3501  AAAGGCCGCG TTGCTGGCGT TTTTCCATAG GCTCCGCCCC CCTGACGAGC ATCACAAAAA TCGACGCTCA AGTCAGAGGT GGCGAAACCC GACAGGACTA
3601  TAAAGATACC AGGCGTTTCC CCCTGGAAGC TCCCTCGTGC GCTCTCCTGT TCCGACCCTG CCGCTTACCG GATACCTGTC CGCCTTTCTC CCTTCGGGAA
3701  GCGTGGCGCT TTCTCATAGC TCACGCTGTA GGTATCTCAG TTCGGTGTAG GTCGTTCGCT CCAAGCTGGG CTGTGTGCAC CTGTCCCACG TTCAGCCCGA
3801  CCGCTGCGCC TTATCCGGTA ACTATCGTCT TGAGTCCAAC CCGGTAAGAC ACGACTTATC GCCACTGGCA GCAGCCACTG GTAACAGGAT TAGCAGAGCG
3901  AGGTATGTAG GCGGTGCTAC AGAGTTCTTG AAGTGGTGGC CTAACTACGG CTACACTAGA AGAACAGTAT TTGGTATCTG CCTCTGCTG AAGCCAGTTA
4001  CCTTCGGAAA AAGAGTTGGT AGCTCTTGAT CCGGCAAACA AACCACCGCT GGTAGCGGTG GTTTTTTTGT TTGCAAGCAG CAGATTACGC GCAGAAAAAA
4101  AGGATCTCAA GAAGATCCTT TGATCTTTTC TACGGGGTCT GACGCTCAGT GGAACGAAAA CTCACGTTAA GGGATTTTGG TCATGCTAG TTAATTAACA
4201  TTTAAATCAG CGGCCGCAAT TATTTTCATT ACATCTGTGT GTTGGTTTTT TGTGTGAATC TACGCTCTCC ATCAAAACAA
4301  AACGAAACAA AACAAACTAG CAAAATAGGC TGTCCCCAGT GCAAGTGCAG GTGCCAGAAC ATTTCTCTAT CGAA (SEQ ID NO:98)
```

IL2ss.CXCL11(4-73).hIgG4Fc sequence [Alanine substitutions for GAG binding sites – Arg, Lys & His]

```
2301 CACGACCTCC GACCACTCGG CGTACAGCTC GTCCAGGCCG CGCACCCACA CCCAGGCCAG GGTGTTGTCC GGCACCACCT GGTCCTGGAC CGGCTGATG
2401 AACAGGGTCA CGTCGTCCCG GACCACACCG GCGAAGTCGT CCTCCACGAA GTCCCGGGAG AACCCGAGCC GGTCCGGTCCA GAACTCGACC GCTCCCGGCA
2501 CGTCGCGCGC GGTGAGCCAC GGAACGGCAC TGGTCAACTT GGCCATGATG GCTCCTCCTG TCAGGAGAGG AAAGAGAAGA AGGTTAGTAC AATTGCTATA
                                                AseI
2601 GTGAGTTGTA TTATACTATG CAGATATACT ATGCCAATGA TTAATTGTCA AACTAGGGCT GCAGGGTTCA TAGTGCCACT TTTCCTGCAC TGCCCCATCT
2701 CCTGCCCACC CTTTCCCAGG CATAGACAGT CAGTGACTTA CCAAACTCAC AGGAGGGAGA AGGCAGAAGC TTGAGACAGA CCCGCGGGAC CGCCGAACTG
2801 CGAGGGACG TGGCTAGGGC GGCTTCTTTT ATGGTGCGCC GGCCCTCGGA GGCAGGGCGC TCGGGGAGGC CTAGCGGTG GCAGGAGGCG
2901 GGGCCGAAGG CCGTGCCTGA CCAATCCGGA GCACATAGGA GTCTCAGCGC CCCGGCCCAA AGCAAGGGGA AGTCACGCGC CTGTAGCGCC AGCGTGTTGT
3001 GAAATGGGGG CTTGGGGGGG TTGGGGCCCT GACTAGTCAA AACAAACTCC CATTGACGTC AATGGGGTGG AGACTTGGAA ATCCCGGTGA GTCAAACCGC
3101 TATCCACGCC CATTGATGTA CTGCCAAAAC CGCATCATCA TGGTAATAGC GATGACTAAT ACGTAGATGT AGGAAAGTCC CATAAGGTCA
3201 TGTACTGGGC ATAATGCCAG GCGGGCCATT TACCGTCATT GACGTCAATA TTGGCATATG ATACACTTGA TGTACTGCCA AGTGGCAGT
3301 TTACCGTAAA TACTCCACCC ATTGACGTCA ATGGAAAGTC CCTATTGGCG TTACTATGGG AACATACGTC ATTATTGACG CAAATGGGCG GGAACCGTTG
3401 GCGGTCAGCC CAGGCGGGCC ATTTACCGTA AGTTATGTAA CGCCTGCAGG CGCTGACGAG AACATGTGAGC AAAAGGCCAG GGAACCGTAA
3501 AAAGGCCGCG TTGCTGGCGT TTTTCCATAG GCTCCGCCCC CCTGACGAGC ATCACAAAAA TCGACGCTCA AGTCAGAGGT GGCGAAACCC GACAGGACTA
3601 TAAAGATACC AGGCGTTTCC CCCTGGAAGC TCCCTCGTGC GCTCTCCTGT TCCGACCCTG CCGCTTACCG GATACCTGTC CGCCTTTCTC CCTTCGGGAA
3701 GCGTGGCGCT TTCTCATAGC TCACGCTGTA GGTATCTCAG TTCGGTGTAG GTCGTTCGCT CCAAGCTGGG CTGTGTGCAC GAACCCCCG TTCAGCCCGA
3801 CCGCTGCGCC TTATCCGGTA ACTATCGTCT TGAGTCCAAC CCGGTAAGAC ACGACTTATC GCCACTGGCA GCAGCCACTG GTAACAGGAT TAGCAGAGCG
3901 AGGTATGTAG GCGGTGCTAC AGAGTTCTTG AAGTGGTGGC CTAACTACGG CTACACTAGA AGAACAGTAT TGGTATCTG CGCTCTGCTG AAGCCAGTTA
4001 CCTTCGGAAA AAGAGTTGGT AGCTCTTGAT CCGGCAAACA AACCACCGCT GGTAGCGGTG GTTTTTTTGT TTGCAAGCAG CAGATTACGC GCAGAAAAAA
4101 AGGATCTCAA GAAGATCCTT TGATCTTTTC TACGGGGTCT GACGCTCAGT GGAACGAAAA CTCACGTTAA GGGATTTTGG TCATGGCTAG TTAATTAACA
4201 TTTAAATCAG CGGCCGCAAT TATTTTCATT TATTTTCATT ACATCTGTGT GTTGGTTTTT TGTGTGAATC GTAACTAACA TACGCTCTCC ATCAAAACAA
4301 AACGAAACAA AACAAACTAG CAAAATAGGC TGTCCCCAGT GCAAGTGCAG GTGCCAGAAC ATTTCTCTAT CGAA    (SEQ ID NO:99)
```

*FIG.7E (CONT)*

FIG. 8A
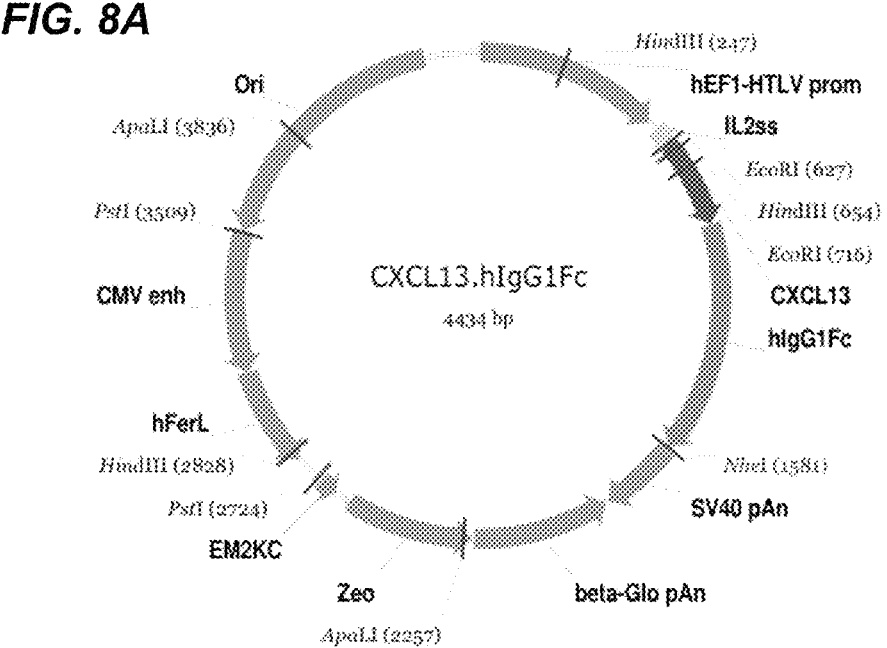
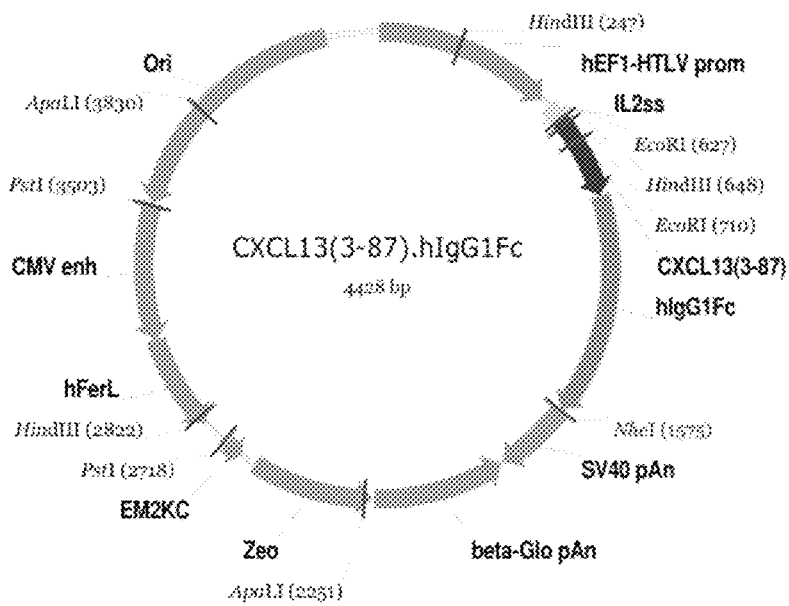
FIG. 8B

FIG. 8C

IL2ss.CXCL13.hIgG1Fc sequence

```
   1 GGATCTGCGA TCGCTCCGGT CCCCGTCAGT GGGCAGAGCG CACATCGCCC ACAGTCCCCG AGAGTTGGG GGGAGGGGTC GGCAATTGAA CGGGTGCCTA
 101 GAGAAGCTGG CCCGGGGTAA ACTGTCGTG TCATGTCGTG GCCAGAACAC AGTGAAGCT CTGGGGGCT TCGAGGGGCT GCCATCTCT CGAGGGTGGG GGAGAACCGT ATATAAGTGC AGTAGTGCC
 201 GTGACGTTC TTTTTCGCAA CGGGTTTGCC GCCAGAACAC AGTGAAGCT CTGTGGTGCC TCTCGAACTG CGTCCGCCGT CTAGGTAAGT CCGCCGCCCT ACCTAGGCC
 301 GCCATCCACG CCGGTTGAGT CGGTTTTGC CGGCTCCCGC ACCTAGGCCT AGCCGGCTCT CCACCCTTTG CTTGCTCAAC TCTACGTCTT TGTCGAGACC
 401 GGGCCCTTGT CGGGCGCTCC CTTGGAGCCT ACCTAGGCCT AGCCGGCTCT CCACCCTTTG CTTGCTCAAC TCTACGTCTT TGTTTCGTTT
                                           KasI
                                           NarI
                                           SfoI
                                           BbeI                                                             IL-2 secretion signal
                                                                                                            MetTyrArg MetGlnLeu LeuSerCysIle
 501 TCTGTTCTGC GCCGTTACAG ATCCAAGCTG TCACCGGCGC CTACCTGAGA TCACCGGCGA AGGAGGGCCA CCATTACAG GATGCAACTC CTGTCTTGCA
           EcoRI                  CXCL13 (1-87)
                                                                                                           AlaLeuSer LeuAlaLeu ValThrAsnSer ValLeuGlu ValTyrTyr ThrSerLeuArg CysArgCys ValGlnGlu SerSerValPhe IleProArg
 601 TTGCACTAAG TCTTGCACTT GTCACGAATT CGGTTCTGGA GGTCTATTAC ACAAGCTTGA TGTCCAAGAG AGCTCAGTCT TTATCCCTAG
           EcoRI
                                                                                                           ArgPheIle AspArgIleGln IleLeuPro ArgGlyAsn GlyCysProArg LysGluIle IleValTrp LysLysAsnLys SerIleVal CysValAsp
 701 ACGCTTCATT GATCGAATTC AAATCTTGCC CCGTGGGAAT GGTTGTCCAA GAAAAGAAAT CATAGTCTGG AAGAAGAACA AGTCAATTGT GTGTGTGAC
                                                                                                                                    human IgG1 Fc
                                                                                                                                     (constant region)
                                                                                                           ProGlnAlaGlu TrpIleGln ArgMetMet GluValLeuArg LysArgSer SerSerThr LeuProVal ProValPheLys ProAspLysThr
 801 CCTCAAGCTG AATGGATACA AAGAATGATG GAAGTATTGA GAAAAGAAG TTCTTCAACT CTACCAGTTC CAGTGTTTAA CCAGAGATT CCCGACAAAA
                                                                                                           HisThrCys ProProCys ProAlaProGlu LeuLeuGly GlyProSer ValPheLeuPhe ProProLys ProLysAsp ThrLeuMetIle SerArgThr
 901 CTCACACATG CCCACCGTGC CCAGCACCTG AACTCCTGG GGGACCGTCA GTCTTCCTCT TCCCCCCAAA ACCCAAGGAC ACCCTCATGA TCTCCCGGAC
                                                                                                           ProGluVal ThrCysValVal ValAspVal SerHisGlu AspProGluVal LysPheAsn TrpTyrVal AspGlyValGlu ValHisAsn AlaLysThr
1001 CCCTGAGGTC ACATGCGTGG TGGTGGACGT GAGCCACGAA GACCCTGAGG TCAAGTTCAA CTGGTACGTG GACGGCGTGG AGTGCATAA TGCCAAGACA
                                                                                                           LysProArgGlu GluGlnTyr AsnSerThr TyrArgValVal SerValLeu ThrValLeu HisGlnAspTrp LeuAsnGly LysGluTyr LysCysLysVal
1101 AAGCCGCGGG AGGAGCAGTA CAACAGCACG TACCGTGTGG TCAGCGTCCT CACCGTCCTG CACCAGGACT GGCTGAATGG CAAGGAGTAC AAGTGCAAGG
                                                                                                           SerAsnLys AlaLeuPro AlaProIleGlu LysThrIle SerLysAla LysGlyGlnPro ArgGluPro GlnValTyr ThrLeuProPro SerArgGlu
1201 TCTCCAACAA AGCCCTCCCA GCCCCCATCG AGAAAACCAT CTCCAAAGCC AAAGGGCAG CCCGAGAACC ACAGGTGTAC ACCCTGCCC CATCCCGGGA
                                                                                                           GluMetThr LysAsnGlnVal SerLeuThr CysLeuVal LysGlyPheTyr ProSerAsp IleAlaVal GluTrpGluSer AsnGlyAsn ProGluAsn
1301 GGAGATGACC AAGAACCAGG TCAGCCTGAC CTGCCTGGTC AAAGGCTTCT ATCCCAGCGA CATCGCCGTG GAGTGGGAGA GCAATGGGCA GCCGGAGAAC
                                                                                                           AsnTyrLysThr ThrProPro ValLeuAsp SerAspGlySer PhePheLeu TyrSerLys LeuThrValAsp LysSerArg TrpGlnGln GlyAsnValPhe
1401 AACTACAAGA CCACGCCTCC CGTGCTGGAC TCCGACGGCT CCTTCTTCCT CTACAGCAAG CTCACCGTGG ACAAGAGCAG GTGGCAGCAG GGGAACGTCT
                                                                                                          BmtI
                                                                                                          NheI
                                                                                                           SerCysSer ValMetHis GluAlaLeuHis AsnHisTyr ThrGlnLys SerLeuSerLeu SerProGly Lys*** (SEQ ID NO:73)
1501 TCTCATGCTC CGTGATGCAC GAGGCTCTGC ACAACCACTA CACGCAGAAG AGCTCTCCC TGTCTCCGGG TAAATGAGTG CTAGCTGGCC AGATCATGATA
1601 AGATACATTG ATGAGTTTGG ACAAACCACA ACTAGAATGC AGTGAAAAAA ATGCTTTATT TGTGAAATTT GTGATGCTAT TGCTTTATTT GTAACCATTA
1701 TAAGCTGCAA TAAACAAGTT AACAACACA ATGCATTCA TTTTATGTTT CAGTTGCAGG GGAGGGTTG GAAGGTTTTT TAAAGCAAGT AAAACCCTTA
1801 CAAATGTGGT ATGGAATTAA TTCTAAAATA CAGCATAGCA AAACTTTAAC CTCCAAATCA AGCCTCTACT TGAATCCTTT TCTGAGGGAT GAATAAGGCA
1901 TAGGCATCAG GGCTGTGTGC CAATGTGCAT TAGCTGTTTG CAGCCTCACC TTCTTTCATG GAGTTAAGAA TATAGTGTAT TTTCCCAAGG TTTGAACTAG
2001 CTCTTCATTT CTTTATGTTT TAAATGCACT GACCTCCCAC ATTCCCCTTC TAGTAAAAATA TTCCAGAAATA AITCATTGCAA TGAAAATAAA
2101 TGTTTTTAT TAGGAGAAT CCAGATGCTC AAGCCCCTTC ATAATATCCC CCAGTTTAGT AGTTGGACTT AGGAACCAA GGAACCTTTA ATAGAAATTG
2201 GACAGCAAGA AAGCGAGCTT CTAGCTGTAC CTCACTGCTG CTCCTCTGCC ACAAAGTGCA CGCAGTTGCC GGCCAGGTCG GCAGGGCGA ACTCCCGCCC
```

*FIG. 8C (CONT)*

```
2301 CCACGGCTGC TCGCCGATCT CGGTCATGGC CGGCCCGGAG GCGTCCCGGA AGTTCGTGGA CACGACCTCC GACCACTCGG CGTACAGCTC GTCCAGGCCG
2401 CGCACCCACA CCCAGGCCAG GGTGTTGTCC GGCACCACCT GGTCCTGGAC CGCGCTGATG CGCCTGGTCA AACAGGGTCA CGTCGTCCCG GACCACACCG GCGAAGTCGT
2501 CCTCCACGAA GTCCCGGAGC AACCCGAGCC GGTCGGTCCA GAACTGACC GCTCCGGCGA CGTCGCGCGC GGTGAGCACC GGAACGGCAC TGGTCAACTT
2601 GGCCATGATG GCTCCTCCTG TCAGGAGAGG AAAGAGAAGA AGGTTAGTAC AATTGCTATA GTGAGTTGTA TTATACTATG CAGATATACT ATGCCAATGA
     AseI
2701 TTAATTGTCA AACTAGGGCT GCAGGGTTCA TAGTGCCACT TTTCCTGCAC TGCCCCATCT CCTGCCCACC CTTTCCCAGG CATAGACAGT CAGTGACTTA
2801 CCAAACTCAC AGGAGGGAGA AGGCAGAAGC TTGAGACAGA CCCGCGGGAC CGCGAACTG CGCGAACTG CGAGGGGACG TGGCTAGGGC GGCTTCTTTT ATGGTGCGCC
2901 GGCCCTCGGA GGCAGGGCGC TCGGGAGGGC CTAGCGGCCA ATCTGCGGTG GCAGGAGGCG AGGCGTTTGT GGGCCGAAGG CCTGCCTGA CCAATCCGGA GCACATAGGA
3001 GTCTCAGCCC CCCGCCCCAA AGCTAGGGGA CTGTAGCGCG CTGTAGCGCC AGGCGTGTTGT AGGCGTGTTGT GAAATGGGGG CTTGGGCCCT GACTAGTCAA
3101 AACAAACTCC CATTGACGTC AATGGGGTGG AGACTTGGAA ATCCCCGTGA GTCAAACCGC TATCCACGCC CTGCCAAAAC CTGCATCATCA
3201 TGGTAATAGC GATGACTAAT ACGTAGATGT AGGAAAGTCC CATAAGGTCA TGTACTGGGC ATAATGCCAG GCGGGCCATT TACCGTCATT
3301 GACGTCAATA GGGGGCGTAC TTGGCATATG TGTACTGCCA AGTGGGCAGT TTACCTCACCC ATTGACGTCA ATGGAAAGTC
3401 CCTATTGGCG TTAATTAAGA ACATACGTC ATTATTGACG TCAATGGGCG GGGACCGTTG GCGGTCAGC CAGGCGGGCC ATTTACCGTA AGTTATGTAA
3501 CGCCTGCAGG TAATTAAGA ATCACAAAAA TCGACGCTCA AAAAGGCCA GGAACCGTAA AAAGGCCGCG TTGCTGGCGT TTTTCCATAG GCTCCGCCCC
3601 CCTGACGAGC ATCACAAAAA TCGACGCTCA AGTCAGAGGT GGCGAAACCC GACAGGACTA TAAAGATACC AGGCGTTTCC CCCTGGAAGC TCCCTCGTGC
3701 GCTCTCCTGT TCCGACCCTG CCGCTTACCG GATACCTGTC CGCCTTTCTC CCTTCGGGAA GCGTGGCGCT TTCTCATAGC TCACGCTGTA GGTATCTCAG
3801 TTCGGTGTAG GTCGTTCGCT CCAAGCTGGG CTGTGTGCAC GAACCCCCCG TTCAGCCCGA CCGCTGCGCC TTATCCGGTA ACTATCGTCT TGAGTCCAAC
3901 CCGTAAGACA ACACTTATC GCCACTGGCA GCAGCCACTG GTAACAGGAT TAGCAGAGCG AGGTATGTAG GCGGTGCTAC AGAGTTCTTG AAGTGGTGGC
4001 CTAACTACGG CTACACTAGA AGAACAGTAT TTGGTATCTG CGCTCTGCTG AAGCCAGTTA CCTTCGGAAA AAGAGTTGGT AGCTCTTGAT CGGCAAACA
4101 AACCACCGCT GGTAGCGGTG GTTTTTTTGT TTGCAAGCAG CAGATTACGC GCAGAAAAAA AGGATCTCAA GAAGATCCTT TGATCTTTTC TACGGGGTCT
4201 GACGCTCAGT GGAACGAAAA CTCACGTTAA GGGATTTTGG TCATGCTAG TTTAATTAACA CGGCCGCAAT AAAATATCTT TATTTTCATT
4301 ACATCTGTGT GTTGGTTTTT TGTGTGAATC TACGCTCTCC ATCAAACTAG AACGAAACAA CAAAACTAG TGTCCCAGT
4401 GCAAGTGCAG GTGCCAGAAC ATTTCTCTAT CGAA   (SEQ ID NO:100)
```

FIG. 8D

IL2ss.CXCL13(3-87).hIgG1Fc sequence

```
   1  GGATCTGCGA TCGCTCCGGT GCCCCTCAGT GGCCAGAGCG CACATCGCCC GGGCAGAGTTGGG AGAAGTTGGG GGGAGGGGTC GGCAATTGAA CGGGTGCCTA
 101  GAGAAGGTGG CCCGGGGTAA ACTGGGAAAG TGATGTCGTG GCCAGAACAC TACTGGCTCC GCCTTTTTCC CAAGGGTGGG GGAGAACCGT ATATAAGTGC AGTAGTCGCC
 201  GTGAACGTTC TTTTTCGCAA CGGGTTTGCC GCCAGAACAC AGCTGAAGCT TCGAGGGGCT TCGACATCTC CTTCACGCGC CCCGCGCCCT ACCTGAGGCG
 301  GCCATCCACG CCGGTTGAGT CCGGTCTGC CGCTCCCGC CTGTGTGCC CCTGAACTG CGTCGCCGT CTAGGTAAGT TTAAAGCTCA GGTCGAGACC
 401  GGGCCTTTGT CCGGCGCTCC CTTGGAGCCT AGCCGGCTCT CCACGTTTG CCTGACCCTG CTTGCTCAAC TCTACGTCTT TGTTTCGTTT

501  TCTGTTCTGC GCCGTTACAG ATCCAAGCTG TGACCGCGC CTACCTGAGA TCACCGGCGA AGGAGGGCCA CCATGTACAG GATGCAACTC CTGTCTTGCA
                                  EcoRI                                              MetTyrArg MetGlnLeu LeuSerCysIle
                          -------- CXCL13 (3-87)                                           IL-2 secretion signal 601  AlaLeuSer LeuAlaLeu ValThrAsnSer GluValTyr TyrThrSer LeuArgCysArg CysValGln GluSerSer ValPheIlePro ArgArgPhe
      TTGCACTAAG TCTTGCACTT GTCACGAATT CGGAGGTCTA TTACACAAGC TTGAGGTGTA GATGTGCCA AGAGAGTCA GTCTTTATCC CTAGAGCTT
 701  IleAspArg IleGlnIleLeu ProArgGly AsnGlyCys ProArgLysLys ProGlyLysLys AsnLysSerIle ValCysVal AspProGln
      CATTGATCGA ATTCAAATCT TGCCCGGTGG GAATGGTTGT CCAAGAAAAG AATATATAGT CTGGAAAGAAG AACAAGTCAA TTGTGTGGT GACCCTCAA
                                                                                                 human IgG1 Fc
                                                                                                (constant region)

801  AlaGluTrpIle GlnArgMet MetGluVal LeuArgLysArg SerSerSer ThrLeuPro ValProValPhe LeuProPro LysThrHisThr
      GCTGAATGGA TACAAAGAAT GATGAAGTA TTGAGAAAAA GAAGTTCTTC AACTTTACCA GTTCCAGTGT TTAAGAGAAA GATTCCCGAC AAAACTCACA
 901  CysProPro CysProAla ProGluLeuLeu GlyGlyPro SerValPhe LeuPhePro LysProLys AspThrLeu MetIleSerArg ThrProGlu
      CATGCCCACC GTGCCCAGCA CCTGAACTCC TGGGGGGACC GTCAGTCTTC CTCTTCCCCC CAAAACCCAA GGACACCCTC ATGATCTCCC GGACCCCTGA
1001  ValThrCys ValValValAsp ValSerHis GluAspPro GluValLysPhe AsnTrpTyr ValAspGly ValGluValHis AsnAlaLys ThrLysPro
      GGTCACATGC GTGGTGGTGG ACGTAAGCCA CGAAGACCCT GAGGTCAAGT TCAACTGGTA CGTGGACGGC GTGGAGGTGC ATAATGCCAA GACAAAGCCG
1101  ArgGluGluGln TyrAsnSer ThrTyrArg ValValSerVal LeuThrVal LeuHisGln AspTrpLeuAsn GlyLysGlu TyrLysCys LysValSerAsn
      CGGGAGGAGC AGTACAACAG CACGTACCGT GTGGTCAGCG TCCTCACCGT CCTGCACCAG GACTGGCTGA ATGGCAAGGA GTACAAGTGC AAGGTCTCCA
1201  LysAlaLeu ProAlaPro IleGluLysThr IleSerLys AlaLysGly GlnProArgGlu ProGlnVal TyrThrLeu ProProSerArg GluGluMet
      ACAAAGCCCT CCCAGCCCCC ATCGAGAAAA CCATCTCCAA AGCCAAAGGG CAGCCCCGAG AACCACAGGT GTACACCCTG CCCCCATCCC GGGAGGAGAT
1301  ThrLysAsn GlnValSerLeu ThrCysLeu ValLysGly PheTyrProSer AspIleAla ValGluTrp GluSerAsnGly GlnProGlu AsnAsnTyr
      GACCAAGAAC CAGGTCAGCC TGACCTGCCT GGTCAAAGGC TTCTATCCCA GCGACATCGC CGTGGAGTGG GAGAGCAATG GCCAGCCGGA GAACAACTAC
1401  LysThrThrPro ProValLeu AspSerAsp GlySerPhePhe LeuTyrSer LysLeuThr ValAspLysSer ArgTrpGln GlnGlyAsn ValPheSerCys
      AAGACCACGC CTCCCGTGCT GGACTCCGAC GGCTCCTTCT TCCTCTACAG CAAGCTCACC GTGGACAAGA GCAGGTGGCA GCAGGGGAAC GTCTTCTCAT
                                                                                                           BmtI
                                                                                                           NheI
1501  SerValMet HisGluAla LeuHisAsnHis TyrThrGln LysSerLeu SerLeuSerPro GlyLys*** (SEQ ID NO:74)
      GCTCCGTGAT GCACGAGGCT CTGCACAACCA CTACACGCA GAAGAGCCTC TCCCTGTCTC CGGGTAAATG AGTGCTAGCT GCCCAGACAT GATAAGATAC
1601  ATTGATGAGT TTGGACAAAC CACAACTAGA ATGCAGTGAA AAAAATGCTT TATTTGTGAA ATTTGTGATG CTATTGCTTT ATTTGTAACC ATTATAAGCT
1701  GCAATAAACA AGTTAACAAC AACAATTGCA TTCATTTTAT GTTTCAGGTT CAGGGGGAGT TGTGGCAGT TTTTTAAAGC AAGTAAAACC TCTACAAATG
             AseI
1801  TGGTATGGAA TTAATTCTAA AATACAGCAT AGCAAAACTT TAACCTCCAA ATCAAGCCTC TACTTGAATC CTTTTCTGAG GGATGAATAA GGCATAGGCA
1901  TCAGGGCCTG TTGCCAATGT GCATTAGCTG TTTGCAGCCT CACCCTTCTT TTTTAGTAA AATAATTTAA ATACATCATT GAATGAAAA TAAATGTTTT
2001  ATTTCTTAT GTTTTAAATG CACTGACCCTG CCACATTCCG TTTTAGTAA AATAATTTAA ATACATCATT GCAATGAAAA TAAATGTTTT
2101  TTATTAGGCA GAATCCAGAT GCTCAAGGCC CTTCATAATA TCCCCCAGTT TAGTAGTTGG ACTTAGGGAA CAAAGGAACC TTTAATAGAA ATTGGACAGC
2201  AAGAAAGCGA GCTTCTAGCT TATCCTCTCT CCTGCTCTC TGCACCCAGT TGCCGCCGGG GTCGGCCCGG GCGAATTCCC GCCCCCACGG
```

```
2301 CTGCTCGCCG ATCTCGGTCA TGGCCCGCCC GGAGGCGTCC CGGAAGTTCG TGGACACGAC CTCCGACCAC TCGGCGTACA GCTCGTCCAG GCCGCGCACC
2401 CACACCCAGG CCAGGGTGTT GTCCGGCACC ACCTGGTCCT GGACCGCGCT GATGAACAGG GTCACGTCGT CCCGGACCAC ACCGGCGAAG TGGTCCTCCA
2501 CGAAGTCCCG GGAGAACCCG AGCCGGTCGG TCCAGAACTC GACCGCTCCG GCGACGTCGC GCCGGTGAG CACCGGAACG GCACTGGTCA ACTTGGCCAT
                                                                                                    AseI
2601 GATGGCTCCT CCTGTCAGGA GAGGAAAGAG GTACAATTGC GTACAATTGC TGTATTATAC TATGCAGATA TACTATGCCA ATGATTAATT
2701 GTCAAACTAG GGCTGCAGGG TTCATAGTGC CACTTTTCCT GCACTGCCCC ATCTCCTGCC CACCCTTTCC CAGGCATAGA CAGTCAGTGA CTTACCAAAC
2801 TCACAGGAGG AAGCTTGAGA CAGACCCGCG CAGAGCCCGC ACTGCGAGGG ACTGCGAGGG GCGGGCTTC GGGCGGCTTC TTTTATGGTG CGCCGGCCCT
2901 CGGAGCAGG GCGCTCCGGG AGGCTACCG GTGGCAGGA GGTGGCAGGA GGCGGGCCCG AAGGCCGTGC CTGACCAATC CCGAGCACAT AGGAGTCTCA
3001 GCCCCCGCC CCAAAGCAAG GGGAAGTCAC GCGCAGCGTG TTGTGAAATG GGGGCTTGGG CCCTGACTAG TCAAAACAAA
3101 CTCCCATTGA CGTCAATGGG GTGGAGACTT GGAAATCCCC GTGAGTCAAA CCGCTATCCA CGGCCATTGA TGTACTGCCA AAACCGCATC ATCATGGTAA
3201 TAGCGATGAC TAATACGTAG ATGTACTGCC AAGTAGGAAA GTCCATAAGG GTCATGTACT CCAGGCGGGC CATTTACCGT CATTGACGTC
3301 GGCGTTACTA TGGGAACATA CGTCATTATT TTGATGTACT GCCAAGTGGG GCCCATTGAC GTCAATGGAA AGTCCCTATT
3401 AATAGGGGGC GTACTTGGCA TATGATACAC GACGTCAATG GCCAAGTGGG CAGTCCCGGT GTTGGGCGGT CAGCCAGGCG GCCCATTTAC CGTAAGTTAT GTAACGCCTG
3501 CAGGTTAATT TGGGAACATA CGTCATTATT GACGTCAATG GGGGGGGTC GCCAAGAACC GTAAAAAGGC CGCGTTGCTG GCGTTTTTCC CCCCCTGAC
3601 GAGCATCACA AAAATCGACG CTCAAGTCAG AGGTGGCGAA ACCCGACAGG ACTATAAAGA TACCAGGCGT TTCCCCCTGG AAGCTCCCTC GTGCGCTCTC
3701 CTGTTCCGAC CCTGCCGCTT ACCGGATACC TGTCCGCCTT TCTCCCTTCG GAAGCGTGG CGCTTTCTCA TAGCTCACGC TGTAGGTATC TCAGTTCGGT
3801 GTAGGTCGTT CGCTCCAAGC TGGGCTGTGT GCACGAACCC CCCGTTCAGC CCGACCGCTG CGCCTTATCC GGTAACTATC GTCTTGAGTC CAACCCGGTA
3901 AGACACGACT TATCGCCACT GGCAGCAGCC ACTGGTAACA GGATTAGCAG AGCGAGGTAT GTAGGCGGTG CTACAGAGTT CTTGAAGTGG TGGCCTAACT
4001 ACGGCTACAC TAGAAGAACA GTATTTGGTA TCTGCGCTCT GCTGAAGCCA GTTACCTTCG GAAAAAGAGT TGGTAGCTCT TGATCCCGGCA AACAAACCAC
4101 CGCTGGTAGC GGTGGTTTTT TTGTTGCAA GCAGCAGATT ACGCGCAGAA AAAAAGGATC TCAAGAAGAT CCTTTGATCT TTTCTACGGG GTCTGACGCT
4201 CAGTGGAACG AAAACTCACG TTAAGGGATT TTGGTCATGG CTAGTTAATT AACATTAAA TCACGGCCG CAATAAAATA TCTTTATTTT CATTACATCT
4301 GTGTGTTGGT TTTTTGTGTG AATCGTAACT CTCCATCAAA ACAAAACGAA CTAGCAAAT CAGTGCAAGT
4401 GCAGGTGCCA GAACATTTCT CTATCGAA
             (SEQ ID NO:101)
```

IL2ss.CXCL13(3-87)hIgG1Fc sequence [Alanine substitutions for removal of GAG binding sites – Lys & His]

```
2301  CTGCTCGCCG ATCTCGGTCA TGGCCCGGCCC GGAGGCGTCC CGGAAGTTCG TGGACACGAC CTCCGACCAC TCGGCGTACA GCTCGTCCAG GCCGCGCACC
2401  CACACCCAGG CCAGGGTGTT GTCCGGCACC ACCTGGTCCT GCCGCGCGCT GATGAACAGG GTCACGTCGT CCCGGACCAC ACCGGCGAAG TCGTCCTCCA
2501  CGAAGTCCCG GGAGAACCCG AGCCGGTCGG TCCAGAACTC CCAGAACTC GACCGCTCCG GCGCGGTGAG GCGCGGAACG CACCGGAAGG GCACTGGTCA ACTTGGCCAT
                                                                                                                  AseI
2601  GATGGCTCCT CCTGTCAGGA GAGGAAAGAG AAGAAGGTTA GTACAATTGC TATAGTGAGT TGTATTATAC TATGCAGATA TACTATGCCA ATGATTAATT
2701  GTCAAACTAG GGCTGCAGGG TTCATAGTGC AAGCTTGAGA CACTGCCCC GCACTGCCCC ATCTCCTGCC CACCCTTTCC CAGGCATAGA CAGTCAGTGA CTTACCAAAC
2801  TCACAGGAGG AGAAGGCAG AAGCTTGAGA CAGACCCGCG GCACCGCCGA ACTGCGAGGG GACGTGGCTA GGGCGGCTTC TTTTATGGTG CGCCGGCCCT
2901  CGGAGGCAGG GCGCTCGGGG AGGCCTAGCC GCCAATCTGC GGTGGCAGGA AGGCCGTGC CTGACCAATC CGGAGCACAT AGGAGTTCA
3001  GCCCCCGCC CCAAAGCAAG GGGAAGTCAC GCGCATCGTG TTGTGAAATG GGGGCTTGGG GGGGTTGGGG CCCTGACTAG TCAAAACAAA
3101  CTCCCATTGA CGTCAATGGG GTGGAGACTT GGAAATCCCC CGGCTATCCA CGCCCATTGA TGTACTGCCA AAACCGCATC ATCATGGTAA
3201  TAGCGATGAC TAATACGTAG AAGTAGGAAA GTCATGTACT GTGAGTCAAA CCAGGCGGGC CATTTACCGT CATTGACGTC
3301  AATAGGGGC GTACTTGGCA TTGATGTACT TGGGCATTGA GTCCCATAAG CAGTTTACCG TAAATACTCC ACCCATTGAC GTCAATGGAA AGTCCCTATT
3401  GGCGTTACTA TGGGAACATA CGTCATTATT GACGTCAATG GGCGGGGGTC GTTGGGCGGT CAGCCAGGCG GGCCATTTAC CGTAAGTTAT GTAACGCCTG
3501  CAGGTTAATT AAGAACATGT GAGCAAAAGG CCAGCAAAAG GCCAGGAACC GTAAAAAGGC CGCGTTGCTG GCGTTTTTCC ATAGGCTCCG CCCCCCTGAC
3601  GAGCATCACA AAAATCGACG CTCAAGTCAG AGGTGGCGAA ACCCGACAGG ACTATAAAGA TACCAGGCGT TTCCCCCTGG AAGCTCCCTC GTGCGCTCTC
3701  CTGTTCCGAC CCTGCCGCTT ACCGGATACC TGTCCGCTTT TCTCCCTTCG GGAAGCGTGG CGCTTTCTCA TAGCTCACGC TGTAGGTATC TCAGTTCGGT
3801  GTAGGTCGTT CGCTCCAAGC TGGGCTGTGT GCACGAACCC CCGTTCAGCC CGACCGCTG CGCCTTATCC GGTAACTATC GTCTTGAGTC CAACCCGGTA
3901  AGACACGACT TATCGCCACT GGCAGCAGCC ACTGGTAACA GGATTAGCAG AGCGAGGTAT GTAGGCGGTG CTACAGAGTT CTTGAAGTGG TGGCCTAACT
4001  ACGGCTACAC TAGAAGAACA GTATTTGGTA TCTGCGCTCT GCTGAAGCCA GTTACCTTCG GAAAAGAGT TGGTAGCTCT TGATCCGGCA AACAAACCAC
4101  CGCTGGTAGC GGTGGTTTTT TTGTTTGCAA GCAGCAGATT ACGCGCAGAA AAAAAGGATC TCAAGAAGAT CCTTTGATCT TTTCTACGGG GTCTGACGCT
4201  CAGTGGAACG AAAACTCACG TTAAGGGATT TTGGTCATGA CTAGTTAATT AACATTTAAA TCAGCGCCG CAATAAAATA TCTTTATTTT CATTACATCT
4301  GTGTGTTGGT TTTTTGTGTG AATCGTAACT AACATACGCT CTCCATCAAA ACAAAACGAA ACAAAACAAA TCAAAACAAA CTAGCAAAAT AGGCTGTCCC CAGTGCAAGT
4401  GCAGGTGCCA GAACATTTCT CTATCGAA    (SEQ ID NO:102)
```

*FIG. 8E (CONT)*

*FIG. 9A*
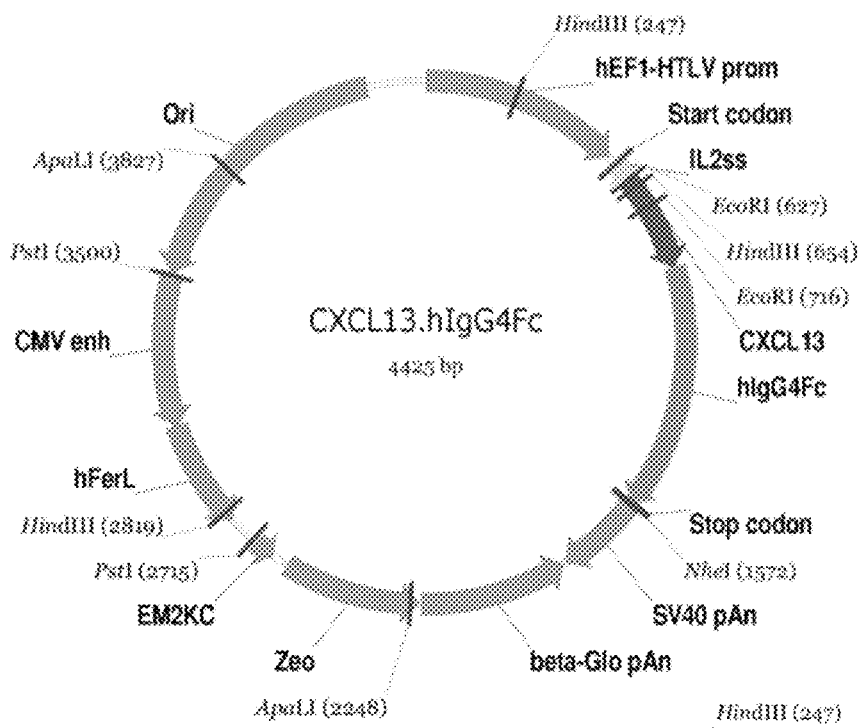
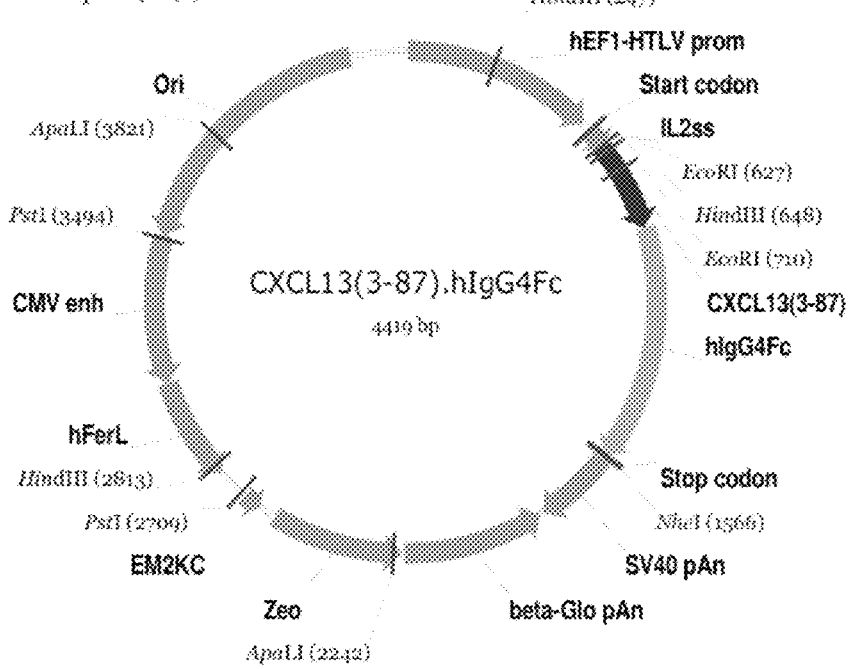
*FIG. 9B*

FIG. 9C

IL2ss.CXCL13.hIgG4Fc sequence

```
   1 GGATCTGCGA TCGCTCCGGT GCCCGTCAGT GGGCAGAGCG CACATCGCCC ACAGTCCCCG AGAAGTTGGG GGGAGGGGTC GGCAATTGAA CGGTGCCTA
 101 GAGAAGGTGG CGCGGGGTAA ACTGGGAAAG TGATGTCGTG TACTGGCTCC GCCTTTTCC CGAGGGTGG CGAGGGTGG GGAGAACCGT ATATAAGTGC AGTAGTGCC
 201 GTGAACGTTC TTTTTCGCAA CGGGTTTGCC GCCAGAACAC AGTCGAAGCT TCGAGGGGCT CGCATCTCTC CGCACGCGC CTTCACGCGC CCGCCGCCCT ACCTGAGGCC
 301 GCCATCCACG CCGGTTGAGT CGGGTTCTGC GCCTCCCCGC CTGTGGTGCC TCCTGAACTG CGTCCGCGT CTAGTAAGT TTAAAGCTCA GGTCGAGACC
 401 GGGCCTTTGT CCGGCCGCTCC CTTGGAGCCT ACCTAGACTC AGCCGGCTCT AGCCGGCCTG CCACGCTTTG CCTGACCCTG CTTGCTCAAC TCTACGTCTT TGTTTCGTTT

IL-2 secretion signal
                                                                                                    MetTyrArg MetGlnLeu LeuSerCysIle
 501 TCTGTTCTGC GCCGTTACAG ATCCAAGCTG TGACCCGGCC CTACCTCGAGA TCACCGGCGA AGGAGGGCCA CCATGTACAG GATGCAACTC CTGTCTTGCA
                                 EcoRI          ----- CXCL13 (1-87)
        AlaLeuSer LeuAlaLeu ValThrAsnSer ValLeuGlu ValTyrTyr ThrSerLeuArg CysArgCys ValGlnGlu SerSerValPhe IleProArg
 601 TTGCACTAAG TCTTGCACTT GTCACGAATT CGGTTCTGGA GGTCTATTAC ACAAGTCTTGA TGTCCAAGAG AGCTCAGTCT TTATCCCTAG
        ArgPheIle AspArgIleGln IleLeuPro ArgGlyAsn GlyCysProArg LysGlyVal IleValTrp LysLysAsnLys SerIleVal CysValAsp
 701 ACGCTTCATT GATCGAATTC AAATCTTGCC CCGTGGGAAT GGTTGTCCCA GAAAAGAAAT CATAGTCTGG AAGAAGAACA AGTCAATTGT GTGTGTGGAC
                                                                                                        human IgG4 Fc
                                                                                                        (constant region)
        ProGlnAlaGlu TrpIleGln ArgMetMet GluValLeuArg LysArgSer SerSerThr LeuProValPro ValPheLys ArgLysIle ProProProCys
 801 CCTCAAGCTG AATGGATACA AAGAATGATG GAAGTATTGA GAAAAGAAG TCCTCAACT CTACCAGTTC CAGTCTTTAA GAGAAGATT CCCCCCCAT
        ProSerCys ProAlaPro GluPheLeuGly TyrProSer ValPheLeu PheProProLys ProLysAsp ThrLeuMet IleSerArgThr ProGluVal
 901 GCCCATCATG CCCAGCACCT GAGTTCCTGG GGGACCATC AGTCTTCCTG TTCCCCCCAA AACCCAAGGA CACTCTCATG ATCTCCCGGA CCCCTGAGGT
        ThrCysVal ValValAspVal SerGlnGlu AspProGlu ValGlnPheAsn TrpTyrVal AspGlyVal GluValHisAsn AlaLysThr LysProArg
1001 CACGTGCGTG GTGGTGGACG TGAGCCAGGA AGACCCCGAG GTCCAGTTCA ACTGGTACGT GGATGGCGTG GAGGTGCATA ATGCCAAGAC AAAGCCGCGG
        GluGluGlnPhe AsnSerThr TyrArgVal ValSerValLeu ThrValLeu HisGlnAsp TrpLeuAsnGly LysGluTyr LysCysLys ValSerAsnLys
1101 GAGGAGCAGT TCAACAGCAC GTACCGTGTG GTCAGCGTCC TCACCGTCCT GCACCAGGAC TGGCTGAACG GCAAGGAGTA CAAGTGCAAG GTCTCCAACA
        GlyLeuPro SerLysIle GluLysThrIle SerLysAla LysGlyGln ProArgGluPro GlnValTyr ThrLeuPro ProSerGlnGlu GluMetThr
1201 AAGGCCTCCC GTCCTCCATC GAGAAAACCA TCTCCAAAGC CAAAGGGCAG CCCCGAGAGC CACAGGTGTA CACCCTGCCC CCATCCCAGG AGGAGATGAC
        LysAsnGln ValSerLeuThr CysLeuVal LysGlyPhe TyrProSerAsp IleAlaVal GluTrpGlu SerAsnGlyGln ProGluAsn AsnTyrLys
1301 CAAGAACCAG GTCAGCCTGA CCTGCCTGGT CAAAGGCTTC TACCCCAGCG ACATCGCCGT GGAGTGGGAG AGCAATGGGC AGCCGGAGAA CAACTACAAG
        ThrThrProPro ValLeuAsp SerAspGly SerPhePheLeu TyrSerArg LeuThrVal AspLysSerArg TrpGlnGln GlyAsnVal PheSerCysSer
1401 ACCACGCCTC CCGTGCTGGA CTCCGACGGC TCCTTCTTCC TCTACAGCAG GCTAACCGTG GACAAGAGCA GGTGGCAGGA GGGGAATGTC TTCTCATGCT
        ValMetHis GluAlaLeu HisAsnHisTyr ThrGlnLys SerLeuSer LeuSerProGly Lys*** (SEQ ID NO:76)
1501 CCGTGATGCA TGAGGCTCTG CACAACCACT ACACACAGAA GAGCCTCTCC CTGTCTCCGG GTAAATGAGT GCTAGCTGGC CAGACATGAT AAGATACATT
1601 GATGAGTTTG GACAAACCAC AACTAGAATG CAGTGAAAAA AATGCTTTAT TTGTGAAATT TGTCATGCTA TTGCTTTATT TGTAACCATT ATAAGCTGCA
1701 ATAAACAAGT TAACACAAC AATTGCATTC ATTTTATGTT TCAGGTTCAG GGGGAGGTGT GGGAGGTTTT TAAAGCAAG TAAAACCTCT ACAAAGTGG
        AseI
1801 TATGGAATTA ATTCTAAAAT ACAGCATAGC AAAACTTTAA CCCTCAAATC AAGCCTCTAC TTGAATCCTT TTCTGAGGGA TGAATAAGGC ATAGGCATCA
1901 GGGCTGTTTG CCAATGTGCA TTAGCTGTTT GCACCCTCAC CTTCCTCCAA GGAGTTTAAG ATATAGTGTA TTTTCCCAAG GTTTGAACTA GCTCTTCATT
2001 TCTTTATGTT TTAAATGCAT TGACCTCCCA CATTCCCTT TTAGTAAAAT ATTCAGAAAT AATTAAATA CATCATTGCA AGAACCTTTT ATGTTTTTA
2101 TTAGCCAGAA TCCAGATGCT CAAGGCCCTT CATAATATCC CCAGTTTAG TAGTTGGACT CCCAAAGTGC AGAACAA AGGAACCTTT AATAGAAATT GGACAGCAAG
2201 AAAGGGAGCT TCTAGCTTAT CCTCCTCCCT GCTCCTCTGC CACAAAGTGC ACGGCAGTGGC CGGCAGGGCG AACTCCCGCC CCGCAGGCTG
```

```
2301 CTCGCCGATC TCGGTCATGG CCGGCCCGGA AAGTTCGTGG ACACGACCTC CGACCACTCG GCGTACAGCT CGTCCAGGCC GCGCACCCAC
2401 ACCCAGGCCA GGGTGTTGTC CGGCACCACC TGGTCCTGGA CCGCGCTGAT GAACAGGGTC ACGTCGTCCC GGACCACACC GGCGAAGTCG TCCTCCACGA
2501 AGTCCGGGGA GAACCCGAGC CGGTCGGTCC AGAACTCGAC CGCTCCGGCG ACGTCGCGCG CGGTGAGCAC CGGAACGGCA CTGGTCAACT TGGCCATGAT
                                                                                                    AseI
2601 GGCTCCTCCT GTCAGGAGAG CCGGCCCGGA GAAAGAGAAG CAATTGCTAT AGTGAGTTGT ATTATACTAT GCAGATATAC TATGCCAATG ATTAATTGTC
2701 AAACTAGGGC TGCAGGGTTC ATAGTGCCAC TTTTCCTGCA CTGCCCCATC TCCTGCCCAC CCTTTCCCAG GCATAGACAG TCAGTGACTT ACCAAACTCA
2801 CAGGAGGGAG AAGGCAGAAG CTTGAGACAG ACCCGCGGGA CCGCGCAACT CCGGCTAGGG GTGGCTAGGG GTCGCTAGGG TATGGTGCGC CGGCCCTCGG
2901 AGGCAGGGCG CTCGGGAGGG CCTAGCGGGT AATCTGCGGT GGGGACGAGG GGGGCCGAAG CCCGTAGGGG GTCGTGTTTG GCCTAGCGCG CAGCGTGTTG ACCAATCCGG AGCACATAGG AGTCTCAGCC
3001 CCCGCCCCA AGCAAGGGTG AAGTCACGCG CCTGTAGCGC CAGCGTGTTG TGAAATGGGG 3CTTGGGGGG CCATTGATGT ACTGCCAAAA AAACAAACTC
3101 CCATTGACGT CAATGGGTG GACACTTGGA AATCCCCGTG AGTCAAACCG CTATCCACGC CCATTGATGT ACTGCCAAAA CCGCATCATC ATGCTAATAG
3201 CGATGACTAA TACGTAGATG TACTGCCAAG TAGGAAAGTC CCATAAGGTC ATGTACTGGG CTATCCACGC GCGGGCCAT TTACCGTCAT TGACGTCAAT
3301 AGGGGCGTA CTTGGCATAT GATACACTTG ATGTACTGCC AAGTGGGCAG TTTTACCGTAA AATACTCCACC CATTGACGTC AATGGAAAGT CCCTATTGGC
3401 GTTACTATGG GAACATACGT CATTATTGAC GTCAATGGGC GGGGGTCGTT CCAGGCGGTCAG CATTTACCGT AAGTTATGTA ACGCCTGCAG
3501 GTTAATTAAG AACATGTGAG CAAAAGGCCA GCAAAAGGCC AGGAACCGTA AAAAGGCCGC GTTGCTGGCG TTTTTCCATA GGCTCCGCCC CCCTGACGAG
3601 CATCACAAAA ATCGACGCTC AAGTCAGAGG TGGCGAAACC CGACAGGACT ATAAAGATAC CAGGCGTTTC CCCCTGGAAG CTCCCTCGTG CGCTCTCCTG
3701 TTCCGACCCT GCCGCTTACC GGATACCTGT CCGCCTTTCT CCCTTCGGGA AGCGTGGCGC TTTCTCATAG CTCACGCTGT AGTATCTCAG GTTCGGTGTA
3801 GGTCGTTCGC TCCAAGCTGG GCTGTGTGCA CGAACCCCCC GTTCAGCCCG ACCGCTGCGC CTTATCCGGT AACTATCGTC TTGAGTCCAA CCCGGTAAGA
3901 CACGACTTAT CGCCACTGGC AGCAGCCACT GGTAACAGGA TTAGCAGAGC GAGGTATGTA GGCGGTGCTA CAGAGTTCTT GAAGTGGTGG CCTAACTACG
4001 GCTACACTAG AAGAACAGTA TTTGGTATCT GCGCTCTGCT GAAGCCAGTT ACCTTCGGAA AAAGAGTTGG TAGCTCTTGA TCCGGCAAAC AAACCACCGC
4101 TGGTAGCGGT GGTTTTTTTG TTTGCAAGCA GCAGATTACG CGCAGAAAAA AAGGATCTCA AGAAGATCCT TTGATCTTTT CTACGGGGTC TGACGCTCAG
4201 TGGAACGAAA ACTCACGTTA AGGGATTTTG GTCATGAGCTA GTTAATTAAC ATTTAAATCA GCGGCCGCAA TAAAATATCT TTATTTTCAT TACATCTGTG
4301 TGTTGGTTTT TTGTGTGAAT CGTAACTAAC ATACGCTCTC CATCAAAAACA AAACGAAACA GCAAAATAGG CTGTCCCCAG TGCAAGTGCA
4401 GGTGCCAGAA CATTTCTCTA TCGAA (SEQ ID NO:103)
```

IL2ss.CXCL13(3-87).hIgG4Fc sequence

```
   1 GGATCTGCGA TCGCTCCGGT GCCGTCAGT GGGCAGAGCG CACATCGCCC ACAGTCCCCG AGAAGTTGGG GGGAGGGGTC GGCAATTGAA CGGGTGCCTA
 101 GAGAAGGTGG CGCGGGGTAA ACTGGGAAAG TGATGTGGGT TACTGGCTCC GCCTTTTTCC GGAGGGGTGG GGAGAACCGT ATATAAGTGC AGTAGTCGCC
 201 GTGAACGTTC TTTTTGCAAA CGGGTTTGCC GCCAGAACAC AGCTGAAGCT TCGAGGGGCT CGCATCTCTC CTTCACGCGC CCCGCGCCCT ACCTGAGGCC
 301 GCCATCCACG CCGGTTGAGT CGCGTTCTGC CCCCTTCTGC CTGTGGTGCC CTGTGGTGCC CGTCCGGCGT CTAGGTAAGT TTAAGCTCA GGTCGAGACC
 401 GGGCCTTTGT CCGGGCGTCC CTTGGAGCCT ACCTAGACTC AGCCGGCTCT CCACGGCTTTG CCTGACCCTG CTTGCTCAAC TCTACGTCTT TGTTTCGTTT
                                                 NarI
                                                 KasI
                                                 StoI
                                                 BbeI                                          IL-2 secretion signal
                                                                                        MetTyrArg MetGlnLeu LeuSerCysIle
 501 TCTGTTTCTGC GCCGTTACAG ATCCAAGCTG TGAGCTGAGA CTACCTGAGA TCACCGGCGA AGGAGGGCCA CCATGTACAG GATGCAACTC CTGTCTTGCA
                            EcoRI              --------- CXCL13 (3-87) -----
                                                           AlaLeuSer LeuAlaLeu ValThrAsnSer GluValTyr TyrThrSer LeuArgCysArg CysValGln GluSerSer ValPheIlePro ArgArgPhe
 601 TTGCACTAAG TCTTGCACTT GTCACGAATT CCGAGGTCTA TTACACAAGC TTGAGGTGTA GATGTGTCCA AGAGAGCTCA GTCTTTATCC CTAGACGTT
                                                           IleAspArg IleGlnIleLeu ProArgGly AsnGlyCys ProArgLysGlu IleIleVal TrpLysLys AsnLysSerIle ValCysVal AspProGln
 701 CATTGATCGA ATTCAAATCT TGCCCCGTGG GAATGGTTGT CCAAGAAAAG AAATCATAGT CTGGAAGAAG AACAAGTCAA TTGTGTGTGT GGACCCCAA
                                                 --------- human IgG4 Fc (constant region) ----------
                                                           AlaGluTrpIle GlnArgMet MetGluVal LeuArgLysArg SerSerSer ThrLeuPro ValProLysAsp ThrLeuMet IleSerArg ThrProGluVal ThrCysVal
 801 GCTGAATGGA TACAAGGAAT GATGGAAGTA TTGAGAAGA GAAGTCTTC AACCTACCA GTTCCAGTGT TTAAGACAA CCTTGATGAT CAGCAGAGT CACCTGTGTG
                                                           ValValVal AspValSerGln GluAspPro GluValGln PheAsnTrpTyr ValAspGly ValGluVal HisAsnAlaLys ThrLysPro ArgGluGlu
 901 CAGTCCCAGC ACCTGAGTTC CTGGGGGAC CATCAGTCTT CCTGTTCCCC CCAAAACCCA AGGACACTCT CATGATCTCC CGGACCCTG AGGTCACGTG
                                                           GlnPheAsnSer ThrTyrArg ValValSer ValLeuThrVal LeuHisGln AspTrpLeu AsnGlyLysGlu TyrLysCys LysValSer AsnLysGlyLeu
1001 CGTGGTGGTG GACGTGAGCC AGGAAGACCC CGAGGTCCAG TTCAACTGGT ACGTGGATGG CGTGGAGGTG CATAATGCCA AGACAAAGCC GCGGGAGGAG
                                                           ProSerSerIle GluLysThr IleSerLys AlaLysGly GlnProArg GluProGlnVal TyrThrLeu ProProSer GlnGluGluMet ThrLysAsn
1101 CAGTTCAACA GCACGTACCG TGTGGTCAGC GTCCTCACCG TCCTGCACCA GGACTGGCTG AACGGCAAGG AGTACAAGTG CAAGGTCTCC AACAAGGCC
                                                           GlnValSer LeuThrCysLeu ValLysGly PheTyrPro SerAspIleAla ValGluTrp GluSerAsn GlyGlnProGlu AsnAsnTyr LysThrThr
1201 TCCCGTCCTC CATCGAGAAA ACCATCTCCA AAGCCAAAGG GCAGCCCCGA GAGCCACAGG TGTACACCCT GCCCCCATCC CAGGAGGAGA TGACCAAGAA
                                                           ProProValLeu AspSerAsp GlySerPhe PheLeuTyrSer ArgLeuThr ValAspLys SerArgTrpGln GluGlyAsn ValPheSer CysSerValMet
1301 CCAGGTCAGC CTGACCTGCC TGGTCAAAGG CTTCTACCCC AGCGACATCG CCGTGGAGTG GGAGAGCAAT GGGCAGCCGG AGAACAACTA CAAGACCACG
                                                           HisGluAla LeuHisAsn HisTyrThrGln LysSerLeu SerLeuSer LeuGlyLys***(SEQ ID NO:77)
1401 CCTCCCGTGC TGGACTCCGA CGGCTCCTTC TTCCTCTACA GCAGGCTAAC CGTGGACAAG AGCAGGTGGC AGGAGGGGAA TGTCTTCTCA TGCTCCGTGA
                                                           BmtI
                                                           NheI
1501 TGCATGAGGC TCTGCACAAC CACTACACAC AGAAGAGCCT CTCCCTGTCT CCGGGTAAAT GAGTGCTAGC TGGCCAGACA TGATAAGATA CATTGATGAG
1601 TTTGGACAAA CCACAACTAG AATGCAGTGA AAAAAATGCT TTATTTGTGA AATTTGTGAT GCTATTGCTT TATTTGTAAC CATTATAAGC TGCAATAAAC
1701 AAGTTAACAA CAACAATTGC ATTCATTTTA TGTTTCAGGT TCAGGGGGAG GTGTGGGAGG TTTTTTAAAG CAAGTAAAAC CTCTACAAAT GTGGTATGGA
     AseI
1801 ATTAATTCTA AAATACAGCA TAGCAAAACT TTAACCTCCA AATCAAGCCT TCTACTTCTT TCATGGAGTT TCATGATATAG CCGGTAAAT CCTTTTCTGA GGGATGAATA AGGCATAGGC ATCAGGGCT
1901 GTTGCCAATG TGCATTAGCT GTTTGCAGCC CCCATTCC CTTCTTTAAT AATCCCCAGT TTAGTAGTTG GACTTAGGGA ACAAAGGAAC CAAGGTTGA TGCAATGAAT CTGCCCCAGG ACTAGCTCTT CATTTCTTA
2001 TGTTTTAAAT GCACTGACCT CACACATTCC CTTCATAAT ATCCCCAGT TTAGTAGTTG GACTTAGGGA ACAAAGGAAC TGCAATGAAA CTTTAATAGA AATTGGACAG AATTGGACAG AATAAATGTTT TTTATTAGGC
2101 AGAATCCAGA TGCTCAAGGC CTCCCAAAA GTGCAGGAC TTGCCGGGCS GGTCGGCCAG GTCGCCCAG GGCGAACTCC CGCCCCACG CGGCCCACG CGCCCCACG GGCCCCACG CAAGAAAGCG
2201 AGCTTCTAGC TTATCTGCAC TCCTCCGCCC CTGCCACAAA GTGGACACGA CCTCCGACCA CTCGGCGTAC GGCTGCGTCC GCCGGCGCAC CCACACCCAG
2301 GATCTCGGTC ATGGGCCGGC CGGAGGGGTC CCGGAAGTTC GTGGACACGA
```

```
2401 GCCAGGGTGT TGTCCGGCAC CACCTGGTCC TGGACCGCGC TGATGAACAG GGTCACGTCG TCCCGACCA CACCGGCGAA GTCGTCCTCC ACGAAGTCCC
2501 GGGAGAACCC GAGCCGGTCG GTCCAGAACT CGACCGCTCC CGACCGGTGA CGCGCGGTGA GCACCGGAAC GCACCGGAAC GGCACTGGTC AACTTGGCCA TGATGGCTCC
                                                                                                    AseI
2601 TCCTGTCAGG AGAGGAAAGA GAAGAAGGTT AGTACAATTG CTATAGTGAG TTGTATTATA CTATGCAGAT ATACTATGCC AATGATTAAT TGTCAAACTA
2701 GGGCTGCAGG GTTCATAGTG CCACTTTTCC TGCACTGCCC CATCTCCTGC CCACCCTTTC CCAGCATAG ACAGTCAGTG ACTTACCAAA CTCACAGGAG
2801 GGAGAAGGCA GAAGCTTGAG ACAGACCCGC GGGACCCGCG AACTGCGAGG GGAAGTGGCT AGGGCGGCTT CTTTTATGGT GCCCCGGCCC TCGGAGGCAG
2901 GGCGCTCGGG GAGGCCTAGC GGCCAATCTG CGGTGGCAGG AGGCGGGGCC GAAGCCGTG CCTGACCAAT CGGAGCACA TAGGAGTCTC AGCCCCCGC
3001 CCCAAAGCAA GGGGAAGTCA CGCGGCCTGTA GCCCCAGCGT GTTGTGAAAT ACCGCTATCC GGGGGCTTGG ACGTACTGCC AAAACCCGAT GTCAAAACAA ACTCCCATTG
3101 ACGTCAATGG GGTGGAGACT TGGAAATCCC CGTGAGTCAA ACCGCTATCC ATGTACTGCC ACGCCCATTG ATGTACTGCC AAAACCGAT CATCATGGTA ATAGCGATGA
3201 CTAATACGTA GATGTACTGC CAAGTAGGAA AGTCCCATAA GGTCATGTAC TGGGCATAAT GCCAGGCGGG CCATTACCG TCATTGACGT CAATAGGGGG
3301 CGTACTTGGC ATATGATACA CTTGATGTAC TGCCAAGTGG GCAGTTTACC GTAAATACTC CACCCATTGA CGTCAATGGA AGTCCCTAT GGCGGTTAAT
3401 ATGGGAACAT ACGTCATTAT TGACGTCAAT GGGCGGGGGT CGTTGGGCGG TCAGCCAGGC CACCCATTGA CGTAAGTTA TGTAACGCCT GCAGTTAAT
3501 TAAGAACATG TGAGCAAAAG GCCAGCAAAA GGCGGGGAAC CCGCGTTTTC GGGCGTTTTC CCCCCCTGA CGAGCATCAC CGAGCATCAC
3601 AAAAATCGAC GCTCAAGTCA GAGGTGGCGA AACCCGACAG GACTATAAAG ATACCAGGCG TTTCCCCTG GAAGCTCCCT CGTGCGCTCT CCTGTTCCGA
3701 CCCTGCCGCT TACCGGATAC CTGTCCGCCT TTCTCCCTTC GGGAAGCGTG GCGCTTTCTC ATAGCTCACG CTGTAGGTAT CTCAGTTCGG TGTAGGTCGT
3801 TCGCTCCAAG CTGGGCTGTG TGCACGAACC CCCCGTTCAG CCCGACCGCT GCGCCTTATC CGGTAACTAT CGTCTTGAGT CCAACCCGGT AAGACACGAC
3901 TTATCGCCAC TGGCAGCAGC CACTGGTAAC AGGATTAGCA GAGCGAGGTA TGTAGGCGGT GCTACAGAGT TCTTGAAGTG GTGGCCTAAC TACGGCTACA
4001 CTAGAAGAAC AGTATTTGGT ATCTGCGCTC TGCTGAAGCC AGTTACCTTC GGAAAAAGAG TTGGTAGCTC TTGATCCGGC AAACAAACCA CCGCTGGTAG
4101 CGGTGGTTTT TTTGTTTGCA AGCAGCAGAT TACGCGCAGA AAAAAAGGAT CTCAAGAAGA TCCTTTGATC TTTTCTACGG GGTCTGACGC TCAGTGGAAC
4201 GAAAACTCAC GTTAAGGGAT TTTGGTCATG GCTAGTTAAT TAACATTTAA ATCAGCGGCC GCAATAAAAT ATCTTTATTT TCATTACATC TGTGTGTTGG
4301 TTTTTTGTGT GAATCGTAAC TAACATACGC TCTCCATCAA AACAAAACGA AACAAAACAA ACTAGCAAAA TAGGCTGTCC CCAGTGCAAG TGCAGGTGCC
4401 AGAACATTTC TCTATCGAA (SEQ ID NO: 104)
```

IL2ss.CXCL13(3-87).hIgG4Fc sequence [Alanine substitutions for removal of GAG binding sites – Lys & His]

```
2301 GATCTCGGTC ATGGCCGGCC CGGAGGCGTC GTGGACACGA CCTCCGACCA CTCGGCGTAC AGCTCGTCCA GGCCGCGCAC CCACACCCAG
2401 GCCAGGGTGT TGTCCGGCAC CACCTGGTCC TGGACCGCGC TGATGAACAG GGTCACGTCG TCCCGGACCA CACCGGCGAA GTCGTCCTCC ACGAAGTCCC
2501 GGGAGAACCC GAGCCGGTCG GTCCAGAACT CGACCGCTCC GGCGACGTCG CGCGCGGTGA GCACCGGAAC GGCACTGGTC AACTGGCCA  TGATGGCTCC
                                                                                         AseI
2601 TCCTGTCAGG AGAGAAAGA  GAAGAAGGTT AGTACAATTG CTATAGTGAG TTGTATTATA CTATCCAGAT ATACTATGCC AATGATTAAT TGTCAAACTA
2701 GGGCTGCAGG GTTCATAGTG CCACTTTTCC TGCACTGCCC CATCTCCTGC CCAGGCATAG ACAGTCAGTG ACTTACCAAA CTCACAGGAG
2801 GGAGAAGGCA GAAGTTGAG  ACAGACCCGC GGGACGCCGG AACTGCGAGG AGGGCCGGCT CTTTTATGGT GCGCCGGCCC TCGGAGGCAG
2901 GGCGCTCGGG GAGGCCTAGC GGCCAATCTG CGGTGGCAGG AGGGCCGTG  CCTGACCCAT CCGGAGCACA TAGGAGTCTC AGCCCCCGC
3001 CCCAAGCAA  GGGGAAGTCA CGCGCCTGTA GCGCCAGCGT GTTGTGAAAT GGGGGCTTGG GCCCTGACTA GTCAAAACAA ACTCCCATTG
3101 ACGTCAATGG GGTGAGACT  TGGAAATCCC CGTGAGTATC ACCGGCTATCC ATGTACTGCC AAAACCGCAT CATCAAGGTA ATAGCGATGA
3201 CTAATACGTA GATGTACTGC CAAGTAGGAA GTCCCATAGG GCAGTTTACC TGGGCATAAT GCCAGGCGGG CCATTTACCG CAATAGGGGG
3301 CGTACTTGGC ATATGATACA CTTGATGTAC TGCCAAGTGG GCAGTTTACC GTAAATACTC CACCATTGA  AAGTCCCTAT TGGCGTTACT
3401 ATGGAACAT  ACGTCATTAT TGACGTCAAT GGGCGGGGGT CGTTGGGCGG TCAGCCAGGC CACCCATTGA CGTCAATGGA TGTAACGCCT GCAGTTAAT
3501 TAAGAACATG TGAGCAAAAG GCCAGCAAA  GGCCAGGAAC CGTAAAAAGG CCGCGTTGCT GGCGTTTTTC CATAGGCTCC GCCCCCTGA  CGAGCATCAC
3601 AAAAATCGAC GCTCAAGTCA GAGGTGGCGA AACCCGACAG GACTATAAAG ATACCAGGCG TTTCCCCCTG GAAGCTCCCT CGTGCGCTCT CCTGTTCCGA
3701 CCCTGCCGCT TACCGGATAC CTGTCCGCCT TTCTCCCTTC CGGCTTTCTC ATAGCTCACG CTGTAGGTAT CTCAGTTCGG TGTAGGTCGT
3801 TCGCTCCAAG CTGGGCTGTG TGCACGAACC CCCCGTTCAG CCCGACCGCT GCGCCTTATC CGGTAACTAT CGTCTTGAGT CCAACCCGGT AAGACACGAC
3901 TTATCGCCAC TGGCAGCAGC CACTGGTAAC AGGATTAGCA GAGCGAGGTA TGTAGGCGGT GCTACAGAGT TCTTGAAGTG GTGGCCTAAC TACGGCTACA
4001 CTAGAAGAAC AGTATTTGGT ATCTGCGCTC TGCTGAAGCC AGTTACCTTC GGAAAAAGAG TTGGTAGCTC TTGATCCGGC AAACAAACCA CCGCTGGTAG
4101 CGGTGGTTTT TTTGTTTGCA AGCAGCAGAT TACGCGCAGA AAAAAAGGAT CTCAAGAAGA TCCTTTGATC TTTTCTACGG GGTCTGACGC TCAGTGGAAC
4201 GAAAACTCAC GTTAAGGGAT TTTGGTCATG GCTAGTTAAT TAACATTTAA ATCAGCGGCC GCAATAAAAT ATCTTTATTT TCATTACATC TGTGTGTTGG
4301 TTTTTTGTGT GAATCGTAAC TAACATACGC TCTCCATCAA AACAAAACGA AACAAAACAA ACTAGCAAAA TAGGCTGTCC CCAGTGCAAG TGCAGGTGCC
4401 AGAACATTTC TCTATCGAA  (SEQ ID NO:105)
```

*FIG. 9E (CONT)*

↖ indicate potential sites for pegylation of CXCL11.

FIG. 12

CCL1    NP_002972    SEQ ID NO:1
mqiittalvc lllagmwped vdsksmqvpf srccfsfaeq eiplrailcy rntssicsne
glifklkrgk eacaldtvgw vqrhrkmlrh cpskrk

CCL2    NP_002973    SEQ ID NO:2
mkvsaallcl lliaatfipq glaqpdaina pvtccynftn rkisvqrlas yrritsskcp
keavifktiv akeicadpkq kwvqdsmdhl dkqtqtpkt

CCL3    NP_002974    SEQ ID NO:3
mqvstaalav llctmalcnq fsaslaadtp taccfsytsr qipqnfiady fetssqcskp
gvifltkrsr qvcadpseew vqkyvsdlel sa

CCL4    NP_002975    SEQ ID NO:4
mklcvtvlsl lmlvaafcsp alsapmgsdp ptaccfsyta rklprnfvvd yyetsslcsq
pavvfqtkrs kqvcadpses wvqeyvydle ln

CCL4L1    NP_001001435    SEQ ID NO:5
mklcvtvlsl lvlvaafcsl alsapmgsdp ptaccfsyta rklprnfvvd yyetsslcsq
pavvfqtkrg kqvcadpses wvqeyvydle ln

CCL5    NP_002976    SEQ ID NO:6
mkvsaaalav iliatalcap asaspyssdt tpccfayiar plprahikey fytsgkcsnp
avvfvtrknr qvcanpekkw vreyinslem s

CCL7    NP_006264    SEQ ID NO:7
mkasaallcl lltaaafspq glaqpvgint sttccyrfin kkipkqrles yrrttsshcp
reavifktkl dkeicadptq kwvqdfmkhl dkktqtpkl

CCL8    NP_005614    SEQ ID NO:8
mkvsaallcl llmaatfspq glaqpdsvsi pitccfnvin rkipiqrles ytritniqcp
keavifktkr gkevcadpke rwvrdsmkhl dqifqnlkp

CCL11    CAG33702    SEQ ID NO:9
mkvsaallwl lliaaafspq glaqpasvpt tccfnlanrk iplqrlesyr ritsgkcpqk
avifktklak dicadpkkkw vqdsmkyldq ksptpkp

CCL13    NP_005399    SEQ ID NO:10
mkvsavllcl llmtaafnpq glaqpdalnv pstccftfss kkislqrlks yvittsrcpq
kavifrtklg keicadpkek wvqnymkhlg rkahtlkt

CCL14-1    NP_116739    SEQ ID NO:11
mkisvaaipf fllitialgt ktesssrgpy hpseccftyt tykiprqrim dyyetnsqcs
kpgivfitkr ghsvctnpsd kwvqdyikdm ken

CCL14-2    NP_116738    SEQ ID NO:12
mkisvaaipf fllitialgt ktesssqtgg kpkvvkiqlk lvggpyhpse ccftyttyki
prqrimdyye tnsqcskpgi vfitkrghsv ctnpsdkwvq dyikdmken

FIG. 12 (CONT)

CCL15  NP_116741  SEQ ID NO:13
mkvsvaalsc lmlvavlgsq aqfindaete lmmsklplen pvvlnsfhfa adcctsyisq
sipcslmksy fetssecskp gvifltkkgr qvcakpsgpg vqdcmkklkp ysi

CCL16  NP_004581  SEQ ID NO:14
mkvseaalsl lvliliitsa srsqpkvpew vntpstcclk yyekvlprrl vvgyrkalnc
hlpaiifvtk rnrevctnpn ddwvqeyikd pnlpllptrn lstvkiitak ngqpqllnsq

CCL17  NP_002978  SEQ ID NO:15
maplkmlalv tlllgaslqh ihaargtnvg reccleyfkg aiplrklktw yqtsedcsrd
aivfvtvqgr aicsdpnnkr vknavkylqs lers

CCL18  NP_002979  SEQ ID NO:16
mkglaaallv lvctmalcsc aqvgtnkelc clvytswqip qkfivdyset spqcpkpgvi
lltkrgrqic adpnkkwvqk yisdlklna

CCL19  NP_006265  SEQ ID NO:17
mallalsll vlwtspaptl sgtndaedcc lsvtqkpipg yivrnfhyll ikdgcrvpav
vfttlrgrql cappdqpwve riiqrlqrts akmkrrss

CCL20-1  NP_004582  SEQ ID NO:18
mcctkslla almsvlllhl cgeseaasnf dcclgytdri lhpkfivgft rqlanegcdi
naiifhtkkk lsvcanpkqt wvkyivrlls kkvknm

CCL20-2  NP_001123518  SEQ ID NO:19
mcctkslla almsvlllhl cgeseasnfd cclgytdril hpkfivgftr qlanegcdin
aiifhtkkkl svcanpkqtw vkyivrllsk kvknm

CCL21  NP_002980  SEQ ID NO:20
maqslalsll ilvlafgipr tqgsdggaqd cclkysqrki pakvvrsyrk qepslgcsip
ailflprkrs qaelcadpke lwvqqlmqhl dktpspqkpa qgcrkdrgas ktgkkgkgsk
gckrtersqt pkgp

CCL22  NP_002981  SEQ ID NO:21
mdrlqtallv vlvilavalq ateagpygan medsvccrdy vryrlplrvv khfywtsdsc
prpgvvlltf rdkeicadpr vpwvkmilnk lsq

CCL23-1  NP_665905  SEQ ID NO:22
mkvsvaalsc lmlvtalgsq arvtkdaete fmmsklplen pvlldrfhat sadccisytp
rsipcslles yfetnsecsk pgvifltkkg rrfcanpsdk qvqvcvrmlk ldtriktrkn

CCL23-2  NP_005055  SEQ ID NO:23
mkvsvaalsc lmlvtalgsq arvtkdaete fmmsklplen pvlldmlwrr kigpqmtlsh
aagfhatsad ccisytprsi pcsllesyfe tnsecskpgv ifltkkgrrf canpsdkqvq
vcvrmlkldt riktrkn

CCL24  NP_002982  SEQ ID NO:24
maglmtivts llflgvcahh iiptgsvvip spccmffvsk ripenrvvsy qlssrstclk
agvifttkkg qqfcgdpkqe wvqrymknld akqkkaspra ravavkgpvq rypgnqttc

FIG. 12 (CONT)

CCL25-1   NP_005615   SEQ ID NO:25
mnlwllaclv agflgawapa vhtqgvfedc clayhypigw avlrrawtyr iqevsgscnl
paaifylpkr hrkvcgnpks revqramkll darnkvfakl hhntqtfqag phavkklssg
nsklssskfs npissskrnv sllisansgl

CCL25-2   NP_683686   SEQ ID NO:26
mnlwllaclv agflgawapa vhtqgvfedc clayhypigw avlrrawtyr iqevsgscnl
paairpscck evefwklqvi ivqv

CCL25-3   EAW68951   SEQ ID NO:27
mnlwllaclv agflgawapa vhtqgvfedc clayhypigw avlrrawtyr iqevsgscnl
paairpscck evefwklqvi iiqv

CCL26   NP_006063   SEQ ID NO:28
mmglslasav llasllslhl gtatrgsdis ktccfqyshk plpwtwvrsy eftsnscsqr
avifttkrgk kvcthprkkw vqkyisllkt pkql

CCL27   NP_006655   SEQ ID NO:29
mkgpptfcsl lllslllspd ptaafllpps tacctqlyrk plsdkllrkv iqvelqeadg
dchlqafvlh laqrsicihp qnpslsqwfe hqerklhgtl pklnfgmlrk mg

CCL28   NP_683513   SEQ ID NO:30
mqqrglaiva lavcaalhas eailpiassc ctevshhisr rllervnmcr iqradgdcdl
aavilhvkrr ricvsphnht vkqwmkvqaa kkngkgnvch rkkhhgkrns nrahqgkhet
yghktpy

CXCL1   NP_001502   SEQ ID NO:31
maraalsaap snprllrval lllllvaagr raagasvate lrcqclqtlq gihpkniqsv
nvkspgphca qteviatlkn grkaclnpas pivkkiiekm lnsdksn

CXCL2   NP_002080   SEQ ID NO:32
maratlsaap snprllrval lllllvaasr raagaplate lrcqclqtlq gihlkniqsv
kvkspgphca qteviatlkn gqkaclnpas pmvkkiiekm lkngksn

CXCL3   NP_002081   SEQ ID NO:33
mahatlsaap snprllrval lllllvaasr raagasvvte lrcqclqtlq gihlkniqsv
nvrspgphca qteviatlkn gkkaclnpas pmvqkiieki lnkgstn

CXCL4   NP_002610   SEQ ID NO:34
mssaagfcas rpgllflgll llplvvafas aeaeedgdlq clcvkttsqv rprhitslev
ikagphcpta qliatlkngr kicldlqapl ykkiikklle s

CXCL5   NP_002985   SEQ ID NO:35
msllssraar vpgpssslca llvlllltq pgpiasagpa aavlrelrcv clqttgvhp
kmisnlqvfa igpqcskvev vaslkngkei cldpeapflk kviqkildgg nken

CXCL6   NP_002984   SEQ ID NO:36
mslpssraar vpgpsgslca llalllltp pgplasagpv savltelrct clrvtlrvnp
ktigklqvfp agpqcskvev vaslkngkqv cldpeapflk kviqkildsg nkkn

FIG. 12 (CONT)

CXCL7          NP_002695          SEQ ID NO:37
mslrldttps cnsarplhal qvllllslll talasstkgq tkrnlakgke esldsdlyae
lrcmciktts gihpkniqsl evigkgthcn qveviatlkd grkicldpda prikkivqkk
lagdesad

CXCL8          NP_000575          SEQ ID NO:38
mtsklavall aaflisaalc egavlprsak elrcqcikty skpfhpkfik elrviesgph
canteiivkl sdgrelcldp kenwvqrvve kflkraens

CXCL9          NP_002407          SEQ ID NO:39
mkksgvlfll giillvligv qgtpvvrkgr cscistnqgt ihlqslkdlk qfapspscek
ieiiatlkng vqtclnpdsa dvkelikkwe kqvsqkkkqk ngkkhqkkkv lkvrksqrsr
qkktt

CXCL10         NP_001556          SEQ ID NO:40
mnqtailicc lifltlsgiq gvplsrtvrc tcisisnqpv nprsleklei ipasqfcprv
eiiatmkkkg ekrclnpesk aiknllkavs kerskrsp

CXCL11         NP_005400          SEQ ID NO:41
msvkgmaial avilcatvvq gfpmfkrgrc lcigpgvkav kvadiekasi mypsnncdki
eviitlkenk gqrclnpksk qarliikkve rknf

CXCL12         NP_000600          SEQ ID NO:42
mnakvvvvlv lvltalclsd gkpvslsyrc pcrffeshva ranvkhlkil ntpncalqiv
arlknnnrqv cidpklkwiq eylekalnkr fkm

CXCL13         NP_006410          SEQ ID NO:43
mkfistslll mllvsslspv qgvlevyyts lrcrcvqess vfiprrfidr iqilprgngc
prkeiivwkk nksivcvdpq aewiqrmmev lrkrsssstlp vpvfkrkip

CXCL16         NP_071342          SEQ ID NO:44
msgsqsevap spqsprspem grdlrpgsrv llllllllllv yltqpgngne gsvtgscycg
krissdspps vqfmnrlrkh lrayhrclyy trfqllswsv cggnkdpwvq elmscldlke
cghaysgiva hqkhllptsp pisqasegas sdihtpaqml lstlqstqrp tlpvgslssd
keltrpnett ihtaghslaa gpeagenqkq peknagptar tsatvpvlcl laiifiltaa
lsyvlckrrr gqspqsspdl pvhyipvapd snt

XCL1           AAH69817           SEQ ID NO:45
mrllilallg icsltayive gvgsevsdkr tcvslttqrl pvsriktyti tegslravif
itkrglkvca dpqatwvrdv vrsmdrksnt rnnmiqtkpt gtqqstntav tltg

XCL2           NP_003166          SEQ ID NO:46
mrllilallg icsltayive gvgsevshrr tcvslttqrl pvsriktyti tegslravif
itkrglkvca dpqatwvrdv vrsmdrksnt rnnmiqtkpt gtqqstntav tltg

FIG. 12 (CONT)

CX3CL1    NP_002987    SEQ ID NO:47
mapislswll rlatfchltv llagqhhgvt kcnitcskmt skipvallih yqqnqascgk
raiiletrqh rlfcadpkeq wvkdamqhld rqaaaltrng gtfekqigev kprttpaagg
mdesvvlepe atgessslep tpssqeaqra lgtspelptg vtgssgtrlp ptpkaqdggp
vgtelfrvpp vstaatwqss aphqpgpslw aeaktseaps tqdpstqast asspapeena
psegqrvwgq gqsprpensl ereemgpvpa htdafqdwgp gsmahvsvvp vssegtpsre
pvasgswtpk aeepihatmd pqrlgvlitp vpdaqaatrr qavgllaflg llfclgvamf
tyqslqgcpr kmagemaegl ryiprscgsn syvlvpv

IgG1Fc    CBX54381.1    SEQ ID NO:48
sepkscdkth tcppcpapel lggpsvflfp pkpkdtlmis rtpevtcvvv dvshedpevk
fnwyvdgvev hnaktkpree qynstyrvvs vltvlhqdwl ngkeykckvs nkalpapiek
tiskakgqpr epqvytlpps rdeltknqvs ltclvkgfyp sdiavewesn gqpennykkt
ppvldsdgsf flyskltvdk srwqqgnvfs csvmhealhn hytqkslsls pgk

IgG2Fc    CBX54382.1    SEQ ID NO:49
erkccvecpp cpappvagps vflfppkpkd tlmisrtpev tcvvvdvshe dpevqfnwyv
dgvevhnakt kpreeqfnst frvvsvltvv hqdwlngkey kckvsnkglp apiektiskt
kgqprepqvy tlppsreemt knqvsltclv kgfypsdiav ewesngqpen nykttppmld
sdgsfflysk ltvdksrwqq gnvfscsvmh ealhnhytqk slslspgk

IgG3Fc    CBX54383.1    SEQ ID NO:50
elktplgdtt htcprcpepk scdtpppcpr cpepkscdtp ppcprcpepk scdtpppcpr
cpapellggp svflfppkpk dtlmisrtpe vtcvvvdvsh edpevqfkwy vdgvevhnak
tkpreeqfns tfrvvsvltv lhqdwlngke ykckvsnkal papiektisk tkgqprepqv
ytlppsreem tknqvsltcl vkgfypsdia vewessgqpe nnynttppml dsdgsfflys
kltvdksrwq qgnifscsvm healhnrftq kslslspgk

IgG4Fc    CBX54384.1    SEQ ID NO:51
eskygppcps cpapeflggp svflfppkpk dtlmisrtpe vtcvvvdvsq edpevqfnwy
vdgvevhnak tkpreeqfns tyrvvsvltv vhqdwlngke ykckvsnkgl pssiektisk
akgqprepqv ytlppsqeem tknqvsltcl vkgfypsdia vewesngqpe nnykttppvl
dsdgsfflys rltvdksrwq egnvfscsvm healnhytq kslslslgk

SEQUENCE LISTING

<160> NUMBER OF SEQ ID NOS: 106

<210> SEQ ID NO 1
<211> LENGTH: 96
<212> TYPE: PRT
<213> ORGANISM: Homo sapiens

<400> SEQUENCE: 1

Met Gln Ile Ile Thr Thr Ala Leu Val Cys Leu Leu Leu Ala Gly Met
1               5                   10                  15

Trp Pro Glu Asp Val Asp Ser Lys Ser Met Gln Val Pro Phe Ser Arg
            20                  25                  30

Cys Cys Phe Ser Phe Ala Glu Gln Glu Ile Pro Leu Arg Ala Ile Leu
        35                  40                  45

Cys Tyr Arg Asn Thr Ser Ser Ile Cys Ser Asn Glu Gly Leu Ile Phe
    50                  55                  60

Lys Leu Lys Arg Gly Lys Glu Ala Cys Ala Leu Asp Thr Val Gly Trp
65                  70                  75                  80

Val Gln Arg His Arg Lys Met Leu Arg His Cys Pro Ser Lys Arg Lys
                85                  90                  95

<210> SEQ ID NO 2
<211> LENGTH: 99
<212> TYPE: PRT
<213> ORGANISM: Homo sapiens

<400> SEQUENCE: 2

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr

<210> SEQ ID NO 3
<211> LENGTH: 92
<212> TYPE: PRT
<213> ORGANISM: Homo sapiens

<400> SEQUENCE: 3

Met Gln Val Ser Thr Ala Ala Leu Ala Val Leu Leu Cys Thr Met Ala
1               5                   10                  15

Leu Cys Asn Gln Phe Ser Ala Ser Leu Ala Ala Asp Thr Pro Thr Ala
            20                  25                  30

Cys Cys Phe Ser Tyr Thr Ser Arg Gln Ile Pro Gln Asn Phe Ile Ala
        35                  40                  45

Asp Tyr Phe Glu Thr Ser Ser Gln Cys Ser Lys Pro Gly Val Ile Phe
    50                  55                  60

Leu Thr Lys Arg Ser Arg Gln Val Cys Ala Asp Pro Ser Glu Glu Trp
65                  70                  75                  80

Val Gln Lys Tyr Val Ser Asp Leu Glu Leu Ser Ala
                    85                  90

<210> SEQ ID NO 4
<211> LENGTH: 92
<212> TYPE: PRT
<213> ORGANISM: Homo sapiens

<400> SEQUENCE: 4

Met Lys Leu Cys Val Thr Val Leu Ser Leu Leu Met Leu Val Ala Ala
1               5                   10                  15

Phe Cys Ser Pro Ala Leu Ser Ala Pro Met Gly Ser Asp Pro Pro Thr
                20                  25                  30

Ala Cys Cys Phe Ser Tyr Thr Ala Arg Lys Leu Pro Arg Asn Phe Val
            35                  40                  45

Val Asp Tyr Tyr Glu Thr Ser Ser Leu Cys Ser Gln Pro Ala Val Val
        50                  55                  60

Phe Gln Thr Lys Arg Ser Lys Gln Val Cys Ala Asp Pro Ser Glu Ser
65                  70                  75                  80

Trp Val Gln Glu Tyr Val Tyr Asp Leu Glu Leu Asn
                85                  90

<210> SEQ ID NO 5
<211> LENGTH: 92
<212> TYPE: PRT
<213> ORGANISM: Homo sapiens

<400> SEQUENCE: 5

Met Lys Leu Cys Val Thr Val Leu Ser Leu Leu Val Leu Val Ala Ala
1               5                   10                  15

Phe Cys Ser Leu Ala Leu Ser Ala Pro Met Gly Ser Asp Pro Pro Thr
                20                  25                  30

Ala Cys Cys Phe Ser Tyr Thr Ala Arg Lys Leu Pro Arg Asn Phe Val
            35                  40                  45

Val Asp Tyr Tyr Glu Thr Ser Ser Leu Cys Ser Gln Pro Ala Val Val
        50                  55                  60

Phe Gln Thr Lys Arg Gly Lys Gln Val Cys Ala Asp Pro Ser Glu Ser
65                  70                  75                  80

Trp Val Gln Glu Tyr Val Tyr Asp Leu Glu Leu Asn
                85                  90

<210> SEQ ID NO 6
<211> LENGTH: 91
<212> TYPE: PRT
<213> ORGANISM: Homo sapiens

<400> SEQUENCE: 6

Met Lys Val Ser Ala Ala Ala Leu Ala Val Ile Leu Ile Ala Thr Ala
1               5                   10                  15

Leu Cys Ala Pro Ala Ser Ala Ser Pro Tyr Ser Ser Asp Thr Thr Pro
                20                  25                  30

Cys Cys Phe Ala Tyr Ile Ala Arg Pro Leu Pro Arg Ala His Ile Lys
            35                  40                  45

Glu Tyr Phe Tyr Thr Ser Gly Lys Cys Ser Asn Pro Ala Val Val Phe
        50                  55                  60

Val Thr Arg Lys Asn Arg Gln Val Cys Ala Asn Pro Glu Lys Lys Trp
65                  70                  75                  80

Val Arg Glu Tyr Ile Asn Ser Leu Glu Met Ser

-continued

```
                    85                  90

<210> SEQ ID NO 7
<211> LENGTH: 99
<212> TYPE: PRT
<213> ORGANISM: Homo sapiens

<400> SEQUENCE: 7

Met Lys Ala Ser Ala Ala Leu Leu Cys Leu Leu Leu Thr Ala Ala Ala
1               5                   10                  15

Phe Ser Pro Gln Gly Leu Ala Gln Pro Val Gly Ile Asn Thr Ser Thr
                20                  25                  30

Thr Cys Cys Tyr Arg Phe Ile Asn Lys Lys Ile Pro Lys Gln Arg Leu
            35                  40                  45

Glu Ser Tyr Arg Arg Thr Thr Ser Ser His Cys Pro Arg Glu Ala Val
        50                  55                  60

Ile Phe Lys Thr Lys Leu Asp Lys Glu Ile Cys Ala Asp Pro Thr Gln
65                  70                  75                  80

Lys Trp Val Gln Asp Phe Met Lys His Leu Asp Lys Lys Thr Gln Thr
                85                  90                  95

Pro Lys Leu

<210> SEQ ID NO 8
<211> LENGTH: 99
<212> TYPE: PRT
<213> ORGANISM: Homo sapiens

<400> SEQUENCE: 8

Met Lys Val Ser Ala Ala Leu Leu Cys Leu Leu Leu Met Ala Ala Thr
1               5                   10                  15

Phe Ser Pro Gln Gly Leu Ala Gln Pro Asp Ser Val Ser Ile Pro Ile
                20                  25                  30

Thr Cys Cys Phe Asn Val Ile Asn Arg Lys Ile Pro Ile Gln Arg Leu
            35                  40                  45

Glu Ser Tyr Thr Arg Ile Thr Asn Ile Gln Cys Pro Lys Glu Ala Val
        50                  55                  60

Ile Phe Lys Thr Lys Arg Gly Lys Glu Val Cys Ala Asp Pro Lys Glu
65                  70                  75                  80

Arg Trp Val Arg Asp Ser Met Lys His Leu Asp Gln Ile Phe Gln Asn
                85                  90                  95

Leu Lys Pro

<210> SEQ ID NO 9
<211> LENGTH: 97
<212> TYPE: PRT
<213> ORGANISM: Homo sapiens

<400> SEQUENCE: 9

Met Lys Val Ser Ala Ala Leu Leu Trp Leu Leu Leu Ile Ala Ala Ala
1               5                   10                  15

Phe Ser Pro Gln Gly Leu Ala Gly Pro Ala Ser Val Pro Thr Thr Cys
                20                  25                  30

Cys Phe Asn Leu Ala Asn Arg Lys Ile Pro Leu Gln Arg Leu Glu Ser
            35                  40                  45

Tyr Arg Arg Ile Thr Ser Gly Lys Cys Pro Gln Lys Ala Val Ile Phe
        50                  55                  60

Lys Thr Lys Leu Ala Lys Asp Ile Cys Ala Asp Pro Lys Lys Lys Trp
```

```
                65                  70                  75                  80
Val Gln Asp Ser Met Lys Tyr Leu Asp Gln Lys Ser Pro Thr Pro Lys
                    85                  90                  95

Pro

<210> SEQ ID NO 10
<211> LENGTH: 98
<212> TYPE: PRT
<213> ORGANISM: Homo sapiens

<400> SEQUENCE: 10

Met Lys Val Ser Ala Val Leu Leu Cys Leu Leu Met Thr Ala Ala
1               5                   10                  15

Phe Asn Pro Gln Gly Leu Ala Gln Pro Asp Ala Leu Asn Val Pro Ser
                20                  25                  30

Thr Cys Cys Phe Thr Phe Ser Ser Lys Lys Ile Ser Leu Gln Arg Leu
            35                  40                  45

Lys Ser Tyr Val Ile Thr Thr Ser Arg Cys Pro Gln Lys Ala Val Ile
        50                  55                  60

Phe Arg Thr Lys Leu Gly Lys Glu Ile Cys Ala Asp Pro Lys Glu Lys
65                  70                  75                  80

Trp Val Gln Asn Tyr Met Lys His Leu Gly Arg Lys Ala His Thr Leu
                85                  90                  95

Lys Thr

<210> SEQ ID NO 11
<211> LENGTH: 93
<212> TYPE: PRT
<213> ORGANISM: Homo sapiens

<400> SEQUENCE: 11

Met Lys Ile Ser Val Ala Ala Ile Pro Phe Phe Leu Leu Ile Thr Ile
1               5                   10                  15

Ala Leu Gly Thr Lys Thr Glu Ser Ser Ser Arg Gly Pro Tyr His Pro
                20                  25                  30

Ser Glu Cys Cys Phe Thr Tyr Thr Thr Tyr Lys Ile Pro Arg Gln Arg
            35                  40                  45

Ile Met Asp Tyr Tyr Glu Thr Asn Ser Gln Cys Ser Lys Pro Gly Ile
        50                  55                  60

Val Phe Ile Thr Lys Arg Gly His Ser Val Cys Thr Asn Pro Ser Asp
65                  70                  75                  80

Lys Trp Val Gln Asp Tyr Ile Lys Asp Met Lys Glu Asn
                85                  90

<210> SEQ ID NO 12
<211> LENGTH: 109
<212> TYPE: PRT
<213> ORGANISM: Homo sapiens

<400> SEQUENCE: 12

Met Lys Ile Ser Val Ala Ala Ile Pro Phe Phe Leu Leu Ile Thr Ile
1               5                   10                  15

Ala Leu Gly Thr Lys Thr Glu Ser Ser Ser Gln Thr Gly Gly Lys Pro
                20                  25                  30

Lys Val Val Lys Ile Gln Leu Lys Leu Val Gly Gly Pro Tyr His Pro
            35                  40                  45

Ser Glu Cys Cys Phe Thr Tyr Thr Thr Tyr Lys Ile Pro Arg Gln Arg
```

```
                50                  55                  60
Ile Met Asp Tyr Tyr Glu Thr Asn Ser Gln Cys Ser Lys Pro Gly Ile
 65                  70                  75                  80

Val Phe Ile Thr Lys Arg Gly His Ser Val Cys Thr Asn Pro Ser Asp
                 85                  90                  95

Lys Trp Val Gln Asp Tyr Ile Lys Asp Met Lys Glu Asn
                100                 105

<210> SEQ ID NO 13
<211> LENGTH: 113
<212> TYPE: PRT
<213> ORGANISM: Homo sapiens

<400> SEQUENCE: 13

Met Lys Val Ser Val Ala Ala Leu Ser Cys Leu Met Leu Val Ala Val
 1               5                  10                  15

Leu Gly Ser Gln Ala Gln Phe Ile Asn Asp Ala Glu Thr Glu Leu Met
                20                  25                  30

Met Ser Lys Leu Pro Leu Glu Asn Pro Val Val Leu Asn Ser Phe His
                35                  40                  45

Phe Ala Asp Cys Cys Thr Ser Tyr Ile Ser Gln Ser Ile Pro Cys
 50                  55                  60

Ser Leu Met Lys Ser Tyr Phe Glu Thr Ser Ser Glu Cys Ser Lys Pro
 65                  70                  75                  80

Gly Val Ile Phe Leu Thr Lys Lys Gly Arg Gln Val Cys Ala Lys Pro
                 85                  90                  95

Ser Gly Pro Gly Val Gln Asp Cys Met Lys Lys Leu Lys Pro Tyr Ser
                100                 105                 110

Ile

<210> SEQ ID NO 14
<211> LENGTH: 120
<212> TYPE: PRT
<213> ORGANISM: Homo sapiens

<400> SEQUENCE: 14

Met Lys Val Ser Glu Ala Ala Leu Ser Leu Leu Val Leu Ile Leu Ile
 1               5                  10                  15

Ile Thr Ser Ala Ser Arg Ser Gln Pro Lys Val Pro Glu Trp Val Asn
                20                  25                  30

Thr Pro Ser Thr Cys Cys Leu Lys Tyr Tyr Glu Lys Val Leu Pro Arg
                35                  40                  45

Arg Leu Val Val Gly Tyr Arg Lys Ala Leu Asn Cys His Leu Pro Ala
 50                  55                  60

Ile Ile Phe Val Thr Lys Arg Asn Arg Glu Val Cys Thr Asn Pro Asn
 65                  70                  75                  80

Asp Asp Trp Val Gln Glu Tyr Ile Lys Asp Pro Asn Leu Pro Leu Leu
                 85                  90                  95

Pro Thr Arg Asn Leu Ser Thr Val Lys Ile Ile Thr Ala Lys Asn Gly
                100                 105                 110

Gln Pro Gln Leu Leu Asn Ser Gln
                115                 120

<210> SEQ ID NO 15
<211> LENGTH: 94
<212> TYPE: PRT
<213> ORGANISM: Homo sapiens
```

<400> SEQUENCE: 15

Met Ala Pro Leu Lys Met Leu Ala Leu Val Thr Leu Leu Leu Gly Ala
1               5                   10                  15

Ser Leu Gln His Ile His Ala Ala Arg Gly Thr Asn Val Gly Arg Glu
            20                  25                  30

Cys Cys Leu Glu Tyr Phe Lys Gly Ala Ile Pro Leu Arg Lys Leu Lys
        35                  40                  45

Thr Trp Tyr Gln Thr Ser Glu Asp Cys Ser Arg Asp Ala Ile Val Phe
    50                  55                  60

Val Thr Val Gln Gly Arg Ala Ile Cys Ser Asp Pro Asn Asn Lys Arg
65                  70                  75                  80

Val Lys Asn Ala Val Lys Tyr Leu Gln Ser Leu Glu Arg Ser
                85                  90

<210> SEQ ID NO 16
<211> LENGTH: 89
<212> TYPE: PRT
<213> ORGANISM: Homo sapiens

<400> SEQUENCE: 16

Met Lys Gly Leu Ala Ala Ala Leu Leu Val Leu Val Cys Thr Met Ala
1               5                   10                  15

Leu Cys Ser Cys Ala Gln Val Gly Thr Asn Lys Glu Leu Cys Cys Leu
            20                  25                  30

Val Tyr Thr Ser Trp Gln Ile Pro Gln Lys Phe Ile Val Asp Tyr Ser
        35                  40                  45

Glu Thr Ser Pro Gln Cys Pro Lys Pro Gly Val Ile Leu Leu Thr Lys
    50                  55                  60

Arg Gly Arg Gln Ile Cys Ala Asp Pro Asn Lys Lys Trp Val Gln Lys
65                  70                  75                  80

Tyr Ile Ser Asp Leu Lys Leu Asn Ala
                85

<210> SEQ ID NO 17
<211> LENGTH: 98
<212> TYPE: PRT
<213> ORGANISM: Homo sapiens

<400> SEQUENCE: 17

Met Ala Leu Leu Leu Ala Leu Ser Leu Leu Val Leu Trp Thr Ser Pro
1               5                   10                  15

Ala Pro Thr Leu Ser Gly Thr Asn Asp Ala Glu Asp Cys Cys Leu Ser
            20                  25                  30

Val Thr Gln Lys Pro Ile Pro Gly Tyr Ile Val Arg Asn Phe His Tyr
        35                  40                  45

Leu Leu Ile Lys Asp Gly Cys Arg Val Pro Ala Val Val Phe Thr Thr
    50                  55                  60

Leu Arg Gly Arg Gln Leu Cys Ala Pro Pro Asp Gln Pro Trp Val Glu
65                  70                  75                  80

Arg Ile Ile Gln Arg Leu Gln Arg Thr Ser Ala Lys Met Lys Arg Arg
                85                  90                  95

Ser Ser

<210> SEQ ID NO 18
<211> LENGTH: 96
<212> TYPE: PRT

<213> ORGANISM: Homo sapiens

<400> SEQUENCE: 18

Met Cys Cys Thr Lys Ser Leu Leu Leu Ala Ala Leu Met Ser Val Leu
1               5                   10                  15

Leu Leu His Leu Cys Gly Glu Ser Glu Ala Ala Ser Asn Phe Asp Cys
            20                  25                  30

Cys Leu Gly Tyr Thr Asp Arg Ile Leu His Pro Lys Phe Ile Val Gly
        35                  40                  45

Phe Thr Arg Gln Leu Ala Asn Glu Gly Cys Asp Ile Asn Ala Ile Ile
    50                  55                  60

Phe His Thr Lys Lys Lys Leu Ser Val Cys Ala Asn Pro Lys Gln Thr
65                  70                  75                  80

Trp Val Lys Tyr Ile Val Arg Leu Leu Ser Lys Lys Val Lys Asn Met
                85                  90                  95

<210> SEQ ID NO 19
<211> LENGTH: 95
<212> TYPE: PRT
<213> ORGANISM: Homo sapiens

<400> SEQUENCE: 19

Met Cys Cys Thr Lys Ser Leu Leu Leu Ala Ala Leu Met Ser Val Leu
1               5                   10                  15

Leu Leu His Leu Cys Gly Glu Ser Glu Ala Ser Asn Phe Asp Cys Cys
            20                  25                  30

Leu Gly Tyr Thr Asp Arg Ile Leu His Pro Lys Phe Ile Val Gly Phe
        35                  40                  45

Thr Arg Gln Leu Ala Asn Glu Gly Cys Asp Ile Asn Ala Ile Ile Phe
    50                  55                  60

His Thr Lys Lys Lys Leu Ser Val Cys Ala Asn Pro Lys Gln Thr Trp
65                  70                  75                  80

Val Lys Tyr Ile Val Arg Leu Leu Ser Lys Lys Val Lys Asn Met
                85                  90                  95

<210> SEQ ID NO 20
<211> LENGTH: 134
<212> TYPE: PRT
<213> ORGANISM: Homo sapiens

<400> SEQUENCE: 20

Met Ala Gln Ser Leu Ala Leu Ser Leu Leu Ile Leu Val Leu Ala Phe
1               5                   10                  15

Gly Ile Pro Arg Thr Gln Gly Ser Asp Gly Gly Ala Gln Asp Cys Cys
            20                  25                  30

Leu Lys Tyr Ser Gln Arg Lys Ile Pro Ala Lys Val Val Arg Ser Tyr
        35                  40                  45

Arg Lys Gln Glu Pro Ser Leu Gly Cys Ser Ile Pro Ala Ile Leu Phe
    50                  55                  60

Leu Pro Arg Lys Arg Ser Gln Ala Glu Leu Cys Ala Asp Pro Lys Glu
65                  70                  75                  80

Leu Trp Val Gln Gln Leu Met Gln His Leu Asp Lys Thr Pro Ser Pro
                85                  90                  95

Gln Lys Pro Ala Gln Gly Cys Arg Lys Asp Arg Gly Ala Ser Lys Thr
            100                 105                 110

Gly Lys Lys Gly Lys Gly Ser Lys Gly Cys Lys Arg Thr Glu Arg Ser
        115                 120                 125

```
Gln Thr Pro Lys Gly Pro
        130

<210> SEQ ID NO 21
<211> LENGTH: 93
<212> TYPE: PRT
<213> ORGANISM: Homo sapiens

<400> SEQUENCE: 21

Met Asp Arg Leu Gln Thr Ala Leu Leu Val Val Val Leu Leu Ala
1               5                   10                  15

Val Ala Leu Gln Ala Thr Glu Ala Gly Pro Tyr Gly Ala Asn Met Glu
                20                  25                  30

Asp Ser Val Cys Cys Arg Asp Tyr Val Arg Tyr Arg Leu Pro Leu Arg
            35                  40                  45

Val Val Lys His Phe Tyr Trp Thr Ser Asp Ser Cys Pro Arg Pro Gly
        50                  55                  60

Val Val Leu Leu Thr Phe Arg Asp Lys Glu Ile Cys Ala Asp Pro Arg
65                  70                  75                  80

Val Pro Trp Val Lys Met Ile Leu Asn Lys Leu Ser Gln
                85                  90

<210> SEQ ID NO 22
<211> LENGTH: 120
<212> TYPE: PRT
<213> ORGANISM: Homo sapiens

<400> SEQUENCE: 22

Met Lys Val Ser Val Ala Ala Leu Ser Cys Leu Met Leu Val Thr Ala
1               5                   10                  15

Leu Gly Ser Gln Ala Arg Val Thr Lys Asp Ala Glu Thr Glu Phe Met
                20                  25                  30

Met Ser Lys Leu Pro Leu Glu Asn Pro Val Leu Leu Asp Arg Phe His
            35                  40                  45

Ala Thr Ser Ala Asp Cys Cys Ile Ser Tyr Thr Pro Arg Ser Ile Pro
        50                  55                  60

Cys Ser Leu Leu Glu Ser Tyr Phe Glu Thr Asn Ser Glu Cys Ser Lys
65                  70                  75                  80

Pro Gly Val Ile Phe Leu Thr Lys Lys Gly Arg Arg Phe Cys Ala Asn
                85                  90                  95

Pro Ser Asp Lys Gln Val Gln Val Cys Val Arg Met Leu Lys Leu Asp
            100                 105                 110

Thr Arg Ile Lys Thr Arg Lys Asn
        115                 120

<210> SEQ ID NO 23
<211> LENGTH: 137
<212> TYPE: PRT
<213> ORGANISM: Homo sapiens

<400> SEQUENCE: 23

Met Lys Val Ser Val Ala Ala Leu Ser Cys Leu Met Leu Val Thr Ala
1               5                   10                  15

Leu Gly Ser Gln Ala Arg Val Thr Lys Asp Ala Glu Thr Glu Phe Met
                20                  25                  30

Met Ser Lys Leu Pro Leu Glu Asn Pro Val Leu Leu Asp Met Leu Trp
            35                  40                  45
```

```
Arg Arg Lys Ile Gly Pro Gln Met Thr Leu Ser His Ala Ala Gly Phe
 50                  55                  60

His Ala Thr Ser Ala Asp Cys Cys Ile Ser Tyr Thr Pro Arg Ser Ile
 65                  70                  75                  80

Pro Cys Ser Leu Leu Glu Ser Tyr Phe Glu Thr Asn Ser Glu Cys Ser
                 85                  90                  95

Lys Pro Gly Val Ile Phe Leu Thr Lys Lys Gly Arg Arg Phe Cys Ala
                100                 105                 110

Asn Pro Ser Asp Lys Gln Val Gln Val Cys Val Arg Met Leu Lys Leu
                115                 120                 125

Asp Thr Arg Ile Lys Thr Arg Lys Asn
                130                 135

<210> SEQ ID NO 24
<211> LENGTH: 119
<212> TYPE: PRT
<213> ORGANISM: Homo sapiens

<400> SEQUENCE: 24

Met Ala Gly Leu Met Thr Ile Val Thr Ser Leu Leu Phe Leu Gly Val
 1               5                  10                  15

Cys Ala His His Ile Ile Pro Thr Gly Ser Val Val Ile Pro Ser Pro
                 20                  25                  30

Cys Cys Met Phe Phe Val Ser Lys Arg Ile Pro Glu Asn Arg Val Val
                 35                  40                  45

Ser Tyr Gln Leu Ser Ser Arg Ser Thr Cys Leu Lys Ala Gly Val Ile
 50                  55                  60

Phe Thr Thr Lys Lys Gly Gln Gln Phe Cys Gly Asp Pro Lys Gln Glu
 65                  70                  75                  80

Trp Val Gln Arg Tyr Met Lys Asn Leu Asp Ala Lys Gln Lys Lys Ala
                 85                  90                  95

Ser Pro Arg Ala Arg Ala Val Ala Val Lys Gly Pro Val Gln Arg Tyr
                100                 105                 110

Pro Gly Asn Gln Thr Thr Cys
                115

<210> SEQ ID NO 25
<211> LENGTH: 150
<212> TYPE: PRT
<213> ORGANISM: Homo sapiens

<400> SEQUENCE: 25

Met Asn Leu Trp Leu Leu Ala Cys Leu Val Ala Gly Phe Leu Gly Ala
 1               5                  10                  15

Trp Ala Pro Ala Val His Thr Gln Gly Val Phe Glu Asp Cys Cys Leu
                 20                  25                  30

Ala Tyr His Tyr Pro Ile Gly Trp Ala Val Leu Arg Arg Ala Trp Thr
                 35                  40                  45

Tyr Arg Ile Gln Glu Val Ser Gly Ser Cys Asn Leu Pro Ala Ala Ile
 50                  55                  60

Phe Tyr Leu Pro Lys Arg His Arg Lys Val Cys Gly Asn Pro Lys Ser
 65                  70                  75                  80

Arg Glu Val Gln Arg Ala Met Lys Leu Leu Asp Ala Arg Asn Lys Val
                 85                  90                  95

Phe Ala Lys Leu His His Asn Thr Gln Thr Phe Gln Ala Gly Pro His
                100                 105                 110
```

Ala Val Lys Lys Leu Ser Ser Gly Asn Ser Lys Leu Ser Ser Ser Lys
            115                 120                 125

Phe Ser Asn Pro Ile Ser Ser Lys Arg Asn Val Ser Leu Leu Ile
        130                 135                 140

Ser Ala Asn Ser Gly Leu
145                 150

<210> SEQ ID NO 26
<211> LENGTH: 84
<212> TYPE: PRT
<213> ORGANISM: Homo sapiens

<400> SEQUENCE: 26

Met Asn Leu Trp Leu Leu Ala Cys Leu Val Ala Gly Phe Leu Gly Ala
1               5                   10                  15

Trp Ala Pro Ala Val His Thr Gln Gly Val Phe Glu Asp Cys Cys Leu
            20                  25                  30

Ala Tyr His Tyr Pro Ile Gly Trp Ala Val Leu Arg Arg Ala Trp Thr
        35                  40                  45

Tyr Arg Ile Gln Glu Val Ser Gly Ser Cys Asn Leu Pro Ala Ala Ile
    50                  55                  60

Arg Pro Ser Cys Cys Lys Glu Val Glu Phe Trp Lys Leu Gln Val Ile
65                  70                  75                  80

Ile Val Gln Val

<210> SEQ ID NO 27
<211> LENGTH: 84
<212> TYPE: PRT
<213> ORGANISM: Homo sapiens

<400> SEQUENCE: 27

Met Asn Leu Trp Leu Leu Ala Cys Leu Val Ala Gly Phe Leu Gly Ala
1               5                   10                  15

Trp Ala Pro Ala Val His Thr Gln Gly Val Phe Glu Asp Cys Cys Leu
            20                  25                  30

Ala Tyr His Tyr Pro Ile Gly Trp Ala Val Leu Arg Arg Ala Trp Thr
        35                  40                  45

Tyr Arg Ile Gln Glu Val Ser Gly Ser Cys Asn Leu Pro Ala Ala Ile
    50                  55                  60

Arg Pro Ser Cys Cys Lys Glu Val Glu Phe Trp Lys Leu Gln Val Ile
65                  70                  75                  80

Ile Ile Gln Val

<210> SEQ ID NO 28
<211> LENGTH: 94
<212> TYPE: PRT
<213> ORGANISM: Homo sapiens

<400> SEQUENCE: 28

Met Met Gly Leu Ser Leu Ala Ser Ala Val Leu Leu Ala Ser Leu Leu
1               5                   10                  15

Ser Leu His Leu Gly Thr Ala Thr Arg Gly Ser Asp Ile Ser Lys Thr
            20                  25                  30

Cys Cys Phe Gln Tyr Ser His Lys Pro Leu Pro Trp Thr Trp Val Arg
        35                  40                  45

Ser Tyr Glu Phe Thr Ser Asn Ser Cys Ser Gln Arg Ala Val Ile Phe
    50                  55                  60

```
Thr Thr Lys Arg Gly Lys Lys Val Cys Thr His Pro Arg Lys Lys Trp
 65                  70                  75                  80

Val Gln Lys Tyr Ile Ser Leu Leu Lys Thr Pro Lys Gln Leu
                 85                  90
```

<210> SEQ ID NO 29
<211> LENGTH: 112
<212> TYPE: PRT
<213> ORGANISM: Homo sapiens

<400> SEQUENCE: 29

```
Met Lys Gly Pro Pro Thr Phe Cys Ser Leu Leu Leu Ser Leu Leu
 1               5                  10                  15

Leu Ser Pro Asp Pro Thr Ala Ala Phe Leu Leu Pro Pro Ser Thr Ala
                 20                  25                  30

Cys Cys Thr Gln Leu Tyr Arg Lys Pro Leu Ser Asp Lys Leu Leu Arg
             35                  40                  45

Lys Val Ile Gln Val Glu Leu Gln Glu Ala Asp Gly Asp Cys His Leu
 50                  55                  60

Gln Ala Phe Val Leu His Leu Ala Gln Arg Ser Ile Cys Ile His Pro
 65                  70                  75                  80

Gln Asn Pro Ser Leu Ser Gln Trp Phe Glu His Gln Glu Arg Lys Leu
                 85                  90                  95

His Gly Thr Leu Pro Lys Leu Asn Phe Gly Met Leu Arg Lys Met Gly
                100                 105                 110
```

<210> SEQ ID NO 30
<211> LENGTH: 127
<212> TYPE: PRT
<213> ORGANISM: Homo sapiens

<400> SEQUENCE: 30

```
Met Gln Gln Arg Gly Leu Ala Ile Val Ala Leu Ala Val Cys Ala Ala
 1               5                  10                  15

Leu His Ala Ser Glu Ala Ile Leu Pro Ile Ala Ser Ser Cys Cys Thr
                 20                  25                  30

Glu Val Ser His His Ile Ser Arg Arg Leu Leu Glu Arg Val Asn Met
             35                  40                  45

Cys Arg Ile Gln Arg Ala Asp Gly Asp Cys Asp Leu Ala Ala Val Ile
 50                  55                  60

Leu His Val Lys Arg Arg Arg Ile Cys Val Ser Pro His Asn His Thr
 65                  70                  75                  80

Val Lys Gln Trp Met Lys Val Gln Ala Ala Lys Lys Asn Gly Lys Gly
                 85                  90                  95

Asn Val Cys His Arg Lys Lys His His Gly Lys Arg Asn Ser Asn Arg
                100                 105                 110

Ala His Gln Gly Lys His Glu Thr Tyr Gly His Lys Thr Pro Tyr
            115                 120                 125
```

<210> SEQ ID NO 31
<211> LENGTH: 107
<212> TYPE: PRT
<213> ORGANISM: Homo sapiens

<400> SEQUENCE: 31

```
Met Ala Arg Ala Ala Leu Ser Ala Ala Pro Ser Asn Pro Arg Leu Leu
 1               5                  10                  15

Arg Val Ala Leu Leu Leu Leu Leu Leu Val Ala Ala Gly Arg Arg Ala
```

```
            20                  25                  30
Ala Gly Ala Ser Val Ala Thr Glu Leu Arg Cys Gln Cys Leu Gln Thr
            35                  40                  45

Leu Gln Gly Ile His Pro Lys Asn Ile Gln Ser Val Asn Val Lys Ser
        50                  55                  60

Pro Gly Pro His Cys Ala Gln Thr Glu Val Ile Ala Thr Leu Lys Asn
65                  70                  75                  80

Gly Arg Lys Ala Cys Leu Asn Pro Ala Ser Pro Ile Val Lys Lys Ile
                85                  90                  95

Ile Glu Lys Met Leu Asn Ser Asp Lys Ser Asn
            100                 105

<210> SEQ ID NO 32
<211> LENGTH: 107
<212> TYPE: PRT
<213> ORGANISM: Homo sapiens

<400> SEQUENCE: 32

Met Ala Arg Ala Thr Leu Ser Ala Ala Pro Ser Asn Pro Arg Leu Leu
1               5                   10                  15

Arg Val Ala Leu Leu Leu Leu Leu Val Ala Ala Ser Arg Arg Ala
            20                  25                  30

Ala Gly Ala Pro Leu Ala Thr Glu Leu Arg Cys Gln Cys Leu Gln Thr
            35                  40                  45

Leu Gln Gly Ile His Leu Lys Asn Ile Gln Ser Val Lys Val Lys Ser
        50                  55                  60

Pro Gly Pro His Cys Ala Gln Thr Glu Val Ile Ala Thr Leu Lys Asn
65                  70                  75                  80

Gly Gln Lys Ala Cys Leu Asn Pro Ala Ser Pro Met Val Lys Lys Ile
                85                  90                  95

Ile Glu Lys Met Leu Lys Asn Gly Lys Ser Asn
            100                 105

<210> SEQ ID NO 33
<211> LENGTH: 107
<212> TYPE: PRT
<213> ORGANISM: Homo sapiens

<400> SEQUENCE: 33

Met Ala His Ala Thr Leu Ser Ala Ala Pro Ser Asn Pro Arg Leu Leu
1               5                   10                  15

Arg Val Ala Leu Leu Leu Leu Leu Val Ala Ala Ser Arg Arg Ala
            20                  25                  30

Ala Gly Ala Ser Val Val Thr Glu Leu Arg Cys Gln Cys Leu Gln Thr
            35                  40                  45

Leu Gln Gly Ile His Leu Lys Asn Ile Gln Ser Val Asn Val Arg Ser
        50                  55                  60

Pro Gly Pro His Cys Ala Gln Thr Glu Val Ile Ala Thr Leu Lys Asn
65                  70                  75                  80

Gly Lys Lys Ala Cys Leu Asn Pro Ala Ser Pro Met Val Gln Lys Ile
                85                  90                  95

Ile Glu Lys Ile Leu Asn Lys Gly Ser Thr Asn
            100                 105

<210> SEQ ID NO 34
<211> LENGTH: 101
<212> TYPE: PRT
```

-continued

<213> ORGANISM: Homo sapiens

<400> SEQUENCE: 34

Met Ser Ser Ala Ala Gly Phe Cys Ala Ser Arg Pro Gly Leu Leu Phe
1               5                   10                  15

Leu Gly Leu Leu Leu Leu Pro Leu Val Val Ala Phe Ala Ser Ala Glu
            20                  25                  30

Ala Glu Glu Asp Gly Asp Leu Gln Cys Leu Cys Val Lys Thr Thr Ser
        35                  40                  45

Gln Val Arg Pro Arg His Ile Thr Ser Leu Glu Val Ile Lys Ala Gly
    50                  55                  60

Pro His Cys Pro Thr Ala Gln Leu Ile Ala Thr Leu Lys Asn Gly Arg
65                  70                  75                  80

Lys Ile Cys Leu Asp Leu Gln Ala Pro Leu Tyr Lys Lys Ile Ile Lys
                85                  90                  95

Lys Leu Leu Glu Ser
            100

<210> SEQ ID NO 35
<211> LENGTH: 114
<212> TYPE: PRT
<213> ORGANISM: Homo sapiens

<400> SEQUENCE: 35

Met Ser Leu Leu Ser Ser Arg Ala Ala Arg Val Pro Gly Pro Ser Ser
1               5                   10                  15

Ser Leu Cys Ala Leu Leu Val Leu Leu Leu Leu Thr Gln Pro Gly Gly
            20                  25                  30

Pro Ile Ala Ser Ala Gly Pro Ala Ala Ala Val Leu Arg Glu Leu Arg
        35                  40                  45

Cys Val Cys Leu Gln Thr Thr Gln Gly Val His Pro Lys Met Ile Ser
    50                  55                  60

Asn Leu Gln Val Phe Ala Ile Gly Pro Gln Cys Ser Lys Val Glu Val
65                  70                  75                  80

Val Ala Ser Leu Lys Asn Gly Lys Glu Ile Cys Leu Asp Pro Glu Ala
                85                  90                  95

Pro Phe Leu Lys Lys Val Ile Gln Lys Ile Leu Asp Gly Gly Asn Lys
            100                 105                 110

Glu Asn

<210> SEQ ID NO 36
<211> LENGTH: 114
<212> TYPE: PRT
<213> ORGANISM: Homo sapiens

<400> SEQUENCE: 36

Met Ser Leu Pro Ser Ser Arg Ala Ala Arg Val Pro Gly Pro Ser Gly
1               5                   10                  15

Ser Leu Cys Ala Leu Leu Ala Leu Leu Leu Leu Thr Pro Pro Gly Gly
            20                  25                  30

Pro Leu Ala Ser Ala Gly Pro Val Ser Ala Val Leu Thr Glu Leu Arg
        35                  40                  45

Cys Thr Cys Leu Arg Val Thr Leu Arg Val Asn Pro Lys Thr Ile Gly
    50                  55                  60

Lys Leu Gln Val Phe Pro Ala Gly Pro Gln Cys Ser Lys Val Glu Val
65                  70                  75                  80

```
Val Ala Ser Leu Lys Asn Gly Lys Gln Val Cys Leu Asp Pro Glu Ala
             85                  90                  95

Pro Phe Leu Lys Lys Val Ile Gln Lys Ile Leu Asp Ser Gly Asn Lys
            100                 105                 110

Lys Asn

<210> SEQ ID NO 37
<211> LENGTH: 128
<212> TYPE: PRT
<213> ORGANISM: Homo sapiens

<400> SEQUENCE: 37

Met Ser Leu Arg Leu Asp Thr Thr Pro Ser Cys Asn Ser Ala Arg Pro
1               5                   10                  15

Leu His Ala Leu Gln Val Leu Leu Leu Ser Leu Leu Leu Thr Ala
             20                  25                  30

Leu Ala Ser Ser Thr Lys Gly Gln Thr Lys Arg Asn Leu Ala Lys Gly
             35                  40                  45

Lys Glu Glu Ser Leu Asp Ser Asp Leu Tyr Ala Glu Leu Arg Cys Met
         50                  55                  60

Cys Ile Lys Thr Thr Ser Gly Ile His Pro Lys Asn Ile Gln Ser Leu
65                  70                  75                  80

Glu Val Ile Gly Lys Gly Thr His Cys Asn Gln Val Glu Val Ile Ala
             85                  90                  95

Thr Leu Lys Asp Gly Arg Lys Ile Cys Leu Asp Pro Asp Ala Pro Arg
            100                 105                 110

Ile Lys Lys Ile Val Gln Lys Lys Leu Ala Gly Asp Glu Ser Ala Asp
            115                 120                 125

<210> SEQ ID NO 38
<211> LENGTH: 99
<212> TYPE: PRT
<213> ORGANISM: Homo sapiens

<400> SEQUENCE: 38

Met Thr Ser Lys Leu Ala Val Ala Leu Leu Ala Ala Phe Leu Ile Ser
1               5                   10                  15

Ala Ala Leu Cys Glu Gly Ala Val Leu Pro Arg Ser Ala Lys Glu Leu
             20                  25                  30

Arg Cys Gln Cys Ile Lys Thr Tyr Ser Lys Pro Phe His Pro Lys Phe
             35                  40                  45

Ile Lys Glu Leu Arg Val Ile Glu Ser Gly Pro His Cys Ala Asn Thr
         50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
             85                  90                  95

Glu Asn Ser

<210> SEQ ID NO 39
<211> LENGTH: 125
<212> TYPE: PRT
<213> ORGANISM: Homo sapiens

<400> SEQUENCE: 39

Met Lys Lys Ser Gly Val Leu Phe Leu Leu Gly Ile Ile Leu Leu Val
1               5                   10                  15
```

-continued

Leu Ile Gly Val Gln Gly Thr Pro Val Val Arg Lys Gly Arg Cys Ser
            20                  25                  30

Cys Ile Ser Thr Asn Gln Gly Thr Ile His Leu Gln Ser Leu Lys Asp
        35                  40                  45

Leu Lys Gln Phe Ala Pro Ser Pro Ser Cys Glu Lys Ile Glu Ile Ile
 50                  55                  60

Ala Thr Leu Lys Asn Gly Val Gln Thr Cys Leu Asn Pro Asp Ser Ala
65                  70                  75                  80

Asp Val Lys Glu Leu Ile Lys Lys Trp Glu Lys Gln Val Ser Gln Lys
                85                  90                  95

Lys Lys Gln Lys Asn Gly Lys Lys His Gln Lys Lys Val Leu Lys
            100                 105                 110

Val Arg Lys Ser Gln Arg Ser Arg Gln Lys Lys Thr Thr
            115                 120                 125

<210> SEQ ID NO 40
<211> LENGTH: 98
<212> TYPE: PRT
<213> ORGANISM: Homo sapiens

<400> SEQUENCE: 40

Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
            20                  25                  30

Ile Ser Ile Ser Asn Gln Pro Val Asn Pro Arg Ser Leu Glu Lys Leu
        35                  40                  45

Glu Ile Ile Pro Ala Ser Gln Phe Cys Pro Arg Val Glu Ile Ile Ala
 50                  55                  60

Thr Met Lys Lys Lys Gly Glu Lys Arg Cys Leu Asn Pro Glu Ser Lys
65                  70                  75                  80

Ala Ile Lys Asn Leu Leu Lys Ala Val Ser Lys Glu Arg Ser Lys Arg
                85                  90                  95

Ser Pro

<210> SEQ ID NO 41
<211> LENGTH: 94
<212> TYPE: PRT
<213> ORGANISM: Homo sapiens

<400> SEQUENCE: 41

Met Ser Val Lys Gly Met Ala Ile Ala Leu Ala Val Ile Leu Cys Ala
1               5                   10                  15

Thr Val Val Gln Gly Phe Pro Met Phe Lys Arg Gly Arg Cys Leu Cys
            20                  25                  30

Ile Gly Pro Gly Val Lys Ala Val Lys Val Ala Asp Ile Glu Lys Ala
        35                  40                  45

Ser Ile Met Tyr Pro Ser Asn Asn Cys Asp Lys Ile Glu Val Ile Ile
 50                  55                  60

Thr Leu Lys Glu Asn Lys Gly Gln Arg Cys Leu Asn Pro Lys Ser Lys
65                  70                  75                  80

Gln Ala Arg Leu Ile Ile Lys Lys Val Glu Arg Lys Asn Phe
                85                  90

<210> SEQ ID NO 42
<211> LENGTH: 93
<212> TYPE: PRT

-continued

<213> ORGANISM: Homo sapiens

<400> SEQUENCE: 42

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
                35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Arg Phe Lys Met
                85                  90

<210> SEQ ID NO 43
<211> LENGTH: 109
<212> TYPE: PRT
<213> ORGANISM: Homo sapiens

<400> SEQUENCE: 43

Met Lys Phe Ile Ser Thr Ser Leu Leu Leu Met Leu Leu Val Ser Ser
1               5                   10                  15

Leu Ser Pro Val Gln Gly Val Leu Glu Val Tyr Tyr Thr Ser Leu Arg
            20                  25                  30

Cys Arg Cys Val Gln Glu Ser Ser Val Phe Ile Pro Arg Arg Phe Ile
        35                  40                  45

Asp Arg Ile Gln Ile Leu Pro Arg Gly Asn Gly Cys Pro Arg Lys Glu
    50                  55                  60

Ile Ile Val Trp Lys Lys Asn Lys Ser Ile Val Cys Val Asp Pro Gln
65                  70                  75                  80

Ala Glu Trp Ile Gln Arg Met Met Glu Val Leu Arg Lys Arg Ser Ser
                85                  90                  95

Ser Thr Leu Pro Val Pro Val Phe Lys Arg Lys Ile Pro
            100                 105

<210> SEQ ID NO 44
<211> LENGTH: 273
<212> TYPE: PRT
<213> ORGANISM: Homo sapiens

<400> SEQUENCE: 44

Met Ser Gly Ser Gln Ser Glu Val Ala Pro Ser Pro Gln Ser Pro Arg
1               5                   10                  15

Ser Pro Glu Met Gly Arg Asp Leu Arg Pro Gly Ser Arg Val Leu Leu
            20                  25                  30

Leu Leu Leu Leu Leu Leu Leu Val Tyr Leu Thr Gln Pro Gly Asn Gly
        35                  40                  45

Asn Glu Gly Ser Val Thr Gly Ser Cys Tyr Cys Gly Lys Arg Ile Ser
    50                  55                  60

Ser Asp Ser Pro Pro Ser Val Gln Phe Met Asn Arg Leu Arg Lys His
65                  70                  75                  80

Leu Arg Ala Tyr His Arg Cys Leu Tyr Tyr Thr Arg Phe Gln Leu Leu
                85                  90                  95

Ser Trp Ser Val Cys Gly Gly Asn Lys Asp Pro Trp Val Gln Glu Leu
            100                 105                 110

```
Met Ser Cys Leu Asp Leu Lys Glu Cys Gly His Ala Tyr Ser Gly Ile
            115                 120                 125
Val Ala His Gln Lys His Leu Leu Pro Thr Ser Pro Pro Ile Ser Gln
        130                 135                 140
Ala Ser Glu Gly Ala Ser Ser Asp Ile His Thr Pro Ala Gln Met Leu
145                 150                 155                 160
Leu Ser Thr Leu Gln Ser Thr Gln Arg Pro Thr Leu Pro Val Gly Ser
                165                 170                 175
Leu Ser Ser Asp Lys Glu Leu Thr Arg Pro Asn Glu Thr Thr Ile His
                180                 185                 190
Thr Ala Gly His Ser Leu Ala Ala Gly Pro Glu Ala Gly Glu Asn Gln
                195                 200                 205
Lys Gln Pro Glu Lys Asn Ala Gly Pro Thr Ala Arg Thr Ser Ala Thr
        210                 215                 220
Val Pro Val Leu Cys Leu Leu Ala Ile Ile Phe Ile Leu Thr Ala Ala
225                 230                 235                 240
Leu Ser Tyr Val Leu Cys Lys Arg Arg Arg Gly Gln Ser Pro Gln Ser
                245                 250                 255
Ser Pro Asp Leu Pro Val His Tyr Ile Pro Val Ala Pro Asp Ser Asn
                260                 265                 270
Thr

<210> SEQ ID NO 45
<211> LENGTH: 114
<212> TYPE: PRT
<213> ORGANISM: Homo sapiens

<400> SEQUENCE: 45

Met Arg Leu Leu Ile Leu Ala Leu Leu Gly Ile Cys Ser Leu Thr Ala
1               5                   10                  15
Tyr Ile Val Glu Gly Val Gly Ser Glu Val Ser Asp Lys Arg Thr Cys
            20                  25                  30
Val Ser Leu Thr Thr Gln Arg Leu Pro Val Ser Arg Ile Lys Thr Tyr
        35                  40                  45
Thr Ile Thr Glu Gly Ser Leu Arg Ala Val Ile Phe Ile Thr Lys Arg
    50                  55                  60
Gly Leu Lys Val Cys Ala Asp Pro Gln Ala Thr Trp Val Arg Asp Val
65                  70                  75                  80
Val Arg Ser Met Asp Arg Lys Ser Asn Thr Arg Asn Asn Met Ile Gln
                85                  90                  95
Thr Lys Pro Thr Gly Thr Gln Gln Ser Thr Asn Thr Ala Val Thr Leu
            100                 105                 110
Thr Gly

<210> SEQ ID NO 46
<211> LENGTH: 114
<212> TYPE: PRT
<213> ORGANISM: Homo sapiens

<400> SEQUENCE: 46

Met Arg Leu Leu Ile Leu Ala Leu Leu Gly Ile Cys Ser Leu Thr Ala
1               5                   10                  15
Tyr Ile Val Glu Gly Val Gly Ser Glu Val Ser His Arg Arg Thr Cys
            20                  25                  30
Val Ser Leu Thr Thr Gln Arg Leu Pro Val Ser Arg Ile Lys Thr Tyr
```

```
                    35                  40                  45
Thr Ile Thr Glu Gly Ser Leu Arg Ala Val Ile Phe Ile Thr Lys Arg
 50                  55                  60

Gly Leu Lys Val Cys Ala Asp Pro Gln Ala Thr Trp Val Arg Asp Val
 65                  70                  75                  80

Val Arg Ser Met Asp Arg Lys Ser Asn Thr Arg Asn Asn Met Ile Gln
                 85                  90                  95

Thr Lys Pro Thr Gly Thr Gln Gln Ser Thr Asn Thr Ala Val Thr Leu
                100                 105                 110

Thr Gly

<210> SEQ ID NO 47
<211> LENGTH: 397
<212> TYPE: PRT
<213> ORGANISM: Homo sapiens

<400> SEQUENCE: 47

Met Ala Pro Ile Ser Leu Ser Trp Leu Leu Arg Leu Ala Thr Phe Cys
  1               5                  10                  15

His Leu Thr Val Leu Leu Ala Gly Gln His His Gly Val Thr Lys Cys
                 20                  25                  30

Asn Ile Thr Cys Ser Lys Met Thr Ser Lys Ile Pro Val Ala Leu Leu
                 35                  40                  45

Ile His Tyr Gln Gln Asn Gln Ala Ser Cys Gly Lys Arg Ala Ile Ile
 50                  55                  60

Leu Glu Thr Arg Gln His Arg Leu Phe Cys Ala Asp Pro Lys Glu Gln
 65                  70                  75                  80

Trp Val Lys Asp Ala Met Gln His Leu Asp Arg Gln Ala Ala Ala Leu
                 85                  90                  95

Thr Arg Asn Gly Gly Thr Phe Glu Lys Gln Ile Gly Glu Val Lys Pro
                100                 105                 110

Arg Thr Thr Pro Ala Ala Gly Gly Met Asp Glu Ser Val Val Leu Glu
                115                 120                 125

Pro Glu Ala Thr Gly Glu Ser Ser Ser Leu Glu Pro Thr Pro Ser Ser
130                 135                 140

Gln Glu Ala Gln Arg Ala Leu Gly Thr Ser Pro Glu Leu Pro Thr Gly
145                 150                 155                 160

Val Thr Gly Ser Ser Gly Thr Arg Leu Pro Pro Thr Pro Lys Ala Gln
                165                 170                 175

Asp Gly Gly Pro Val Gly Thr Glu Leu Phe Arg Val Pro Pro Val Ser
                180                 185                 190

Thr Ala Ala Thr Trp Gln Ser Ser Ala Pro His Gln Pro Gly Pro Ser
                195                 200                 205

Leu Trp Ala Glu Ala Lys Thr Ser Glu Ala Pro Ser Thr Gln Asp Pro
210                 215                 220

Ser Thr Gln Ala Ser Thr Ala Ser Ser Pro Ala Pro Glu Glu Asn Ala
225                 230                 235                 240

Pro Ser Glu Gly Gln Arg Val Trp Gly Gln Gly Gln Ser Pro Arg Pro
                245                 250                 255

Glu Asn Ser Leu Glu Arg Glu Glu Met Gly Pro Val Pro Ala His Thr
                260                 265                 270

Asp Ala Phe Gln Asp Trp Gly Pro Gly Ser Met Ala His Val Ser Val
                275                 280                 285

Val Pro Val Ser Ser Glu Gly Thr Pro Ser Arg Glu Pro Val Ala Ser
```

```
                290             295             300
Gly Ser Trp Thr Pro Lys Ala Glu Pro Ile His Ala Thr Met Asp
305                 310                 315                 320

Pro Gln Arg Leu Gly Val Leu Ile Thr Pro Val Pro Asp Ala Gln Ala
                325                 330                 335

Ala Thr Arg Arg Gln Ala Val Gly Leu Ala Phe Leu Gly Leu Leu
                340                 345                 350

Phe Cys Leu Gly Val Ala Met Phe Thr Tyr Gln Ser Leu Gln Gly Cys
                355                 360                 365

Pro Arg Lys Met Ala Gly Glu Met Ala Glu Gly Leu Arg Tyr Ile Pro
                370                 375                 380

Arg Ser Cys Gly Ser Asn Ser Tyr Val Leu Val Pro Val
385                 390                 395

<210> SEQ ID NO 48
<211> LENGTH: 233
<212> TYPE: PRT
<213> ORGANISM: Homo sapiens

<400> SEQUENCE: 48

Ser Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
                20                  25                  30

Pro Lys Asp Thr Leu Met Ile Ser Arg Thr Pro Glu Val Thr Cys Val
                35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
                100                 105                 110

Ala Leu Pro Ala Pro Ile Glu Lys Thr Ile Ser Lys Ala Lys Gly Gln
                115                 120                 125

Pro Arg Glu Pro Gln Val Tyr Thr Leu Pro Pro Ser Arg Asp Glu Leu
                130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
                180                 185                 190

Tyr Ser Lys Leu Thr Val Asp Lys Ser Arg Trp Gln Gln Gly Asn Val
                195                 200                 205

Phe Ser Cys Ser Val Met His Glu Ala Leu His Asn His Tyr Thr Gln
                210                 215                 220

Lys Ser Leu Ser Leu Ser Pro Gly Lys
225                 230

<210> SEQ ID NO 49
<211> LENGTH: 228
<212> TYPE: PRT
<213> ORGANISM: Homo sapiens
```

<400> SEQUENCE: 49

```
Glu Arg Lys Cys Cys Val Glu Cys Pro Pro Cys Pro Ala Pro Pro Val
1               5                   10                  15
Ala Gly Pro Ser Val Phe Leu Phe Pro Pro Lys Pro Lys Asp Thr Leu
            20                  25                  30
Met Ile Ser Arg Thr Pro Glu Val Thr Cys Val Val Val Asp Val Ser
        35                  40                  45
His Glu Asp Pro Glu Val Gln Phe Asn Trp Tyr Val Asp Gly Val Glu
    50                  55                  60
Val His Asn Ala Lys Thr Lys Pro Arg Glu Glu Gln Phe Asn Ser Thr
65                  70                  75                  80
Phe Arg Val Val Ser Val Leu Thr Val Val His Gln Asp Trp Leu Asn
                85                  90                  95
Gly Lys Glu Tyr Lys Cys Lys Val Ser Asn Lys Gly Leu Pro Ala Pro
            100                 105                 110
Ile Glu Lys Thr Ile Ser Lys Thr Lys Gly Gln Pro Arg Glu Pro Gln
        115                 120                 125
Val Tyr Thr Leu Pro Pro Ser Arg Glu Glu Met Thr Lys Asn Gln Val
    130                 135                 140
Ser Leu Thr Cys Leu Val Lys Gly Phe Tyr Pro Ser Asp Ile Ala Val
145                 150                 155                 160
Glu Trp Glu Ser Asn Gly Gln Pro Glu Asn Asn Tyr Lys Thr Thr Pro
                165                 170                 175
Pro Met Leu Asp Ser Asp Gly Ser Phe Phe Leu Tyr Ser Lys Leu Thr
            180                 185                 190
Val Asp Lys Ser Arg Trp Gln Gln Gly Asn Val Phe Ser Cys Ser Val
        195                 200                 205
Met His Glu Ala Leu His Asn His Tyr Thr Gln Lys Ser Leu Ser Leu
    210                 215                 220
Ser Pro Gly Lys
225
```

<210> SEQ ID NO 50
<211> LENGTH: 279
<212> TYPE: PRT
<213> ORGANISM: Homo sapiens

<400> SEQUENCE: 50

```
Glu Leu Lys Thr Pro Leu Gly Asp Thr Thr His Thr Cys Pro Arg Cys
1               5                   10                  15
Pro Glu Pro Lys Ser Cys Asp Thr Pro Pro Cys Pro Arg Cys Pro
            20                  25                  30
Glu Pro Lys Ser Cys Asp Thr Pro Pro Cys Pro Arg Cys Pro Glu
        35                  40                  45
Pro Lys Ser Cys Asp Thr Pro Pro Cys Pro Arg Cys Pro Ala Pro
    50                  55                  60
Glu Leu Leu Gly Gly Pro Ser Val Phe Leu Phe Pro Pro Lys Pro Lys
65                  70                  75                  80
Asp Thr Leu Met Ile Ser Arg Thr Pro Glu Val Thr Cys Val Val Val
                85                  90                  95
Asp Val Ser His Glu Asp Pro Glu Val Gln Phe Lys Trp Tyr Val Asp
            100                 105                 110
Gly Val Glu Val His Asn Ala Lys Thr Lys Pro Arg Glu Glu Gln Phe
        115                 120                 125
```

```
Asn Ser Thr Phe Arg Val Val Ser Val Leu Thr Val Leu His Gln Asp
        130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Met Thr Lys
                180                 185                 190

Asn Gln Val Ser Leu Thr Cys Leu Val Lys Gly Phe Tyr Pro Ser Asp
                195                 200                 205

Ile Ala Val Glu Trp Glu Ser Ser Gly Gln Pro Glu Asn Asn Tyr Asn
210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
                260                 265                 270

Leu Ser Leu Ser Pro Gly Lys
        275

<210> SEQ ID NO 51
<211> LENGTH: 229
<212> TYPE: PRT
<213> ORGANISM: Homo sapiens

<400> SEQUENCE: 51

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
        50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Val His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
                180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
210                 215                 220
```

Leu Ser Leu Gly Lys
225

<210> SEQ ID NO 52
<211> LENGTH: 303
<212> TYPE: PRT
<213> ORGANISM: Artificial Sequence
<220> FEATURE:
<223> OTHER INFORMATION: CCL2-IgG1Fc

<400> SEQUENCE: 52

```
Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr Asp Lys Thr His
65                  70                  75                  80

Thr Cys Pro Pro Cys Pro Ala Pro Glu Leu Leu Gly Gly Pro Ser Val
                85                  90                  95

Phe Leu Phe Pro Pro Lys Pro Lys Asp Thr Leu Met Ile Ser Arg Thr
            100                 105                 110

Pro Glu Val Thr Cys Val Val Val Asp Val Ser His Glu Asp Pro Glu
        115                 120                 125

Val Lys Phe Asn Trp Tyr Val Asp Gly Val Glu Val His Asn Ala Lys
    130                 135                 140

Thr Lys Pro Arg Glu Glu Gln Tyr Asn Ser Thr Tyr Arg Val Val Ser
145                 150                 155                 160

Val Leu Thr Val Leu His Gln Asp Trp Leu Asn Gly Lys Glu Tyr Lys
                165                 170                 175

Cys Lys Val Ser Asn Lys Ala Leu Pro Ala Pro Ile Glu Lys Thr Ile
            180                 185                 190

Ser Lys Ala Lys Gly Gln Pro Arg Glu Pro Gln Val Tyr Thr Leu Pro
        195                 200                 205

Pro Ser Arg Glu Glu Met Thr Lys Asn Gln Val Ser Leu Thr Cys Leu
    210                 215                 220

Val Lys Gly Phe Tyr Pro Ser Asp Ile Ala Val Glu Trp Glu Ser Asn
225                 230                 235                 240

Gly Gln Pro Glu Asn Asn Tyr Lys Thr Thr Pro Pro Val Leu Asp Ser
                245                 250                 255

Asp Gly Ser Phe Phe Leu Tyr Ser Lys Leu Thr Val Asp Lys Ser Arg
            260                 265                 270

Trp Gln Gln Gly Asn Val Phe Ser Cys Ser Val Met His Glu Ala Leu
        275                 280                 285

His Asn His Tyr Thr Gln Lys Ser Leu Ser Leu Ser Pro Gly Lys
    290                 295                 300
```

<210> SEQ ID NO 53
<211> LENGTH: 309
<212> TYPE: PRT
<213> ORGANISM: Artificial Sequence
<220> FEATURE:
<223> OTHER INFORMATION: CCL2(5-76)-IgG1Fc

<400> SEQUENCE: 53

```
Ala Leu Ser Leu Ala Leu Val Thr Asn Ser Ile Asn Ala Pro Val Thr
1               5                   10                  15

Cys Cys Tyr Asn Phe Thr Asn Arg Lys Ile Ser Val Gln Arg Leu Ala
            20                  25                  30

Ser Tyr Arg Arg Ile Thr Ser Ser Lys Cys Pro Lys Glu Ala Val Ile
        35                  40                  45

Phe Lys Thr Ile Val Ala Lys Glu Ile Cys Ala Asp Pro Lys Gln Lys
50                  55                  60

Trp Val Gln Asp Ser Met Asp His Leu Asp Lys Gln Thr Gln Thr Pro
65                  70                  75                  80

Lys Thr Asp Lys Thr His Thr Cys Pro Pro Cys Pro Ala Pro Glu Leu
                85                  90                  95

Leu Gly Gly Pro Ser Val Phe Leu Phe Pro Pro Lys Pro Lys Asp Thr
            100                 105                 110

Leu Met Ile Ser Arg Thr Pro Glu Val Thr Cys Val Val Val Asp Val
        115                 120                 125

Ser His Glu Asp Pro Glu Val Lys Phe Asn Trp Tyr Val Asp Gly Val
130                 135                 140

Glu Val His Asn Ala Lys Thr Lys Pro Arg Glu Glu Gln Tyr Asn Ser
145                 150                 155                 160

Thr Tyr Arg Val Val Ser Val Leu Thr Val Leu His Gln Asp Trp Leu
                165                 170                 175

Asn Gly Lys Glu Tyr Lys Cys Lys Val Ser Asn Lys Ala Leu Pro Ala
            180                 185                 190

Pro Ile Glu Lys Thr Ile Ser Lys Ala Lys Gly Gln Pro Arg Glu Pro
        195                 200                 205

Gln Val Tyr Thr Leu Pro Pro Ser Arg Glu Glu Met Thr Lys Asn Gln
210                 215                 220

Val Ser Leu Thr Cys Leu Val Lys Gly Phe Tyr Pro Ser Asp Ile Ala
225                 230                 235                 240

Val Glu Trp Glu Ser Asn Gly Gln Pro Glu Asn Asn Tyr Lys Thr Thr
                245                 250                 255

Pro Pro Val Leu Asp Ser Asp Gly Ser Phe Phe Leu Tyr Ser Lys Leu
            260                 265                 270

Thr Val Asp Lys Ser Arg Trp Gln Gln Gly Asn Val Phe Ser Cys Ser
        275                 280                 285

Val Met His Glu Ala Leu His Asn His Tyr Thr Gln Lys Ser Leu Ser
290                 295                 300

Leu Ser Pro Gly Lys
305
```

<210> SEQ ID NO 54
<211> LENGTH: 299
<212> TYPE: PRT
<213> ORGANISM: Artificial Sequence
<220> FEATURE:
<223> OTHER INFORMATION: CCL2(5-76K/H-A)-IgG1Fc

<400> SEQUENCE: 54

```
Ile Asn Ala Pro Val Thr Cys Cys Tyr Asn Phe Thr Asn Arg Lys Ile
1               5                   10                  15

Ser Val Gln Arg Leu Ala Ser Tyr Arg Arg Ile Thr Ser Ser Lys Cys
            20                  25                  30

Pro Lys Glu Ala Val Ile Phe Lys Thr Ile Val Ala Ala Glu Ile Cys
```

```
                35                  40                  45
Ala Asp Pro Ala Gln Ala Trp Val Gln Asp Ser Met Asp Ala Leu Asp
 50                  55                  60

Ala Gln Thr Gln Thr Pro Ala Thr Asp Lys Thr His Thr Cys Pro Pro
 65                  70                  75                  80

Cys Pro Ala Pro Glu Leu Leu Gly Gly Pro Ser Val Phe Leu Phe Pro
                 85                  90                  95

Pro Lys Pro Lys Asp Thr Leu Met Ile Ser Arg Thr Pro Glu Val Thr
            100                 105                 110

Cys Val Val Val Asp Val Ser His Glu Asp Pro Glu Val Lys Phe Asn
        115                 120                 125

Trp Tyr Val Asp Gly Val Glu Val His Asn Ala Lys Thr Lys Pro Arg
    130                 135                 140

Glu Glu Gln Tyr Asn Ser Thr Tyr Arg Val Val Ser Val Leu Thr Val
145                 150                 155                 160

Leu His Gln Asp Trp Leu Asn Gly Lys Glu Tyr Lys Cys Lys Val Ser
                165                 170                 175

Asn Lys Ala Leu Pro Ala Pro Ile Glu Lys Thr Ile Ser Lys Ala Lys
            180                 185                 190

Gly Gln Pro Arg Glu Pro Gln Val Tyr Thr Leu Pro Pro Ser Arg Glu
        195                 200                 205

Glu Met Thr Lys Asn Gln Val Ser Leu Thr Cys Leu Val Lys Gly Phe
    210                 215                 220

Tyr Pro Ser Asp Ile Ala Val Glu Trp Glu Ser Asn Gly Gln Pro Glu
225                 230                 235                 240

Asn Asn Tyr Lys Thr Thr Pro Pro Val Leu Asp Ser Asp Gly Ser Phe
                245                 250                 255

Phe Leu Tyr Ser Lys Leu Thr Val Asp Lys Ser Arg Trp Gln Gln Gly
            260                 265                 270

Asn Val Phe Ser Cys Ser Val Met His Glu Ala Leu His Asn His Tyr
        275                 280                 285

Thr Gln Lys Ser Leu Ser Leu Ser Pro Gly Lys
    290                 295

<210> SEQ ID NO 55
<211> LENGTH: 289
<212> TYPE: PRT
<213> ORGANISM: Artificial Sequence
<220> FEATURE:
<223> OTHER INFORMATION: CCL7-IgG1Fc

<400> SEQUENCE: 55

Phe Ile Asn Lys Lys Ile Pro Lys Gln Arg Leu Glu Ser Tyr Arg Arg
 1               5                  10                  15

Thr Thr Ser Ser His Cys Pro Arg Glu Ala Val Ile Phe Lys Thr Lys
             20                  25                  30

Leu Asp Lys Glu Ile Cys Ala Asp Pro Thr Gln Lys Trp Val Gln Asp
         35                  40                  45

Phe Met Lys His Leu Asp Lys Lys Thr Gln Thr Pro Lys Leu Asp Lys
     50                  55                  60

Thr His Thr Cys Pro Pro Cys Pro Ala Pro Glu Leu Leu Gly Gly Pro
 65                  70                  75                  80

Ser Val Phe Leu Phe Pro Pro Lys Pro Lys Asp Thr Leu Met Ile Ser
                 85                  90                  95

Arg Thr Pro Glu Val Thr Cys Val Val Val Asp Val Ser His Glu Asp
```

```
                 100                 105                 110
Pro Glu Val Lys Phe Asn Trp Tyr Val Asp Gly Val Glu Val His Asn
            115                 120                 125

Ala Lys Thr Lys Pro Arg Glu Glu Gln Tyr Asn Ser Thr Tyr Arg Val
130                 135                 140

Val Ser Val Leu Thr Val Leu His Gln Asp Trp Leu Asn Gly Lys Glu
145                 150                 155                 160

Tyr Lys Cys Lys Val Ser Asn Lys Ala Leu Pro Ala Pro Ile Glu Lys
                165                 170                 175

Thr Ile Ser Lys Ala Lys Gly Gln Pro Arg Glu Pro Gln Val Tyr Thr
            180                 185                 190

Leu Pro Pro Ser Arg Glu Glu Met Thr Lys Asn Gln Val Ser Leu Thr
            195                 200                 205

Cys Leu Val Lys Gly Phe Tyr Pro Ser Asp Ile Ala Val Glu Trp Glu
    210                 215                 220

Ser Asn Gly Gln Pro Glu Asn Asn Tyr Lys Thr Thr Pro Pro Val Leu
225                 230                 235                 240

Asp Ser Asp Gly Ser Phe Phe Leu Tyr Ser Lys Leu Thr Val Asp Lys
                245                 250                 255

Ser Arg Trp Gln Gln Gly Asn Val Phe Ser Cys Ser Val Met His Glu
            260                 265                 270

Ala Leu His Asn His Tyr Thr Gln Lys Ser Leu Ser Leu Ser Pro Gly
            275                 280                 285

Lys

<210> SEQ ID NO 56
<211> LENGTH: 293
<212> TYPE: PRT
<213> ORGANISM: Artificial Sequence
<220> FEATURE:
<223> OTHER INFORMATION: CCL7(5-76)-IgGFc

<400> SEQUENCE: 56

Cys Cys Tyr Arg Phe Ile Asn Lys Lys Ile Pro Lys Gln Arg Leu Glu
1               5                   10                  15

Ser Tyr Arg Arg Thr Thr Ser Ser His Cys Pro Arg Glu Ala Val Ile
            20                  25                  30

Phe Lys Thr Lys Leu Asp Lys Glu Ile Cys Ala Asp Pro Thr Gln Lys
        35                  40                  45

Trp Val Gln Asp Phe Met Lys His Leu Asp Lys Lys Thr Gln Thr Pro
50                  55                  60

Lys Leu Asp Lys Thr His Thr Cys Pro Pro Cys Pro Ala Pro Glu Leu
65                  70                  75                  80

Leu Gly Gly Pro Ser Val Phe Leu Phe Pro Pro Lys Pro Lys Asp Thr
                85                  90                  95

Leu Met Ile Ser Arg Thr Pro Glu Val Thr Cys Val Val Val Asp Val
            100                 105                 110

Ser His Glu Asp Pro Glu Val Lys Phe Asn Trp Tyr Val Asp Gly Val
        115                 120                 125

Glu Val His Asn Ala Lys Thr Lys Pro Arg Glu Glu Gln Tyr Asn Ser
    130                 135                 140

Thr Tyr Arg Val Val Ser Val Leu Thr Val Leu His Gln Asp Trp Leu
145                 150                 155                 160

Asn Gly Lys Glu Tyr Lys Cys Lys Val Ser Asn Lys Ala Leu Pro Ala
                165                 170                 175
```

```
Pro Ile Glu Lys Thr Ile Ser Lys Ala Lys Gly Gln Pro Arg Glu Pro
            180                 185                 190

Gln Val Tyr Thr Leu Pro Pro Ser Arg Glu Glu Met Thr Lys Asn Gln
        195                 200                 205

Val Ser Leu Thr Cys Leu Val Lys Gly Phe Tyr Pro Ser Asp Ile Ala
210                 215                 220

Val Glu Trp Glu Ser Asn Gly Gln Pro Glu Asn Asn Tyr Lys Thr Thr
225                 230                 235                 240

Pro Pro Val Leu Asp Ser Asp Gly Ser Phe Phe Leu Tyr Ser Lys Leu
                245                 250                 255

Thr Val Asp Lys Ser Arg Trp Gln Gln Gly Asn Val Phe Ser Cys Ser
            260                 265                 270

Val Met His Glu Ala Leu His Asn His Tyr Thr Gln Lys Ser Leu Ser
        275                 280                 285

Leu Ser Pro Gly Lys
    290

<210> SEQ ID NO 57
<211> LENGTH: 289
<212> TYPE: PRT
<213> ORGANISM: Artificial Sequence
<220> FEATURE:
<223> OTHER INFORMATION: CCL7(5-76K/H-A)-IgGFc

<400> SEQUENCE: 57

Phe Ile Asn Lys Lys Ile Pro Lys Gln Arg Leu Glu Ser Tyr Arg Arg
1               5                   10                  15

Thr Thr Ser Ser His Cys Pro Arg Glu Ala Val Ile Phe Ala Thr Ala
            20                  25                  30

Leu Asp Ala Glu Ile Cys Ala Asp Pro Thr Gln Ala Trp Val Gln Asp
        35                  40                  45

Phe Met Ala Ala Leu Asp Ala Ala Thr Gln Thr Pro Ala Leu Asp Lys
    50                  55                  60

Thr His Thr Cys Pro Pro Cys Pro Ala Pro Glu Leu Leu Gly Gly Pro
65                  70                  75                  80

Ser Val Phe Leu Phe Pro Pro Lys Pro Lys Asp Thr Leu Met Ile Ser
                85                  90                  95

Arg Thr Pro Glu Val Thr Cys Val Val Val Asp Val Ser His Glu Asp
            100                 105                 110

Pro Glu Val Lys Phe Asn Trp Tyr Val Asp Gly Val Glu Val His Asn
        115                 120                 125

Ala Lys Thr Lys Pro Arg Glu Glu Gln Tyr Asn Ser Thr Tyr Arg Val
    130                 135                 140

Val Ser Val Leu Thr Val Leu His Gln Asp Trp Leu Asn Gly Lys Glu
145                 150                 155                 160

Tyr Lys Cys Lys Val Ser Asn Lys Ala Leu Pro Ala Pro Ile Glu Lys
                165                 170                 175

Thr Ile Ser Lys Ala Lys Gly Gln Pro Arg Glu Pro Gln Val Tyr Thr
            180                 185                 190

Leu Pro Pro Ser Arg Glu Glu Met Thr Lys Asn Gln Val Ser Leu Thr
        195                 200                 205

Cys Leu Val Lys Gly Phe Tyr Pro Ser Asp Ile Ala Val Glu Trp Glu
    210                 215                 220

Ser Asn Gly Gln Pro Glu Asn Asn Tyr Lys Thr Thr Pro Pro Val Leu
225                 230                 235                 240
```

Asp Ser Asp Gly Ser Phe Phe Leu Tyr Ser Lys Leu Thr Val Asp Lys
            245                 250                 255

Ser Arg Trp Gln Gln Gly Asn Val Phe Ser Cys Ser Val Met His Glu
        260                 265                 270

Ala Leu His Asn His Tyr Thr Gln Lys Ser Leu Ser Leu Ser Pro Gly
        275                 280                 285

Lys

<210> SEQ ID NO 58
<211> LENGTH: 303
<212> TYPE: PRT
<213> ORGANISM: Artificial Sequence
<220> FEATURE:
<223> OTHER INFORMATION: CCL8-IgG1Fc

<400> SEQUENCE: 58

Gln Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
            20                  25                  30

Asn Ile Gln Cys Pro Lys Glu Ala Val Ile Phe Lys Thr Lys Arg Gly
        35                  40                  45

Lys Glu Val Cys Ala Asp Pro Lys Glu Arg Trp Val Arg Asp Ser Met
50                  55                  60

Lys His Leu Asp Gln Ile Phe Gln Asn Leu Lys Pro Asp Lys Thr His
65                  70                  75                  80

Thr Cys Pro Pro Cys Pro Ala Pro Glu Leu Leu Gly Gly Pro Ser Val
                85                  90                  95

Phe Leu Phe Pro Pro Lys Pro Lys Asp Thr Leu Met Ile Ser Arg Thr
            100                 105                 110

Pro Glu Val Thr Cys Val Val Val Asp Val Ser His Glu Asp Pro Glu
        115                 120                 125

Val Lys Phe Asn Trp Tyr Val Asp Gly Val Glu Val His Asn Ala Lys
130                 135                 140

Thr Lys Pro Arg Glu Glu Gln Tyr Asn Ser Thr Tyr Arg Val Val Ser
145                 150                 155                 160

Val Leu Thr Val Leu His Gln Asp Trp Leu Asn Gly Lys Glu Tyr Lys
                165                 170                 175

Cys Lys Val Ser Asn Lys Ala Leu Pro Ala Pro Ile Glu Lys Thr Ile
            180                 185                 190

Ser Lys Ala Lys Gly Gln Pro Arg Glu Pro Gln Val Tyr Thr Leu Pro
        195                 200                 205

Pro Ser Arg Glu Glu Met Thr Lys Asn Gln Val Ser Leu Thr Cys Leu
210                 215                 220

Val Lys Gly Phe Tyr Pro Ser Asp Ile Ala Val Glu Trp Glu Ser Asn
225                 230                 235                 240

Gly Gln Pro Glu Asn Asn Tyr Lys Thr Thr Pro Pro Val Leu Asp Ser
                245                 250                 255

Asp Gly Ser Phe Phe Leu Tyr Ser Lys Leu Thr Val Asp Lys Ser Arg
            260                 265                 270

Trp Gln Gln Gly Asn Val Phe Ser Cys Ser Val Met His Glu Ala Leu
        275                 280                 285

His Asn His Tyr Thr Gln Lys Ser Leu Ser Leu Ser Pro Gly Lys
    290                 295                 300

<210> SEQ ID NO 59
<211> LENGTH: 299
<212> TYPE: PRT
<213> ORGANISM: Artificial Sequence
<220> FEATURE:
<223> OTHER INFORMATION: CCL8(5-76)-IgG1Fc

<400> SEQUENCE: 59

```
Val Ser Ile Pro Ile Thr Cys Cys Phe Asn Val Ile Asn Arg Lys Ile
1               5                   10                  15

Pro Ile Gln Arg Leu Glu Ser Tyr Thr Arg Ile Thr Asn Ile Gln Cys
            20                  25                  30

Pro Lys Glu Ala Val Ile Phe Lys Thr Lys Arg Gly Lys Glu Val Cys
        35                  40                  45

Ala Asp Pro Lys Glu Arg Trp Val Arg Asp Ser Met Lys His Leu Asp
    50                  55                  60

Gln Ile Phe Gln Asn Leu Lys Pro Asp Lys Thr His Thr Cys Pro Pro
65                  70                  75                  80

Cys Pro Ala Pro Glu Leu Leu Gly Gly Pro Ser Val Phe Leu Phe Pro
                85                  90                  95

Pro Lys Pro Lys Asp Thr Leu Met Ile Ser Arg Thr Pro Glu Val Thr
            100                 105                 110

Cys Val Val Val Asp Val Ser His Glu Asp Pro Glu Val Lys Phe Asn
        115                 120                 125

Trp Tyr Val Asp Gly Val Glu Val His Asn Ala Lys Thr Lys Pro Arg
    130                 135                 140

Glu Glu Gln Tyr Asn Ser Thr Tyr Arg Val Val Ser Val Leu Thr Val
145                 150                 155                 160

Leu His Gln Asp Trp Leu Asn Gly Lys Glu Tyr Lys Cys Lys Val Ser
                165                 170                 175

Asn Lys Ala Leu Pro Ala Pro Ile Glu Lys Thr Ile Ser Lys Ala Lys
            180                 185                 190

Gly Gln Pro Arg Glu Pro Gln Val Tyr Thr Leu Pro Pro Ser Arg Glu
        195                 200                 205

Glu Met Thr Lys Asn Gln Val Ser Leu Thr Cys Leu Val Lys Gly Phe
    210                 215                 220

Tyr Pro Ser Asp Ile Ala Val Glu Trp Glu Ser Asn Gly Gln Pro Glu
225                 230                 235                 240

Asn Asn Tyr Lys Thr Thr Pro Pro Val Leu Asp Ser Asp Gly Ser Phe
                245                 250                 255

Phe Leu Tyr Ser Lys Leu Thr Val Asp Lys Ser Arg Trp Gln Gln Gly
            260                 265                 270

Asn Val Phe Ser Cys Ser Val Met His Glu Ala Leu His Asn His Tyr
        275                 280                 285

Thr Gln Lys Ser Leu Ser Leu Ser Pro Gly Lys
    290                 295
```

<210> SEQ ID NO 60
<211> LENGTH: 265
<212> TYPE: PRT
<213> ORGANISM: Artificial Sequence
<220> FEATURE:
<223> OTHER INFORMATION: CCL8(5-76K/H-A)-IgG1Fc

<400> SEQUENCE: 60

```
Val Ser Ile Pro Ile Thr Cys Cys Phe Asn Val Ile Asn Arg Lys Ile
1               5                   10                  15
```

```
Pro Ile Gln Arg Leu Glu Ser Tyr Thr Arg Ile Thr Asn Ile Gln Cys
            20                  25                  30

Pro Lys Glu Ala Val Ile Phe Lys Thr Ala Ala Gly Ala Glu Val Cys
        35                  40                  45

Ala Asp Pro Ala Glu Ala Trp Val Ala Asp Ser Met Ala Ala Leu Asp
 50                  55                  60

Gln Ile Phe Gln Asn Leu Ala Pro Asp Lys Thr His Thr Cys Pro Pro
 65                  70                  75                  80

Cys Pro Ala Pro Glu Leu Leu Gly Gly Pro Ser Val Phe Leu Phe Pro
                 85                  90                  95

Pro Lys Pro Lys Asp Thr Leu Met Ile Ser Arg Thr Pro Glu Val Thr
                100                 105                 110

Cys Val Val Val Asp Val Ser His Glu Asp Pro Glu Val Lys Phe Asn
            115                 120                 125

Trp Tyr Val Asp Gly Val Glu Val His Asn Ala Lys Thr Lys Pro Arg
130                 135                 140

Glu Glu Gln Tyr Asn Ser Thr Tyr Arg Val Val Ser Val Leu Thr Val
145                 150                 155                 160

Leu His Gln Asp Trp Leu Asn Gly Lys Glu Tyr Lys Cys Lys Val Ser
                165                 170                 175

Asn Lys Ala Leu Pro Ala Pro Ile Glu Lys Thr Ile Ser Lys Ala Lys
            180                 185                 190

Gly Gln Pro Arg Glu Pro Gln Val Tyr Thr Leu Pro Pro Ser Arg Glu
        195                 200                 205

Glu Met Thr Lys Asn Gln Val Ser Leu Thr Cys Leu Val Lys Gly Phe
    210                 215                 220

Tyr Pro Ser Asp Ile Ala Val Glu Trp Glu Ser Asn Gly Gln Pro Glu
225                 230                 235                 240

Asn Asn Tyr Lys Thr Thr Pro Pro Val Leu Asp Ser Asp Gly Ser Phe
                245                 250                 255

Lys Ser Leu Ser Leu Ser Pro Gly Lys
                260                 265

<210> SEQ ID NO 61
<211> LENGTH: 302
<212> TYPE: PRT
<213> ORGANISM: Artificial Sequence
<220> FEATURE:
<223> OTHER INFORMATION: CCL13-IgG1Fc

<400> SEQUENCE: 61

Gln Pro Asp Ala Leu Asn Val Pro Ser Thr Cys Cys Phe Thr Phe Ser
 1               5                  10                  15

Ser Lys Lys Ile Ser Leu Gln Arg Leu Lys Ser Tyr Val Ile Thr Thr
            20                  25                  30

Ser Arg Cys Pro Gln Lys Ala Val Ile Phe Arg Thr Lys Leu Gly Lys
        35                  40                  45

Glu Ile Cys Ala Asp Pro Lys Glu Lys Trp Val Gln Asn Tyr Met Lys
 50                  55                  60

His Leu Gly Arg Lys Ala His Thr Leu Lys Thr Asp Lys Thr His Thr
 65                  70                  75                  80

Cys Pro Pro Cys Pro Ala Pro Glu Leu Leu Gly Gly Pro Ser Val Phe
                 85                  90                  95

Leu Phe Pro Pro Lys Pro Lys Asp Thr Leu Met Ile Ser Arg Thr Pro
                100                 105                 110
```

Glu Val Thr Cys Val Val Val Asp Val Ser His Glu Asp Pro Glu Val
            115                 120                 125

Lys Phe Asn Trp Tyr Val Asp Gly Val Glu Val His Asn Ala Lys Thr
130                 135                 140

Lys Pro Arg Glu Glu Gln Tyr Asn Ser Thr Tyr Arg Val Val Ser Val
145                 150                 155                 160

Leu Thr Val Leu His Gln Asp Trp Leu Asn Gly Lys Glu Tyr Lys Cys
            165                 170                 175

Lys Val Ser Asn Lys Ala Leu Pro Ala Pro Ile Glu Lys Thr Ile Ser
            180                 185                 190

Lys Ala Lys Gly Gln Pro Arg Glu Pro Gln Val Tyr Thr Leu Pro Pro
            195                 200                 205

Ser Arg Glu Glu Met Thr Lys Asn Gln Val Ser Leu Thr Cys Leu Val
            210                 215                 220

Lys Gly Phe Tyr Pro Ser Asp Ile Ala Val Glu Trp Glu Ser Asn Gly
225                 230                 235                 240

Gln Pro Glu Asn Asn Tyr Lys Thr Thr Pro Pro Val Leu Asp Ser Asp
            245                 250                 255

Gly Ser Phe Phe Leu Tyr Ser Lys Leu Thr Val Asp Lys Ser Arg Trp
            260                 265                 270

Gln Gln Gly Asn Val Phe Ser Cys Ser Val Met His Glu Ala Leu His
            275                 280                 285

Asn His Tyr Thr Gln Lys Ser Leu Ser Leu Ser Pro Gly Lys
            290                 295                 300

<210> SEQ ID NO 62
<211> LENGTH: 298
<212> TYPE: PRT
<213> ORGANISM: Artificial Sequence
<220> FEATURE:
<223> OTHER INFORMATION: CCL13(5-75)-IgG1Fc

<400> SEQUENCE: 62

Leu Asn Val Pro Ser Thr Cys Cys Phe Thr Phe Ser Ser Lys Lys Ile
1               5                   10                  15

Ser Leu Gln Arg Leu Lys Ser Tyr Val Ile Thr Thr Ser Arg Cys Pro
            20                  25                  30

Gln Lys Ala Val Ile Phe Arg Thr Lys Leu Gly Lys Glu Ile Cys Ala
            35                  40                  45

Asp Pro Lys Glu Lys Trp Val Gln Asn Tyr Met Lys His Leu Gly Arg
50                  55                  60

Lys Ala His Thr Leu Lys Thr Asp Lys Thr His Thr Cys Pro Pro Cys
65                  70                  75                  80

Pro Ala Pro Glu Leu Leu Gly Gly Pro Ser Val Phe Leu Phe Pro Pro
            85                  90                  95

Lys Pro Lys Asp Thr Leu Met Ile Ser Arg Thr Pro Glu Val Thr Cys
            100                 105                 110

Val Val Val Asp Val Ser His Glu Asp Pro Glu Val Lys Phe Asn Trp
            115                 120                 125

Tyr Val Asp Gly Val Glu Val His Asn Ala Lys Thr Lys Pro Arg Glu
130                 135                 140

Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
            165                 170                 175

```
Lys Ala Leu Pro Ala Pro Ile Glu Lys Thr Ile Ser Lys Ala Lys Gly
            180                 185                 190

Gln Pro Arg Glu Pro Gln Val Tyr Thr Leu Pro Pro Ser Arg Glu Glu
            195                 200                 205

Met Thr Lys Asn Gln Val Ser Leu Thr Cys Leu Val Lys Gly Phe Tyr
    210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
                245                 250                 255

Leu Tyr Ser Lys Leu Thr Val Asp Lys Ser Arg Trp Gln Gln Gly Asn
            260                 265                 270

Val Phe Ser Cys Ser Val Met His Glu Ala Leu His Asn His Tyr Thr
        275                 280                 285

Gln Lys Ser Leu Ser Leu Ser Pro Gly Lys
    290                 295

<210> SEQ ID NO 63
<211> LENGTH: 298
<212> TYPE: PRT
<213> ORGANISM: Artificial Sequence
<220> FEATURE:
<223> OTHER INFORMATION: CCL13(5-75K/H-A)-IgG1Fc

<400> SEQUENCE: 63

Leu Asn Val Pro Ser Thr Cys Cys Phe Thr Phe Ser Ser Lys Lys Ile
1               5                   10                  15

Ser Leu Gln Arg Leu Lys Ser Tyr Val Ile Thr Thr Ser Arg Cys Pro
            20                  25                  30

Gln Lys Ala Val Ile Phe Arg Thr Ala Leu Gly Ala Glu Ile Cys Ala
        35                  40                  45

Asp Pro Ala Glu Ala Trp Val Gln Asn Tyr Met Ala Ala Leu Gly Arg
    50                  55                  60

Lys Ala Ala Thr Leu Ala Thr Asp Lys Thr His Thr Cys Pro Pro Cys
65                  70                  75                  80

Pro Ala Pro Glu Leu Leu Gly Gly Pro Ser Val Phe Leu Phe Pro Pro
                85                  90                  95

Lys Pro Lys Asp Thr Leu Met Ile Ser Arg Thr Pro Glu Val Thr Cys
            100                 105                 110

Val Val Val Asp Val Ser His Glu Asp Pro Glu Val Lys Phe Asn Trp
        115                 120                 125

Tyr Val Asp Gly Val Glu Val His Asn Ala Lys Thr Lys Pro Arg Glu
    130                 135                 140

Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
                165                 170                 175

Lys Ala Leu Pro Ala Pro Ile Glu Lys Thr Ile Ser Lys Ala Lys Gly
            180                 185                 190

Gln Pro Arg Glu Pro Gln Val Tyr Thr Leu Pro Pro Ser Arg Glu Glu
            195                 200                 205

Met Thr Lys Asn Gln Val Ser Leu Thr Cys Leu Val Lys Gly Phe Tyr
    210                 215                 220

Pro Ser Asp Ile Ala Val Glu Trp Glu Ser Asn Gly Gln Pro Glu Asn
225                 230                 235                 240
```

Asn Tyr Lys Thr Thr Pro Pro Val Leu Asp Ser Asp Gly Ser Phe Phe
            245                 250                 255

Leu Tyr Ser Lys Leu Thr Val Asp Lys Ser Arg Trp Gln Gln Gly Asn
        260                 265                 270

Val Phe Ser Cys Ser Val Met His Glu Ala Leu His Asn His Tyr Thr
    275                 280                 285

Gln Lys Ser Leu Ser Leu Ser Pro Gly Lys
290                 295

<210> SEQ ID NO 64
<211> LENGTH: 345
<212> TYPE: PRT
<213> ORGANISM: Artificial Sequence
<220> FEATURE:
<223> OTHER INFORMATION: CCL25-IgG1Fc

<400> SEQUENCE: 64

Thr Gln Gly Val Phe Glu Asp Cys Cys Leu Ala Tyr His Tyr Pro Ile
1               5                   10                  15

Gly Trp Ala Val Leu Arg His Ala Trp Thr Tyr Arg Ile Gln Glu Val
            20                  25                  30

Ser Gly Ser Cys Asn Leu Pro Ala Ala Ile Phe Tyr Leu Pro Lys Arg
        35                  40                  45

His Arg Lys Val Cys Gly Asn Pro Lys Ser Arg Glu Val Gln Arg Ala
    50                  55                  60

Met Lys Leu Leu Asp Ala Arg Asn Lys Val Phe Ala Lys Leu Arg His
65                  70                  75                  80

Asn Thr Gln Thr Phe Gln Gly Pro His Ala Val Lys Lys Leu Ser Ser
                85                  90                  95

Gly Asn Ser Lys Leu Ser Ser Ser Lys Phe Ser Asn Pro Ile Ser Ser
            100                 105                 110

Ser Lys Arg Asn Val Ser Asp Lys Thr His Thr Cys Pro Pro Cys Pro
        115                 120                 125

Ala Pro Glu Leu Leu Gly Gly Pro Ser Val Phe Leu Phe Pro Pro Lys
    130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Gln Tyr Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
    210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Glu Glu Met
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
        275                 280                 285

Tyr Lys Thr Thr Pro Pro Val Leu Asp Ser Asp Gly Ser Phe Phe Leu
    290                 295                 300

```
Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
                340                 345

<210> SEQ ID NO 65
<211> LENGTH: 342
<212> TYPE: PRT
<213> ORGANISM: Artificial Sequence
<220> FEATURE:
<223> OTHER INFORMATION: CCL25(4-127)-IgG1Fc

<400> SEQUENCE: 65

Val Phe Glu Asp Cys Cys Leu Ala Tyr His Tyr Pro Ile Gly Trp Ala
1               5                   10                  15

Val Leu Arg His Ala Trp Thr Tyr Arg Ile Gln Glu Val Ser Gly Ser
                20                  25                  30

Cys Asn Leu Pro Ala Ala Ile Phe Tyr Leu Pro Lys Arg His Arg Lys
                35                  40                  45

Val Cys Gly Asn Pro Lys Ser Arg Glu Val Gln Arg Ala Met Lys Leu
    50                  55                  60

Leu Asp Ala Arg Asn Lys Val Phe Ala Lys Leu Arg His Asn Thr Gln
65                  70                  75                  80

Thr Phe Gln Gly Pro His Ala Val Lys Lys Leu Ser Ser Gly Asn Ser
                85                  90                  95

Lys Leu Ser Ser Ser Lys Phe Ser Asn Pro Ile Ser Ser Ser Lys Arg
                100                 105                 110

Asn Val Ser Asp Lys Thr His Thr Cys Pro Pro Cys Pro Ala Pro Glu
                115                 120                 125

Leu Leu Gly Gly Pro Ser Val Phe Leu Phe Pro Pro Lys Pro Lys Asp
130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
                180                 185                 190

Ser Thr Tyr Arg Val Val Ser Val Leu Thr Val Leu His Gln Asp Trp
                195                 200                 205

Leu Asn Gly Lys Glu Tyr Lys Cys Lys Val Ser Asn Lys Ala Leu Pro
210                 215                 220

Ala Pro Ile Glu Lys Thr Ile Ser Lys Ala Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
                260                 265                 270

Ala Val Glu Trp Glu Ser Asn Gly Gln Pro Glu Asn Asn Tyr Lys Thr
                275                 280                 285

Thr Pro Pro Val Leu Asp Ser Asp Gly Ser Phe Phe Leu Tyr Ser Lys
                290                 295                 300

Leu Thr Val Asp Lys Ser Arg Trp Gln Gln Gly Asn Val Phe Ser Cys
305                 310                 315                 320
```

```
Ser Val Met His Glu Ala Leu His Asn His Tyr Thr Gln Lys Ser Leu
            325                 330                 335

Ser Leu Ser Pro Gly Lys
            340

<210> SEQ ID NO 66
<211> LENGTH: 342
<212> TYPE: PRT
<213> ORGANISM: Artificial Sequence
<220> FEATURE:
<223> OTHER INFORMATION: CCL25(4-127K/H-A)-IgG1Fc

<400> SEQUENCE: 66

Val Phe Glu Asp Cys Cys Leu Ala Tyr His Tyr Pro Ile Gly Trp Ala
1               5                   10                  15

Val Leu Arg His Ala Trp Thr Tyr Arg Ile Gln Glu Val Ser Gly Ser
            20                  25                  30

Cys Asn Leu Pro Ala Ala Ile Phe Tyr Leu Pro Ala Ala Ala Ala Ala
        35                  40                  45

Val Cys Gly Asn Pro Ala Ser Ala Glu Val Gln Ala Ala Met Ala Leu
    50                  55                  60

Leu Asp Ala Ala Asn Ala Val Phe Ala Ala Leu Ala Ala Asn Thr Gln
65                  70                  75                  80

Thr Phe Gln Gly Pro Ala Ala Val Ala Ala Leu Ser Ser Gly Asn Ser
                85                  90                  95

Ala Leu Ser Ser Ser Ala Phe Ser Asn Pro Ile Ser Ser Ser Ala Ala
            100                 105                 110

Asn Val Ser Asp Lys Thr His Thr Cys Pro Pro Cys Pro Ala Pro Glu
        115                 120                 125

Leu Leu Gly Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Ala Leu Pro
    210                 215                 220

Ala Pro Ile Glu Lys Thr Ile Ser Lys Ala Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Val Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335
```

Ser Leu Ser Pro Gly Lys
            340

<210> SEQ ID NO 67
<211> LENGTH: 300
<212> TYPE: PRT
<213> ORGANISM: Artificial Sequence
<220> FEATURE:
<223> OTHER INFORMATION: CXCL11-IgG1Fc

<400> SEQUENCE: 67

Phe Pro Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Gln Ala Arg Leu Ile
    50                  55                  60

Ile Lys Lys Val Glu Arg Lys Asn Phe Asp Lys Thr His Thr Cys Pro
65                  70                  75                  80

Pro Cys Pro Ala Pro Glu Leu Leu Gly Gly Pro Ser Val Phe Leu Phe
                85                  90                  95

Pro Pro Lys Pro Lys Asp Thr Leu Met Ile Ser Arg Thr Pro Glu Val
            100                 105                 110

Thr Cys Val Val Val Asp Val Ser His Glu Asp Pro Glu Val Lys Phe
        115                 120                 125

Asn Trp Tyr Val Asp Gly Val Glu Val His Asn Ala Lys Thr Lys Pro
    130                 135                 140

Arg Glu Glu Gln Tyr Asn Ser Thr Tyr Arg Val Val Ser Val Leu Thr
145                 150                 155                 160

Val Leu His Gln Asp Trp Leu Asn Gly Lys Glu Tyr Lys Cys Lys Val
                165                 170                 175

Ser Asn Lys Ala Leu Pro Ala Pro Ile Glu Lys Thr Ile Ser Lys Ala
            180                 185                 190

Lys Gly Gln Pro Arg Glu Pro Gln Val Tyr Thr Leu Pro Pro Ser Arg
        195                 200                 205

Glu Glu Met Thr Lys Asn Gln Val Ser Leu Thr Cys Leu Val Lys Gly
    210                 215                 220

Phe Tyr Pro Ser Asp Ile Ala Val Glu Trp Glu Ser Asn Gly Gln Pro
225                 230                 235                 240

Glu Asn Asn Tyr Lys Thr Thr Pro Pro Val Leu Asp Ser Asp Gly Ser
                245                 250                 255

Phe Phe Leu Tyr Ser Lys Leu Thr Val Asp Lys Ser Arg Trp Gln Gln
            260                 265                 270

Gly Asn Val Phe Ser Cys Ser Val Met His Glu Ala Leu His Asn His
        275                 280                 285

Tyr Thr Gln Lys Ser Leu Ser Leu Ser Pro Gly Lys
    290                 295                 300

<210> SEQ ID NO 68
<211> LENGTH: 297
<212> TYPE: PRT
<213> ORGANISM: Artificial Sequence
<220> FEATURE:
<223> OTHER INFORMATION: CXCL11(4-73)-IgG1Fc

```
<400> SEQUENCE: 68

Phe Lys Arg Gly Arg Cys Leu Cys Ile Gly Pro Gly Val Lys Ala Val
1               5                   10                  15

Lys Val Ala Asp Ile Glu Lys Ala Ser Ile Met Tyr Pro Ser Asn Asn
                20                  25                  30

Cys Asp Lys Ile Glu Val Ile Ile Thr Leu Lys Glu Asn Lys Gly Gln
            35                  40                  45

Arg Cys Leu Asn Pro Lys Ser Lys Gln Ala Arg Leu Ile Ile Lys Lys
    50                  55                  60

Val Glu Arg Lys Asn Phe Asp Lys Thr His Thr Cys Pro Pro Cys Pro
65                  70                  75                  80

Ala Pro Glu Leu Leu Gly Gly Pro Ser Val Phe Leu Phe Pro Pro Lys
                85                  90                  95

Pro Lys Asp Thr Leu Met Ile Ser Arg Thr Pro Glu Val Thr Cys Val
            100                 105                 110

Val Val Asp Val Ser His Glu Asp Pro Glu Val Lys Phe Asn Trp Tyr
        115                 120                 125

Val Asp Gly Val Glu Val His Asn Ala Lys Thr Lys Pro Arg Glu Glu
130                 135                 140

Gln Tyr Asn Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Ala Leu Pro Ala Pro Ile Glu Lys Thr Ile Ser Lys Ala Lys Gly Gln
            180                 185                 190

Pro Arg Glu Pro Gln Val Tyr Thr Leu Pro Pro Ser Arg Glu Glu Met
        195                 200                 205

Thr Lys Asn Gln Val Ser Leu Thr Cys Leu Val Lys Gly Phe Tyr Pro
210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255

Tyr Ser Lys Leu Thr Val Asp Lys Ser Arg Trp Gln Gln Gly Asn Val
            260                 265                 270

Phe Ser Cys Ser Val Met His Glu Ala Leu His Asn His Tyr Thr Gln
        275                 280                 285

Lys Ser Leu Ser Leu Ser Pro Gly Lys
    290                 295

<210> SEQ ID NO 69
<211> LENGTH: 297
<212> TYPE: PRT
<213> ORGANISM: Artificial Sequence
<220> FEATURE:
<223> OTHER INFORMATION: CXCL11(4-73K/H-A)-IgG1Fc

<400> SEQUENCE: 69

Phe Lys Arg Gly Arg Cys Leu Cys Ile Gly Pro Gly Val Lys Ala Val
1               5                   10                  15

Lys Val Ala Asp Ile Glu Ala Ala Ser Ile Met Tyr Pro Ser Asn Asn
                20                  25                  30

Cys Asp Lys Ile Glu Val Ile Ile Thr Leu Ala Glu Asn Ala Gly Gln
            35                  40                  45

Ala Cys Leu Asn Pro Ala Ser Ala Gln Ala Ala Leu Ile Ile Ala Ala
```

```
            50                  55                  60
Val Glu Ala Ala Asn Phe Asp Lys Thr His Thr Cys Pro Pro Cys Pro
 65                  70                  75                  80

Ala Pro Glu Leu Leu Gly Gly Pro Ser Val Phe Leu Phe Pro Pro Lys
                 85                  90                  95

Pro Lys Asp Thr Leu Met Ile Ser Arg Thr Pro Glu Val Thr Cys Val
            100                 105                 110

Val Val Asp Val Ser His Glu Asp Pro Glu Val Lys Phe Asn Trp Tyr
            115                 120                 125

Val Asp Gly Val Glu Val His Asn Ala Lys Thr Lys Pro Arg Glu Glu
        130                 135                 140

Gln Tyr Asn Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Ala Leu Pro Ala Pro Ile Glu Lys Thr Ile Ser Lys Ala Lys Gly Gln
            180                 185                 190

Pro Arg Glu Pro Gln Val Tyr Thr Leu Pro Pro Ser Arg Glu Glu Met
        195                 200                 205

Thr Lys Asn Gln Val Ser Leu Thr Cys Leu Val Lys Gly Phe Tyr Pro
210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255

Tyr Ser Lys Leu Thr Val Asp Lys Ser Arg Trp Gln Gln Gly Asn Val
            260                 265                 270

Phe Ser Cys Ser Val Met His Glu Ala Leu His Asn His Tyr Thr Gln
        275                 280                 285

Lys Ser Leu Ser Leu Ser Pro Gly Lys
    290                 295

<210> SEQ ID NO 70
<211> LENGTH: 297
<212> TYPE: PRT
<213> ORGANISM: Artificial Sequence
<220> FEATURE:
<223> OTHER INFORMATION: CXCL11-IgG4Fc

<400> SEQUENCE: 70

Phe Pro Met Phe Lys Arg Gly Arg Cys Leu Cys Ile Gly Pro Gly Val
 1               5                  10                  15

Lys Ala Val Lys Val Ala Asp Ile Glu Lys Ala Ser Ile Met Tyr Pro
                20                  25                  30

Ser Asn Asn Cys Asp Lys Ile Glu Val Ile Ile Thr Leu Lys Glu Asn
            35                  40                  45

Lys Gly Gln Arg Cys Leu Asn Pro Lys Ser Lys Gln Ala Arg Leu Ile
        50                  55                  60

Ile Lys Lys Val Glu Arg Lys Asn Phe Pro Cys Pro Ser Cys Pro
 65                  70                  75                  80

Ala Pro Glu Phe Leu Gly Gly Pro Ser Val Phe Leu Phe Pro Pro Lys
                 85                  90                  95

Pro Lys Asp Thr Leu Met Ile Ser Arg Thr Pro Glu Val Thr Cys Val
            100                 105                 110

Val Val Asp Val Ser Gln Glu Asp Pro Glu Val Gln Phe Asn Trp Tyr
```

```
                 115                 120                 125
Val Asp Gly Val Glu Val His Asn Ala Lys Thr Lys Pro Arg Glu Glu
130                 135                 140

Gln Phe Asn Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Gly Leu Pro Ser Ser Ile Glu Lys Thr Ile Ser Lys Ala Lys Gly Gln
            180                 185                 190

Pro Arg Glu Pro Gln Val Tyr Thr Leu Pro Pro Ser Gln Glu Glu Met
        195                 200                 205

Thr Lys Asn Gln Val Ser Leu Thr Cys Leu Val Lys Gly Phe Tyr Pro
210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255

Tyr Ser Arg Leu Thr Val Asp Lys Ser Arg Trp Gln Glu Gly Asn Val
            260                 265                 270

Phe Ser Cys Ser Val Met His Glu Ala Leu His Asn His Tyr Thr Gln
        275                 280                 285

Lys Ser Leu Ser Leu Ser Pro Gly Lys
    290                 295

<210> SEQ ID NO 71
<211> LENGTH: 294
<212> TYPE: PRT
<213> ORGANISM: Artificial Sequence
<220> FEATURE:
<223> OTHER INFORMATION: CXCL11(4-73)-IgG4Fc

<400> SEQUENCE: 71

Phe Lys Arg Gly Arg Cys Leu Cys Ile Gly Pro Gly Val Lys Ala Val
1               5                   10                  15

Lys Val Ala Asp Ile Glu Lys Ala Ser Ile Met Tyr Pro Ser Asn Asn
            20                  25                  30

Cys Asp Lys Ile Glu Val Ile Ile Thr Leu Lys Glu Asn Lys Gly Gln
        35                  40                  45

Arg Cys Leu Asn Pro Lys Ser Lys Gln Ala Arg Leu Ile Ile Lys Lys
    50                  55                  60

Val Glu Arg Lys Asn Phe Pro Pro Cys Pro Ser Cys Pro Ala Pro Glu
65                  70                  75                  80

Phe Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
            100                 105                 110

Val Ser Gln Glu Asp Pro Glu Val Gln Phe Asn Trp Tyr Val Asp Gly
        115                 120                 125

Val Glu Val His Asn Ala Lys Thr Lys Pro Arg Glu Glu Gln Phe Asn
130                 135                 140

Ser Thr Tyr Arg Val Val Ser Val Leu Thr Val Leu His Gln Asp Trp
145                 150                 155                 160

Leu Asn Gly Lys Glu Tyr Lys Cys Lys Val Ser Asn Lys Gly Leu Pro
                165                 170                 175

Ser Ser Ile Glu Lys Thr Ile Ser Lys Ala Lys Gly Gln Pro Arg Glu
```

```
              180                 185                 190
Pro Gln Val Tyr Thr Leu Pro Pro Ser Gln Glu Glu Met Thr Lys Asn
            195                 200                 205

Gln Val Ser Leu Thr Cys Leu Val Lys Gly Phe Tyr Pro Ser Asp Ile
        210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Arg
                245                 250                 255

Leu Thr Val Asp Lys Ser Arg Trp Gln Glu Gly Asn Val Phe Ser Cys
            260                 265                 270

Ser Val Met His Glu Ala Leu His Asn His Tyr Thr Gln Lys Ser Leu
        275                 280                 285

Ser Leu Ser Pro Gly Lys
        290

<210> SEQ ID NO 72
<211> LENGTH: 294
<212> TYPE: PRT
<213> ORGANISM: Artificial Sequence
<220> FEATURE:
<223> OTHER INFORMATION: CXCL11(4-73K/H-A)-IgG4Fc

<400> SEQUENCE: 72

Phe Lys Arg Gly Arg Cys Leu Cys Ile Gly Pro Gly Val Lys Ala Val
1               5                   10                  15

Lys Val Ala Asp Ile Glu Ala Ala Ser Ile Met Tyr Pro Ser Asn Asn
            20                  25                  30

Cys Asp Lys Ile Glu Val Ile Ile Thr Leu Ala Glu Asn Ala Gly Gln
        35                  40                  45

Ala Cys Leu Asn Pro Ala Ser Ala Gln Ala Ala Leu Ile Ile Ala Ala
    50                  55                  60

Val Glu Ala Ala Asn Phe Pro Pro Cys Pro Ser Cys Pro Ala Pro Glu
65                  70                  75                  80

Phe Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
            100                 105                 110

Val Ser Gln Glu Asp Pro Glu Val Gln Phe Asn Trp Tyr Val Asp Gly
        115                 120                 125

Val Glu Val His Asn Ala Lys Thr Lys Pro Arg Glu Glu Gln Phe Asn
    130                 135                 140

Ser Thr Tyr Arg Val Val Ser Val Leu Thr Val Leu His Gln Asp Trp
145                 150                 155                 160

Leu Asn Gly Lys Glu Tyr Lys Cys Lys Val Ser Asn Lys Gly Leu Pro
                165                 170                 175

Ser Ser Ile Glu Lys Thr Ile Ser Lys Ala Lys Gly Gln Pro Arg Glu
            180                 185                 190

Pro Gln Val Tyr Thr Leu Pro Pro Ser Gln Glu Glu Met Thr Lys Asn
        195                 200                 205

Gln Val Ser Leu Thr Cys Leu Val Lys Gly Phe Tyr Pro Ser Asp Ile
    210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Arg
```

```
                         245                 250                 255
Leu Thr Val Asp Lys Ser Arg Trp Gln Glu Gly Asn Val Phe Ser Cys
            260                 265                 270
Ser Val Met His Glu Ala Leu His Asn His Tyr Thr Gln Lys Ser Leu
            275                 280                 285
Ser Leu Ser Pro Gly Lys
            290

<210> SEQ ID NO 73
<211> LENGTH: 314
<212> TYPE: PRT
<213> ORGANISM: Artificial Sequence
<220> FEATURE:
<223> OTHER INFORMATION: CXCL13-IgG1Fc

<400> SEQUENCE: 73

Val Leu Glu Val Tyr Tyr Thr Ser Leu Arg Cys Arg Cys Val Gln Glu
1               5                   10                  15
Ser Ser Val Phe Ile Pro Arg Arg Phe Ile Asp Arg Ile Gln Ile Leu
            20                  25                  30
Pro Arg Gly Asn Gly Cys Pro Arg Lys Glu Ile Ile Val Trp Lys Lys
        35                  40                  45
Asn Lys Ser Ile Val Cys Val Asp Pro Gln Ala Glu Trp Ile Gln Arg
50                  55                  60
Met Met Glu Val Leu Arg Lys Arg Ser Ser Thr Leu Pro Val Pro
65                  70                  75                  80
Val Phe Lys Arg Lys Ile Pro Asp Lys Thr His Thr Cys Pro Pro Cys
                85                  90                  95
Pro Ala Pro Glu Leu Leu Gly Gly Pro Ser Val Phe Leu Phe Pro Pro
            100                 105                 110
Lys Pro Lys Asp Thr Leu Met Ile Ser Arg Thr Pro Glu Val Thr Cys
        115                 120                 125
Val Val Val Asp Val Ser His Glu Asp Pro Glu Val Lys Phe Asn Trp
    130                 135                 140
Tyr Val Asp Gly Val Glu Val His Asn Ala Lys Thr Lys Pro Arg Glu
145                 150                 155                 160
Glu Gln Tyr Asn Ser Thr Tyr Arg Val Val Ser Val Leu Thr Val Leu
                165                 170                 175
His Gln Asp Trp Leu Asn Gly Lys Glu Tyr Lys Cys Lys Val Ser Asn
            180                 185                 190
Lys Ala Leu Pro Ala Pro Ile Glu Lys Thr Ile Ser Lys Ala Lys Gly
        195                 200                 205
Gln Pro Arg Glu Pro Gln Val Tyr Thr Leu Pro Pro Ser Arg Glu Glu
    210                 215                 220
Met Thr Lys Asn Gln Val Ser Leu Thr Cys Leu Val Lys Gly Phe Tyr
225                 230                 235                 240
Pro Ser Asp Ile Ala Val Glu Trp Glu Ser Asn Gly Gln Pro Glu Asn
                245                 250                 255
Asn Tyr Lys Thr Thr Pro Pro Val Leu Asp Ser Asp Gly Ser Phe Phe
            260                 265                 270
Leu Tyr Ser Lys Leu Thr Val Asp Lys Ser Arg Trp Gln Gln Gly Asn
        275                 280                 285
Val Phe Ser Cys Ser Val Met His Glu Ala Leu His Asn His Tyr Thr
    290                 295                 300
Gln Lys Ser Leu Ser Leu Ser Pro Gly Lys
305                 310
```

<210> SEQ ID NO 74
<211> LENGTH: 312
<212> TYPE: PRT
<213> ORGANISM: Artificial Sequence
<220> FEATURE:
<223> OTHER INFORMATION: CXCL13(3-87)-IgG1Fc

<400> SEQUENCE: 74

Glu Val Tyr Tyr Thr Ser Leu Arg Cys Arg Cys Val Gln Glu Ser Ser
1               5                   10                  15

Val Phe Ile Pro Arg Arg Phe Ile Asp Arg Ile Gln Ile Leu Pro Arg
            20                  25                  30

Gly Asn Gly Cys Pro Arg Lys Glu Ile Ile Val Trp Lys Lys Asn Lys
        35                  40                  45

Ser Ile Val Cys Val Asp Pro Gln Ala Glu Trp Ile Gln Arg Met Met
    50                  55                  60

Glu Val Leu Arg Lys Arg Ser Ser Ser Thr Leu Pro Val Pro Val Phe
65                  70                  75                  80

Lys Arg Lys Ile Pro Asp Lys Thr His Thr Cys Pro Pro Cys Pro Ala
                85                  90                  95

Pro Glu Leu Leu Gly Gly Pro Ser Val Phe Leu Phe Pro Pro Lys Pro
            100                 105                 110

Lys Asp Thr Leu Met Ile Ser Arg Thr Pro Glu Val Thr Cys Val Val
        115                 120                 125

Val Asp Val Ser His Glu Asp Pro Glu Val Lys Phe Asn Trp Tyr Val
    130                 135                 140

Asp Gly Val Glu Val His Asn Ala Lys Thr Lys Pro Arg Glu Glu Gln
145                 150                 155                 160

Tyr Asn Ser Thr Tyr Arg Val Val Ser Val Leu Thr Val Leu His Gln
                165                 170                 175

Asp Trp Leu Asn Gly Lys Glu Tyr Lys Cys Lys Val Ser Asn Lys Ala
            180                 185                 190

Leu Pro Ala Pro Ile Glu Lys Thr Ile Ser Lys Ala Lys Gly Gln Pro
        195                 200                 205

Arg Glu Pro Gln Val Tyr Thr Leu Pro Pro Ser Arg Glu Glu Met Thr
    210                 215                 220

Lys Asn Gln Val Ser Leu Thr Cys Leu Val Lys Gly Phe Tyr Pro Ser
225                 230                 235                 240

Asp Ile Ala Val Glu Trp Glu Ser Asn Gly Gln Pro Glu Asn Asn Tyr
                245                 250                 255

Lys Thr Thr Pro Pro Val Leu Asp Ser Asp Gly Ser Phe Phe Leu Tyr
            260                 265                 270

Ser Lys Leu Thr Val Asp Lys Ser Arg Trp Gln Gln Gly Asn Val Phe
        275                 280                 285

Ser Cys Ser Val Met His Glu Ala Leu His Asn His Tyr Thr Gln Lys
    290                 295                 300

Ser Leu Ser Leu Ser Pro Gly Lys
305                 310

<210> SEQ ID NO 75
<211> LENGTH: 312
<212> TYPE: PRT
<213> ORGANISM: Artificial Sequence
<220> FEATURE:
<223> OTHER INFORMATION: CXCL13(3-87K/H-A)-IgG1Fc

<400> SEQUENCE: 75

```
Glu Val Tyr Tyr Thr Ser Leu Arg Cys Arg Cys Val Gln Glu Ser Ser
1               5                   10                  15

Val Phe Ile Pro Arg Arg Phe Ile Asp Ala Ile Gln Ile Leu Pro Arg
            20                  25                  30

Gly Asn Gly Cys Pro Arg Lys Glu Ile Ile Val Trp Ala Ala Asn Ala
        35                  40                  45

Ser Ile Val Cys Val Asp Pro Gln Ala Glu Trp Ile Gln Ala Met Met
    50                  55                  60

Glu Val Leu Ala Ala Ser Ser Ser Thr Leu Pro Val Pro Val Phe
65                  70                  75                  80

Ala Ala Ala Ile Pro Asp Lys Thr His Thr Cys Pro Pro Cys Pro Ala
                85                  90                  95

Pro Glu Leu Leu Gly Gly Pro Ser Val Phe Leu Phe Pro Pro Lys Pro
            100                 105                 110

Lys Asp Thr Leu Met Ile Ser Arg Thr Pro Glu Val Thr Cys Val Val
        115                 120                 125

Val Asp Val Ser His Glu Asp Pro Glu Val Lys Phe Asn Trp Tyr Val
    130                 135                 140

Asp Gly Val Glu Val His Asn Ala Lys Thr Lys Pro Arg Glu Glu Gln
145                 150                 155                 160

Tyr Asn Ser Thr Tyr Arg Val Val Ser Val Leu Thr Val Leu His Gln
                165                 170                 175

Asp Trp Leu Asn Gly Lys Glu Tyr Lys Cys Lys Val Ser Asn Lys Ala
            180                 185                 190

Leu Pro Ala Pro Ile Glu Lys Thr Ile Ser Lys Ala Lys Gly Gln Pro
        195                 200                 205

Arg Glu Pro Gln Val Tyr Thr Leu Pro Pro Ser Arg Glu Glu Met Thr
    210                 215                 220

Lys Asn Gln Val Ser Leu Thr Cys Leu Val Lys Gly Phe Tyr Pro Ser
225                 230                 235                 240

Asp Ile Ala Val Glu Trp Glu Ser Asn Gly Gln Pro Glu Asn Asn Tyr
                245                 250                 255

Lys Thr Thr Pro Pro Val Leu Asp Ser Asp Gly Ser Phe Phe Leu Tyr
            260                 265                 270

Ser Lys Leu Thr Val Asp Lys Ser Arg Trp Gln Gln Gly Asn Val Phe
        275                 280                 285

Ser Cys Ser Val Met His Glu Ala Leu His Asn His Tyr Thr Gln Lys
    290                 295                 300

Ser Leu Ser Leu Ser Pro Gly Lys
305                 310
```

<210> SEQ ID NO 76
<211> LENGTH: 311
<212> TYPE: PRT
<213> ORGANISM: Artificial Sequence
<220> FEATURE:
<223> OTHER INFORMATION: CXCL13-IgG4Fc

<400> SEQUENCE: 76

```
Val Leu Glu Val Tyr Tyr Thr Ser Leu Arg Cys Arg Cys Val Gln Glu
1               5                   10                  15

Ser Ser Val Phe Ile Pro Arg Arg Phe Ile Asp Arg Ile Gln Ile Leu
            20                  25                  30
```

```
Pro Arg Gly Asn Gly Cys Pro Arg Lys Glu Ile Ile Val Trp Lys Lys
            35                  40                  45

Asn Lys Ser Ile Val Cys Val Asp Pro Gln Ala Glu Trp Ile Gln Arg
 50                  55                  60

Met Met Glu Val Leu Arg Lys Arg Ser Ser Thr Leu Pro Val Pro
 65                  70                  75                  80

Val Phe Lys Arg Lys Ile Pro Pro Cys Pro Ser Cys Pro Ala Pro
                85                  90                  95

Glu Phe Leu Gly Gly Pro Ser Val Phe Leu Phe Pro Pro Lys Pro Lys
                100                 105                 110

Asp Thr Leu Met Ile Ser Arg Thr Pro Glu Val Thr Cys Val Val Val
            115                 120                 125

Asp Val Ser Gln Glu Asp Pro Glu Val Gln Phe Asn Trp Tyr Val Asp
130                 135                 140

Gly Val Glu Val His Asn Ala Lys Thr Lys Pro Arg Glu Glu Gln Phe
145                 150                 155                 160

Asn Ser Thr Tyr Arg Val Val Ser Val Leu Thr Val Leu His Gln Asp
                165                 170                 175

Trp Leu Asn Gly Lys Glu Tyr Lys Cys Lys Val Ser Asn Lys Gly Leu
            180                 185                 190

Pro Ser Ser Ile Glu Lys Thr Ile Ser Lys Ala Lys Gly Gln Pro Arg
            195                 200                 205

Glu Pro Gln Val Tyr Thr Leu Pro Pro Ser Gln Glu Glu Met Thr Lys
210                 215                 220

Asn Gln Val Ser Leu Thr Cys Leu Val Lys Gly Phe Tyr Pro Ser Asp
225                 230                 235                 240

Ile Ala Val Glu Trp Glu Ser Asn Gly Gln Pro Glu Asn Asn Tyr Lys
                245                 250                 255

Thr Thr Pro Pro Val Leu Asp Ser Asp Gly Ser Phe Phe Leu Tyr Ser
            260                 265                 270

Arg Leu Thr Val Asp Lys Ser Arg Trp Gln Glu Gly Asn Val Phe Ser
            275                 280                 285

Cys Ser Val Met His Glu Ala Leu His Asn His Tyr Thr Gln Lys Ser
290                 295                 300

Leu Ser Leu Ser Pro Gly Lys
305                 310

<210> SEQ ID NO 77
<211> LENGTH: 309
<212> TYPE: PRT
<213> ORGANISM: Artificial Sequence
<220> FEATURE:
<223> OTHER INFORMATION: CXCL13(3-87)-IgG4Fc

<400> SEQUENCE: 77

Glu Val Tyr Tyr Thr Ser Leu Arg Cys Arg Cys Val Gln Glu Ser Ser
1               5                   10                  15

Val Phe Ile Pro Arg Arg Phe Ile Asp Arg Ile Gln Ile Leu Pro Arg
                20                  25                  30

Gly Asn Gly Cys Pro Arg Lys Glu Ile Ile Val Trp Lys Lys Asn Lys
            35                  40                  45

Ser Ile Val Cys Val Asp Pro Gln Ala Glu Trp Ile Gln Arg Met Met
 50                  55                  60

Glu Val Leu Arg Lys Arg Ser Ser Thr Leu Pro Val Pro Val Phe
 65                  70                  75                  80
```

```
Lys Arg Lys Ile Pro Pro Cys Pro Ser Cys Pro Ala Pro Glu Phe
                85              90              95
Leu Gly Gly Pro Ser Val Phe Leu Phe Pro Pro Lys Pro Lys Asp Thr
            100             105             110
Leu Met Ile Ser Arg Thr Pro Glu Val Thr Cys Val Val Val Asp Val
            115             120             125
Ser Gln Glu Asp Pro Glu Val Gln Phe Asn Trp Tyr Val Asp Gly Val
    130             135             140
Glu Val His Asn Ala Lys Thr Lys Pro Arg Glu Glu Gln Phe Asn Ser
145             150             155             160
Thr Tyr Arg Val Val Ser Val Leu Thr Val Leu His Gln Asp Trp Leu
                165             170             175
Asn Gly Lys Glu Tyr Lys Cys Lys Val Ser Asn Lys Gly Leu Pro Ser
            180             185             190
Ser Ile Glu Lys Thr Ile Ser Lys Ala Lys Gly Gln Pro Arg Glu Pro
        195             200             205
Gln Val Tyr Thr Leu Pro Pro Ser Gln Glu Glu Met Thr Lys Asn Gln
    210             215             220
Val Ser Leu Thr Cys Leu Val Lys Gly Phe Tyr Pro Ser Asp Ile Ala
225             230             235             240
Val Glu Trp Glu Ser Asn Gly Gln Pro Glu Asn Asn Tyr Lys Thr Thr
                245             250             255
Pro Pro Val Leu Asp Ser Asp Gly Ser Phe Phe Leu Tyr Ser Arg Leu
            260             265             270
Thr Val Asp Lys Ser Arg Trp Gln Glu Gly Asn Val Phe Ser Cys Ser
        275             280             285
Val Met His Glu Ala Leu His Asn His Tyr Thr Gln Lys Ser Leu Ser
    290             295             300
Leu Ser Pro Gly Lys
305

<210> SEQ ID NO 78
<211> LENGTH: 309
<212> TYPE: PRT
<213> ORGANISM: Artificial Sequence
<220> FEATURE:
<223> OTHER INFORMATION: CXCL13(3-87K/H-A)-IgG4Fc

<400> SEQUENCE: 78

Glu Val Tyr Tyr Thr Ser Leu Arg Cys Arg Cys Val Gln Glu Ser Ser
1               5               10              15
Val Phe Ile Pro Arg Arg Phe Ile Asp Ala Ile Gln Ile Leu Pro Arg
                20              25              30
Gly Asn Gly Cys Pro Arg Lys Glu Ile Ile Val Trp Ala Ala Asn Ala
            35              40              45
Ser Ile Val Cys Val Asp Pro Gln Ala Glu Trp Ile Gln Ala Met Met
    50              55              60
Glu Val Leu Ala Ala Ala Ser Ser Ser Thr Leu Pro Val Pro Val Phe
65              70              75              80
Ala Ala Ala Ile Pro Pro Cys Pro Ser Cys Pro Ala Pro Glu Phe
                85              90              95
Leu Gly Gly Pro Ser Val Phe Leu Phe Pro Pro Lys Pro Lys Asp Thr
            100             105             110
Leu Met Ile Ser Arg Thr Pro Glu Val Thr Cys Val Val Val Asp Val
            115             120             125
```

Ser Gln Glu Asp Pro Glu Val Gln Phe Asn Trp Tyr Val Asp Gly Val
    130                 135                 140
Glu Val His Asn Ala Lys Thr Lys Pro Arg Glu Glu Gln Phe Asn Ser
145                 150                 155                 160
Thr Tyr Arg Val Val Ser Val Leu Thr Val Leu His Gln Asp Trp Leu
                165                 170                 175
Asn Gly Lys Glu Tyr Lys Cys Lys Val Ser Asn Lys Gly Leu Pro Ser
            180                 185                 190
Ser Ile Glu Lys Thr Ile Ser Lys Ala Lys Gly Gln Pro Arg Glu Pro
        195                 200                 205
Gln Val Tyr Thr Leu Pro Pro Ser Gln Glu Met Thr Lys Asn Gln
    210                 215                 220
Val Ser Leu Thr Cys Leu Val Lys Gly Phe Tyr Pro Ser Asp Ile Ala
225                 230                 235                 240
Val Glu Trp Glu Ser Asn Gly Gln Pro Glu Asn Asn Tyr Lys Thr Thr
                245                 250                 255
Pro Pro Val Leu Asp Ser Asp Gly Ser Phe Phe Leu Tyr Ser Arg Leu
            260                 265                 270
Thr Val Asp Lys Ser Arg Trp Gln Glu Gly Asn Val Phe Ser Cys Ser
        275                 280                 285
Val Met His Glu Ala Leu His Asn His Tyr Thr Gln Lys Ser Leu Ser
    290                 295                 300
Leu Ser Pro Gly Lys
305

<210> SEQ ID NO 79
<211> LENGTH: 4401
<212> TYPE: DNA
<213> ORGANISM: Artificial Sequence
<220> FEATURE:
<223> OTHER INFORMATION: pCCL2-IgG1Fc

<400> SEQUENCE: 79

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gcctttttcc cgagggtggg ggagaaccgt     180
atataagtgc agtagtcgcc gtgaacgttc ttttcgcaa cgggtttgcc gccagaacac      240
agctgaagct cgagggggct cgcatctctc cttcacgcgc ccgccgccct acctgaggcc     300
gccatccacg ccggttgagt cgcgttctgc cgcctcccgc tgtggtgcc tcctgaactg      360
cgtccgccgt ctaggtaagt ttaaagctca ggtcgagacc gggcctttgt ccggcgctcc     420
cttggagcct acctgactc agccggctct ccacgctttg cctgaccctg cttgctcaac      480
tctacgtctt tgtttcgttt ctgttctgc gccgttacag atccaagctg tgaccggcgc      540
ctacctgaga tcaccggcga aggagggcca ccatgtacag gatgcaactc ctgtcttgca     600
ttgcactaag tcttgcactt gtcacgaatt cgcagccaga tgcaatcaat gccccagtca     660
cctgctgtta aacttcacc aataggaaga tctcagtgca gaggctcgcg agctatagaa      720
gaatcaccag cagcaagtgt cccaaagaag ctgtgatctt caagaccatt gtggccaagg    780
agatctgtgc tgaccccaag cagaagtggg ttcaggattc catggaccac tggacaagc     840
aaacccaaac tccgaagact gacaaaactc acacatgccc accgtgccca gcacctgaac    900
tcctgggggg accgtcagtc ttcctcttcc cccaaaaacc caaggacacc ctcatgatct    960
cccggacccc tgaggtcaca tgcgtggtgg tggacgtgag ccacgaagac cctgaggtca   1020
```

```
agttcaactg gtacgtggac ggcgtggagg tgcataatgc aagacaaag   ccgcgggagg    1080 agcagtacaa cagcacgtac cgtgtggtca gcgtcctcac cgtcctgcac caggactggc    1140
tgaatggcaa ggagtacaag tgcaaggtct ccaacaaagc cctcccagcc cccatcgaga    1200
aaaccatctc caaagccaaa gggcagcccc gagaaccaca ggtgtacacc ctgcccccat    1260
cccgggagga gatgaccaag aaccaggtca gcctgacctg cctggtcaaa ggcttctatc    1320
ccagcgacat cgccgtggag tgggagagca atgggcagcc ggagaacaac tacaagacca    1380
cgcctcccgt gctggactcc gacggctcct tcttcctcta cagcaagctc accgtggaca    1440
agagcaggtg gcagcagggg aacgtcttct catgctccgt gatgcacgag gctctgcaca    1500
accactacac gcagaagagc ctctccctgt ctccgggtaa atgagtgcta gctggccaga    1560
catgataaga tacattgatg agtttggaca aaccacaact agaatgcagt gaaaaaaatg    1620
ctttatttgt gaaatttgtg atgctattgc tttatttgta accattataa gctgcaataa    1680
acaagttaac aacaacaatt gcattcattt tatgtttcag gttcagggg  aggtgtggga     1740 ggttttttaa agcaagtaaa acctctacaa atgtggtatg gaattaattc taaaatacag    1800
catagcaaaa ctttaacctc caaatcaagc ctctacttga atccttttct gagggatgaa    1860
taaggcatag gcatcagggg ctgttgccaa tgtgcattag ctgtttgcag cctcaccttc    1920
tttcatggag tttaagatat agtgtatttt cccaaggttt gaactagctc ttcatttctt    1980
tatgttttaa atgcactgac ctcccacatt ccctttttag taaaatattc agaaataatt    2040
taaatacatc attgcaatga aaataaatgt ttttattag  gcagaatcca gatgctcaag     2100
gcccttcata atatccccca gtttagtagt tggacttagg gaacaaagga acctttaata    2160
gaaattggac agcaagaaag cgagcttcta gcttatcctc agtcctgctc ctctgccaca    2220
aagtgcacgc agttgccggc cgggtcgcgc agggcgaact cccgccccca cggctgctcg    2280
ccgatctcgg tcatggccgg cccggaggcg tcccggaagt tcgtggacac gacctccgac    2340
cactcggcgt acagctcgtc caggccgcgc acccacaccc aggccagggt gttgtccggc    2400
accacctggt cctggaccgc gctgatgaac agggtcacgt cgtcccggac cacaccggcg    2460
aagtcgtcct ccacgaagtc ccgggagaac ccgagccggt cggtccagaa ctcgaccgct    2520
ccggcgacgt cgcgcgcggt gagcaccgga acggcactgg tcaacttggc catgatggct    2580
cctcctgtca ggagaggaaa gagaagaagg ttagtacaat tgctatagtg agttgtatta    2640
tactatgcag atatactatg ccaatgatta attgtcaaac tagggctgca gggttcatag    2700
tgccactttt cctgcactgc cccatctcct gcccacccct tcccaggcat agacagtcag    2760
tgacttacca aactcacagg agggagaagg cagaagcttg agacagaccc gcgggaccgc    2820
cgaactgcga gggacgtgg  ctagggcggc ttcttttatg gtgcgccggc cctcggaggc    2880
agggcgctcg gggaggccta gcggccaatc tgcggtggca ggaggcgggg ccgaaggccg    2940
tgcctgacca atccggagca cataggagtc tcagcccccc gccccaaagc aaggggaagt    3000
cacgcgcctg tagcgccagc gtgttgtgaa atgggggctt ggggggggttg gggccctgac    3060 tagtcaaaac aaactcccat tgacgtcaat ggggtggaga cttggaaatc cccgtgagtc    3120
aaaccgctat ccacgcccat tgatgtactg ccaaaaccgc atcatcatgg taatagcgat    3180
gactaatacg tagatgtact gccaagtagg aaagtcccat aaggtcatgt actgggcata    3240
atgccaggcg ggccatttac cgtcattgac gtcaataggg ggcgtacttg gcatatgata    3300
cacttgatgt actgccaagt gggcagttta ccgtaaatac tccacccatt gacgtcaatg    3360
```

| | |
|---|---|
| gaaagtccct attggcgtta ctatgggaac atacgtcatt attgacgtca atgggcgggg | 3420 |
| gtcgttgggc ggtcagccag gcgggccatt taccgtaagt tatgtaacgc ctgcaggtta | 3480 |
| attaagaaca tgtgagcaaa aggccagcaa aaggccagga accgtaaaaa ggccgcgttg | 3540 |
| ctggcgtttt tccataggct ccgcccccct gacgagcatc acaaaaatcg acgctcaagt | 3600 |
| cagaggtggc gaaacccgac aggactataa agataccagg cgtttccccc tggaagctcc | 3660 |
| ctcgtgcgct ctcctgttcc gaccctgccg cttaccggat acctgtccgc ctttctccct | 3720 |
| tcgggaagcg tggcgctttc tcatagctca cgctgtaggt atctcagttc ggtgtaggtc | 3780 |
| gttcgctcca agctgggctg tgtgcacgaa ccccccgttc agcccgaccg ctgcgcctta | 3840 |
| tccggtaact atcgtcttga gtccaacccg gtaagacacg acttatcgcc actggcagca | 3900 |
| gccactggta acaggattag cagagcgagg tatgtaggcg gtgctacaga gttcttgaag | 3960 |
| tggtggccta actacggcta cactagaaga acagtatttg gtatctgcgc tctgctgaag | 4020 |
| ccagttacct tcggaaaaag agttggtagc tcttgatccg gcaaacaaac caccgctggt | 4080 |
| agcggtggtt tttttgtttg caagcagcag attacgcgca gaaaaaaagg atctcaagaa | 4140 |
| gatcctttga tcttttctac ggggtctgac gctcagtgga acgaaaactc acgttaaggg | 4200 |
| attttggtca tggctagtta attaacattt aaatcagcgg ccgcaataaa atatctttat | 4260 |
| tttcattaca tctgtgtgtt ggttttttgt gtgaatcgta actaacatac gctctccatc | 4320 |
| aaaacaaaac gaaacaaaac aaactagcaa ataggctgt ccccagtgca agtgcaggtg | 4380 |
| ccagaacatt tctctatcga a | 4401 |

<210> SEQ ID NO 80
<211> LENGTH: 4389
<212> TYPE: DNA
<213> ORGANISM: Artificial Sequence
<220> FEATURE:
<223> OTHER INFORMATION: pCCL2(5-76)-IgG1Fc

<400> SEQUENCE: 80

| | |
|---|---|
| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gcctttttcc cgagggtggg ggagaaccgt | 180 |
| atataagtgc agtagtcgcc gtgaacgttc tttttcgcaa cgggtttgcc gccagaacac | 240 |
| agctgaagct tcgaggggct cgcatctctc cttcacgcgc ccgccgccct acctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg tgaccggcgc | 540 |
| ctacctgaga tcaccggcga aggagggcca ccatgtacag gatgcaactc ctgtcttgca | 600 |
| ttgcactaag tcttgcactt gtcacgaatt cgatcaatgc cccagtcacc tgctgttata | 660 |
| acttccaccaa taggaagatc tcagtgcaga ggctcgcgag ctatagaaga atcaccagca | 720 |
| gcaagtgtcc caagaagct gtgatcttca agaccattgt ggccaaggag atctgtgctg | 780 |
| accccaagca gaagtgggtt caggattcca tggaccacct ggacaagcaa acccaaactc | 840 |
| cgaagactga caaaactcac acatgcccac cgtgcccagc acctgaactc ctggggggac | 900 |
| cgtcagtctt cctcttcccc ccaaaaccca aggacaccct catgatctcc cggacccctg | 960 |
| aggtcacatg cgtggtggtg gacgtgagcc acgaagaccc tgaggtcaag ttcaactggt | 1020 |

-continued

```
acgtggacgg cgtggaggtg cataatgcca agacaaagcc gcgggaggag cagtacaaca     1080
gcacgtaccg tgtggtcagc gtcctcaccg tcctgcacca ggactggctg aatggcaagg     1140
agtacaagtg caaggtctcc aacaaagccc tcccagcccc catcgagaaa accatctcca     1200
aagccaaagg gcagccccga gaaccacagg tgtacaccct gcccccatcc cgggaggaga     1260
tgaccaagaa ccaggtcagc ctgacctgcc tggtcaaagg cttctatccc agcgacatcg     1320
ccgtggagtg ggagagcaat gggcagccgg agaacaacta caagaccacg cctcccgtgc     1380
tggactccga cggctccttc ttcctctaca gcaagctcac cgtggacaag agcaggtggc     1440 agcagggaa cgtcttctca tgctccgtga tgcacgaggc tctgcacaac cactacacgc     1500
agaagagcct ctccctgtct ccgggtaaat gagtgctagc tggccagaca tgataagata     1560
cattgatgag tttggacaaa ccacaactag aatgcagtga aaaaaatgct ttatttgtga     1620
aatttgtgat gctattgctt tatttgtaac cattataagc tgcaataaac aagttaacaa     1680
caacaattgc attcatttta tgtttcaggt tcaggggag gtgtgggagg ttttttaaag     1740
caagtaaaac ctctacaaat gtggtatgga attaattcta aaatacagca tagcaaaact     1800
ttaacctcca aatcaagcct ctacttgaat ccttttctga gggatgaata aggcataggc     1860
atcaggggct gttgccaatg tgcattagct gtttgcagcc tcaccttctt tcatggagtt     1920
taagatatag tgtattttcc caaggtttga actagctctt catttcttta tgttttaaat     1980
gcactgacct cccacattcc cttttagta aatattcag aaataattta aatacatcat     2040
tgcaatgaaa ataatgtttt ttattaggc agaatccaga tgctcaaggc ccttcataat     2100 atccccagt ttagtagttg gacttaggga acaaggaac ctttaataga aattggacag     2160
caagaaagcg agcttctagc ttatcctcag tcctgctcct ctgccacaaa gtgcacgcag     2220
ttgccggccg ggtcgcgcag ggcgaactcc cgccccacg gctgctcgcc gatctcggtc     2280
atggccggcc cggaggcgtc ccggaagttc gtggacacga cctccgacca ctcggcgtac     2340
agctcgtcca ggccgcgcac ccacacccag gccaggtgt tgtccggcac cacctggtcc     2400
tggaccgcgc tgatgaacag ggtcacgtcg tcccggacca caccggcgaa gtcgtcctcc     2460
acgaagtccc gggagaaccc gagccggtcg gtccagaact cgaccgctcc ggcgacgtcg     2520
cgcgcggtga gcaccggaac ggcactggtc aacttggcca tgatggctcc tcctgtcagg     2580
agaggaaaga gaagaaggtt agtacaattg ctatagtgag ttgtattata ctatgcagat     2640
atactatgcc aatgattaat tgtcaaacta gggctgcagg gttcatagtg ccactttttcc     2700 tgcactgccc catctcctgc ccacccttc ccaggcatag acagtcagtg acttaccaaa     2760
ctcacaggag ggagaaggca gaagcttgag acagaccgc gggaccgccg aactgcgagg     2820
ggacgtggct agggcggctt cttttatggt gcgccggccc tcggaggcag ggcgctcggg     2880
gaggcctagc ggccaatctg cggtggcagg aggcggggcc gaaggccgtg cctgaccaat     2940
ccggagcaca taggagtctc agccccccgc cccaaagcaa ggggaagtca cgcgcctgta     3000
gcgccagcgt gttgtgaaat gggggcttgg gggggttggg gccctgacta gtcaaaacaa     3060
actcccattg acgtcaatgg ggtggagact tggaaatccc cgtgagtcaa accgctatcc     3120
acgcccattg atgtactgcc aaaaccgcat catcatggta atagcgatga ctaatacgta     3180
gatgtactgc caagtaggaa agtcccataa ggtcatgtac tgggcataat gccaggcggg     3240
ccatttaccg tcattgacgt cataggggg cgtacttggc atatgataca cttgatgtac     3300
tgccaagtgg gcagtttacc gtaaatactc cacccattga cgtcaatgga aagtccctat     3360
```

| | |
|---|---:|
| tggcgttact atgggaacat acgtcattat tgacgtcaat gggcgggggt cgttgggcgg | 3420 |
| tcagccaggc gggccattta ccgtaagtta tgtaacgcct gcaggttaat taagaacatg | 3480 |
| tgagcaaaag gccagcaaaa ggccaggaac cgtaaaaagg ccgcgttgct ggcgtttttc | 3540 |
| cataggctcc gcccccctga cgagcatcac aaaaatcgac gctcaagtca gaggtggcga | 3600 |
| aacccgacag gactataaag ataccaggcg tttccccctg gaagctccct cgtgcgctct | 3660 |
| cctgttccga ccctgccgct taccggatac ctgtccgcct ttctcccttc gggaagcgtg | 3720 |
| gcgctttctc atagctcacg ctgtaggtat ctcagttcgg tgtaggtcgt tcgctccaag | 3780 |
| ctgggctgtg tgcacgaacc ccccgttcag cccgaccgct cgccttatc cggtaactat | 3840 |
| cgtcttgagt ccaacccggt aagacacgac ttatcgccac tggcagcagc cactggtaac | 3900 |
| aggattagca gagcgaggta tgtaggcggt gctacagagt tcttgaagtg gtggcctaac | 3960 |
| tacggctaca ctagaagaac agtatttggt atctgcgctc tgctgaagcc agttaccttc | 4020 |
| ggaaaaagag ttggtagctc ttgatccggc aaacaaacca ccgctggtag cggtggtttt | 4080 |
| tttgtttgca agcagcagat tacgcgcaga aaaaaggat ctcaagaaga tcctttgatc | 4140 |
| ttttctacgg ggtctgacgc tcagtggaac gaaaactcac gttaagggat tttggtcatg | 4200 |
| gctagttaat taacatttaa atcagcggcc gcaataaaat atctttattt tcattacatc | 4260 |
| tgtgtgttgg ttttttgtgt gaatcgtaac taacatacgc tctccatcaa acaaaacga | 4320 |
| aacaaaacaa actagcaaaa taggctgtcc ccagtgcaag tgcaggtgcc agaacatttc | 4380 |
| tctatcgaa | 4389 |

<210> SEQ ID NO 81
<211> LENGTH: 4389
<212> TYPE: DNA
<213> ORGANISM: Artificial Sequence
<220> FEATURE:
<223> OTHER INFORMATION: pCCL2(5-76K/H-A)-IgG1Fc

<400> SEQUENCE: 81

| | |
|---|---:|
| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gcctttttcc cgagggtggg ggagaaccgt | 180 |
| atataagtgc agtagtcgcc gtgaacgttc tttttcgcaa cgggtttgcc gccagaacac | 240 |
| agctgaagct tcgaggggct cgcatctctc cttcacgcgc ccgccgccct acctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg tgaccggcgc | 540 |
| ctacctgaga tcaccggcga aggagggcca ccatgtacag gatgcaactc ctgtcttgca | 600 |
| ttgcactaag tcttgcactt gtcacgaatt cgatcaatgc cccagtcacc tgctgttata | 660 |
| acttcaccaa taggaagatc tcagtgcaga ggctcgcgag ctatagaaga atcaccagca | 720 |
| gcaagtgtcc caagaagct gtgatcttca agaccattgt ggccgcggag atctgtgctg | 780 |
| accccgctca ggcctgggtt caggattcca tggacgctct ggacgcccaa acccaaactc | 840 |
| cggcgactga caaaactcac acatgcccac cgtgcccagc acctgaactc ctggggggac | 900 |
| cgtcagtctt cctcttcccc ccaaaaccca aggacaccct catgatctcc cggacccctg | 960 |
| aggtcacatg cgtggtggtg gacgtgagcc acgaagaccc tgaggtcaag ttcaactggt | 1020 |

```
acgtggacgg cgtggaggtg cataatgcca agacaaagcc gcgggaggag cagtacaaca   1080
gcacgtaccg tgtggtcagc gtcctcaccg tcctgcacca ggactggctg aatggcaagg   1140
agtacaagtg caaggtctcc aacaaagccc tcccagcccc catcgagaaa accatctcca   1200
aagccaaagg gcagccccga gaaccacagg tgtacaccct gccccatcc cgggaggaga    1260 tgaccaagaa ccaggtcagc ctgacctgcc tggtcaaagg cttctatccc agcgacatcg   1320
ccgtggagtg ggagagcaat gggcagccgg agaacaacta caagaccacg cctcccgtgc   1380
tggactccga cggctccttc ttcctctaca gcaagctcac cgtggacaag agcaggtggc   1440 agcagggaa cgtcttctca tgctccgtga tgcacgaggc tctgcacaac cactacacgc    1500
agaagagcct ctccctgtct ccgggtaaat gagtgctagc tggccagaca tgataagata   1560
cattgatgag tttggacaaa ccacaactag aatgcagtga aaaaaatgct ttatttgtga   1620
aatttgtgat gctattgctt tatttgtaac cattataagc tgcaataaac aagttaacaa   1680
caacaattgc attcatttta tgtttcaggt tcaggggag gtgtgggagg ttttttaaag    1740
caagtaaaac ctctacaaat gtggtatgga attaattcta aaatacagca tagcaaaact   1800
ttaacctcca aatcaagcct ctacttgaat ccttttctga gggatgaata aggcataggc   1860
atcaggggct gttgccaatg tgcattagct gtttgcagcc tcaccttctt tcatggagtt   1920
taagatatag tgtattttcc caaggtttga actagctctt catttcttta tgttttaaat   1980
gcactgacct cccacattcc ctttttagta aaatattcag aaataattta aatacatcat   2040
tgcaatgaaa ataatgtttt tttattaggc agaatccaga tgctcaaggc ccttcataat   2100
atcccccagt ttagtagttg gacttaggga acaaaggaac ctttaataga aattggacag   2160
caagaaagcg agcttctagc ttatcctcag tcctgctcct ctgccacaaa gtgcacgcag   2220
ttgccggccg ggtcgcgcag ggcgaactcc cgccccacg gctgctcgcc gatctcggtc    2280
atggccggcc cggaggcgtc ccggaagttc gtggacacga cctccgacca ctcggcgtac   2340
agctcgtcca ggccgcgcac ccacacccag gccaggtgt tgtccggcac cacctggtcc    2400
tggaccgcgc tgatgaacag ggtcacgtcg tcccggacca caccggcgaa gtcgtcctcc   2460
acgaagtccc gggagaaccc gagccggtcg gtccagaact cgaccgctcc ggcgacgtcg   2520
cgcgcggtga gcaccggaac ggcactggtc aacttggcca tgatggctcc tcctgtcagg   2580
agaggaaaga gaagaaggtt agtacaattg ctatagtgag ttgtattata ctatgcagat   2640
atactatgcc aatgattaat tgtcaaacta gggctgcagg gttcatagtg ccactttcc    2700 tgcactgccc catctcctgc ccaccctttc ccaggcatag acagtcagtg acttaccaaa   2760
ctcacaggag ggagaaggca gaagcttgag acagaccgc gggaccgccg aactgcgagg    2820
ggacgtggct agggcggctt cttttatggt gcgccggccc tcggaggcag ggcgctcggg   2880
gaggcctagc ggccaatctg cggtggcagg aggcggggcc gaaggccgtg cctgaccaat   2940
ccggagcaca taggagtctc agccccccgc cccaaagcaa ggggaagtca cgcgcctgta   3000
gcgccagcgt gttgtgaaat ggggggcttgg gggggttggg gccctgacta gtcaaaacaa   3060
actcccattg acgtcaatgg ggtggagact tggaaatccc cgtgagtcaa accgctatcc   3120
acgcccattg atgtactgcc aaaaccgcat catcatggta atagcgatga ctaatacgta   3180
gatgtactgc caagtaggaa agtcccataa ggtcatgtac tgggcataat gccaggcggg   3240
ccatttaccg tcattgacgt caatagggg cgtacttggc atatgataca cttgatgtac    3300
tgccaagtgg gcagtttacc gtaaatactc cacccattga cgtcaatgga aagtccctat   3360
```

| | |
|---|---|
| tggcgttact atgggaacat acgtcattat tgacgtcaat gggcgggggt cgttgggcgg | 3420 |
| tcagccaggc gggccattta ccgtaagtta tgtaacgcct gcaggttaat taagaacatg | 3480 |
| tgagcaaaag gccagcaaaa ggccaggaac cgtaaaaagg ccgcgttgct ggcgtttttc | 3540 |
| cataggctcc gccccctga cgagcatcac aaaaatcgac gctcaagtca gaggtggcga | 3600 |
| aacccgacag gactataaag ataccaggcg tttccccctg gaagctccct cgtgcgctct | 3660 |
| cctgttccga ccctgccgct taccggatac ctgtccgcct ttctcccttc gggaagcgtg | 3720 |
| gcgctttctc atagctcacg ctgtaggtat ctcagttcgg tgtaggtcgt tcgctccaag | 3780 |
| ctgggctgtg tgcacgaacc ccccgttcag cccgaccgct cgccttatc cggtaactat | 3840 |
| cgtcttgagt ccaacccggt aagacacgac ttatcgccac tggcagcagc cactggtaac | 3900 |
| aggattagca gagcgaggta tgtaggcggt gctacagagt tcttgaagtg gtggcctaac | 3960 |
| tacggctaca ctagaagaac agtatttggt atctgcgctc tgctgaagcc agttaccttc | 4020 |
| ggaaaaagag ttggtagctc ttgatccggc aaacaaacca ccgctggtag cggtggtttt | 4080 |
| tttgtttgca agcagcagat tacgcgcaga aaaaaggat ctcaagaaga tcctttgatc | 4140 |
| ttttctacgg ggtctgacgc tcagtggaac gaaaactcac gttaagggat tttggtcatg | 4200 |
| gctagttaat taacatttaa atcagcggcc gcaataaaat atctttattt tcattacatc | 4260 |
| tgtgtgttgg ttttttgtgt gaatcgtaac taacatacgc tctccatcaa aacaaaacga | 4320 |
| aacaaaacaa actagcaaaa taggctgtcc ccagtgcaag tgcaggtgcc agaacatttc | 4380 |
| tctatcgaa | 4389 |

<210> SEQ ID NO 82
<211> LENGTH: 4371
<212> TYPE: DNA
<213> ORGANISM: Artificial Sequence
<220> FEATURE:
<223> OTHER INFORMATION: pCCL7-IgG1Fc

<400> SEQUENCE: 82

| | |
|---|---|
| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gcctttttcc cgagggtggg ggagaaccgt | 180 |
| atataagtgc agtagtcgcc gtgaacgttc ttttttcgcaa cgggtttgcc gccagaacac | 240 |
| agctgaagct tcgaggggct cgcatctctc cttcacgcgc ccgccgccct acctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg tgaccggcgc | 540 |
| ctacctgaga tcaccggcga aggagggcca ccatgtacag gatgcaactc ctgtcttgca | 600 |
| ttgcactaag tcttgcactt gtcacgaatt cgtgctgcta cagatttatc aataagaaaa | 660 |
| tccctaagca gaggctggag agctacagaa ggaccaccag tagccactgt ccccgggaag | 720 |
| ctgtaatctt caagaccaaa ctggacaagg agatctgtgc tgaccccaca cagaagtggg | 780 |
| tccaggactt tatgaagcac ctggacaaga aacccaaac tccaaagctt gacaaaactc | 840 |
| acacatgccc accgtgccca gcacctgaac tcctgggggg accgtcagtc ttcctcttcc | 900 |
| ccccaaaacc caaggacacc ctcatgatct cccggacccc tgaggtcaca tgcgtggtgg | 960 |
| tggacgtgag ccacgaagac cctgaggtca agttcaactg gtacgtggac ggcgtggagg | 1020 |

```
tgcataatgc caagacaaag ccgcgggagg agcagtacaa cagcacgtac cgtgtggtca   1080
gcgtcctcac cgtcctgcac caggactggc tgaatggcaa ggagtacaag tgcaaggtct   1140
ccaacaaagc cctcccagcc cccatcgaga aaccatctc caaagccaaa gggcagcccc    1200
gagaaccaca ggtgtacacc ctgccccat cccgggagga gatgaccaag aaccaggtca    1260
gcctgacctg cctggtcaaa ggcttctatc ccagcgacat cgccgtggag tgggagagca   1320
atgggcagcc ggagaacaac tacaagacca cgcctcccgt gctggactcc gacggctcct   1380
tcttcctcta cagcaagctc accgtggaca agagcaggtg gcagcagggg aacgtcttct   1440
catgctccgt gatgcacgag gctctgcaca accactacac gcagaagagc ctctccctgt   1500
ctccgggtaa atgagtgcta gctggccaga catgataaga tacattgatg agtttggaca   1560
aaccacaact agaatgcagt gaaaaaaatg ctttatttgt gaaatttgtg atgctattgc   1620
tttatttgta accattataa gctgcaataa acaagttaac aacaacaatt gcattcattt   1680
tatgtttcag gttcaggggg aggtgtggga ggttttttaa agcaagtaaa acctctacaa   1740
atgtggtatg gaattaattc taaaatacag catagcaaaa ctttaacctc caaatcaagc   1800
ctctacttga atccttttct gagggatgaa taaggcatag gcatcagggg ctgttgccaa   1860
tgtgcattag ctgtttgcag cctcaccttc tttcatggag tttaagatat agtgtatttt   1920
cccaaggttt gaactagctc ttcatttctt tatgttttaa atgcactgac ctcccacatt   1980
ccctttttag taaaatattc agaaataatt taaatacatc attgcaatga aaataaatgt   2040
tttttattag gcagaatcca gatgctcaag gcccttcata atatccccca gtttagtagt   2100
tggacttagg gaacaaagga acctttaata gaaattggac agcaagaaag cgagcttcta   2160
gcttatcctc agtcctgctc ctctgccaca aagtgcacgc agttgccggc cgggtcgcgc   2220
agggcgaact cccgccccca cggctgctcg ccgatctcgg tcatggccgg cccggaggcg   2280
tcccggaagt tcgtggacac gacctccgac cactcggcgt acagctcgtc caggccgcgc   2340
acccacaccc aggccagggt gttgtccggc accacctggt cctggaccgc gctgatgaac   2400
agggtcacgt cgtcccggac cacaccggcg aagtcgtcct ccacgaagtc ccgggagaac   2460
ccgagccggt cggtccagaa ctcgaccgct ccggcgacgt cgcgcgcggt gagcaccgga   2520
acggcactgg tcaacttggc catgatggct cctcctgtca ggagaggaaa gagaagaagg   2580
ttagtacaat tgctatagtg agttgtatta tactatgcag atatactatg ccaatgatta   2640
attgtcaaac tagggctgca gggttcatag tgccactttt cctgcactgc cccatctcct   2700
gcccacccct tcccaggcat agacagtcag tgacttacca aactcacagg agggagaagg   2760
cagaagcttg agacagaccc gcgggaccgc cgaactgcga ggggacgtgg ctagggcggc   2820
ttcttttatg gtgcgccggc cctcggaggc agggcgctcg ggaggccta gcggccaatc    2880 tgcggtggca ggaggcgggg ccgaaggccg tgcctgacca atccggagca cataggagtc   2940
tcagcccccc gccccaaagc aaggggaagt cacgcgcctg tagcgccagc gtgttgtgaa   3000
atgggggctt ggggggggttg gggccctgac tagtcaaaac aaactcccat tgacgtcaat   3060
ggggtggaga cttggaaatc cccgtgagtc aaaccgctat ccacgcccat tgatgtactg   3120
ccaaaaccgc atcatcatgg taatagcgat gactaatacg tagatgtact gccaagtagg   3180
aaagtcccat aaggtcatgt actgggcata atgccaggcg ggccatttac cgtcattgac   3240
gtcaataggg ggcgtacttg gcatatgata cacttgatgt actgccaagt gggcagttta   3300
ccgtaaatac tccacccatt gacgtcaatg gaaagtccct attggcgtta ctatgggaac   3360
```

```
atacgtcatt attgacgtca atgggcgggg gtcgttgggc ggtcagccag gcgggccatt      3420
taccgtaagt tatgtaacgc ctgcaggtta attaagaaca tgtgagcaaa aggccagcaa      3480
aaggccagga accgtaaaaa ggccgcgttg ctggcgtttt tccataggct ccgcccccct      3540
gacgagcatc acaaaaatcg acgctcaagt cagaggtggc gaaacccgac aggactataa      3600
agataccagg cgtttccccc tggaagctcc ctcgtgcgct ctcctgttcc gaccctgccg      3660
cttaccggat acctgtccgc ctttctccct tcgggaagcg tggcgctttc tcatagctca      3720
cgctgtaggt atctcagttc ggtgtaggtc gttcgctcca agctgggctg tgtgcacgaa      3780
ccccccgttc agcccgaccg ctgcgcctta tccggtaact atcgtcttga gtccaacccg      3840
gtaagacacg acttatcgcc actggcagca gccactggta acaggattag cagagcgagg      3900
tatgtaggcg gtgctacaga gttcttgaag tggtggccta actacggcta cactagaaga      3960
acagtatttg gtatctgcgc tctgctgaag ccagttacct tcggaaaaag agttggtagc      4020
tcttgatccg gcaaacaaac caccgctggt agcggtggtt tttttgtttg caagcagcag      4080
attacgcgca gaaaaaaagg atctcaagaa gatcctttga tcttttctac ggggtctgac      4140
gctcagtgga acgaaaactc acgttaaggg attttggtca tggctagtta attaacattt      4200
aaatcagcgg ccgcaataaa atatctttat tttcattaca tctgtgtgtt ggttttttgt      4260
gtgaatcgta actaacatac gctctccatc aaaacaaaac gaaacaaaac aaactagcaa      4320
aataggctgt ccccagtgca agtgcaggtg ccagaacatt tctctatcga a              4371
```

<210> SEQ ID NO 83
<211> LENGTH: 4359
<212> TYPE: DNA
<213> ORGANISM: Artificial Sequence
<220> FEATURE:
<223> OTHER INFORMATION: pCCL7(5-76)-IgG1Fc

<400> SEQUENCE: 83

```
ggatctgcga tcgctccggt gcccgtcagt gggcagagcg cacatcgccc acagtccccg        60
agaagttggg gggaggggtc ggcaattgaa cgggtgccta gagaaggtgg cgcggggtaa       120
actgggaaag tgatgtcgtg tactggctcc gcctttttcc cgagggtggg ggagaaccgt       180
atataagtgc agtagtcgcc gtgaacgttc tttttcgcaa cgggtttgcc gccagaacac       240
agctgaagct tcgaggggct cgcatctctc cttcacgcgc ccgccgccct acctgaggcc       300
gccatccacg ccggttgagt cgcgttctgc cgcctcccgc ctgtggtgcc tcctgaactg       360
cgtccgccgt ctaggtaagt ttaaagctca ggtcgagacc gggcctttgt ccggcgctcc       420
cttggagcct acctagactc agccggctct ccacgctttg cctgaccctg cttgctcaac       480
tctacgtctt tgtttcgttt tctgttctgc gccgttacag atccaagctg tgaccggcgc       540
ctacctgaga tcaccggcga aggagggcca ccatgtacag gatgcaactc ctgtcttgca       600
ttgcactaag tcttgcactt gtcacgaatt cgtttatcaa taagaaaatc cctaagcaga       660
ggctggagag ctacagaagg accaccagta gccactgtcc ccgggaagct gtaatcttca       720
agaccaaact ggacaaggag atctgtgctg accccacaca gaagtgggtc caggacttta       780
tgaagcacct ggacaagaaa acccaaactc aaagcttgaa caaaactcac acatgcccac       840
cgtgcccagc acctgaactc ctgggggac cgtcagtctt cctcttcccc ccaaaaccca       900
aggacaccct catgatctcc cggacccctg aggtcacatg cgtggtggtg gacgtgagcc       960
acgaagaccc tgaggtcaag ttcaactggt acgtggacgg cgtggaggtg cataatgcca      1020
agacaaagcc gcgggaggag cagtacaaca gcacgtaccg tgtggtcagc gtcctcaccg      1080
```

-continued

```
tcctgcacca ggactggctg aatggcaagg agtacaagtg caaggtctcc aacaaagccc      1140
tcccagcccc catcgagaaa accatctcca aagccaaagg gcagccccga gaaccacagg      1200
tgtacaccct gcccccatcc cgggaggaga tgaccaagaa ccaggtcagc ctgacctgcc      1260
tggtcaaagg cttctatccc agcgacatcg ccgtggagtg ggagagcaat gggcagccgg      1320
agaacaacta caagaccacg cctcccgtgc tggactccga cggctccttc ttcctctaca      1380
gcaagctcac cgtggacaag agcaggtggc agcaggggaa cgtcttctca tgctccgtga      1440
tgcacgaggc tctgcacaac cactacacgc agaagagcct ctccctgtct ccgggtaaat      1500
gagtgctagc tggccagaca tgataagata cattgatgag tttggacaaa ccacaactag      1560
aatgcagtga aaaaaatgct ttatttgtga aatttgtgat gctattgctt tatttgtaac      1620
cattataagc tgcaataaac aagttaacaa caacaattgc attcatttta tgtttcaggt      1680
tcagggggag gtgtgggagg ttttttaaag caagtaaaac ctctacaaat gtggtatgga      1740
attaattcta aaatacagca tagcaaaact ttaacctcca aatcaagcct ctacttgaat      1800
ccttttctga gggatgaata aggcataggc atcagggggct gttgccaatg tgcattagct      1860
gtttgcagcc tcaccttctt tcatggagtt taagatatag tgtattttcc caaggtttga      1920
actagctctt catttcttta tgttttaaat gcactgacct cccacattcc cttttagta      1980
aaatattcag aaataattta aatacatcat tgcaatgaaa ataaatgttt tttattaggc      2040
agaatccaga tgctcaaggc ccttcataat atccccagt ttagtagttg gacttaggga      2100
acaaaggaac ctttaataga aattggacag caagaaagcg agcttctagc ttatcctcag      2160
tcctgctcct ctgccacaaa gtgcacgcag ttgccggccg ggtcgcgcag ggcgaactcc      2220
cgcccccacg gctgctcgcc gatctcggtc atggccggcc cggaggcgtc ccggaagttc      2280
gtggacacga cctccgacca ctcggcgtac agctcgtcca ggccgcgcac ccacacccag      2340
gccagggtgt tgtccggcac cacctggtcc tggaccgcgc tgatgaacag ggtcacgtcg      2400
tcccggacca caccggcgaa gtcgtcctcc acgaagtccc gggagaaccc gagccggtcg      2460
gtccagaact cgaccgctcc ggcgacgtcg cgcgcggtga gcaccggaac ggcactggtc      2520
aacttggcca tgatggctcc tcctgtcagg agaggaaaga gaagaaggtt agtacaattg      2580
ctatagtgag ttgtattata ctatgcagat atactatgcc aatgattaat tgtcaaacta      2640
gggctgcagg gttcatagtg ccacttttcc tgcactgccc catctcctgc ccacccttc      2700
ccaggcatag acagtcagtg acttaccaaa ctcacaggag ggagaaggca gaagcttgag      2760
acagacccgc gggaccgccg aactgcgagg ggacgtggct agggcggctt cttttatggt      2820
gcgccggccc tcggaggcag ggcgctcggg gaggcctagc ggccaatctg cggtggcagg      2880
aggcggggcc gaaggccgtg cctgaccaat ccggagcaca taggagtctc agccccccgc      2940
cccaaagcaa ggggaagtca cgcgcctgta gcgccagcgt gttgtgaaat gggggcttgg      3000
gggggttggg gccctgacta gtcaaaacaa actcccattg acgtcaatgg ggtggagact      3060
tggaaatccc cgtgagtcaa accgctatcc acgcccattg atgtactgcc aaaaccgcat      3120
catcatggta atagcgatga ctaatacgta gatgtactgc caagtaggaa agtcccataa      3180
ggtcatgtac tgggcataat gccagcgggg ccatttaccg tcattgacgt caatagggggg      3240
cgtacttggc atatgataca cttgatgtac tgccaagtgg gcagtttacc gtaaatactc      3300
cacccattga cgtcaatgga aagtcctat tggcgttact atgggaacat acgtcattat      3360
tgacgtcaat gggcgggggt cgttgggcgg tcagccaggc gggccattta ccgtaagtta      3420
```

| | |
|---|---|
| tgtaacgcct gcaggttaat taagaacatg tgagcaaaag gccagcaaaa ggccaggaac | 3480 |
| cgtaaaaagg ccgcgttgct ggcgtttttc cataggctcc gccccctga cgagcatcac | 3540 |
| aaaaatcgac gctcaagtca gaggtggcga acccgacag gactataaag ataccaggcg | 3600 |
| tttccccctg gaagctccct cgtgcgctct cctgttccga ccctgccgct taccggatac | 3660 |
| ctgtccgcct ttctcccttc gggaagcgtg gcgctttctc atagctcacg ctgtaggtat | 3720 |
| ctcagttcgg tgtaggtcgt tcgctccaag ctgggctgtg tgcacgaacc cccgttcag | 3780 |
| cccgaccgct gcgccttatc cggtaactat cgtcttgagt ccaacccggt aagacacgac | 3840 |
| ttatcgccac tggcagcagc cactggtaac aggattagca gagcgaggta tgtaggcggt | 3900 |
| gctacagagt tcttgaagtg gtggcctaac tacggctaca ctagaagaac agtatttggt | 3960 |
| atctgcgctc tgctgaagcc agttaccttc ggaaaaagag ttggtagctc ttgatccggc | 4020 |
| aaacaaacca ccgctggtag cggtggtttt tttgtttgca agcagcagat tacgcgcaga | 4080 |
| aaaaaaggat ctcaagaaga tcctttgatc ttttctacgg ggtctgacgc tcagtggaac | 4140 |
| gaaaactcac gttaagggat tttggtcatg ctagttaat taacatttaa atcagcggcc | 4200 |
| gcaataaaat atctttattt tcattacatc tgtgtgttgg ttttttgtgt gaatcgtaac | 4260 |
| taacatacgc tctccatcaa acaaaacga aacaaaacaa actagcaaaa taggctgtcc | 4320 |
| ccagtgcaag tgcaggtgcc agaacatttc tctatcgaa | 4359 |

<210> SEQ ID NO 84
<211> LENGTH: 4359
<212> TYPE: DNA
<213> ORGANISM: Artificial Sequence
<220> FEATURE:
<223> OTHER INFORMATION: pCCL7(5-76K/H-A)-IgG1Fc

<400> SEQUENCE: 84

| | |
|---|---|
| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gcctttttcc cgagggtggg ggagaaccgt | 180 |
| atataagtgc agtagtcgcc gtgaacgttc tttttcgcaa cgggtttgcc gccagaacac | 240 |
| agctgaagct cgaggggct cgcatctctc cttcacgcgc ccgccgccct acctgaggcc | 300 |
| gccatccacg ccgttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg tgaccggcgc | 540 |
| ctacctgaga tcaccggcga aggagggcca ccatgtacag gatgcaactc ctgtcttgca | 600 |
| ttgcactaag tcttgcactt gtcacgaatt cgtttatcaa taagaaaatc cctaagcaga | 660 |
| ggctggagag ctacagaagg accaccagta gccactgtcc ccgggaagct gtaatcttcg | 720 |
| ccaccgcgct ggacgctgag atctgtgctg accccacaca ggcctgggtc caggactta | 780 |
| tggctgccct ggacgcggct acccaaactc agcccttga caaaactcac acatgcccac | 840 |
| cgtgcccagc acctgaactc ctggggggac cgtcagtctt cctcttcccc ccaaaaccca | 900 |
| aggacaccct catgatctcc cggacccctg aggtcacatg cgtggtggtg gacgtgagcc | 960 |
| acgaagaccc tgaggtcaag ttcaactggt acgtggacgg cgtggaggtg cataatgcca | 1020 |
| agacaaagcc gcgggaggag cagtacaaca gcacgtaccg tgtggtcagc gtcctcaccg | 1080 |
| tcctgcacca ggactggctg aatggcaagg agtacaagtg caaggtctcc aacaaagccc | 1140 |

-continued

| | |
|---|---|
| tcccagcccc catcgagaaa accatctcca aagccaaagg gcagccccga gaaccacagg | 1200 |
| tgtacaccct gccccatcc cgggaggaga tgaccaagaa ccaggtcagc ctgacctgcc | 1260 |
| tggtcaaagg cttctatccc agcgacatcg ccgtggagtg ggagagcaat gggcagccgg | 1320 |
| agaacaacta caagaccacg cctcccgtgc tggactccga cggctccttc ttcctctaca | 1380 |
| gcaagctcac cgtggacaag agcaggtggc agcaggggaa cgtcttctca tgctccgtga | 1440 |
| tgcacgaggc tctgcacaac cactacacgc agaagagcct ctccctgtct ccgggtaaat | 1500 |
| gagtgctagc tggccagaca tgataagata cattgatgag tttggacaaa ccacaactag | 1560 |
| aatgcagtga aaaaaatgct ttatttgtga aatttgtgat gctattgctt tatttgtaac | 1620 |
| cattataagc tgcaataaac aagttaacaa caacaattgc attcatttta tgtttcaggt | 1680 |
| tcaggggag gtgtgggagg ttttttaaag caagtaaaac ctctacaaat gtggtatgga | 1740 |
| attaattcta aaatacagca tagcaaaact ttaacctcca aatcaagcct ctacttgaat | 1800 |
| ccttttctga gggatgaata aggcataggc atcaggggct gttgccaatg tgcattagct | 1860 |
| gtttgcagcc tcaccttctt tcatggagtt taagatatag tgtattttcc caaggtttga | 1920 |
| actagctctt catttcttta tgttttaaat gcactgacct cccacattcc ctttttagta | 1980 |
| aaatattcag aaataattta aatacatcat tgcaatgaaa ataaatgttt tttattaggc | 2040 |
| agaatccaga tgctcaaggc ccttcataat atccccagt ttagtagttg gacttaggga | 2100 |
| acaaaggaac ctttaataga aattggacag caagaaagcg agcttctagc ttatcctcag | 2160 |
| tcctgctcct ctgccacaaa gtgcacgcag ttgccggccg ggtcgcgcag ggcgaactcc | 2220 |
| cgcccccacg gctgctcgcc gatctcggtc atggccggcc cggaggcgtc ccggaagttc | 2280 |
| gtggacacga cctccgacca ctcggcgtac agctcgtcca ggccgcgcac ccacacccag | 2340 |
| gccagggtgt tgtccggcac cacctggtcc tggaccgcgc tgatgaacag ggtcacgtcg | 2400 |
| tcccggacca caccggcgaa gtcgtcctcc acgaagtccc gggagaaccc gagccggtcg | 2460 |
| gtccagaact cgaccgctcc ggcgacgtcg cgcgcggtga gcaccggaac ggcactggtc | 2520 |
| aacttggcca tgatggctcc tcctgtcagg agaggaaaga gaagaaggtt agtacaattg | 2580 |
| ctatagtgag ttgtattata ctatgcagat atactatgcc aatgattaat tgtcaaacta | 2640 |
| gggctgcagg gttcatagtg ccacttttcc tgcactgccc catctcctgc ccacccttc | 2700 |
| ccaggcatag acagtcagtg acttaccaaa ctcacaggag ggagaaggca gaagcttgag | 2760 |
| acagacccgc gggaccgccg aactgcgagg ggacgtggct agggcggctt cttttatggt | 2820 |
| gcgccggccc tcgaggcag ggcgctcggg gaggcctagc ggccaatctg cggtggcagg | 2880 |
| aggcggggcc gaaggccgtg cctgaccaat ccggagcaca taggagtctc agccccccgc | 2940 |
| cccaaagcaa gggggaagtca cgcgcctgta gcgccagcgt gttgtgaaat gggggcttgg | 3000 |
| gggggttggg gccctgacta gtcaaaacaa actcccattg acgtcaatgg ggtggagact | 3060 |
| tggaaatccc cgtgagtcaa accgctatcc acgccccattg atgtactgcc aaaaccgcat | 3120 |
| catcatggta atagcgatga ctaatacgta gatgtactgc caagtaggaa agtcccataa | 3180 |
| ggtcatgtac tgggcataat gccaggcggg ccatttaccg tcattgacgt caataggggg | 3240 |
| cgtacttggc atatgataca cttgatgtac tgccaagtgg gcagtttacc gtaaatactc | 3300 |
| cacccattga cgtcaatgga aagtccctat tggcgttact atgggaacat acgtcattat | 3360 |
| tgacgtcaat gggcggggt cgttggcgg tcagccaggc gggccattta ccgtaagtta | 3420 |
| tgtaacgcct gcaggttaat taagaacatg tgagcaaaag gccagcaaaa ggccaggaac | 3480 |

| | |
|---|---:|
| cgtaaaaagg ccgcgttgct ggcgttttc cataggctcc gcccccctga cgagcatcac | 3540 |
| aaaaatcgac gctcaagtca gaggtggcga aacccgacag gactataaag ataccaggcg | 3600 |
| tttccccctg gaagctccct cgtgcgctct cctgttccga ccctgccgct taccggatac | 3660 |
| ctgtccgcct ttctcccttc gggaagcgtg gcgctttctc atagctcacg ctgtaggtat | 3720 |
| ctcagttcgg tgtaggtcgt tcgctccaag ctgggctgtg tgcacgaacc ccccgttcag | 3780 |
| cccgaccgct gcgccttatc cggtaactat cgtcttgagt ccaacccggt aagacacgac | 3840 |
| ttatcgccac tggcagcagc cactggtaac aggattagca gagcgaggta tgtaggcggt | 3900 |
| gctacagagt tcttgaagtg gtggcctaac tacggctaca ctagaagaac agtatttggt | 3960 |
| atctgcgctc tgctgaagcc agttaccttc ggaaaaagag ttggtagctc ttgatccggc | 4020 |
| aaacaaacca ccgctggtag cggtggtttt tttgtttgca agcagcagat tacgcgcaga | 4080 |
| aaaaaggat ctcaagaaga tcctttgatc ttttctacgg ggtctgacgc tcagtggaac | 4140 |
| gaaaactcac gttaagggat tttggtcatg ctagttaat taacatttaa atcagcggcc | 4200 |
| gcaataaaat atctttattt tcattacatc tgtgtgttgg ttttttgtgt gaatcgtaac | 4260 |
| taacatacgc tctccatcaa aacaaaacga aacaaaacaa actagcaaaa taggctgtcc | 4320 |
| ccagtgcaag tgcaggtgcc agaacatttc tctatcgaa | 4359 |

<210> SEQ ID NO 85
<211> LENGTH: 4401
<212> TYPE: DNA
<213> ORGANISM: Artificial Sequence
<220> FEATURE:
<223> OTHER INFORMATION: pCCL8-IgG1Fc

<400> SEQUENCE: 85

| | |
|---|---:|
| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gccttttcc cgagggtggg ggagaaccgt | 180 |
| atataagtgc agtagtcgcc gtgaacgttc tttttcgcaa cgggtttgcc gccagaacac | 240 |
| agctgaagct tcgaggggct cgcatctctc cttcacgcgc ccgccgccct aacctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg tgaccggcgc | 540 |
| ctacctgaga tcaccggcga aggagggcca ccatgtacag gatgcaactc ctgtcttgca | 600 |
| ttgcactaag tcttgcactt gtcacgaatt cgcagccaga ttcagtttcc attccaatca | 660 |
| cctgctgctt taacgtgatc aataggaaaa ttcctatcca gaggctggag agctacacaa | 720 |
| gaatcaccaa catccaatgt cccaaggaag ctgtgatctt caagaccaaa cggggcaagg | 780 |
| aggtctgtgc tgaccccaag gagagatggg tcagggattc catgaagcat ctggaccaaa | 840 |
| tatttcaaaa tctgaagcca gacaaaactc acacatgccc accgtgccca gcacctgaac | 900 |
| tcctgggggg accgtcagtc ttcctcttcc ccccaaaacc caaggacacc ctcatgatct | 960 |
| cccggacccc tgaggtcaca tgcgtggtgg tggacgtgag ccacgaagac cctgaggtca | 1020 |
| agttcaactg gtacgtggac ggcgtggagg tgcataatgc caagacaaag ccgcgggagg | 1080 |
| agcagtacaa cagcacgtac cgtgtggtca gcgtcctcac cgtcctgcac caggactggc | 1140 |
| tgaatggcaa ggagtacaag tgcaaggtct ccaacaaagc cctcccagcc cccatcgaga | 1200 |

-continued

| | |
|---|---|
| aaaccatctc caaagccaaa gggcagcccc gagaaccaca ggtgtacacc ctgcccccat | 1260 |
| cccgggagga gatgaccaag aaccaggtca gcctgacctg cctggtcaaa ggcttctatc | 1320 |
| ccagcgacat cgccgtggag tgggagagca atgggcagcc ggagaacaac tacaagacca | 1380 |
| cgcctcccgt gctggactcc gacggctcct tcttcctcta cagcaagctc accgtggaca | 1440 |
| agagcaggtg gcagcagggg aacgtcttct catgctccgt gatgcacgag gctctgcaca | 1500 |
| accactacac gcagaagagc ctctccctgt ctccgggtaa atgagtgcta gctggccaga | 1560 |
| catgataaga tacattgatg agtttggaca aaccacaact agaatgcagt gaaaaaaatg | 1620 |
| ctttatttgt gaaatttgtg atgctattgc tttatttgta accattataa gctgcaataa | 1680 |
| acaagttaac aacaacaatt gcattcattt tatgtttcag gttcaggggg aggtgtggga | 1740 |
| ggttttttaa agcaagtaaa acctctacaa atgtggtatg gaattaattc taaaatacag | 1800 |
| catagcaaaa ctttaacctc caaatcaagc ctctacttga atccttttct gagggatgaa | 1860 |
| taaggcatag gcatcagggg ctgttgccaa tgtgcattag ctgtttgcag cctcaccttc | 1920 |
| tttcatggag tttaagatat agtgtatttt cccaaggttt gaactagctc ttcatttctt | 1980 |
| tatgttttaa atgcactgac ctcccacatt ccctttttag taaaatattc agaataatt | 2040 |
| taaatacatc attgcaatga aaataaatgt tttttattag gcagaatcca gatgctcaag | 2100 |
| gcccttcata atatcccca gtttagtagt tggacttagg gaacaaagga acctttaata | 2160 |
| gaaattggac agcaagaaag cgagcttcta gcttatcctc agtcctgctc ctctgccaca | 2220 |
| aagtgcacgc agttgccggc cgggtcgcgc agggcgaact cccgcccca cggctgctcg | 2280 |
| ccgatctcgg tcatggccgg cccggaggcg tcccggaagt tcgtggacac gacctccgac | 2340 |
| cactcggcgt acagctcgtc caggccgcgc acccacaccc aggccagggt gttgtccggc | 2400 |
| accacctggt cctggaccgc gctgatgaac agggtcacgt cgtcccggac cacaccggcg | 2460 |
| aagtcgtcct ccacgaagtc ccgggagaac ccgagccggt cggtccagaa ctcgaccgct | 2520 |
| ccggcgacgt cgcgcgcggt gagcaccgga acggcactgg tcaacttggc catgatggct | 2580 |
| cctcctgtca ggagaggaaa gagaagaagg ttagtacaat tgctatagtg agttgtatta | 2640 |
| tactatgcag atatactatg ccaatgatta attgtcaaac tagggctgca gggttcatag | 2700 |
| tgccactttt cctgcactgc cccatctcct gcccacccct tcccaggcat agacagtcag | 2760 |
| tgacttacca aactcacagg agggagaagg cagaagcttg agacagaccc gcgggaccgc | 2820 |
| cgaactgcga ggggacgtgg ctagggcggc ttcttttatg gtgcgccggc cctcggaggc | 2880 |
| agggcgctcg gggaggccta gcggccaatc tgcggtggca ggaggcgggg ccgaaggccg | 2940 |
| tgcctgacca atccggagca cataggagtc tcagcccccc gccccaaagc aaggggaagt | 3000 |
| cacgcgcctg tagcgccagc gtgttgtgaa atggggcctt ggggggttg gggccctgac | 3060 |
| tagtcaaaac aaactcccat tgacgtcaat ggggtggaga cttggaaatc cccgtgagtc | 3120 |
| aaaccgctat ccacgcccat tgatgtactg ccaaaaccgc atcatcatgg taatagcgat | 3180 |
| gactaatacg tagatgtact gccaagtagg aaagtcccat aaggtcatgt actgggcata | 3240 |
| atgccaggcg ggccatttac cgtcattgac gtcaataggg ggcgtacttg gcatatgata | 3300 |
| cacttgatgt actgccaagt gggcagttta ccgtaaatac tccacccatt gacgtcaatg | 3360 |
| gaaagtccct attggcgtta ctatgggaac atacgtcatt attgacgtca atgggcgggg | 3420 |
| gtcgttgggc ggtcagccag gcgggccatt taccgtaagt tatgtaacgc ctgcaggtta | 3480 |
| attaagaaca tgtgagcaaa aggccagcaa aaggccagga accgtaaaaa ggccgcgttg | 3540 |

| | |
|---|---|
| ctggcgtttt tccataggct ccgccccct gacgagcatc acaaaaatcg acgctcaagt | 3600 |
| cagaggtggc gaaacccgac aggactataa agataccagg cgtttccccc tggaagctcc | 3660 |
| ctcgtgcgct ctcctgttcc gaccctgccg cttaccggat acctgtccgc ctttctccct | 3720 |
| tcgggaagcg tggcgctttc tcatagctca cgctgtaggt atctcagttc ggtgtaggtc | 3780 |
| gttcgctcca agctgggctg tgtgcacgaa ccccccgttc agcccgaccg ctgcgcctta | 3840 |
| tccggtaact atcgtcttga gtccaacccg gtaagacacg acttatcgcc actggcagca | 3900 |
| gccactggta acaggattag cagagcgagg tatgtaggcg gtgctacaga gttcttgaag | 3960 |
| tggtggccta actacggcta cactagaaga acagtatttg gtatctgcgc tctgctgaag | 4020 |
| ccagttacct tcggaaaaag agttggtagc tcttgatccg gcaaacaaac caccgctggt | 4080 |
| agcggtggtt tttttgtttg caagcagcag attacgcgca gaaaaaaagg atctcaagaa | 4140 |
| gatcctttga tcttttctac ggggtctgac gctcagtgga acgaaaactc acgttaaggg | 4200 |
| attttggtca tggctagtta attaacattt aaatcagcgg ccgcaataaa atatctttat | 4260 |
| tttcattaca tctgtgtgtt ggttttttgt gtgaatcgta actaacatac gctctccatc | 4320 |
| aaaacaaaac gaaacaaaac aaactagcaa ataggctgt ccccagtgca agtgcaggtg | 4380 |
| ccagaacatt tctctatcga a | 4401 |

<210> SEQ ID NO 86
<211> LENGTH: 4389
<212> TYPE: DNA
<213> ORGANISM: Artificial Sequence
<220> FEATURE:
<223> OTHER INFORMATION: pCCL8(5-76)-IgG1Fc

<400> SEQUENCE: 86

| | |
|---|---|
| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gccttttcc cgagggtggg ggagaaccgt | 180 |
| atataagtgc agtagtcgcc gtgaacgttc ttttcgcaa cgggtttgcc gccagaacac | 240 |
| agctgaagct tcgaggggct cgcatctctc cttcacgcgc ccgccgccct aactgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg tgaccggcgc | 540 |
| ctacctgaga tcaccggcga aggagggcca ccatgtacag gatgcaactc ctgtcttgca | 600 |
| ttgcactaag tcttgcactt gtcacgaatt cggtttccat tccatcacc tgctgcttta | 660 |
| acgtgatcaa taggaaaatt cctatccaga ggctggagag ctacacaaga atcaccaaca | 720 |
| tccaatgtcc caaggaagct gtgatcttca gaccaaacg gggcaaggag gtctgtgctg | 780 |
| accccaagga gagatgggtc agggattcca tgaagcatct ggaccaaata tttcaaaatc | 840 |
| tgaagccaga caaaactcac acatgcccac cgtgcccagc acctgaactc ctggggggac | 900 |
| cgtcagtctt cctcttcccc ccaaaaccca aggacaccct catgatctcc cggacccctg | 960 |
| aggtcacatg cgtggtggtg gacgtgagcc acgaagaccc tgaggtcaag ttcaactggt | 1020 |
| acgtggacgg cgtggaggtg cataatgcca agacaaagcc gcgggaggag cagtacaaca | 1080 |
| gcacgtaccg tgtggtcagc gtcctcaccg tcctgcacca ggactggctg aatggcaagg | 1140 |
| agtacaagtg caaggtctcc aacaaagccc tcccagcccc catcgagaaa accatctcca | 1200 |

```
aagccaaagg gcagcccga  gaaccacagg tgtacaccct gccccatcc  cggaggaga   1260 tgaccaagaa ccaggtcagc ctgacctgcc tggtcaaagg cttctatccc agcgacatcg  1320
ccgtggagtg ggagagcaat gggcagccgg agaacaacta caagaccacg cctcccgtgc  1380
tggactccga cggctccttc ttcctctaca gcaagctcac cgtggacaag agcaggtggc  1440
agcaggggaa cgtcttctca tgctccgtga tgcacgaggc tctgcacaac cactacacgc  1500
agaagagcct ctccctgtct ccgggtaaat gagtgctagc tggccagaca tgataagata  1560
cattgatgag tttggacaaa ccacaactag aatgcagtga aaaaaatgct ttatttgtga  1620
aatttgtgat gctattgctt tatttgtaac cattataagc tgcaataaac aagttaacaa  1680
caacaattgc attcatttta tgtttcaggt tcaggggag  gtgtgggagg tttttaaag   1740 caagtaaaac ctctacaaat gtggtatgga attaattcta aaatacagca tagcaaaact  1800
ttaacctcca aatcaagcct ctacttgaat cctttctga  gggatgaata aggcataggc  1860
atcaggggct gttgccaatg tgcattagct gtttgcagcc tcaccttctt tcatggagtt  1920
taagatatag tgtattttcc caaggtttga actagctctt catttcttta tgttttaaat  1980
gcactgacct cccacattcc cttttagta  aaatattcag aaataattta aatacatcat  2040
tgcaatgaaa ataaatgttt tttattaggc agaatccaga tgctcaaggc ccttcataat  2100
atcccccagt ttagtagttg gacttaggga acaaaggaac ctttaataga aattggacag  2160
caagaaagcg agcttctagc ttatcctcag tcctgctcct ctgccacaaa gtgcacgcag  2220
ttgccggccg gtcgcgcag  ggcgaactcc cgccccacg  gctgctcgcc gatctcggtc  2280
atggccggcc cggaggcgtc ccggaagttc gtggacacga cctccgacca ctcggcgtac  2340
agctcgtcca ggccgcgcac ccacacccag gccagggtgt tgtccggcac cacctggtcc  2400
tggaccgcgc tgatgaacag ggtcacgtcg tcccggacca caccggcgaa gtcgtcctcc  2460
acgaagtccc gggagaaccc gagccggtcg gtccagaact cgaccgctcc ggcgacgtcg  2520
cgcgcggtga gcaccggaac ggcactggtc aacttggcca tgatggctcc tcctgtcagg  2580
agaggaaaga gaagaaggtt agtacaattg ctatagtgag ttgtattata ctatgcagat  2640
atactatgcc aatgattaat tgtcaaacta gggctgcagg gttcatagtg ccactttcc   2700 tgcactgccc catctcctgc ccacccttc  ccaggcatag acagtcagtg acttaccaaa  2760
ctcacaggag ggagaaggca gaagcttgag acagacccgc gggaccgccg aactgcgagg  2820
ggacgtggct agggcggctt cttttatggt gcgccggccc tcggaggcag ggcgctcggg  2880
gaggcctagc ggccaatctg cggtggcagg aggcggggcc gaaggccgtg cctgaccaat  2940
ccggagcaca taggagtctc agccccccgc cccaaagcaa ggggaagtca cgcgcctgta  3000
gcgccagcgt gttgtgaaat gggggcttgg ggggttggg  gccctgacta gtcaaaacaa  3060
actcccattg acgtcaatgg ggtggagact tggaaatccc cgtgagtcaa accgctatcc  3120
acgcccattg atgtactgcc aaaaccgcat catcatggta atagcgatga ctaatacgta  3180
gatgtactgc caagtaggaa agtcccataa ggtcatgtac tgggcataat gccaggcggg  3240
ccatttaccg tcattgacgt caataggggg cgtacttggc atatgataca cttgatgtac  3300
tgccaagtgg gcagtttacc gtaaatactc cacccattga cgtcaatgga aagtccctat  3360
tggcgttact atgggaacat acgtcattat tgacgtcaat gggcggggt  cgttgggcgg  3420 tcagccaggc gggccattta ccgtaagtta tgtaacgcct gcaggttaat taagaacatg  3480
tgagcaaaag gccagcaaaa ggccaggaac cgtaaaaagg ccgcgttgct ggcgtttttc  3540
```

| | |
|---|---|
| cataggctcc gcccccctga cgagcatcac aaaaatcgac gctcaagtca gaggtggcga | 3600 |
| aacccgacag gactataaag ataccaggcg tttccccctg gaagctccct cgtgcgctct | 3660 |
| cctgttccga ccctgccgct taccggatac ctgtccgcct ttctcccttc gggaagcgtg | 3720 |
| gcgctttctc atagctcacg ctgtaggtat ctcagttcgg tgtaggtcgt tcgctccaag | 3780 |
| ctgggctgtg tgcacgaacc ccccgttcag cccgaccgct gcgccttatc cggtaactat | 3840 |
| cgtcttgagt ccaacccggt aagacacgac ttatcgccac tggcagcagc cactggtaac | 3900 |
| aggattagca gagcgaggta tgtaggcggt gctacagagt tcttgaagtg gtggcctaac | 3960 |
| tacggctaca ctagaagaac agtatttggt atctgcgctc tgctgaagcc agttaccttc | 4020 |
| ggaaaaagag ttggtagctc ttgatccggc aaacaaacca ccgctggtag cggtggtttt | 4080 |
| tttgtttgca agcagcagat tacgcgcaga aaaaaaggat ctcaagaaga tcctttgatc | 4140 |
| ttttctacgg ggtctgacgc tcagtggaac gaaaactcac gttaagggat tttggtcatg | 4200 |
| gctagttaat taacatttaa atcagcggcc gcaataaaat atctttatttt tcattacatc | 4260 |
| tgtgtgttgg ttttttgtgt gaatcgtaac taacatacg tctccatcaa aacaaaacga | 4320 |
| aacaaaacaa actagcaaaa taggctgtcc ccagtgcaag tgcaggtgcc agaacatttc | 4380 |
| tctatcgaa | 4389 |

<210> SEQ ID NO 87
<211> LENGTH: 4389
<212> TYPE: DNA
<213> ORGANISM: Artificial Sequence
<220> FEATURE:
<223> OTHER INFORMATION: pCCL8(5-76K/H-A)-IgG1Fc

<400> SEQUENCE: 87

| | |
|---|---|
| ggatctgcga tcgctccggt gcccgtcagt gggcagagcg cacatcgccc acagtccccg | 60 |
| agaagttggg gggagggggtc ggcaattgaa cgggtgccta gagaaggtgg cgcggggtaa | 120 |
| actgggaaag tgatgtcgtg tactggctcc gccttttttcc cgagggtggg ggagaaccgt | 180 |
| atataagtgc agtagtcgcc gtgaacgttc ttttttcgcaa cgggtttgcc gccagaacac | 240 |
| agctgaagct tcgaggggct cgcatctctc cttcacgcgc ccgccgccct acctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggccttttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg tgaccggcgc | 540 |
| ctacctgaga tcaccggcga aggagggcca ccatgtacag gatgcaactc ctgtcttgca | 600 |
| ttgcactaag tcttgcactt gtcacgaatt cggtttccat tccaatcacc tgctgcttta | 660 |
| acgtgatcaa taggaaaatt cctatccaga ggctggagag ctacacaaga atcaccaaca | 720 |
| tccaatgtcc caaggaagct gtgatcttca agaccgccgc gggcgctgag gtctgtgctg | 780 |
| accccgccga ggcgtgggtc gctgattcca tggccgcgct ggaccaaata tttcaaaatc | 840 |
| tggctccaga caaaactcac acatgcccac cgtgcccagc acctgaactc ctggggggac | 900 |
| cgtcagtctt cctcttcccc ccaaaaccca aggacaccct catgatctcc cggacccctg | 960 |
| aggtcacatg cgtggtggtg gacgtgagcc acgaagaccc tgaggtcaag ttcaactggt | 1020 |
| acgtggacgg cgtggaggtg cataatgcca agacaaagcc gcgggaggag cagtacaaca | 1080 |
| gcacgtaccg tgtggtcagc gtcctcaccg tcctgcacca ggactggctg aatggcaagg | 1140 |
| agtacaagtg caaggtctcc aacaaagccc tcccagcccc catcgagaaa accatctcca | 1200 |

```
aagccaaagg gcagccccga gaaccacagg tgtacaccct gcccccatcc cgggaggaga    1260
tgaccaagaa ccaggtcagc ctgacctgcc tggtcaaagg cttctatccc agcgacatcg    1320
ccgtggagtg ggagagcaat gggcagccgg agaacaacta caagaccacg cctcccgtgc    1380
tggactccga cggctccttc ttcctctaca gcaagctcac cgtggacaag agcaggtggc    1440
agcaggggaa cgtcttctca tgctccgtga tgcacgaggc tctgcacaac cactacacgc    1500
agaagagcct ctccctgtct ccgggtaaat gagtgctagc tggccagaca tgataagata    1560
cattgatgag tttggacaaa ccacaactag aatgcagtga aaaaaatgct ttatttgtga    1620
aatttgtgat gctattgctt tatttgtaac cattataagc tgcaataaac aagttaacaa    1680
caacaattgc attcatttta tgtttcaggt tcaggggag gtgtgggagg tttttaaag     1740 caagtaaaac ctctacaaat gtggtatgga attaattcta aaatacagca tagcaaaact    1800
ttaacctcca aatcaagcct ctacttgaat ccttttctga gggatgaata aggcataggc    1860
atcaggggct gttgccaatg tgcattagct gtttgcagcc tcaccttctt tcatggagtt    1920
taagatatag tgtattttcc caaggtttga actagctctt catttcttta tgttttaaat    1980
gcactgacct cccacattcc cttttagta aatattcag aaataattta aatacatcat      2040
tgcaatgaaa ataaatgttt tttattaggc agaatccaga tgctcaaggc ccttcataat    2100 atccccagt ttagtagttg gacttaggga acaaaggaac ctttaataga aattggacag    2160
caagaaagcg agcttctagc ttatcctcag tcctgctcct ctgccacaaa gtgcacgcag    2220
ttgccggccg ggtcgcgcag ggcgaactcc cgccccacg gctgctcgcc gatctcggtc     2280
atggccggcc cggaggcgtc ccggaagttc gtggacacga cctccgacca ctcggcgtac    2340
agctcgtcca ggccgcgcac ccacacccag gccagggtgt tgtccggcac cacctggtcc    2400
tggaccgcgc tgatgaacag ggtcacgtcg tcccggacca caccggcgaa gtcgtcctcc    2460
acgaagtccc gggagaaccc gagccggtcg gtccagaact cgaccgctcc ggcgacgtcg    2520
cgcgcggtga gcaccggaac ggcactggtc aacttggcca tgatggctcc tcctgtcagg    2580
agaggaaaga gaagaaggtt agtacaattg ctatagtgag ttgtattata ctatgcagat    2640
atactatgcc aatgattaat tgtcaaacta gggctgcagg gttcatagtg ccactttcc     2700 tgcactgccc catctcctgc ccacccttc ccaggcatag acagtcagtg acttaccaaa    2760
ctcacaggag ggagaaggca gaagcttgag acagacccgc gggaccgccg aactgcgagg    2820
ggacgtggct agggcggctt cttttatggt gcgccggccc tcggaggcag ggcgctcggg    2880
gaggcctagc ggccaatctg cggtggcagg aggcggggcc gaaggccgtg cctgaccaat    2940
ccggagcaca taggagtctc agccccccgc cccaaagcaa ggggaagtca cgcgcctgta    3000
gcgccagcgt gttgtgaaat gggggcttgg ggggttggg gccctgacta gtcaaaacaa     3060
actcccattg acgtcaatgg ggtggagact tggaaatccc cgtgagtcaa accgctatcc    3120
acgcccattg atgtactgcc aaaaccgcat catcatggta atagcgatga ctaatacgta    3180
gatgtactgc caagtaggaa agtcccataa ggtcatgtac tgggcataat gccaggcggg    3240
ccatttaccg tcattgacgt caatagggg cgtacttggc atatgataca cttgatgtac     3300
tgccaagtgg gcagtttacc gtaaatactc cacccattga cgtcaatgga aagtccctat    3360
tggcgttact atgggaacat acgtcattat tgacgtcaat gggcggggt cgttgggcgg     3420 tcagccaggc gggccattta ccgtaagtta tgtaacgcct gcaggttaat taagaacatg    3480
tgagcaaaag gccagcaaaa ggccaggaac cgtaaaaagg ccgcgttgct ggcgtttttc    3540
```

| | |
|---|---|
| cataggctcc gccccctga cgagcatcac aaaaatcgac gctcaagtca gaggtggcga | 3600 |
| aacccgacag gactataaag ataccaggcg tttcccctg gaagctccct cgtgcgctct | 3660 |
| cctgttccga ccctgccgct taccggatac ctgtccgcct ttctcccttc gggaagcgtg | 3720 |
| gcgctttctc atagctcacg ctgtaggtat ctcagttcgg tgtaggtcgt tcgctccaag | 3780 |
| ctgggctgtg tgcacgaacc ccccgttcag cccgaccgct gcgccttatc cggtaactat | 3840 |
| cgtcttgagt ccaacccggt aagacacgac ttatcgccac tggcagcagc cactggtaac | 3900 |
| aggattagca gagcgaggta tgtaggcggt gctacagagt tcttgaagtg gtggcctaac | 3960 |
| tacggctaca ctagaagaac agtatttggt atctgcgctc tgctgaagcc agttaccttc | 4020 |
| ggaaaagag ttggtagctc ttgatccggc aaacaaacca ccgctggtag cggtggtttt | 4080 |
| tttgtttgca agcagcagat tacgcgcaga aaaaaggat ctcaagaaga tcctttgatc | 4140 |
| ttttctacgg ggtctgacgc tcagtggaac gaaaactcac gttaagggat tttggtcatg | 4200 |
| gctagttaat taacatttaa atcagcggcc gcaataaaat atctttattt tcattacatc | 4260 |
| tgtgtgttgg ttttttgtgt gaatcgtaac taacatacg tctccatcaa aacaaaacga | 4320 |
| aacaaaacaa actagcaaaa taggctgtcc ccagtgcaag tgcaggtgcc agaacatttc | 4380 |
| tctatcgaa | 4389 |

<210> SEQ ID NO 88
<211> LENGTH: 4398
<212> TYPE: DNA
<213> ORGANISM: Artificial Sequence
<220> FEATURE:
<223> OTHER INFORMATION: pCCL13-IgG1Fc

<400> SEQUENCE: 88

| | |
|---|---|
| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gcctttttcc cgagggtggg ggagaaccgt | 180 |
| atataagtgc agtagtcgcc gtgaacgttc ttttcgcaa cgggtttgcc gccagaacac | 240 |
| agctgaagct tcgaggggct cgcatctctc cttcacgcgc ccgccgccct acctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg tgaccggcgc | 540 |
| ctacctgaga tcaccggcga aggagggcca ccatgtacag gatgcaactc ctgtcttgca | 600 |
| ttgcactaag tcttgcactt gtcacgaatt cgcagccaga tgcactcaac gtcccatcta | 660 |
| cttgctgctt cacatttagc agtaagaaga tctccttgca gaggctgaag agctatgtga | 720 |
| tcaccaccag caggtgtccc cagaaggctg tcatcttcag aaccaaactg gcaaggagaa | 780 |
| tctgtgctga cccaaaggag aagtgggtcc agaattatat gaaacacctg gccggaaag | 840 |
| ctcacaccct gaagactgac aaaactcaca catgcccacc gtgcccagca cctgaactcc | 900 |
| tggggggacc gtcagtcttc ctcttcccc caaaacccaa ggacaccctc atgatctccc | 960 |
| ggacccctga ggtcacatgc gtggtggtgg acgtgagcca cgaagaccct gaggtcaagt | 1020 |
| tcaactggta cgtggacggc gtggaggtgc ataatgccaa gacaaagccg cgggaggagc | 1080 |
| agtacaacag cacgtaccgt gtggtcagcg tcctcaccgt cctgcaccag gactggctga | 1140 |
| atggcaagga gtacaagtgc aaggtctcca acaaagccct cccagccccc atcgagaaaa | 1200 |

```
ccatctccaa agccaaaggg cagccccgag aaccacaggt gtacaccctg cccccatccc    1260
gggaggagat gaccaagaac caggtcagcc tgacctgcct ggtcaaaggc ttctatccca    1320
gcgacatcgc cgtggagtgg gagagcaatg ggcagccgga gaacaactac aagaccacgc    1380
ctcccgtgct ggactccgac ggctccttct tcctctacag caagctcacc gtggacaaga    1440
gcaggtggca gcaggggaac gtcttctcat gctccgtgat gcacgaggct ctgcacaacc    1500
actacacgca gaagagcctc tccctgtctc cgggtaaatg agtgctagct ggccagacat    1560
gataagatac attgatgagt ttggacaaac cacaactaga atgcagtgaa aaaaatgctt    1620
tatttgtgaa atttgtgatg ctattgcttt atttgtaacc attataagct gcaataaaca    1680
agttaacaac aacaattgca ttcattttat gtttcaggtt caggggagg tgtgggaggt    1740 tttttaaagc aagtaaaacc tctacaaatg tggtatggaa ttaattctaa aatacagcat    1800
agcaaaactt taacctccaa atcaagcctc tacttgaatc cttttctgag ggatgaataa    1860
ggcataggca tcaggggctg ttgccaatgt gcattagctg tttgcagcct caccttcttt    1920
catggagttt aagatatagt gtattttccc aaggtttgaa ctagctcttc atttctttat    1980
gttttaaatg cactgacctc ccacattccc tttttagtaa aatattcaga ataatttaa     2040 atacatcatt gcaatgaaaa taaatgtttt ttattaggca gaatccagat gctcaaggcc    2100
cttcataata tcccccagtt tagtagttgg acttagggaa caaggaacc tttaatagaa     2160 attggacagc aagaaagcga gcttctagct tatcctcagt cctgctcctc tgccacaaag    2220
tgcacgcagt tgccggccgg gtcgcgcagg gcgaactccc gcccccacgg ctgctcgccg    2280
atctcggtca tggccggccc ggaggcgtcc cggaagttcg tggacacgac ctccgaccac    2340
tcggcgtaca gctcgtccag gccgcgcacc cacacccagg ccagggtgtt gtccggcacc    2400
acctggtcct ggaccgcgct gatgaacagg gtcacgtcgt cccggaccac accggcgaag    2460
tcgtcctcca cgaagtcccg ggagaacccg agccggtcgg tccagaactc gaccgctccg    2520
gcgacgtcgc gcgcggtgag caccggaacg gcactggtca acttggccat gatggctcct    2580
cctgtcagga gaggaaagag aagaaggtta gtacaattgc tatagtgagt tgtattatac    2640
tatgcagata tactatgcca atgattaatt gtcaaactag ggctgcaggg ttcatagtgc    2700
cactttccct gcactgcccc atctcctgcc cacccttcc caggcataga cagtcagtga    2760
cttaccaaac tcacaggagg gagaaggcag aagcttgaga cagacccgcg ggaccgccga    2820
actgcgaggg gacgtggcta gggcggcttc ttttatggtg cgccggccct cggaggcagg    2880
gcgctcgggg aggcctagcg gccaatctgc ggtggcagga ggcggggccg aaggccgtgc    2940
ctgaccaatc cggagcacat aggagtctca gcccccgcc ccaaagcaag gggaagtcac    3000
gcgcctgtag cgccagcgtg ttgtgaaatg ggggcttggg ggggttgggg ccctgactag    3060
tcaaaacaaa ctcccattga cgtcaatggg gtggagactt ggaaatcccc gtgagtcaaa    3120
ccgctatcca cgcccattga tgtactgcca aaaccgcatc atcatggtaa tagcgatgac    3180
taatacgtag atgtactgcc aagtaggaaa gtcccataag gtcatgtact gggcataatg    3240
ccaggcgggc catttaccgt cattgacgtc aataggggc gtacttggca tatgatacac    3300
ttgatgtact gccaagtggg cagtttaccg taaatactcc acccattgac gtcaatggaa    3360
agtccctatt ggcgttacta tgggaacata cgtcattatt gacgtcaatg ggcgggggtc    3420
gttgggcggt cagccaggcg ggccatttac cgtaagttat gtaacgcctg caggttaatt    3480
aagaacatgt gagcaaaagg ccagcaaaag gccaggaacc gtaaaaaggc cgcgttgctg    3540
```

```
gcgtttttcc ataggctccg cccccctgac gagcatcaca aaaatcgacg ctcaagtcag      3600
aggtggcgaa acccgacagg actataaaga taccaggcgt ttccccctgg aagctccctc      3660
gtgcgctctc ctgttccgac cctgccgctt accggatacc tgtccgcctt tctcccttcg      3720
ggaagcgtgg cgctttctca tagctcacgc tgtaggtatc tcagttcggt gtaggtcgtt      3780
cgctccaagc tgggctgtgt gcacgaaccc cccgttcagc ccgaccgctg cgccttatcc      3840
ggtaactatc gtcttgagtc caacccggta agacacgact tatcgccact ggcagcagcc      3900
actggtaaca ggattagcag agcgaggtat gtaggcggtg ctacagagtt cttgaagtgg      3960
tggcctaact acggctacac tagaagaaca gtatttggta tctgcgctct gctgaagcca      4020
gttaccttcg gaaaaagagt tggtagctct tgatccggca acaaaccac cgctggtagc       4080
ggtggttttt ttgtttgcaa gcagcagatt acgcgcagaa aaaaggatc tcaagaagat       4140
cctttgatct tttctacggg gtctgacgct cagtggaacg aaaactcacg ttaagggatt      4200
ttggtcatgg ctagttaatt aacatttaaa tcagcggccg caataaaata tctttatttt      4260
cattacatct gtgtgttggt tttttgtgtg aatcgtaact aacatacgct ctccatcaaa      4320
acaaaacgaa acaaaacaaa ctagcaaaat aggctgtccc cagtgcaagt gcaggtgcca      4380
gaacatttct ctatcgaa                                                    4398

<210> SEQ ID NO 89
<211> LENGTH: 4386
<212> TYPE: DNA
<213> ORGANISM: Artificial Sequence
<220> FEATURE:
<223> OTHER INFORMATION: pCCL13(5-75)-IgG1Fc

<400> SEQUENCE: 89
ggatctgcga tcgctccggt gcccgtcagt gggcagagcg cacatcgccc acagtccccg        60
agaagttggg gggaggggtc ggcaattgaa cgggtgccta gagaaggtgg cgcggggtaa       120
actgggaaag tgatgtcgtg tactggctcc gccttttcc cgagggtggg ggagaaccgt        180
atataagtgc agtagtcgcc gtgaacgttc tttttcgcaa cgggtttgcc gccagaacac       240
agctgaagct tcgagggct cgcatctctc cttcacgcgc ccgccgccct acctgaggcc        300
gccatccacg ccggttgagt cgcgttctgc cgcctcccgc ctgtggtgcc tcctgaactg       360
cgtccgccgt ctaggtaagt ttaaagctca ggtcgagacc gggcctttgt ccggcgctcc      420
cttggagcct acctagactc agccggctct ccacgctttg cctgaccctg cttgctcaac      480
tctacgtctt tgtttcgttt tctgttctgc gccgttacag atccaagctg tgaccggcgc      540
ctacctgaga tcaccggcga aggagggcca ccatgtacag gatgcaactc ctgtcttgca      600
ttgcactaag tcttgcactt gtcacgaatt cgctcaacgt cccatctact tgctgcttca      660
catttagcag taagaagatc tccttgcaga ggctgaagag ctatgtgatc accaccagca      720
ggtgtcccca gaaggctgtc atcttcagaa ccaaactggg caaggagatc tgtgctgacc      780
caaaggagaa gtgggtccag aattatatga acacctgggg ccggaaagct cacacctga      840
agactgacaa aactcacaca tgcccaccgt gcccagcacc tgaactcctg ggggaccgt       900
cagtcttcct cttcccccca aaacccaagg acaccctcat gatctcccgg acccctgagg     960
tcacatgcgt ggtggtggac gtgagccacg aagaccctga ggtcaagttc aactggtacg     1020
tggacggcgt ggaggtgcat aatgccaaga caaagccgcg ggaggagcag tacaacagca     1080
cgtaccgtgt ggtcagcgtc ctcaccgtcc tgcaccagga ctggctgaat ggcaaggagt     1140
acaagtgcaa ggtctccaac aaagccctcc cagcccccat cgagaaaacc atctccaaag     1200
```

```
ccaaagggca gccccgagaa ccacaggtgt acaccctgcc cccatcccgg gaggagatga    1260
ccaagaacca ggtcagcctg acctgcctgg tcaaaggctt ctatcccagc gacatcgccg    1320
tggagtggga gagcaatggg cagccggaga acaactacaa gaccacgcct cccgtgctgg    1380
actccgacgg ctccttcttc ctctacagca agctcaccgt ggacaagagc aggtggcagc    1440
aggggaacgt cttctcatgc tccgtgatgc acgaggctct gcacaaccac tacacgcaga    1500
agagcctctc cctgtctccg ggtaaatgag tgctagctgg ccagacatga taagatacat    1560
tgatgagttt ggacaaacca aactagaat gcagtgaaaa aaatgcttta tttgtgaaat     1620
ttgtgatgct attgctttat ttgtaaccat tataagctgc aataaacaag ttaacaacaa    1680
caattgcatt cattttatgt ttcaggttca gggggaggtg tgggaggttt tttaaagcaa    1740 gtaaacctc tacaaatgtg gtatggaatt aattctaaaa tacagcatag caaaacttta    1800
acctccaaat caagcctcta cttgaatcct tttctgaggg atgaataagg cataggcatc    1860
aggggctgtt gccaatgtgc attagctgtt tgcagcctca ccttctttca tggagtttaa    1920
gatatagtgt attttcccaa ggtttgaact agctcttcat ttctttatgt tttaaatgca    1980
ctgacctccc acattccctt tttagtaaaa tattcagaaa taatttaaat acatcattgc    2040
aatgaaaata aatgtttttt attaggcaga atccagatgc tcaaggccct tcataatatc    2100
ccccagttta gtagttggac ttagggaaca aaggaaccTt taatagaaat tggacagcaa    2160
gaaagcgagc ttctagctta tcctcagtcc tgctcctctg ccacaaagtg cacgcagttg    2220
ccggccgggt cgcgcagggc gaactcccgc ccccacggct gctcgccgat ctcggtcatg    2280
gccggcccgg aggcgtcccg gaagttcgtg gacacgacct ccgaccactc ggcgtacagc    2340
tcgtccaggc cgcgcaccca cacccaggcc agggtgttgt ccggcaccac ctggtcctgg    2400
accgcgctga tgaacagggt cacgtcgtcc cggaccacac cggcgaagtc gtcctccacg    2460
aagtcccggg agaacccgag ccggtcggtc cagaactcga ccgctccggc gacgtcgcgc    2520
gcggtgagca ccggaacggc actggtcaac ttggccatga tggctcctcc tgtcaggaga    2580
ggaaagagaa gaaggttagt acaattgcta tagtgagttg tattatacta tgcagatata    2640
ctatgccaat gattaattgt caaactaggg ctgcagggtt catagtgcca ctttcctgc     2700 actgccccat ctcctgccca cccttttccca ggcatagaca gtcagtgact taccaaactc    2760
acaggaggga gaaggcagaa gcttgagaca gacccgcggg accgccgaac tgcgagggga    2820
cgtggctagg gcggcttctt ttatggtgcg ccggccctcg gaggcagggc gctcggggag    2880
gcctagcggc caatctgcgg tggcaggagg cggggccgaa ggccgtgcct gaccaatccg    2940
gagcacatag gagtctcagc cccccgcccc aaagcaaggg gaagtcacgc gcctgtagcg    3000
ccagcgtgtt gtgaaatggg ggcttggggg ggttggggcc ctgactagtc aaaacaaact    3060
cccattgacg tcaatggggt ggagacttgg aaatccccgt gagtcaaacc gctatccacg    3120
cccattgatg tactgccaaa accgcatcat catggtaata gcgatgacta atacgtagat    3180
gtactgccaa gtaggaaagt cccataaggt catgtactgg gcataatgcc aggcgggcca    3240
tttaccgtca ttgacgtcaa taggggggcg acttggcata tgatacactt gatgtactgc    3300
caagtgggca gtttaccgta aatactccac ccattgacgt caatggaaag tccctattgg    3360
cgttactatg ggaacatacg tcattattga cgtcaatggg cggggtcgt tgggcggtca     3420 gccaggcggg ccatttaccg taagttatgt aacgcctgca ggttaattaa gaacatgtga    3480
gcaaaaggcc agcaaaaggc caggaaccgt aaaaaggccg cgttgctggc gttttttccat   3540
```

| | |
|---|---|
| aggctccgcc cccctgacga gcatcacaaa atcgacgct caagtcagag gtggcgaaac | 3600 |
| ccgacaggac tataaagata ccaggcgttt ccccctggaa gctccctcgt gcgctctcct | 3660 |
| gttccgaccc tgccgcttac cggatacctg tccgcctttc tcccttcggg aagcgtggcg | 3720 |
| ctttctcata gctcacgctg taggtatctc agttcggtgt aggtcgttcg ctccaagctg | 3780 |
| ggctgtgtgc acgaaccccc cgttcagccc gaccgctgcg ccttatccgg taactatcgt | 3840 |
| cttgagtcca acccggtaag acacgactta tcgccactgg cagcagccac tggtaacagg | 3900 |
| attagcagag cgaggtatgt aggcggtgct acagagttct tgaagtggtg gcctaactac | 3960 |
| ggctacacta agaacagt atttggtatc tgcgctctgc tgaagccagt taccttcgga | 4020 |
| aaaagagttg gtagctcttg atccggcaaa caaaccaccg ctggtagcgg tggttttttt | 4080 |
| gtttgcaagc agcagattac gcgcagaaaa aaggatctc aagaagatcc tttgatcttt | 4140 |
| tctacggggt ctgacgctca gtggaacgaa aactcacgtt aagggatttt ggtcatggct | 4200 |
| agttaattaa catttaaatc agcggccgca ataaatatc tttatttca ttacatctgt | 4260 |
| gtgttggttt tttgtgtgaa tcgtaactaa catacgctcc catcaaaac aaaacgaaac | 4320 |
| aaaacaaact agcaaaatag gctgtcccca gtgcaagtgc aggtgccaga catttctct | 4380 |
| atcgaa | 4386 |

<210> SEQ ID NO 90
<211> LENGTH: 4386
<212> TYPE: DNA
<213> ORGANISM: Artificial Sequence
<220> FEATURE:
<223> OTHER INFORMATION: pCCL13(5-75K/H-A)-IgG1Fc

<400> SEQUENCE: 90

| | |
|---|---|
| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gcctttttcc cgagggtggg ggagaaccgt | 180 |
| atataagtgc agtagtcgcc gtgaacgttc ttttcgcaa cgggtttgcc gccagaacac | 240 |
| agctgaagct tcgaggggct cgcatctctc cttcacgcgc ccgccgccct acctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg tgaccggcgc | 540 |
| ctacctgaga tcaccggcga aggagggcca ccatgtacag gatgcaactc ctgtcttgca | 600 |
| ttgcactaag tcttgcactt gtcacgaatt cgctcaacgt cccatctact tgctgcttca | 660 |
| catttagcag taagaagatc tccttgcaga ggctgaagag ctatgtgatc accaccagca | 720 |
| ggtgtcccca gaaggctgtc atcttcagaa ccgccctggg cgcggagatc tgtgctgacc | 780 |
| cagccgaggc ctgggtccag aattatatgg cggctctggg ccgaaagct gccaccctgg | 840 |
| ctactgacaa aactcacaca tgcccaccgt gcccagcacc tgaactcctg ggggaccgt | 900 |
| cagtcttcct cttccccca aaacccaagg acaccctcat gatctcccgg acccctgagg | 960 |
| tcacatgcgt ggtggtggac gtgagccacg aagaccctga ggtcaagttc aactggtacg | 1020 |
| tggacggcgt ggaggtgcat aatgccaaga caaagccgcg ggaggagcag tacaacagca | 1080 |
| cgtaccgtgt ggtcagcgtc ctcaccgtcc tgcaccagga ctggctgaat ggcaaggagt | 1140 |
| acaagtgcaa ggtctccaac aaagccctcc cagcccccat cgagaaaacc atctccaaag | 1200 |

```
ccaaagggca gccccgagaa ccacaggtgt acaccctgcc cccatcccgg gaggagatga   1260
ccaagaacca ggtcagcctg acctgcctgg tcaaaggctt ctatcccagc gacatcgccg   1320
tggagtggga gagcaatggg cagccggaga caaactacaa gaccacgcct cccgtgctgg   1380
actccgacgg ctccttcttc ctctacagca agctcaccgt ggacaagagc aggtggcagc   1440
aggggaacgt cttctcatgc tccgtgatgc acgaggctct gcacaaccac tacacgcaga   1500
agagcctctc cctgtctccg ggtaaatgag tgctagctgg ccagacatga taagatacat   1560
tgatgagttt ggacaaacca caactagaat gcagtgaaaa aaatgcttta tttgtgaaat   1620
ttgtgatgct attgctttat ttgtaaccat tataagctgc aataaacaag ttaacaacaa   1680
caattgcatt cattttatgt ttcaggttca gggggaggtg tgggaggttt tttaaagcaa   1740
gtaaaacctc tacaaatgtg gtatggaatt aattctaaaa tacagcatag caaaacttta   1800
acctccaaat caagcctcta cttgaatcct tttctgaggg atgaataagg cataggcatc   1860
aggggctgtt gccaatgtgc attagctgtt tgcagcctca ccttctttca tggagtttaa   1920
gatatagtgt attttcccaa ggtttgaact agctcttcat ttctttatgt tttaaatgca   1980
ctgacctccc acattccctt tttagtaaaa tattcagaaa taatttaaat acatcattgc   2040
aatgaaaata aatgtttttt attaggcaga atccagatgc tcaaggccct tcataatatc   2100
ccccagttta gtagttggac ttagggaaca aaggaacctt taatagaaat tggacagcaa   2160
gaaagcgagc ttctagctta tcctcagtcc tgctcctctg ccacaaagtg cacgcagttg   2220
ccggccgggt cgcgcagggc gaactcccgc ccccacggct gctcgccgat ctcggtcatg   2280
gccggcccgg aggcgtcccg gaagttcgtg gacacgacct ccgaccactc ggcgtacagc   2340
tcgtccaggc cgcgcaccca cacccaggcc agggtgttgt ccggcaccac ctggtcctgg   2400
accgcgctga tgaacagggt cacgtcgtcc cggaccacac cggcgaagtc gtcctccacg   2460
aagtcccggg agaacccgag ccggtcggtc cagaactcga ccgctccggc gacgtcgcgc   2520
gcggtgagca ccggaacggc actggtcaac ttggccatga tggctcctcc tgtcaggaga   2580
ggaaagagaa gaaggttagt acaattgcta tagtgagttg tattatacta tgcagatata   2640
ctatgccaat gattaattgt caaactaggg ctgcagggtt catagtgcca cttttcctgc   2700
actgccccat ctcctgccca ccctttccca ggcatagaca gtcagtgact taccaaactc   2760
acaggaggga gaaggcagaa gcttgagaca gacccgcggg accgccgaac tgcgagggga   2820
cgtggctagg gcggcttctt ttatggtgcg ccggccctcg gaggcagggc gctcggggag   2880
gcctagcggc caatctgcgg tggcaggagg cggggccgaa ggccgtgcct gaccaatccg   2940
gagcacatag gagtctcagc cccccgcccc aaagcaaggg gaagtcacgc gcctgtagcg   3000
ccagcgtgtt gtgaaatggg ggcttggggg ggttggggcc ctgactagtc aaaacaaact   3060
cccattgacg tcaatggggt ggagacttgg aaatccccgt gagtcaaacc gctatccacg   3120
cccattgatg tactgccaaa accgcatcat catggtaata gcgatgacta atacgtagat   3180
gtactgccaa gtaggaaagt cccataaggt catgtactgg gcataatgcc aggcgggcca   3240
tttaccgtca ttgacgtcaa tagggggcgt acttggcata tgatacactt gatgtactgc   3300
caagtgggca gtttaccgta aatactccac ccattgacgt caatggaaag tccctattgg   3360
cgttactatg ggaacatacg tcattattga cgtcaatggg cggggtcgt tgggcggtca   3420 gccaggcggg ccatttaccg taagttatgt aacgcctgca ggttaattaa gaacatgtga   3480
gcaaaaggcc agcaaaaggc caggaaccgt aaaaaggccg cgttgctggc gttttccat   3540
```

| aggctccgcc | cccctgacga | gcatcacaaa | aatcgacgct | caagtcagag | gtggcgaaac | 3600 |
| ccgacaggac | tataaagata | ccaggcgttt | ccccctggaa | gctccctcgt | gcgctctcct | 3660 |
| gttccgaccc | tgccgcttac | cggatacctg | tccgcctttc | tcccttcggg | aagcgtggcg | 3720 |
| ctttctcata | gctcacgctg | taggtatctc | agttcggtgt | aggtcgttcg | ctccaagctg | 3780 |
| ggctgtgtgc | acgaaccccc | cgttcagccc | gaccgctgcg | ccttatccgg | taactatcgt | 3840 |
| cttgagtcca | acccggtaag | acacgactta | tcgccactgg | cagcagccac | tggtaacagg | 3900 |
| attagcagag | cgaggtatgt | aggcggtgct | acagagttct | tgaagtggtg | gcctaactac | 3960 |
| ggctacacta | gaagaacagt | atttggtatc | tgcgctctgc | tgaagccagt | taccttcgga | 4020 |
| aaaagagttg | gtagctcttg | atccggcaaa | caaaccaccg | ctggtagcgg | tggtttttt | 4080 |
| gtttgcaagc | agcagattac | gcgcagaaaa | aaaggatctc | aagaagatcc | tttgatcttt | 4140 |
| tctacggggt | ctgacgctca | gtggaacgaa | aactcacgtt | aagggatttt | ggtcatggct | 4200 |
| agttaattaa | catttaaatc | agcggccgca | ataaaatatc | tttatttca | ttacatctgt | 4260 |
| gtgttggttt | tttgtgtgaa | tcgtaactaa | catacgctcc | ccatcaaaac | aaaacgaaac | 4320 |
| aaaacaaact | agcaaaatag | gctgtcccca | gtgcaagtgc | aggtgccaga | acatttctct | 4380 |
| atcgaa | | | | | | 4386 |

<210> SEQ ID NO 91
<211> LENGTH: 4527
<212> TYPE: DNA
<213> ORGANISM: Artificial Sequence
<220> FEATURE:
<223> OTHER INFORMATION: pCCL25-IgG1Fc

<400> SEQUENCE: 91

| ggatctgcga | tcgctccggt | gcccgtcagt | gggcagagcg | cacatcgccc | acagtccccg | 60 |
| agaagttggg | gggaggggtc | ggcaattgaa | cgggtgccta | gagaaggtgg | cgcggggtaa | 120 |
| actgggaaag | tgatgtcgtg | tactggctcc | gccttttcc | cgagggtggg | ggagaaccgt | 180 |
| atataagtgc | agtagtcgcc | gtgaacgttc | ttttcgcaa | cgggtttgcc | gccagaacac | 240 |
| agctgaagct | tcgaggggct | cgcatctctc | cttcacgcgc | ccgccgccct | acctgaggcc | 300 |
| gccatccacg | ccggttgagt | cgcgttctgc | cgcctcccgc | ctgtggtgcc | tcctgaactg | 360 |
| cgtccgccgt | ctaggtaagt | ttaaagctca | ggtcgagacc | gggcctttgt | ccggcgctcc | 420 |
| cttggagcct | acctagactc | agccggctct | ccacgctttg | cctgaccctg | cttgctcaac | 480 |
| tctacgtctt | tgtttcgttt | tctgttctgc | gccgttacag | atccaagctg | tgaccggcgc | 540 |
| ctacctgaga | tcaccggcga | aggagggcca | ccatgtacag | gatgcaactc | ctgtcttgca | 600 |
| ttgcactaag | tcttgcactt | gtcacgaatt | cgacccaagg | tgtctttgag | gactgctgcc | 660 |
| tggcctacca | ctacccatt | gggtgggctg | tgctccggca | cgcctggact | taccggatcc | 720 |
| aggaggtgag | cgggagctgc | aatctgcctg | ctgcgatatt | ctacctcccc | aagagacaca | 780 |
| ggaaggtgtg | tgggaacccc | aaaagcaggg | aggtgcagag | agccatgaag | ctcctggatg | 840 |
| ctcgaaataa | ggttttgca | aagctccgcc | acaacacgca | gaccttccaa | ggccctcatg | 900 |
| ctgtaaagaa | gttgagttct | ggaaactcca | agttatcatc | gtccaagttt | agcaatccca | 960 |
| tcagcagcag | caagaggaat | gtctccgaca | aaactcacac | atgcccaccg | tgcccagcac | 1020 |
| ctgaactcct | gggggaccg | tcagtcttcc | tcttccccc | aaaacccaag | gacaccctca | 1080 |
| tgatctcccg | gacccctgag | gtcacatgcg | tggtggtgga | cgtgagccac | gaagaccctg | 1140 |
| aggtcaagtt | caactggtac | gtggacggcg | tggaggtgca | taatgccaag | acaaagccgc | 1200 |

```
gggaggagca gtacaacagc acgtaccgtg tggtcagcgt cctcaccgtc ctgcaccagg    1260
actggctgaa tggcaaggag tacaagtgca aggtctccaa caaagccctc ccagccccca    1320
tcgagaaaac catctccaaa gccaagggc agccccgaga accacaggtg tacaccctgc    1380
ccccatcccg ggaggagatg accaagaacc aggtcagcct gacctgcctg gtcaaaggct    1440
tctatcccag cgacatcgcc gtggagtggg agagcaatgg gcagccggag aacaactaca    1500
agaccacgcc tcccgtgctg gactccgacg gctccttctt cctctacagc aagctcaccg    1560
tggacaagag caggtggcag caggggaacg tcttctcatg ctccgtgatg cacgaggctc    1620
tgcacaacca ctacacgcag aagagcctct ccctgtctcc gggtaaatga gtgctagctg    1680
gccagacatg ataagataca ttgatgagtt tggacaaacc acaactagaa tgcagtgaaa    1740
aaaatgcttt atttgtgaaa tttgtgatgc tattgcttta tttgtaacca ttataagctg    1800
caataaacaa gttaacaaca acaattgcat tcattttatg tttcaggttc agggggaggt    1860
gtgggaggtt ttttaaagca agtaaaaacct ctacaaatgt ggtatggaat taattctaaa    1920
atacagcata gcaaaacttt aacctccaaa tcaagcctct acttgaatcc ttttctgagg    1980
gatgaataag gcataggcat caggggctgt tgccaatgtg cattagctgt ttgcagcctc    2040
accttctttc atggagttta agatatagtg tattttccca aggtttgaac tagctcttca    2100 tttcttatg ttttaaatgc actgacctcc cacattccct ttttagtaaa atattcagaa    2160
ataatttaaa tacatcattg caatgaaaat aaatgttttt tattaggcag aatccagatg    2220
ctcaaggccc ttcataatat cccccagttt agtagttgga cttagggaac aaaggaacct    2280
ttaatagaaa ttggacagca agaaagcgag cttctagctt atcctcagtc ctgctcctct    2340
gccacaaagt gcacgcagtt gccggccggg tcgcgcaggg cgaactcccg ccccacggc    2400 tgctcgccga tctcggtcat ggccggcccg gaggcgtccc ggaagttcgt ggacacgacc    2460
tccgaccact cggcgtacag ctcgtccagg ccgcgcaccc acacccaggc cagggtgttg    2520
tccggcacca cctggtcctg gaccgcgctg atgaacaggg tcacgtcgtc ccggaccaca    2580
ccggcgaagt cgtcctccac gaagtcccgg gagaacccga gccggtcggt ccagaactcg    2640
accgctccgg cgacgtcgcg cgcggtgagc accggaacgg cactggtcaa cttggccatg    2700
atggctcctc ctgtcaggag aggaaagaga agaaggttag tacaattgct atagtgagtt    2760
gtattatact atgcagatat actatgccaa tgattaattg tcaaactagg ctgcagggt    2820 tcatagtgcc actttttcctg cactgcccca tctcctgccc acccttccc aggcatagac    2880 agtcagtgac ttaccaaact cacaggaggg agaaggcaga agcttgagac agacccgcgg    2940
gaccgccgaa ctgcgagggg acgtggctag ggcggcttct tttatggtgc gccggccctc    3000
ggaggcaggg cgctcgggga ggcctagcgg ccaatctgcg gtggcaggag gcggggccga    3060
aggccgtgcc tgaccaatcc ggagcacata ggagtctcag ccccccgccc caaagcaagg    3120
ggaagtcacg cgcctgtagc gccagcgtgt tgtgaaatgg gggcttgggg gggtggggc    3180 cctgactagt caaaacaaac tcccattgac gtcaatgggg tggagacttg gaaatccccg    3240
tgagtcaaac cgctatccac gcccattgat gtactgccaa aaccgcatca tcatggtaat    3300
agcgatgact aatacgtaga gtactgcca agtaggaaag tcccataagg tcatgtactg    3360
ggcataatgc caggcgggcc atttaccgtc attgacgtca atagggggcg tacttggcat    3420
atgatacact tgatgtactg ccaagtgggc agtttaccgt aaatactcca cccattgacg    3480
tcaatggaaa gtccctattg gcgttactat gggaacatac gtcattattg acgtcaatgg    3540
```

```
gcggggtcg ttgggcggtc agccaggcgg gccatttacc gtaagttatg taacgcctgc    3600
aggttaatta agaacatgtg agcaaaaggc cagcaaaagg ccaggaaccg taaaaaggcc    3660
gcgttgctgg cgttttttcca taggctccgc cccctgacg agcatcacaa aaatcgacgc    3720
tcaagtcaga ggtggcgaaa cccgacagga ctataaagat accaggcgtt tcccctgga    3780 agctccctcg tgcgctctcc tgttccgacc ctgccgctta ccggatacct gtccgccttt    3840
ctcccttcgg gaagcgtggc gctttctcat agctcacgct gtaggtatct cagttcggtg    3900
taggtcgttc gctccaagct gggctgtgtg cacgaacccc ccgttcagcc cgaccgctgc    3960
gccttatccg gtaactatcg tcttgagtcc aacccggtaa gacacgactt atcgccactg    4020
gcagcagcca ctggtaacag gattagcaga gcgaggtatg taggcggtgc tacagagttc    4080
ttgaagtggt ggcctaacta cggctacact agaagaacag tatttggtat ctgcgctctg    4140
ctgaagccag ttaccttcgg aaaaagagtt ggtagctctt gatccggcaa acaaaccacc    4200
gctggtagcg tggtttttt tgtttgcaag cagcagatta cgcgcagaaa aaaggatct    4260 caagaagatc ctttgatctt ttctacgggg tctgacgctc agtggaacga aaactcacgt    4320
taagggattt tggtcatggc tagttaatta catttaaat cagcggccgc aataaaatat    4380 ctttatttc attacatctg tgtgttggtt ttttgtgtga atcgtaacta acatacgctc    4440
tccatcaaaa caaaacgaaa caaaacaaac tagcaaaata ggctgtcccc agtgcaagtg    4500
caggtgccag aacatttctc tatcgaa                                       4527
```

<210> SEQ ID NO 92
<211> LENGTH: 4518
<212> TYPE: DNA
<213> ORGANISM: Artificial Sequence
<220> FEATURE:
<223> OTHER INFORMATION: pCCL25(4-127)-IgG1Fc

<400> SEQUENCE: 92

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa    120
actgggaaag tgatgtcgtg tactggctcc gccttttttcc cgagggtggg ggagaaccgt    180
atataagtgc agtagtcgcc gtgaacgttc ttttttcgcaa cgggtttgcc gccagaacac    240
agctgaagct tcgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg taccggcgc     540 ctacctgaga tcaccggcga aggagggcca ccatgtacag gatgcaactc ctgtcttgca    600
ttgcactaag tcttgcactt gtcacgaatt cggtctttga ggactgctgc tggcctacc     660 actacccat gggtgggct gtgctccggc acgcctggac ttaccggatc caggaggtga    720
gcgggagctg caatctgcct gctgcgatat tctacctccc caagagacac aggaaggtgt    780
gtgggaaccc caaaagcagg gaggtgcaga gagccatgaa gctcctggat gctcgaaata    840 aggttttttgc aaagctccgc cacaacacgc agaccttcca aggccctcat gctgtaaaga    900
agttgagttc tggaaactcc aagttatcat cgtccaagtt tagcaatccc atcagcagca    960
gcaagaggaa tgtctccgac aaaactcaca catgcccacc gtgcccagca cctgaactcc    1020 tgggggggacc gtcagtcttc ctcttccccc caaaacccaa ggacaccctc atgatctccc    1080
```

```
ggacccctga ggtcacatgc gtggtggtgg acgtgagcca cgaagaccct gaggtcaagt   1140
tcaactggta cgtggacggc gtggaggtgc ataatgccaa gacaaagccg cgggaggagc   1200
agtacaacag cacgtaccgt gtggtcagcg tcctcaccgt cctgcaccag gactggctga   1260
atggcaagga gtacaagtgc aaggtctcca acaaagccct cccagccccc atcgagaaaa   1320
ccatctccaa agccaagggg cagccccgag aaccacaggt gtacaccctg cccccatccc   1380
gggaggagat gaccaagaac caggtcagcc tgacctgcct ggtcaaaggc ttctatccca   1440
gcgacatcgc cgtggagtgg gagagcaatg ggcagccgga gaacaactac aagaccacgc   1500
ctcccgtgct ggactccgac ggctccttct cctctacag caagctcacc gtggacaaga   1560
gcaggtggca gcaggggaac gtcttctcat gctccgtgat gcacgaggct ctgcacaacc   1620
actacacgca gaagagcctc tccctgtctc cgggtaaatg agtgctagct ggccagacat   1680
gataagatac attgatgagt ttggacaaac cacaactaga atgcagtgaa aaaaatgctt   1740
tatttgtgaa atttgtgatg ctattgcttt atttgtaacc attataagct gcaataaaca   1800
agttaacaac aacaattgca ttcattttat gtttcaggtt caggggagg tgtgggaggt   1860 tttttaaagc aagtaaaacc tctacaaatg tggtatggaa ttaattctaa aatacagcat   1920
agcaaaactt taacctccaa atcaagcctc tacttgaatc cttttctgag ggatgaataa   1980
ggcataggca tcaggggctg ttgccaatgt gcattagctg tttgcagcct caccttcttt   2040
catggagttt aagatatagt gtattttccc aaggtttgaa ctagctcttc atttctttat   2100
gttttaaatg cactgacctc ccacattccc tttttagtaa aatattcaga ataatttaa   2160 atacatcatt gcaatgaaaa taatgttttt ttattaggca gaatccagat gctcaaggcc   2220
cttcataata tcccccagtt tagtagttgg acttagggaa caaggaacc tttaatagaa   2280 attggacagc aagaaagcga gcttctagct tatcctcagt cctgctcctc tgccacaaag   2340
tgcacgcagt gccggccgg gtcgcgcagg gcgaactccc gccccacgg ctgctcgccg   2400 atctcggtca tggccggccc ggaggcgtcc cggaagttcg tggacacgac ctccgaccac   2460
tcggcgtaca gctcgtccag gccgcgcacc cacacccagg ccagggtgtt gtccggcacc   2520
acctggtcct ggaccgcgct gatgaacagg gtcacgtcgt cccggaccac accggcgaag   2580
tcgtcctcca cgaagtcccg ggagaacccg agccggtcgg tccagaactc gaccgctccg   2640
gcgacgtcgc gcgcggtgag caccggaacg gcactggtca acttggccat gatggctcct   2700
cctgtcagga gaggaaagag aagaaggtta gtacaattgc tatagtgagt tgtattatac   2760
tatgcagata tactatgcca atgattaatt gtcaaactag gctgcaggg ttcatagtgc   2820 cactttttcct gcactgcccc atctcctgcc cacccttttcc caggcataga cagtcagtga   2880
cttaccaaac tcacaggagg gagaaggcag aagcttgaga cagacccgcg ggaccgccga   2940
actgcgaggg gacgtggcta gggcggcttc ttttatggtg cgccggccct cggaggcagg   3000
gcgctcgggg aggcctagcg gccaatctgc ggtggcagga ggcggggccg aaggccgtgc   3060
ctgaccaatc cggagcacat aggagtctca gccccccgcc ccaaagcaag ggaagtcac   3120 gcgcctgtag cgccagcgtg ttgtgaaatg ggggcttggg ggggttgggg ccctgactag   3180
tcaaaacaaa ctcccattga cgtcaatggg gtggagactt ggaaatcccc gtgagtcaaa   3240
ccgctatcca cgcccattga tgtactgcca aaaccgcatc atcatggtaa tagcgatgac   3300
taatacgtag atgtactgcc aagtaggaaa gtcccataag gtcatgtact gggcataatg   3360
ccaggcgggc catttaccgt cattgacgtc aatagggggc gtacttggca tatgatacac   3420
```

```
ttgatgtact gccaagtggg cagtttaccg taaatactcc acccattgac gtcaatggaa   3480
agtccctatt ggcgttacta tgggaacata cgtcattatt gacgtcaatg gcgggggtc    3540 gttgggcggt cagccaggcg ggccatttac cgtaagttat gtaacgcctg caggttaatt   3600
aagaacatgt gagcaaaagg ccagcaaaag gccaggaacc gtaaaaaggc cgcgttgctg   3660
gcgtttttcc ataggctccg cccccctgac gagcatcaca aaaatcgacg ctcaagtcag   3720
aggtggcgaa acccgacagg actataaaga taccaggcgt ttccccctgg aagctccctc   3780
gtgcgctctc ctgttccgac cctgccgctt accggatacc tgtccgcctt tctcccttcg   3840
ggaagcgtgg cgctttctca tagctcacgc tgtaggtatc tcagttcggt gtaggtcgtt   3900
cgctccaagc tgggctgtgt gcacgaaccc cccgttcagc ccgaccgctg cgccttatcc   3960
ggtaactatc gtcttgagtc aacccggta agacacgact tatcgccact ggcagcagcc    4020
actggtaaca ggattagcag agcgaggtat gtaggcggtg ctacagagtt cttgaagtgg   4080
tggcctaact acggctacac tagaagaaca gtatttggta tctgcgctct gctgaagcca   4140
gttaccttcg gaaaaagagt tggtagctct tgatccggca aacaaaccac cgctggtagc   4200
ggtggttttt ttgtttgcaa gcagcagatt acgcgcagaa aaaaggatc tcaagaagat    4260 cctttgatct tttctacggg gtctgacgct cagtggaacg aaaactcacg ttaagggatt   4320
ttggtcatgg ctagttaatt aacatttaaa tcagcggccg caataaaata tctttatttt   4380
cattacatct gtgtgttggt ttttgtgtg aatcgtaact aacatacgct ctccatcaaa    4440
acaaaacgaa acaaaacaaa ctagcaaaat aggctgtccc cagtgcaagt gcaggtgcca   4500
gaacatttct ctatcgaa                                                 4518
```

<210> SEQ ID NO 93
<211> LENGTH: 4518
<212> TYPE: DNA
<213> ORGANISM: Artificial Sequence
<220> FEATURE:
<223> OTHER INFORMATION: pCCL25(4-127K/H-A)-IgG1Fc

<400> SEQUENCE: 93

```
ggatctgcga tcgctccggt gcccgtcagt gggcagagcg cacatcgccc acagtccccg    60
agaagttggg gggaggggtc ggcaattgaa cgggtgccta gagaaggtgg cgcggggtaa   120
actgggaaag tgatgtcgtg tactggctcc gcctttttcc cgagggtggg ggagaaccgt   180
atataagtgc agtagtcgcc gtgaacgttc tttttcgcaa cgggtttgcc gccagaacac   240
agctgaagct tcgaggggct cgcatctctc cttcacgcgc ccgccgccct acctgaggcc   300
gccatccacg ccggttgagt gcgttctgc cgcctcccgc ctgtggtgcc tcctgaactg    360
cgtccgccgt ctaggtaagt ttaaagctca ggtcgagacc gggcctttgt ccggcgctcc   420
cttggagcct acctagactc agccggctct ccacgctttg cctgaccctg cttgctcaac   480
tctacgtctt tgtttcgttt tctgttctgc gccgttacag atccaagctg tgaccggcgc   540
ctacctgaga tcaccggcga aggagggcca ccatgtacag gatgcaactc ctgtcttgca   600
ttgcactaag tcttgcactt gtcacgaatt cggtctttga ggactgctgc ctggcctacc   660
actaccccat gggtgggct gtgctccggc acgcctggac ttaccggatc caggaggtga    720
gcgggagctg caatctgcct gctgcgatat tctacctccc cgctgccgct gccgcggtgt   780
gtgggaaccc cgctagcgcc gaggtgcagg ctgccatggc cctcctggat gctgctaatg   840 ccgttttgc agcgctcgct gccaacacgc agacctttcca aggccctgcg gctgtagccg   900
ctttgagttc tggaaactcc gccttatcat cgtccgcgtt tagcaatccc atcagcagca   960
```

```
gcgctgccaa tgtctccgac aaaactcaca catgcccacc gtgcccagca cctgaactcc    1020
tggggggacc gtcagtcttc ctcttccccc caaaacccaa ggacaccctc atgatctccc    1080
ggacccctga ggtcacatgc gtggtggtgg acgtgagcca cgaagaccct gaggtcaagt    1140
tcaactggta cgtggacggc gtggaggtgc ataatgccaa gacaaagccg cgggaggagc    1200
agtacaacag cacgtaccgt gtggtcagcg tcctcaccgt cctgcaccag gactggctga    1260
atggcaagga gtacaagtgc aaggtctcca acaaagccct cccagccccc atcgagaaaa    1320
ccatctccaa agccaaaggg cagccccgag aaccacaggt gtacaccctg cccccatccc    1380
gggaggagat gaccaagaac caggtcagcc tgacctgcct ggtcaaaggc ttctatccca    1440
gcgacatcgc cgtggagtgg gagagcaatg ggcagccgga gaacaactac aagaccacgc    1500
ctcccgtgct ggactccgac ggctccttct cctctacag caagctcacc gtggacaaga    1560
gcaggtggca gcaggggaac gtcttctcat gctccgtgat gcacgaggct ctgcacaacc    1620
actacacgca gaagagcctc tccctgtctc cgggtaaatg agtgctagct ggccagacat    1680
gataagatac attgatgagt ttggacaaac cacaactaga atgcagtgaa aaaaatgctt    1740
tatttgtgaa atttgtgatg ctattgcttt atttgtaacc attataagct gcaataaaca    1800
agttaacaac aacaattgca ttcattttat gtttcaggtt cagggggagg tgtgggaggt    1860
tttttaaagc aagtaaaacc tctacaaatg tggtatggaa ttaattctaa aatacagcat    1920
agcaaaactt aacctccaa atcaagcctc tacttgaatc cttttctgag ggatgaataa    1980
ggcataggca tcaggggctg ttgccaatgt gcattagctg tttgcagcct caccttcttt    2040
catggagttt aagatatagt gtatttttccc aaggtttgaa ctagctcttc atttctttat    2100
gttttaaatg cactgacctc ccacattccc tttttagtaa aatattcaga ataatttaa    2160 atacatcatt gcaatgaaaa taatgttttt ttattaggca gaatccagat gctcaaggcc    2220
cttcataata tcccccagtt tagtagttgg acttagggaa caaaggaacc tttaatagaa    2280
attggacagc aagaaagcga gcttctagct tatcctcagt cctgctcctc tgccacaaag    2340
tgcacgcagt gccggccgg gtcgcgcagg gcgaactccc gccccacgg ctgctcgccg    2400 atctcggtca tggccggccc ggaggcgtcc cggaagttcg tggacacgac ctccgaccac    2460
tcggcgtaca gctcgtccag gccgcgcacc cacacccagg ccagggtgtt gtccggcacc    2520
acctggtcct ggaccgcgct gatgaacagg gtcacgtcgt cccggaccac accggcgaag    2580
tcgtcctcca cgaagtcccg ggagaacccg agccggtcgg tccagaactc gaccgctccg    2640
gcgacgtcgc gcgcggtgag caccggaacg gcactggtca acttggccat gatggctcct    2700
cctgtcagga gaggaaagag aagaaggtta gtacaattgc tatagtgagt tgtattatac    2760
tatgcagata tactatgcca atgattaatt gtcaaactag ggctgcaggg ttcatagtgc    2820 cactttttcct gcactgcccc atctcctgcc caccctttcc caggcataga cagtcagtga    2880
cttaccaaac tcacaggagg gagaaggcag aagcttgaga cagacccgcg ggaccgccga    2940
actgcgaggg gacgtggcta gggcggcttc ttttatggtg cgccggccct cggaggcagg    3000
gcgctcgggg aggcctagcg gccaatctgc ggtggcagga ggcggggccg aaggccgtgc    3060
ctgaccaatc cggagcacat aggagtctca gcccccgcc ccaaagcaag gggaagtcac    3120
gcgcctgtag cgccagcgtg ttgtgaaatg ggggcttggg ggggttgggg ccctgactag    3180
tcaaaacaaa ctcccattga cgtcaatggg gtggagactt ggaaatcccc gtgagtcaaa    3240
ccgctatcca cgcccattga tgtactgcca aaaccgcatc atcatggtaa tagcgatgac    3300
```

```
taatacgtag atgtactgcc aagtaggaaa gtcccataag gtcatgtact gggcataatg    3360
ccaggcgggc catttaccgt cattgacgtc aataggggc gtacttggca tatgatacac     3420
ttgatgtact gccaagtggg cagtttaccg taaatactcc acccattgac gtcaatggaa    3480
agtccctatt ggcgttacta tgggaacata cgtcattatt gacgtcaatg ggcgggggtc    3540
gtttgggcggt cagccaggcg ggccatttac cgtaagttat gtaacgcctg caggttaatt   3600
aagaacatgt gagcaaaagg ccagcaaaag gccaggaacc gtaaaaaggc cgcgttgctg    3660
gcgttttttcc ataggctccg cccccctgac gagcatcaca aaaatcgacg ctcaagtcag   3720
aggtggcgaa acccgacagg actataaaga taccaggcgt ttccccctgg aagctccctc    3780
gtgcgctctc ctgttccgac cctgccgctt accggatacc tgtccgcctt tctcccttcg    3840
ggaagcgtgg cgctttctca tagctcacgc tgtaggtatc tcagttcggt gtaggtcgtt    3900
cgctccaagc tgggctgtgt gcacgaaccc cccgttcagc ccgaccgctg cgccttatcc    3960
ggtaactatc gtcttgagtc caacccggta agacacgact tatcgccact ggcagcagcc    4020
actggtaaca ggattagcag agcgaggtat gtaggcggtg ctacagagtt cttgaagtgg    4080
tggcctaact acggctacac tagaagaaca gtatttggta tctgcgctct gctgaagcca    4140
gttaccttcg gaaaaagagt tggtagctct tgatccggca acaaaccac cgctggtagc     4200
ggtggttttt ttgtttgcaa gcagcagatt acgcgcagaa aaaaggatc tcaagaagat     4260
cctttgatct tttctacggg gtctgacgct cagtggaacg aaaactcacg ttaagggatt    4320
ttggtcatgg ctagttaatt aacatttaaa tcagcggccg caataaaata tctttatttt   4380
cattacatct gtgtgttggt tttttgtgtg aatcgtaact aacatacgct ctccatcaaa    4440
acaaaacgaa acaaaacaaa ctagcaaaat aggctgtccc cagtgcaagt gcaggtgcca    4500
gaacatttct ctatcgaa                                                  4518
```

<210> SEQ ID NO 94
<211> LENGTH: 4392
<212> TYPE: DNA
<213> ORGANISM: Artificial Sequence
<220> FEATURE:
<223> OTHER INFORMATION: pCXCL11-IgG1Fc

<400> SEQUENCE: 94

```
ggatctgcga tcgctccggt gcccgtcagt gggcagagcg cacatcgccc acagtccccg     60
agaagttggg gggaggggtc ggcaattgaa cgggtgccta gagaaggtgg cgcggggtaa    120
actgggaaag tgatgtcgtg tactggctcc gccttttcc cgagggtggg ggagaaccgt     180
atataagtgc agtagtcgcc gtgaacgttc tttttcgcaa cgggtttgcc gccagaacac    240
agctgaagct tcgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg gaccggcgc    540
ctacctgaga tcaccggcga aggagggcca ccatgtacag gatgcaactc ctgtcttgca    600
ttgcactaag tcttgcactt gtcacgaatt cgttccccat gttcaaaaga ggacgctgtc    660
tttgcataag ccctgggta aaagcagtga agtggcaga tattgagaaa gcctccataa    720
tgtacccaag taacaactgt gacaaaatag aagtgattat taccctgaaa gaaaataaag    780
gacaacgatg cctaaatccc aaatcgaagc aagcaaggct tataatcaaa aaagttgaaa    840
```

| | | |
|---|---|---|
| gaaagaattt tgacaaaact cacacatgcc caccgtgccc agcacctgaa ctcctggggg | 900 | |
| gaccgtcagt cttcctcttc cccccaaaac ccaaggacac cctcatgatc tcccggaccc | 960 | |
| ctgaggtcac atgcgtggtg gtggacgtga gccacgaaga ccctgaggtc aagttcaact | 1020 | |
| ggtacgtgga cggcgtggag gtgcataatg ccaagacaaa gccgcgggag gagcagtaca | 1080 | |
| acagcacgta ccgtgtggtc agcgtcctca ccgtcctgca ccaggactgg ctgaatggca | 1140 | |
| aggagtacaa gtgcaaggtc tccaacaaag cccteccage cccategag aaaaccatct | 1200 | |
| ccaaagccaa agggcagccc cgagaaccac aggtgtacac cctgccccca tcccgggagg | 1260 | |
| agatgaccaa gaaccaggtc agcctgacct gcctggtcaa aggcttctat cccagcgaca | 1320 | |
| tcgccgtgga gtgggagagc aatgggcagc cggagaacaa ctacaagacc acgcctcccg | 1380 | |
| tgctggactc cgacggctcc ttcttcctct acagcaagct caccgtggac aagagcaggt | 1440 | |
| ggcagcaggg gaacgtcttc tcatgctccg tgatgcacga ggctctgcac aaccactaca | 1500 | |
| cgcagaagag cctctccctg tctccgggta aatgagtgct agctggccag acatgataag | 1560 | |
| atacattgat gagtttggac aaaccacaac tagaatgcag tgaaaaaaat gctttatttg | 1620 | |
| tgaaatttgt gatgctattg ctttatttgt aaccattata agctgcaata aacaagttaa | 1680 | |
| caacaacaat tgcattcatt ttatgtttca ggttcagggg gaggtgtggg aggttttta | 1740 | |
| aagcaagtaa aacctctaca atgtggtat ggaattaatt ctaaaataca gcatagcaaa | 1800 | |
| actttaacct ccaaatcaag cctctacttg aatccttttc tgagggatga ataaggcata | 1860 | |
| ggcatcaggg gctgttgcca atgtgcatta gctgtttgca gcctcacctt ctttcatgga | 1920 | |
| gtttaagata tagtgtattt tcccaaggtt tgaactagct cttcatttct ttatgtttta | 1980 | |
| aatgcactga cctcccacat tcccttttta gtaaaatatt cagaaataat ttaaatacat | 2040 | |
| cattgcaatg aaaataaatg ttttttatta ggcagaatcc agatgctcaa ggcccttcat | 2100 | |
| aatatccccc agtttagtag ttggacttag ggaacaaagg aacctttaat agaaattgga | 2160 | |
| cagcaagaaa gcgagcttct agcttatcct cagtcctgct cctctgccac aaagtgcacg | 2220 | |
| cagttgccgg ccgggtcgcg cagggcgaac tcccgccccc acggctgctc gccgatctcg | 2280 | |
| gtcatggccg gcccggaggc gtcccggaag ttcgtggaca cgacctccga ccactcggcg | 2340 | |
| tacagctcgt ccaggccgcg cacccacacc caggccaggg tgttgtccgg caccacctgg | 2400 | |
| tcctggaccg cgctgatgaa cagggtcacg tcgtcccgga ccacaccggc gaagtcgtcc | 2460 | |
| tccacgaagt cccgggagaa cccgagccgg tcggtccaga actcgaccgc tccggcgacg | 2520 | |
| tcgcgcgcgg tgagcaccgg aacggcactg gtcaacttgg ccatgatggc tcctcctgtc | 2580 | |
| aggagaggaa agagaagaag gttagtacaa ttgctatagt gagttgtatt atactatgca | 2640 | |
| gatatactat gccaatgatt aattgtcaaa ctagggctgc agggttcata gtgccacttt | 2700 | |
| tcctgcactg ccccatctcc tgcccaccct ttcccaggca tagacagtca gtgacttacc | 2760 | |
| aaactcacag gagggagaag gcagaagctt gagacagacc cgcgggaccg ccgaactgcg | 2820 | |
| aggggacgtg gctagggcgg cttctttat ggtgcgccgg ccctcggagg cagggcgctc | 2880 | |
| ggggaggcct agcggccaat ctgcggtggc aggaggcggg gccgaaggcc gtgcctgacc | 2940 | |
| aatccggagc acataggagt ctcagccccc cgccccaaag caaggggaag tcacgcgcct | 3000 | |
| gtagcgccag cgtgttgtga atgggggct tggggggggtt ggggccctga ctagtcaaaa | 3060 | |
| caaactccca ttgacgtcaa tggggtggag acttggaaat ccccgtgagt caaaccgcta | 3120 | |
| tccacgccca ttgatgtact gccaaaaccg catcatcatg gtaatagcga tgactaatac | 3180 | |

| | |
|---|---|
| gtagatgtac tgccaagtag gaaagtccca taaggtcatg tactgggcat aatgccaggc | 3240 |
| gggccattta ccgtcattga cgtcaatagg gggcgtactt ggcatatgat acacttgatg | 3300 |
| tactgccaag tgggcagttt accgtaaata ctccacccat tgacgtcaat ggaaagtccc | 3360 |
| tattggcgtt actatgggaa catacgtcat tattgacgtc aatgggcggg ggtcgttggg | 3420 |
| cggtcagcca ggcgggccat ttaccgtaag ttatgtaacg cctgcaggtt aattaagaac | 3480 |
| atgtgagcaa aaggccagca aaaggccagg aaccgtaaaa aggccgcgtt gctggcgttt | 3540 |
| ttccataggc tccgcccccc tgacgagcat cacaaaaatc gacgctcaag tcagaggtgg | 3600 |
| cgaaacccga caggactata aagataccag gcgtttcccc ctggaagctc cctcgtgcgc | 3660 |
| tctcctgttc cgaccctgcc gcttaccgga tacctgtccg cctttctccc ttcgggaagc | 3720 |
| gtggcgcttt ctcatagctc acgctgtagg tatctcagtt cggtgtaggt cgttcgctcc | 3780 |
| aagctgggct gtgtgcacga accccccgtt cagcccgacc gctgcgcctt atccggtaac | 3840 |
| tatcgtcttg agtccaaccc ggtaagacac gacttatcgc cactggcagc agccactggt | 3900 |
| aacaggatta gcagagcgag gtatgtaggc ggtgctacag agttcttgaa gtggtggcct | 3960 |
| aactacggct acactagaag aacagtattt ggtatctgcg ctctgctgaa gccagttacc | 4020 |
| ttcggaaaaa gagttggtag ctcttgatcc ggcaaacaaa ccaccgctgg tagcggtggt | 4080 |
| ttttttgttt gcaagcagca gattacgcgc agaaaaaaag gatctcaaga agatcctttg | 4140 |
| atcttttcta cggggtctga cgctcagtgg aacgaaaact cacgttaagg gattttggtc | 4200 |
| atggctagtt aattaacatt taaatcagcg gccgcaataa aatatcttta ttttcattac | 4260 |
| atctgtgtgt tggttttttg tgtgaatcgt aactaacata cgctctccat caaaacaaaa | 4320 |
| cgaaacaaaa caaactagca aaataggctg tccccagtgc aagtgcaggt gccagaacat | 4380 |
| ttctctatcg aa | 4392 |

<210> SEQ ID NO 95
<211> LENGTH: 4383
<212> TYPE: DNA
<213> ORGANISM: Artificial Sequence
<220> FEATURE:
<223> OTHER INFORMATION: pCXCL11(4-73)-IgG1Fc

<400> SEQUENCE: 95

| | |
|---|---|
| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gcctttttcc cgagggtggg ggagaaccgt | 180 |
| atataagtgc agtagtcgcc gtgaacgttc tttttcgcaa cgggtttgcc gccagaacac | 240 |
| agctgaagct tcgaggggct cgcatctctc cttcacgcgc ccgccgccct aacctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg taccggcgc | 540 |
| ctacctgaga tcaccggcga aggagggcca ccatgtacag gatgcaactc ctgtcttgca | 600 |
| ttgcactaag tcttgcactt gtcacgaatt cgttcaaaag aggacgctgt cttttgcatag | 660 |
| gccctggggt aaaagcagtg aaagtggcag atattgagaa agcctccata atgtacccaa | 720 |
| gtaacaactg tgacaaaata gaagtgatta ttaccctgaa agaaaataaa ggacaacgat | 780 |
| gcctaaatcc caaatcgaag caagcaaggc ttataatcaa aaaagttgaa agaaagaatt | 840 |

-continued

```
ttgacaaaac tcacacatgc ccaccgtgcc cagcacctga actcctgggg ggaccgtcag    900
tcttcctctt cccccaaaa cccaaggaca ccctcatgat ctcccggacc cctgaggtca    960
catgcgtggt ggtggacgtg agccacgaag accctgaggt caagttcaac tggtacgtgg   1020
acggcgtgga ggtgcataat gccaagacaa agccgcggga ggagcagtac aacagcacgt   1080
accgtgtggt cagcgtcctc accgtcctgc accaggactg gctgaatggc aaggagtaca   1140
agtgcaaggt ctccaacaaa gcctcccag ccccatcga aaaccatc tccaaagcca      1200
aagggcagcc ccgagaacca caggtgtaca ccctgccccc atcccgggag gagatgacca   1260
agaaccaggt cagcctgacc tgcctggtca aaggcttcta tcccagcgac atcgccgtgg   1320
agtgggagag caatgggcag ccggagaaca actacaagac cacgcctccc gtgctggact   1380
ccgacggctc cttcttcctc tacagcaagc tcaccgtgga caagagcagg tggcagcagg   1440
ggaacgtctt ctcatgctcc gtgatgcacg aggctctgca aaccactac acgcagaaga    1500
gcctctccct gtctccgggt aaatgagtgc tagctggcca gacatgataa gatacattga   1560
tgagtttgga caaaccacaa ctagaatgca gtgaaaaaaa tgctttattt gtgaaatttg   1620
tgatgctatt gctttatttg taaccattat aagctgcaat aaacaagtta acaacaacaa   1680
ttgcattcat tttatgtttc aggttcaggg ggaggtgtgg gaggttttt aaagcaagta    1740
aaacctctac aaatgtggta tggaattaat tctaaaatac agcatagcaa aactttaacc   1800
tccaaatcaa gcctctactt gaatccttt ctgagggatg aataaggcat aggcatcagg    1860
ggctgttgcc aatgtgcatt agctgtttgc agcctcacct tctttcatgg agtttaagat   1920
atagtgtatt ttcccaaggt ttgaactagc tcttcatttc tttatgtttt aaatgcactg   1980
acctcccaca ttccctttt agtaaaatat tcagaaataa tttaaataca tcattgcaat   2040
gaaataaat gttttttatt aggcagaatc cagatgctca aggcccttca taatatcccc    2100
cagtttagta gttggactta gggaacaaag gaacctttaa tagaaattgg acagcaagaa   2160
agcgagcttc tagcttatcc tcagtcctgc tcctctgcca caaagtgcac gcagttgccg   2220
gccgggtcgc gcagggcgaa ctcccgcccc cacggctgct cgccgatctc ggtcatggcc   2280
ggcccggagg cgtcccggaa gttcgtggac acgacctccg accactcggc gtacagctcg   2340
tccaggccgc gcacccacac ccaggccagg gtgttgtccg gcaccacctg gtcctggacc   2400
gcgctgatga acagggtcac gtcgtcccgg accacaccgg cgaagtcgtc ctccacgaag   2460
tcccgggaga acccgagccg gtcggtccag aactcgaccg ctccggcgac gtcgcgcgcg   2520
gtgagcaccg gaacggcact ggtcaacttg gccatgatgg ctcctcctgt caggagagga   2580
aagagaagaa ggttagtaca attgctatag tgagttgtat tatactatgc agatatacta   2640
tgccaatgat taattgtcaa actagggctg cagggttcat agtgccactt ttcctgcact   2700
gccccatctc ctgcccaccc tttcccaggc atagacagtc agtgacttac caaactcaca   2760
ggagggagaa ggcagaagct tgagacagac ccgcgggacc gccgaactgc gaggggacgt   2820
ggctagggcg gcttcttta tggtgcgccg gccctcggag gcagggcgct cggggaggcc    2880
tagcggccaa tctgcggtgg caggaggcgg ggccgaaggc cgtgcctgac caatccggag   2940
cacataggag tctcagcccc ccgccccaaa gcaaggggga gtcacgcgcc tgtagcgcca   3000
gcgtgttgtg aaatggggc ttggggggt tggggccctg actagtcaaa acaaactccc    3060
attgacgtca atgggtgga gacttggaaa tccccgtgag tcaaaccgct atccacgccc    3120
attgatgtac tgccaaaacc gcatcatcat ggtaatagcg atgactaata cgtagatgta   3180
```

```
ctgccaagta ggaaagtccc ataaggtcat gtactgggca taatgccagg cgggccattt     3240
accgtcattg acgtcaatag ggggcgtact tggcatatga tacacttgat gtactgccaa     3300
gtgggcagtt taccgtaaat actccaccca ttgacgtcaa tggaaagtcc ctattggcgt     3360
tactatggga acatacgtca ttattgacgt caatgggcgg gggtcgttgg gcggtcagcc     3420
aggcgggcca tttaccgtaa gttatgtaac gcctgcaggt taattaagaa catgtgagca     3480
aaaggccagc aaaaggccag gaaccgtaaa aaggccgcgt tgctggcgtt tttccatagg     3540
ctccgccccc ctgacgagca tcacaaaaat cgacgctcaa gtcagaggtg gcgaaacccg     3600
acaggactat aaagatacca ggcgtttccc cctggaagct ccctcgtgcg ctctcctgtt     3660
ccgaccctgc cgcttaccgg atacctgtcc gcctttctcc cttcgggaag cgtggcgctt     3720
tctcatagct cacgctgtag gtatctcagt tcggtgtagg tcgttcgctc caagctgggc     3780
tgtgtgcacg aaccccccgt tcagcccgac cgctgcgcct tatccggtaa ctatcgtctt     3840
gagtccaacc cggtaagaca cgacttatcg ccactggcag cagccactgg taacaggatt     3900
agcagagcga ggtatgtagg cggtgctaca gagttcttga agtggtggcc taactacggc     3960
tacactagaa gaacagtatt tggtatctgc gctctgctga agccagttac cttcggaaaa     4020
agagttggta gctcttgatc cggcaaacaa accaccgctg gtagcggtgg tttttttgtt     4080
tgcaagcagc agattacgcg cagaaaaaaa ggatctcaag aagatccttt gatcttttct     4140
acggggtctg acgctcagtg gaacgaaaac tcacgttaag ggattttggt catggctagt     4200
taattaacat ttaaatcagc ggccgcaata aaatatcttt attttcatta catctgtgtg     4260
ttggtttttt gtgtgaatcg taactaacat acgctctcca tcaaaacaaa acgaaacaaa     4320
acaaactagc aaaataggct gtccccagtg caagtgcagg tgccagaaca tttctctatc     4380
gaa                                                                  4383
```

<210> SEQ ID NO 96
<211> LENGTH: 4383
<212> TYPE: DNA
<213> ORGANISM: Artificial Sequence
<220> FEATURE:
<223> OTHER INFORMATION: pCXCL11(4-73K/H-A)-IgG1Fc

<400> SEQUENCE: 96

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gcctttttcc cgagggtggg ggagaaccgt     180
atataagtgc agtagtcgcc gtgaacgttc tttttcgcaa cgggtttgcc gccagaacac     240
agctgaagct cgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg taccggcgc      540
ctacctgaga tcaccggcga aggagggcca ccatgtacag gatgcaactc ctgtcttgca     600
ttgcactaag tcttgcactt gtcacgaatt cgttcaaaag gaacgctgt cttttgcatag     660
gccctggggt aaaagcagtg aaagtggcag atattgaggc gcctccata atgtacccaa     720
gtaacaactg tgacaaaata gaagtgatta ttaccctggc agaaaatgcc ggacaagcat     780
gcctaaatcc cgcctcggca caagcagccc ttataatcgc agccgttgaa gcagccaatt     840
```

```
ttgacaaaac tcacacatgc ccaccgtgcc cagcacctga actcctgggg ggaccgtcag    900
tcttcctctt cccccaaaa cccaaggaca ccctcatgat ctcccggacc cctgaggtca    960
catgcgtggt ggtggacgtg agccacgaag accctgaggt caagttcaac tggtacgtgg   1020
acggcgtgga ggtgcataat gccaagacaa agccgcggga ggagcagtac aacagcacgt   1080
accgtgtggt cagcgtcctc accgtcctgc accaggactg gctgaatggc aaggagtaca   1140
agtgcaaggt ctccaacaaa gcctcccag ccccatcga aaaaccatc tccaaagcca     1200 aagggcagcc ccgagaacca caggtgtaca ccctgccccc atcccgggag gagatgacca   1260
agaaccaggt cagcctgacc tgcctggtca aaggcttcta tcccagcgac atcgccgtgg   1320
agtgggagag caatgggcag ccggagaaca actacaagac cacgcctccc gtgctggact   1380
ccgacggctc cttcttcctc tacagcaagc tcaccgtgga caagagcagg tggcagcagg   1440
ggaacgtctt ctcatgctcc gtgatgcacg aggctctgca caaccactac acgcagaaga   1500
gcctctccct gtctccgggt aaatgagtgc tagctggcca gacatgataa gatacattga   1560
tgagtttgga caaaccacaa ctagaatgca gtgaaaaaaa tgctttattt gtgaaatttg   1620
tgatgctatt gctttatttg taaccattat aagctgcaat aaacaagtta acaacaacaa   1680
ttgcattcat tttatgtttc aggttcaggg ggaggtgtgg gaggtttttt aaagcaagta   1740
aaacctctac aaatgtggta tggaattaat tctaaaatac agcatagcaa aactttaacc   1800
tccaaatcaa gcctctactt gaatccttt ctgagggatg aataaggcat aggcatcagg   1860
ggctgttgcc aatgtgcatt agctgtttgc agcctcacct tctttcatgg agtttaagat   1920
atagtgtatt ttcccaaggt ttgaactagc tcttcatttc tttatgtttt aaatgcactg   1980
acctcccaca ttccctttt agtaaaatat tcagaaataa tttaaataca tcattgcaat   2040
gaaaataaat gttttttatt aggcagaatc cagatgctca aggcccttca taatatcccc   2100
cagtttagta gttggactta gggaacaaag gaacctttaa tagaaattgg acagcaagaa   2160
agcgagcttc tagcttatcc tcagtcctgc tcctctgcca caaagtgcac gcagttgccg   2220
gccgggtcgc gcagggcgaa ctcccgcccc cacggctgct cgccgatctc ggtcatggcc   2280 ggccccggagg cgtcccggaa gttcgtggac acgacctccg accactcggc gtacagctcg   2340
tccaggccgc gcacccacac ccaggccagg gtgttgtccg gcaccacctg gtcctggacc   2400
gcgctgatga acagggtcac gtcgtcccgg accacaccgg cgaagtcgtc ctccacgaag   2460
tcccgggaga cccgagccg gtcggtccag aactcgaccg ctccggcgac gtcgcgcgcg   2520
gtgagcaccg gaacggcact ggtcaacttg gccatgatgg ctcctcctgt caggagagga   2580
aagagaagaa ggttagtaca attgctatag tgagttgtat tatactatgc agatatacta   2640
tgccaatgat taattgtcaa actagggctg cagggttcat agtgccactt ttcctgcact   2700
gccccatctc ctgcccaccc tttcccaggc atagacagtc agtgacttac caaactcaca   2760
ggagggagaa ggcagaagct tgagacagac ccgcgggacc gccgaactgc gaggggacgt   2820
ggctagggcg gcttctttta tggtgcgccg gccctcggag gcagggcgct cggggaggcc   2880
tagcggccaa tctgcggtgg caggaggcgg ggccgaaggc cgtgcctgac caatccggag   2940
cacataggag tctcagcccc ccgccccaaa gcaagggaa gtcacgcgcc tgtagcgcca   3000
gcgtgttgtg aaatgggggc ttggggggt tgggggccctg actagtcaaa acaaactccc   3060
attgacgtca atgggtggaa gacttggaaa tccccgtgag tcaaaccgct atccacgccc   3120
attgatgtac tgccaaaacc gcatcatcat ggtaatagcg atgactaata cgtagatgta   3180
```

| | | |
|---|---|---|
| ctgccaagta ggaaagtccc ataaggtcat gtactgggca taatgccagg cgggccattt | 3240 | |
| accgtcattg acgtcaatag ggggcgtact tggcatatga tacacttgat gtactgccaa | 3300 | |
| gtgggcagtt taccgtaaat actccaccca ttgacgtcaa tggaaagtcc ctattggcgt | 3360 | |
| tactatggga acatacgtca ttattgacgt caatgggcgg gggtcgttgg gcggtcagcc | 3420 | |
| aggcgggcca tttaccgtaa gttatgtaac gcctgcaggt taattaagaa catgtgagca | 3480 | |
| aaaggccagc aaaaggccag gaaccgtaaa aaggccgcgt tgctggcgtt tttccatagg | 3540 | |
| ctccgccccc ctgacgagca tcacaaaaat cgacgctcaa gtcagaggtg gcgaaacccg | 3600 | |
| acaggactat aaagatacca ggcgtttccc cctggaagct ccctcgtgcg ctctcctgtt | 3660 | |
| ccgaccctgc cgcttaccgg atacctgtcc gcctttctcc cttcgggaag cgtggcgctt | 3720 | |
| tctcatagct cacgctgtag gtatctcagt tcggtgtagg tcgttcgctc caagctgggc | 3780 | |
| tgtgtgcacg aaccccccgt tcagcccgac cgctgcgcct tatccggtaa ctatcgtctt | 3840 | |
| gagtccaacc cggtaagaca cgacttatcg ccactggcag cagccactgg taacaggatt | 3900 | |
| agcagagcga ggtatgtagg cggtgctaca gagttcttga agtggtggcc taactacggc | 3960 | |
| tacactagaa gaacagtatt tggtatctgc gctctgctga agccagttac cttcggaaaa | 4020 | |
| agagttggta gctcttgatc cggcaaacaa accaccgctg gtagcggtgg tttttttgtt | 4080 | |
| tgcaagcagc agattacgcg cagaaaaaaa ggatctcaag aagatccttt gatcttttct | 4140 | |
| acggggtctg acgctcagtg gaacgaaaac tcacgttaag ggattttggt catggctagt | 4200 | |
| taattaacat ttaaatcagc ggccgcaata aaatatcttt attttcatta catctgtgtg | 4260 | |
| ttggttttt gtgtgaatcg taactaacat acgctctcca tcaaaacaaa acgaaacaaa | 4320 | |
| acaaactagc aaaataggct gtccccagtg caagtgcagg tgccagaaca tttctctatc | 4380 | |
| gaa | 4383 | |

<210> SEQ ID NO 97
<211> LENGTH: 4383
<212> TYPE: DNA
<213> ORGANISM: Artificial Sequence
<220> FEATURE:
<223> OTHER INFORMATION: pCXCL11-IgG4Fc

<400> SEQUENCE: 97

| | | |
|---|---|---|
| ggatctgcga tcgctccggt gcccgtcagt gggcagagcg cacatcgccc acagtccccg | 60 | |
| agaagttggg gggaggggtc ggcaattgaa cgggtgccta gagaaggtgg cgcggggtaa | 120 | |
| actgggaaag tgatgtcgtg tactggctcc gcctttttcc cgagggtggg ggagaaccgt | 180 | |
| atataagtgc agtagtcgcc gtgaacgttc tttttcgcaa cgggtttgcc gccagaacac | 240 | |
| agctgaagct cgaggggct cgcatctctc cttcacgcgc ccgccgccct aacctgaggcc | 300 | |
| gccatccacg ccggttgagt cgcgttctgc cgcctcccgc ctgtggtgcc tcctgaactg | 360 | |
| cgtccgccgt ctaggtaagt ttaaagctca ggtcgagacc gggcctttgt ccggcgctcc | 420 | |
| cttggagcct acctagactc agccggctct ccacgctttg cctgaccctg cttgctcaac | 480 | |
| tctacgtctt tgtttcgttt tctgttctgc gccgttacag atccaagctg tgaccggcgc | 540 | |
| ctacctgaga tcaccggcga aggagggcca ccatgtacag gatgcaactc ctgtcttgca | 600 | |
| ttgcactaag tcttgcactt gtcacgaatt cgttccccat gttcaaaaga ggacgctgtc | 660 | |
| tttgcatagg ccctggggta aaagcagtga agtggcagat attgagaaag gcctccataa | 720 | |
| tgtacccaag taacaactgt gacaaaatag aagtgattat taccctgaaa gaaataaag | 780 | |
| gacaacgatg cctaaatccc aaatcgaagc aagcaaggct tataatcaaa aaagttgaaa | 840 | |

```
gaaagaattt tcccccatgc ccatcatgcc cagcacctga gttcctgggg ggaccatcag    900
tcttcctgtt ccccccaaaa cccaaggaca ctctcatgat ctcccggacc cctgaggtca    960
cgtgcgtggt ggtggacgtg agccaggaag accccgaggt ccagttcaac tggtacgtgg   1020
atggcgtgga ggtgcataat gccaagacaa agccgcggga ggagcagttc aacagcacgt   1080
accgtgtggt cagcgtcctc accgtcctgc accaggactg gctgaacggc aaggagtaca   1140
agtgcaaggt ctccaacaaa ggcctcccgt cctccatcga gaaaaccatc tccaaagcca   1200
aagggcagcc ccgagagcca caggtgtaca ccctgccccc atcccaggag gagatgacca   1260
agaaccaggt cagcctgacc tgcctggtca aaggcttcta ccccagcgac atcgccgtgg   1320
agtgggagag caatgggcag ccggagaaca actacaagac cacgcctccc gtgctggact   1380
ccgacggctc cttcttcctc tacagcaggc taaccgtgga caagagcagg tggcaggagg   1440
ggaatgtctt ctcatgctcc gtgatgcatg aggctctgca caaccactac acacagaaga   1500
gcctctccct gtctccgggt aaatgagtgc tagctggcca gacatgataa gatacattga   1560
tgagtttgga caaaccacaa ctagaatgca gtgaaaaaaa tgctttattt gtgaaatttg   1620
tgatgctatt gctttatttg taaccattat aagctgcaat aaacaagtta acaacaacaa   1680
ttgcattcat tttatgtttc aggttcaggg ggaggtgtgg gaggttttttt aaagcaagta   1740 aaacctctac aaatgtggta tggaattaat tctaaaatac agcatagcaa aactttaacc   1800
tccaaatcaa gcctctactt gaatccttttt ccgaggcatg aataaggcat aggcatcagg   1860
ggctgttgcc aatgtgcatt agctgtttgc agcctcacct tctttcatgg agtttaagat   1920
atagtgtatt ttcccaaggt ttgaactagc tcttcatttc tttatgtttt aaatgcactg   1980
acctcccaca ttccctttt agtaaaatat tcagaaataa tttaaataca tcattgcaat   2040
gaaaataaat gttttttatt aggcagaatc cagatgctca aggcccttca taatatcccc   2100
cagtttagta gttggactta gggaacaaag gaacctttaa tagaaattgg acagcaagaa   2160
agcgagcttc tagcttatcc tcagtcctgc tcctctgcca caaagtgcac gcagttgccg   2220
gccgggtcgc gcagggcgaa ctcccgcccc cacggctgct cgccgatctc ggtcatggcc   2280
ggcccggagg cgtcccggaa gttcgtggac acgacctccg accactcggc gtacagctcg   2340
tccaggccgc gcacccacac ccaggccagg gtgttgtccg gcaccacctg gtcctggacc   2400
gcgctgatga cagggtcacg tcgtcccgg accacaccgg cgaagtcgtc ctccacgaag   2460
tcccgggaga acccgagccg gtcggtccag aactcgaccg ctccggcgac gtcgcgcgcg   2520
gtgagcaccg gaacggcact ggtcaacttg gccatgatgg ctcctcctgt caggagagga   2580
aagagaagaa ggttagtaca attgctatag tgagttgtat tatactatgc agatatacta   2640
tgccaatgat taattgtcaa actagggctg cagggttcat agtgccactt ttcctgcact   2700
gccccatctc ctgcccaccc tttcccaggc atagacagtc agtgacttac caaactcaca   2760
ggagggagaa ggcagaagct tgagacagac ccgcgggacc gccgaactgc gagggggacgt   2820 ggctagggcg gcttcttttta tggtgcgccg gccctcggag gcagggcgct cggggaggcc   2880
tagcggccaa tctgcggtgg caggaggcgg ggccgaaggc cgtgcctgac caatccggag   2940
cacataggag tctcagcccc ccgccccaaa gcaaggggaa gtcacgcgcc tgtagcgcca   3000
gcgtgttgtg aaatgggggc ttggggggt tggggccctg actagtcaaa acaaactccc   3060
attgacgtca atgggggtgga gacttggaaa tccccgtgag tcaaaccgct atccacgccc   3120
attgatgtac tgccaaaacc gcatcatcat ggtaatagcg atgactaata cgtagatgta   3180
```

| ctgccaagta ggaaagtccc ataaggtcat gtactgggca taatgccagg cgggccattt | 3240 |
| accgtcattg acgtcaatag ggggcgtact tggcatatga tacacttgat gtactgccaa | 3300 |
| gtgggcagtt taccgtaaat actccaccca ttgacgtcaa tggaaagtcc ctattggcgt | 3360 |
| tactatggga acatacgtca ttattgacgt caatgggcgg gggtcgttgg gcggtcagcc | 3420 |
| aggcgggcca tttaccgtaa gttatgtaac gcctgcaggt taattaagaa catgtgagca | 3480 |
| aaaggccagc aaaaggccag gaaccgtaaa aaggccgcgt tgctggcgtt tttccatagg | 3540 |
| ctccgccccc ctgacgagca tcacaaaaat cgacgctcaa gtcagaggtg gcgaaacccg | 3600 |
| acaggactat aaagatacca ggcgtttccc cctggaagct ccctcgtgcg ctctcctgtt | 3660 |
| ccgaccctgc cgcttaccgg atacctgtcc gcctttctcc cttcgggaag cgtggcgctt | 3720 |
| tctcatagct cacgctgtag gtatctcagt tcggtgtagg tcgttcgctc caagctgggc | 3780 |
| tgtgtgcacg aaccccccgt tcagcccgac cgctgcgcct tatccggtaa ctatcgtctt | 3840 |
| gagtccaacc cggtaagaca cgacttatcg ccactggcag cagccactgg taacaggatt | 3900 |
| agcagagcga ggtatgtagg cggtgctaca gagttcttga agtggtggcc taactacggc | 3960 |
| tacactagaa gaacagtatt tggtatctgc gctctgctga agccagttac cttcggaaaa | 4020 |
| agagttggta gctcttgatc cggcaaacaa accaccgctg gtagcggtgg tttttttgtt | 4080 |
| tgcaagcagc agattacgcg cagaaaaaaa ggatctcaag aagatccttt gatcttttct | 4140 |
| acggggtctg acgctcagtg gaacgaaaac tcacgttaag ggattttggt catggctagt | 4200 |
| taattaacat ttaaatcagc ggccgcaata aaatatcttt attttcatta catctgtgtg | 4260 |
| ttggtttttt gtgtgaatcg taactaacat acgctctcca tcaaaacaaa acgaaacaaa | 4320 |
| acaaactagc aaaataggct gtccccagtg caagtgcagg tgccagaaca tttctctatc | 4380 |
| gaa | 4383 |

<210> SEQ ID NO 98
<211> LENGTH: 4374
<212> TYPE: DNA
<213> ORGANISM: Artificial Sequence
<220> FEATURE:
<223> OTHER INFORMATION: pCXCL11(4-73)-IgG4Fc

<400> SEQUENCE: 98

| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gcctttttcc cgagggtggg ggagaaccgt | 180 |
| atataagtgc agtagtcgcc gtgaacgttc tttttcgcaa cgggtttgcc gccagaacac | 240 |
| agctgaagct tcgaggggct cgcatctctc cttcacgcgc ccgccgccct aacctgaggc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg taccggcgc | 540 |
| ctacctgaga tcaccggcga aggagggcca ccatgtacag gatgcaactc ctgtcttgca | 600 |
| ttgcactaag tcttgcactt gtcacgaatt cgttcaaaag aggacgctgt cttgcatag | 660 |
| gccctggggt aaaagcagtg aaagtggcag atattgagaa agcctccata atgtacccaa | 720 |
| gtaacaactg tgacaaaata gaagtgatta ttaccctgaa agaaaataaa ggacaacgat | 780 |
| gcctaaatcc caaatcgaag caagcaaggc ttataatcaa aaaagttgaa agaaagaatt | 840 |

```
ttcccccatg cccatcatgc ccagcacctg agttcctggg gggaccatca gtcttcctgt    900 tcccccaaa acccaaggac actctcatga tctcccggac ccctgaggtc acgtgcgtgg     960
tggtggacgt gagccaggaa gaccccgagg tccagttcaa ctggtacgtg gatggcgtgg  1020
aggtgcataa tgccaagaca aagccgcggg aggagcagtt caacagcacg taccgtgtgg  1080
tcagcgtcct caccgtcctg caccaggact ggctgaacgg caaggagtac aagtgcaagg  1140
tctccaacaa aggcctcccg tcctccatcg agaaaaccat ctccaaagcc aaagggcagc  1200
cccgagagcc acaggtgtac accctgcccc catcccagga ggagatgacc aagaaccagg  1260
tcagcctgac ctgcctggtc aaaggcttct accccagcga catcgccgtg gagtgggaga  1320
gcaatgggca gccggagaac aactacaaga ccacgcctcc cgtgctggac tccgacggct  1380
ccttcttcct ctacagcagg ctaaccgtgg acaagagcag gtggcaggag gggaatgtct  1440
tctcatgctc cgtgatgcat gaggctctgc acaaccacta cacacagaag agcctctccc  1500
tgtctccggg taaatgagtg ctagctggcc agacatgata agatacattg atgagtttgg  1560
acaaaccaca actagaatgc agtgaaaaaa atgctttatt tgtgaaattt gtgatgctat  1620
tgctttattt gtaaccatta taagctgcaa taaacaagtt aacaacaaca attgcattca  1680
ttttatgttt caggttcagg gggaggtgtg ggaggttttt taaagcaagt aaaacctcta  1740
caaatgtggt atggaattaa ttctaaaata cagcatagca aactttaac ctccaaatca   1800 agcctctact tgaatccttt tctgagggat gaataaggca taggcatcag gggctgttgc  1860
caatgtgcat tagctgtttg cagcctcacc ttctttcatg gagtttaaga tatagtgtat  1920
tttcccaagg tttgaactag ctcttcattt ctttatgttt taaatgcact gacctcccac  1980
attccctttt tagtaaaata ttcagaaata atttaaatac atcattgcaa tgaaaataaa  2040 tgtttttat taggcagaat ccagatgctc aaggcccttc ataatatccc ccagtttagt   2100
agttggactt agggaacaaa ggaacccttta atagaaattg gacagcaaga aagcgagctt  2160
ctagcttatc ctcagtcctg ctcctctgcc acaaagtgca cgcagttgcc ggccgggtcg  2220
cgcagggcga actcccgccc ccacggctgc tcgccgatct cggtcatggc cggcccggag  2280
gcgtcccgga agttcgtgga cacgacctcc gaccactcgg cgtacagctc gtccaggccg  2340
cgcacccaca cccaggccag ggtgttgtcc ggcaccacct ggtcctggac cgcgctgatg  2400
aacagggtca cgtcgtcccg gaccacaccg gcgaagtcgt cctccacgaa gtcccggag   2460 aacccgagcc ggtcggtcca gaactcgacc gctccggcga cgtcgcgcgc ggtgagcacc  2520
ggaacggcac tggtcaactt ggccatgatg gctcctcctg tcaggagagg aaagagaaga  2580
aggttagtac aattgctata gtgagttgta ttatactatg cagatatact atgccaatga  2640
ttaattgtca aactagggct gcaggggttca tagtgccact tttcctgcac tgccccatct  2700
cctgcccacc ctttcccagg catagacagt cagtgactta ccaaactcac aggagggaga  2760
aggcagaagc ttgagacaga cccgcgggac cgccgaactg cgaggggacg tggctagggc  2820
ggcttctttt atggtgcgcc ggccctcgga ggcagggcgc tcggggaggc ctagcggcca  2880
atctgcggtg gcaggaggcg gggccgaagg ccgtgcctga ccaatccgga gcacatagga  2940
gtctcagccc cccgccccaa agcaaggga  agtcacgcgc ctgtagcgcc agcgtgttgt  3000
gaaatggggg cttgggggggg ttggggccct gactagtcaa aacaaactcc cattgacgtc  3060 aatgggtgg agacttggaa atccccgtga gtcaaaccgc tatccacgcc cattgatgta   3120
ctgccaaaac cgcatcatca tggtaatagc gatgactaat acgtagatgt actgccaagt  3180
```

-continued

| | |
|---|---|
| aggaaagtcc cataaggtca tgtactgggc ataatgccag gcgggccatt taccgtcatt | 3240 |
| gacgtcaata gggggcgtac ttggcatatg atacacttga tgtactgcca agtgggcagt | 3300 |
| ttaccgtaaa tactccaccc attgacgtca atggaaagtc cctattggcg ttactatggg | 3360 |
| aacatacgtc attattgacg tcaatgggcg gggtcgttg gcggtcagc caggcgggcc | 3420 |
| atttaccgta agttatgtaa cgcctgcagg ttaattaaga acatgtgagc aaaaggccag | 3480 |
| caaaaggcca ggaaccgtaa aaaggccgcg ttgctggcgt ttttccatag gctccgcccc | 3540 |
| cctgacgagc atcacaaaaa tcgacgctca agtcagaggt ggcgaaaccc gacaggacta | 3600 |
| taaagatacc aggcgtttcc ccctggaagc tccctcgtgc gctctcctgt tccgaccctg | 3660 |
| ccgcttaccg gatacctgtc cgcctttctc ccttcgggaa gcgtggcgct ttctcatagc | 3720 |
| tcacgctgta ggtatctcag ttcggtgtag gtcgttcgct ccaagctggg ctgtgtgcac | 3780 |
| gaaccccccg ttcagcccga ccgctgcgcc ttatccggta actatcgtct tgagtccaac | 3840 |
| ccggtaagac acgacttatc gccactggca gcagccactg gtaacaggat tagcagagcg | 3900 |
| aggtatgtag gcggtgctac agagttcttg aagtggtggc ctaactacgg ctacactaga | 3960 |
| agaacagtat ttggtatctg cgctctgctg aagccagtta ccttcggaaa aagagttggt | 4020 |
| agctcttgat ccggcaaaca aaccaccgct ggtagcggtg gttttttgt ttgcaagcag | 4080 |
| cagattacgc gcagaaaaaa aggatctcaa gaagatcctt tgatcttttc tacgggtct | 4140 |
| gacgctcagt ggaacgaaaa ctcacgttaa gggattttgg tcatggctag ttaattaaca | 4200 |
| tttaaatcag cggccgcaat aaaatatctt tattttcatt acatctgtgt gttggttttt | 4260 |
| tgtgtgaatc gtaactaaca tacgctctcc atcaaaacaa aacgaaacaa aacaaactag | 4320 |
| caaaataggc tgtccccagt gcaagtgcag gtgccagaac atttctctat cgaa | 4374 |

<210> SEQ ID NO 99
<211> LENGTH: 4374
<212> TYPE: DNA
<213> ORGANISM: Artificial Sequence
<220> FEATURE:
<223> OTHER INFORMATION: pCXCL11(4-73K/H-A)-IgG4Fc

<400> SEQUENCE: 99

| | |
|---|---|
| ggatctgcga tcgctccggt gcccgtcagt gggcagagcg cacatcgccc acagtccccg | 60 |
| agaagttggg ggagggggtc ggcaattgaa cgggtgccta gagaaggtgg cgcggggtaa | 120 |
| actgggaaag tgatgtcgtg tactggctcc gcctttttcc cgagggtggg ggagaaccgt | 180 |
| atataagtgc agtagtcgcc gtgaacgttc ttttttcgcaa cgggtttgcc gccagaacac | 240 |
| agctgaagct cgaggggct cgcatctctc cttcacgcgc ccgccgccct acctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg tgaccggcgc | 540 |
| ctacctgaga tcaccggcga aggagggcca ccatgtacag gatgcaactc ctgtcttgca | 600 |
| ttgcactaag tcttgcactt gtcacgaatt cgttcaaaag gaggacgctgt ctttgcatag | 660 |
| gccctgggt aaaagcagtg aaagtggcag atattgaggc gcctccata atgtacccaa | 720 |
| gtaacaactg tgacaaaata gaagtgatta ttaccctggc agaaaatgcc ggacaagcat | 780 |
| gcctaaatcc cgcctcggca caagcagccc ttataatcgc agccgttgaa gcagccaatt | 840 |
| ttccccccatg cccatcatgc ccagcacctg agttcctggg gggaccatca gtcttcctgt | 900 |

| | |
|---|---|
| tcccccccaaa acccaaggac actctcatga tctcccggac ccctgaggtc acgtgcgtgg | 960 |
| tggtggacgt gagccaggaa gacccccgagg tccagttcaa ctggtacgtg gatggcgtgg | 1020 |
| aggtgcataa tgccaagaca aagccgcggg aggagcagtt caacagcacg taccgtgtgg | 1080 |
| tcagcgtcct caccgtcctg caccaggact ggctgaacgg caaggagtac aagtgcaagg | 1140 |
| tctccaacaa aggcctcccg tcctccatcg agaaaaccat ctccaaagcc aaagggcagc | 1200 |
| cccgagagcc acaggtgtac accctgcccc catcccagga ggagatgacc aagaaccagg | 1260 |
| tcagcctgac ctgcctggtc aaaggcttct accccagcga catcgccgtg gagtgggaga | 1320 |
| gcaatgggca gccggagaac aactacaaga ccacgcctcc cgtgctggac tccgacggct | 1380 |
| ccttcttcct ctacagcagg ctaaccgtgg acaagagcag gtggcaggag gggaatgtct | 1440 |
| tctcatgctc cgtgatgcat gaggctctgc acaaccacta cacacagaag agcctctccc | 1500 |
| tgtctccggg taaatgagtg ctagctggcc agacatgata agatacattg atgagtttgg | 1560 |
| acaaaccaca actagaatgc agtgaaaaaa atgctttatt tgtgaaattt gtgatgctat | 1620 |
| tgctttattt gtaaccatta taagctgcaa taaacaagtt aacaacaaca attgcattca | 1680 |
| ttttatgttt caggttcagg gggaggtgtg ggaggttttt taaagcaagt aaaacctcta | 1740 |
| caaatgtggt atggaattaa ttctaaaata cagcatagca aaactttaac ctccaaatca | 1800 |
| agcctctact tgaatccttt tctgagggat gaataaggca taggcatcag gggctgttgc | 1860 |
| caatgtgcat tagctgtttg cagcctcacc ttctttcatg gagtttaaga tatagtgtat | 1920 |
| tttcccaagg tttgaactag ctcttcattt ctttatgttt taaatgcact gacctcccac | 1980 |
| attccttttt tagtaaaata ttcagaaata atttaaatac atcattgcaa tgaaaataaa | 2040 |
| tgttttttat taggcagaat ccagatgctc aaggcccttc ataatatccc ccagtttagt | 2100 |
| agttggactt agggaacaaa ggaaccttta atagaaattg gacagcaaga aagcgagctt | 2160 |
| ctagcttatc ctcagtcctg ctcctctgcc acaaagtgca cgcagttgcc ggccgggtcg | 2220 |
| cgcagggcga actcccgccc ccacggctgc tcgccgatct cggtcatggc cggccccggag | 2280 |
| gcgtcccgga agttcgtgga cacgacctcc gaccactcgg cgtacagctc gtccaggccg | 2340 |
| cgcacccaca cccaggccag ggtgttgtcc ggcaccacct ggtcctggac cgcgctgatg | 2400 |
| aacagggtca cgtcgtcccg gaccacaccg gcgaagtcgt cctccacgaa gtcccgggag | 2460 |
| aacccgagcc ggtcggtcca gaactcgacc gctccggcga cgtcgcgcgc ggtgagcacc | 2520 |
| ggaacggcac tggtcaactt ggccatgatg gctcctcctg tcaggagagg aaagagaaga | 2580 |
| aggttagtac aattgctata gtgagttgta ttatactatg cagatatact atgccaatga | 2640 |
| ttaattgtca aactagggct gcagggttca tagtgccact tttcctgcac tgccccatct | 2700 |
| cctgcccacc ctttcccagg catagacagt cagtgactta ccaaactcac aggagggaga | 2760 |
| aggcagaagc ttgagacaga cccgcgggac cgccgaactg cgaggggacg tggctagggc | 2820 |
| ggcttctttt atggtgcgcc ggccctcgga ggcagggcgc tcggggaggc ctagcggcca | 2880 |
| atctgcggtg gcaggaggcg gggccgaagg ccgtgcctga ccaatccgga gcacatagga | 2940 |
| gtctcagccc cccgccccaa agcaagggga agtcacgcgc ctgtagcgcc agcgtgttgt | 3000 |
| gaaatggggg cttggggggg ttgggcccct gactagtcaa aacaaactcc cattgacgtc | 3060 |
| aatggggtgg agacttggaa atccccgtga gtcaaaccgc tatccacgcc cattgatgta | 3120 |
| ctgccaaaac cgcatcatca tggtaatagc gatgactaat acgtagatgt actgccaagt | 3180 |
| aggaaagtcc cataaggtca tgtactgggc ataatgccag gcgggccatt taccgtcatt | 3240 |

| | |
|---|---|
| gacgtcaata gggggcgtac ttggcatatg atacacttga tgtactgcca agtgggcagt | 3300 |
| ttaccgtaaa tactccaccc attgacgtca atggaaagtc cctattggcg ttactatggg | 3360 |
| aacatacgtc attattgacg tcaatgggcg gggtcgttg ggcggtcagc caggcgggcc | 3420 |
| atttaccgta agttatgtaa cgcctgcagg ttaattaaga acatgtgagc aaaaggccag | 3480 |
| caaaaggcca ggaaccgtaa aaaggccgcg ttgctggcgt ttttccatag gctccgcccc | 3540 |
| cctgacgagc atcacaaaaa tcgacgctca agtcagaggt ggcgaaaccc gacaggacta | 3600 |
| taaagatacc aggcgtttcc ccctggaagc tccctcgtgc gctctcctgt tccgaccctg | 3660 |
| ccgcttaccg gatacctgtc cgcctttctc ccttcgggaa gcgtggcgct ttctcatagc | 3720 |
| tcacgctgta ggtatctcag ttcggtgtag gtcgttcgct ccaagctggg ctgtgtgcac | 3780 |
| gaaccccccg ttcagcccga ccgctgcgcc ttatccggta actatcgtct tgagtccaac | 3840 |
| ccggtaagac acgacttatc gccactggca gcagccactg gtaacaggat tagcagagcg | 3900 |
| aggtatgtag gcggtgctac agagttcttg aagtggtggc ctaactacgg ctacactaga | 3960 |
| agaacagtat ttggtatctg cgctctgctg aagccagtta ccttcggaaa aagagttggt | 4020 |
| agctcttgat ccggcaaaca aaccaccgct ggtagcggtg gtttttttgt ttgcaagcag | 4080 |
| cagattacgc gcagaaaaaa aggatctcaa gaagatcctt tgatcttttc tacggggtct | 4140 |
| gacgctcagt ggaacgaaaa ctcacgttaa gggattttgg tcatgctagt taattaaca | 4200 |
| tttaaatcag cggccgcaat aaaatatctt tattttcatt acatctgtgt gttggttttt | 4260 |
| tgtgtgaatc gtaactaaca tacgctctcc atcaaaacaa aacgaaacaa aacaaactag | 4320 |
| caaaataggc tgtccccagt gcaagtgcag gtgccagaac atttctctat cgaa | 4374 |

<210> SEQ ID NO 100
<211> LENGTH: 4434
<212> TYPE: DNA
<213> ORGANISM: Artificial Sequence
<220> FEATURE:
<223> OTHER INFORMATION: pCXCL13-IgG1Fc

<400> SEQUENCE: 100

| | |
|---|---|
| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gcctttttcc cgagggtggg ggagaaccgt | 180 |
| atataagtgc agtagtcgcc gtgaacgttc tttttcgcaa cgggtttgcc gccagaacac | 240 |
| agctgaagct cgaggggct cgcatctctc cttcacgcgc ccgccgccct aacctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggccttttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg tgaccggcgc | 540 |
| ctacctgaga tcaccggcga aggagggcca ccatgtacag gatgcaactc ctgtcttgca | 600 |
| ttgcactaag tcttgcactt gtcacgaatt cggttctgga ggtctattac acaagcttga | 660 |
| ggtgtagatg tgtccaagag agctcagtct ttatccctag acgcttcatt gatcgaattc | 720 |
| aaatcttgcc ccgtgggaat ggttgtccaa gaaaagaaat catagtctgg aagaagaaca | 780 |
| agtcaattgt gtgtgtggac cctcaagctg aatggataca agaatgatg gaagtattga | 840 |
| gaaaagaag ttcttcaact ctaccagtc cagtgtttaa gagaaagatt cccgacaaaa | 900 |
| ctcacacatg cccaccgtgc ccagcacctg aactcctggg gggaccgtca gtcttcctct | 960 |

```
tcccccccaaa acccaaggac accctcatga tctcccggac ccctgaggtc acatgcgtgg    1020
tggtggacgt gagccacgaa gaccctgagg tcaagttcaa ctggtacgtg gacggcgtgg    1080
aggtgcataa tgccaagaca aagccgcggg aggagcagta caacagcacg taccgtgtgg    1140
tcagcgtcct caccgtcctg caccaggact ggctgaatgg caaggagtac aagtgcaagg    1200
tctccaacaa agccctccca gcccccatcg agaaaaccat ctccaaagcc aaagggcagc    1260
cccgagaacc acaggtgtac accctgcccc catcccggga ggagatgacc aagaaccagg    1320
tcagcctgac ctgcctggtc aaaggcttct atcccagcga catcgccgtg gagtgggaga    1380
gcaatgggca gccggagaac aactacaaga ccacgcctcc cgtgctggac tccgacggct    1440
ccttcttcct ctacagcaag ctcaccgtgg acaagagcag gtggcagcag gggaacgtct    1500
tctcatgctc cgtgatgcac gaggctctgc acaaccacta cacgcagaag agcctctccc    1560
tgtctccggg taaatgagtg ctagctggcc agacatgata agatacattg atgagtttgg    1620
acaaaccaca actagaatgc agtgaaaaaa atgctttatt tgtgaaattt gtgatgctat    1680
tgctttattt gtaaccatta taagctgcaa taaacaagtt aacaacaaca attgcattca    1740
ttttatgttt caggttcagg gggaggtgtg ggaggttttt taaagcaagt aaaacctcta    1800
caaatgtggt atggaattaa ttctaaaata cagcatagca aaactttaac ctccaaatca    1860
agcctctact tgaatccttt tctgagggat gaataaggca taggcatcag gggctgttgc    1920
caatgtgcat tagctgtttg cagcctcacc ttctttcatg gagtttaaga tatagtgtat    1980
tttcccaagg tttgaactag ctcttcattt ctttatgttt taaatgcact gacctcccac    2040
attccctttt tagtaaaata ttcagaaata atttaaatac atcattgcaa tgaaaataaa    2100
tgttttttat taggcagaat ccagatgctc aaggcccttc ataatatccc ccagtttagt    2160
agttggactt agggaacaaa ggaacctttta atagaaattg gacagcaaga aagcgagctt    2220
ctagcttatc ctcagtcctg ctcctctgcc acaaagtgca cgcagttgcc ggccgggtcg    2280
cgcagggcga actcccgccc ccacggctgc tcgccgatct cggtcatggc cggccccggag   2340 gcgtcccgga agttcgtgga cacgacctcc gaccactcgg cgtacagctc gtccaggccg    2400
cgcacccaca cccaggccag ggtgttgtcc ggcaccacct ggtcctggac cgcgctgatg    2460
aacagggtca cgtcgtcccg gaccacaccg gcgaagtcgt cctccacgaa gtcccgggag    2520
aacccgagcc ggtcggtcca gaactcgacc gctccggcga cgtcgcgcgc ggtgagcacc    2580
ggaacggcac tggtcaactt ggccatgatg gctcctcctg tcaggagagg aaagagaaga    2640
aggttagtac aattgctata gtgagttgta ttatactatg cagatatact atgccaatga    2700
ttaattgtca aactagggct gcagggttca tagtgccact tttcctgcac tgccccatct    2760
cctgcccacc ctttcccagg catagacagt cagtgactta ccaaactcac aggagggaga    2820
aggcagaagc ttgagacaga cccgcgggac cgccgaactg cgagggacg tggctagggc     2880 ggcttctttt atggtgcgcc ggccctcgga ggcagggcgc tcggggaggc ctagcggcca    2940
atctgcggtg gcaggaggcg gggccgaagg ccgtgcctga ccaatccgga gcacatagga    3000
gtctcagccc cccgccccaa agcaagggga agtcacgcgc ctgtagcgcc agcgtgttgt    3060
gaaatggggg cttgggggggg ttgggcccct gactagtcaa aacaaactcc cattgacgtc    3120
aatggggtgg agacttggaa atccccgtga gtcaaaccgc tatccacgcc cattgatgta    3180
ctgccaaaac cgcatcatca tggtaatagc gatgactaat acgtagatgt actgccaagt    3240
aggaaagtcc cataaggtca tgtactgggc ataatgccag gcgggccatt taccgtcatt    3300
```

| | |
|---|---|
| gacgtcaata gggggcgtac ttggcatatg atacacttga tgtactgcca agtgggcagt | 3360 |
| ttaccgtaaa tactccaccc attgacgtca atggaaagtc cctattggcg ttactatggg | 3420 |
| aacatacgtc attattgacg tcaatgggcg gggtcgttg ggcggtcagc caggcgggcc | 3480 |
| atttaccgta agttatgtaa cgcctgcagg ttaattaaga acatgtgagc aaaaggccag | 3540 |
| caaaaggcca ggaaccgtaa aaaggccgcg ttgctggcgt ttttccatag gctccgcccc | 3600 |
| cctgacgagc atcacaaaaa tcgacgctca agtcagaggt ggcgaaaccc gacaggacta | 3660 |
| taaagatacc aggcgtttcc ccctggaagc tccctcgtgc gctctcctgt tccgaccctg | 3720 |
| ccgcttaccg gatacctgtc cgcctttctc ccttcgggaa gcgtggcgct ttctcatagc | 3780 |
| tcacgctgta ggtatctcag ttcggtgtag gtcgttcgct ccaagctggg ctgtgtgcac | 3840 |
| gaaccccccg ttcagcccga ccgctgcgcc ttatccggta actatcgtct tgagtccaac | 3900 |
| ccggtaagac acgacttatc gccactggca gcagccactg gtaacaggat tagcagagcg | 3960 |
| aggtatgtag gcggtgctac agagttcttg aagtggtggc ctaactacgg ctacactaga | 4020 |
| agaacagtat ttggtatctg cgctctgctg aagccagtta ccttcggaaa aagagttggt | 4080 |
| agctcttgat ccggcaaaca aaccaccgct ggtagcggtg gtttttttgt ttgcaagcag | 4140 |
| cagattacgc gcagaaaaaa aggatctcaa gaagatcctt tgatcttttc tacggggtct | 4200 |
| gacgctcagt ggaacgaaaa ctcacgttaa gggattttgg tcatgctag ttaattaaca | 4260 |
| tttaaatcag cggccgcaat aaaatatctt tattttcatt acatctgtgt gttggttttt | 4320 |
| tgtgtgaatc gtaactaaca tacgctctcc atcaaaacaa aacgaaacaa aacaaactag | 4380 |
| caaaataggc tgtccccagt gcaagtgcag gtgccagaac atttctctat cgaa | 4434 |

<210> SEQ ID NO 101
<211> LENGTH: 4428
<212> TYPE: DNA
<213> ORGANISM: Artificial Sequence
<220> FEATURE:
<223> OTHER INFORMATION: pCXCL13(3-87)-IgG1Fc

<400> SEQUENCE: 101

| | |
|---|---|
| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gccttttcc cgagggtggg ggagaaccgt | 180 |
| atataagtgc agtagtcgcc gtgaacgttc ttttcgcaa cgggtttgcc gccagaacac | 240 |
| agctgaagct tcgaggggct cgcatctctc cttcacgcgc ccgccgccct acctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg taccggcgc | 540 |
| ctacctgaga tcaccggcga aggagggcca ccatgtacag gatgcaactc ctgtcttgca | 600 |
| ttgcactaag tcttgcactt gtcacgaatt cggaggtcta ttacacaagc ttgaggtgta | 660 |
| gatgtgtcca agagagctca gtctttatcc ctagacgctt cattgatcga attcaaatct | 720 |
| tgccccgtgg gaatggttgt ccaagaaaag aaatcatagt ctggaagaag aacaagtcaa | 780 |
| ttgtgtgtgt ggaccctcaa gctgaatgga tacaaagaat gatggaagta ttgagaaaaa | 840 |
| gaagttcttc aactctacca gttccagtgt ttaagagaaa gattcccgac aaaactcaca | 900 |
| catgcccacc gtgcccagca cctgaactcc tggggggacc gtcagtcttc ctcttccccc | 960 |

```
caaaacccaa ggacaccctc atgatctccc ggaccoctga ggtcacatgc gtggtggtgg    1020
acgtgagcca cgaagaccct gaggtcaagt tcaactggta cgtggacggc gtggaggtgc    1080
ataatgccaa gacaaagccg cgggaggagc agtacaacag cacgtaccgt gtggtcagcg    1140
tcctcaccgt cctgcaccag gactggctga atggcaagga gtacaagtgc aaggtctcca    1200
acaaagccct cccagccccc atcgagaaaa ccatctccaa agccaaaggg cagccccgag    1260
aaccacaggt gtacaccctg cccccatccc gggaggagat gaccaagaac caggtcagcc    1320
tgacctgcct ggtcaaaggc ttctatccca gcgacatcgc cgtggagtgg gagagcaatg    1380
ggcagccgga gaacaactac aagaccacgc ctcccgtgct ggactccgac ggctccttct    1440
tcctctacag caagctcacc gtggacaaga gcaggtggca gcagggaac gtcttctcat    1500 gctccgtgat gcacgaggct ctgcacaacc actacacgca gaagagcctc tccctgtctc    1560
cgggtaaatg agtgctagct ggccagacat gataagatac attgatgagt ttggacaaac    1620
cacaactaga atgcagtgaa aaaatgctt tatttgtgaa atttgtgatg ctattgcttt    1680
atttgtaacc attataagct gcaataaaca agttaacaac aacaattgca ttcattttat    1740
gtttcaggtt caggggggagg tgtgggaggt tttttaaagc aagtaaaacc tctacaaatg    1800
tggtatggaa ttaattctaa atacagcat agcaaaactt aacctccaa atcaagcctc    1860 tacttgaatc cttttctgag ggatgaataa ggcataggca tcaggggctg ttgccaatgt    1920
gcattagctg tttgcagcct caccttcttt catggagttt aagatatagt gtattttccc    1980
aaggtttgaa ctagctcttc atttctttat gttttaaatg cactgacctc ccacattccc    2040
tttttagtaa atatttcaga ataatttaa atacatcatt gcaatgaaaa taaatgtttt    2100
ttattaggca gaatccagat gctcaaggcc cttcataata tcccccagtt tagtagttgg    2160
acttagggaa caaaggaacc tttaatagaa attggacagc aagaaagcga gcttctagct    2220
tatcctcagt cctgctcctc tgccacaaag tgcacgcagt tgccggccgg tcgcgcagg    2280 gcgaactccc gcccccacgg ctgctcgccg atctcggtca tggccggccc ggaggcgtcc    2340
cggaagttcg tggacacgac ctccgaccac tcggcgtaca gctcgtccag gccgcgcacc    2400
cacacccagg ccagggtgtt gtccggcacc acctggtcct ggaccgcgct gatgaacagg    2460
gtcacgtcgt cccggaccac accggcgaag tcgtcctcca cgaagtcccg ggagaacccg    2520
agccggtcgg tccagaactc gaccgctccg gcgacgtcgc gcgcggtgag caccggaacg    2580
gcactggtca acttggccat gatggctcct cctgtcagga gaggaaagag aagaaggtta    2640
gtacaattgc tatagtgagt tgtattatac tatgcagata tactatgcca atgattaatt    2700
gtcaaactag ggctgcaggg ttcatagtgc cactttttcct gcactgcccc atctcctgcc    2760 cacccttttcc caggcataga cagtcagtga cttaccaaac tcacaggagg gagaaggcag    2820
aagcttgaga cagacccgcg ggaccgccga actgcgaggg gacgtggcta gggcggcttc    2880
ttttatggtg cgccggccct cggaggcagg gcgctcgggg aggcctagcg gccaatctgc    2940
ggtggcagga ggcggggccg aaggccgtgc ctgaccaatc cggagcacat aggagtctca    3000 gcccccgcc ccaaagcaag gggaagtcac gcgcctgtag cgccagcgtg ttgtgaaatg    3060
ggggcttggg ggggttgggg ccctgactag tcaaaacaaa ctcccattga cgtcaatggg    3120
gtggagactt ggaaatcccc gtgagtcaaa ccgctatcca cgcccattga tgtactgcca    3180
aaaccgcatc atcatggtaa tagcgatgac taatacgtag atgtactgcc aagtaggaaa    3240
gtcccataag gtcatgtact gggcataatg ccaggcgggc catttaccgt cattgacgtc    3300
```

```
aatagggggc gtacttggca tatgatacac ttgatgtact gccaagtggg cagtttaccg    3360
taaatactcc acccattgac gtcaatggaa agtccctatt ggcgttacta tgggaacata    3420
cgtcattatt gacgtcaatg ggcggggtc gttgggcggt cagccaggcg gccatttac     3480
cgtaagttat gtaacgcctg caggttaatt aagaacatgt gagcaaaagg ccagcaaaag    3540
gccaggaacc gtaaaaaggc cgcgttgctg gcgtttttcc ataggctccg ccccctgac    3600
gagcatcaca aaaatcgacg ctcaagtcag aggtggcgaa acccgacagg actataaaga    3660
taccaggcgt ttccccctgg aagctccctc gtgcgctctc ctgttccgac cctgccgctt    3720
accggatacc tgtccgcctt tctcccttcg ggaagcgtgg cgctttctca tagctcacgc    3780
tgtaggtatc tcagttcggt gtaggtcgtt cgctccaagc tgggctgtgt gcacgaaccc    3840
cccgttcagc ccgaccgctg cgccttatcc ggtaactatc gtcttgagtc caacccggta    3900
agacacgact tatcgccact ggcagcagcc actggtaaca ggattagcag agcgaggtat    3960
gtaggcggtg ctacagagtt cttgaagtgg tggcctaact acggctacac tagaagaaca    4020
gtatttggta tctgcgctct gctgaagcca gttaccttcg gaaaaagagt tggtagctct    4080
tgatccggca acaaaccac cgctggtagc ggtggttttt ttgtttgcaa gcagcagatt    4140
acgcgcagaa aaaaggatc tcaagaagat cctttgatct tttctacggg gtctgacgct    4200
cagtggaacg aaaactcacg ttaagggatt ttggtcatgg ctagttaatt aacatttaaa    4260
tcagcggccg caataaaata tctttatttt cattacatct gtgtgttggt tttttgtgtg    4320
aatcgtaact aacatacgct ctccatcaaa acaaaacgaa acaaaacaaa ctagcaaaat    4380
aggctgtccc cagtgcaagt gcaggtgcca gaacatttct ctatcgaa                4428
```

<210> SEQ ID NO 102
<211> LENGTH: 4428
<212> TYPE: DNA
<213> ORGANISM: Artificial Sequence
<220> FEATURE:
<223> OTHER INFORMATION: pCXCL13(3-87K/H-A)-IgG1Fc

<400> SEQUENCE: 102

```
ggatctgcga tcgctccggt gcccgtcagt gggcagagcg cacatcgccc acagtccccg     60
agaagttggg gggaggggtc ggcaattgaa cgggtgccta gagaaggtgg cgcggggtaa    120
actgggaaag tgatgtcgtg tactggctcc gcctttttcc cgagggtggg ggagaaccgt    180
atataagtgc agtagtcgcc gtgaacgttc tttttcgcaa cgggtttgcc gccagaacac    240
agctgaagct tcgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg taccggcgc     540
ctacctgaga tcaccggcga aggagggcca ccatgtacag gatgcaactc ctgtcttgca    600
ttgcactaag tcttgcactt gtcacgaatt cggaggtcta ttacacaagc ttgaggtgta    660
gatgtgtcca agagagctca gtctttatcc ctagacgctt cattgatgcc attcaaatct    720
tgccccgtgg gaatggttgt ccaagaaaag aaatcatagt ctgggctgcg aacgcttcaa    780
ttgtgtgtgt ggaccctcaa gctgaatgga tacaagccat gatggaagta ttggctgcgg    840
ctagttcttc aactctacca gttccagtgt ttgccgctgc gattcccgac aaaactcaca    900
catgcccacc gtgcccagca cctgaactcc tggggggacc gtcagtcttc ctcttccccc    960
```

```
caaaacccaa ggacaccctc atgatctccc ggacccctga ggtcacatgc gtggtggtgg   1020
acgtgagcca cgaagaccct gaggtcaagt tcaactggta cgtggacggc gtggaggtgc   1080
ataatgccaa gacaaagccg cgggaggagc agtacaacag cacgtaccgt gtggtcagcg   1140
tcctcaccgt cctgcaccag gactggctga atggcaagga gtacaagtgc aaggtctcca   1200
acaaagccct cccagccccc atcgagaaaa ccatctccaa agccaaaggg cagccccgag   1260
aaccacaggt gtacaccctg cccccatccc gggaggagat gaccaagaac caggtcagcc   1320
tgacctgcct ggtcaaaggc ttctatccca gcgacatcgc cgtggagtgg gagagcaatg   1380
ggcagccgga gaacaactac aagaccacgc ctcccgtgct ggactccgac ggctccttct   1440
tcctctacag caagctcacc gtggacaaga gcaggtggca gcagggaaac gtcttctcat   1500
gctccgtgat gcacgaggct ctgcacaacc actacacgca gaagagcctc tccctgtctc   1560
cgggtaaatg agtgctagct ggccagacat gataagatac attgatgagt ttggacaaac   1620
cacaactaga atgcagtgaa aaaatgctt tatttgtgaa atttgtgatg ctattgcttt   1680
atttgtaacc attataagct gcaataaaca agttaacaac aacaattgca ttcattttat   1740
gtttcaggtt caggggggagg tgtgggaggt tttttaaagc aagtaaaacc tctacaaatg   1800
tggtatggaa ttaattctaa aatacagcat agcaaaactt taacctccaa atcaagcctc   1860
tacttgaatc cttttctgag ggatgaataa ggcataggca tcaggggctg ttgccaatgt   1920
gcattagctg tttgcagcct caccttcttt catggagttt aagatatagt gtattttccc   1980
aaggtttgaa ctagctcttc atttctttat gttttaaatg cactgacctc ccacattccc   2040
tttttagtaa aatattcaga aataatttaa atacatcatt gcaatgaaaa taaatgtttt   2100
ttattaggca gaatccagat gctcaaggcc cttcataata tcccccagtt tagtagttgg   2160
acttagggaa caaaggaacc tttaatagaa attggacagc aagaaagcga gcttctagct   2220
tatcctcagt cctgctcctc tgccacaaag tgcacgcagt tgccggccgg gtcgcgcagg   2280
gcgaactccc gcccccacgg ctgctcgccg atctcggtca tggccggccc ggaggcgtcc   2340
cggaagttcg tggacacgac ctccgaccac tcggcgtaca gctcgtccag gccgcgcacc   2400
cacacccagg ccagggtgtt gtccggcacc acctggtcct ggaccgcgct gatgaacagg   2460
gtcacgtcgt cccggaccac accggcgaag tcgtcctcca cgaagtcccg ggagaacccg   2520
agccggtcgg tccagaactc gaccgctccg gcgacgtcgc gcgcggtgag caccggaacg   2580
gcactggtca acttggccat gatggctcct cctgtcagga gaggaaagag aagaaggtta   2640
gtacaattgc tatagtgagt tgtattatac tatgcagata tactatgcca atgattaatt   2700
gtcaaactag gctgcagggg ttcatagtgc cacttttcct gcactgcccc atctcctgcc   2760
caccctttcc caggcataga cagtcagtga cttaccaaac tcacaggagg gagaaggcag   2820
aagcttgaga cagacccgcg ggaccgccga actgcgaggg gacgtggcta gggcggcttc   2880
ttttatggtg cgccggccct cggaggcagg gcgctcgggg aggcctagcg gccaatctgc   2940
ggtggcagga ggcggggccg aaggccgtgc ctgaccaatc cggagcacat aggagtctca   3000
gccccccgcc ccaaagcaag gggaagtcac gcgcctgtag cgccagcgtg ttgtgaaatg   3060
ggggcttggg ggggttgggg ccctgactag tcaaaacaaa ctcccattga cgtcaatggg   3120
gtggagactt ggaaatcccc gtgagtcaaa ccgctatcca cgcccattga tgtactgcca   3180
aaaccgcatc atcatggtaa tagcgatgac taatacgtag atgtactgcc aagtaggaaa   3240
gtcccataag gtcatgtact gggcataatg ccaggcgggc catttaccgt cattgacgtc   3300
```

```
aatagggggc gtacttggca tatgatacac ttgatgtact gccaagtggg cagtttaccg    3360
taaatactcc acccattgac gtcaatggaa agtccctatt ggcgttacta tgggaacata    3420
cgtcattatt gacgtcaatg ggcggggtc gttgggcggt cagccaggcg ggccatttac     3480
cgtaagttat gtaacgcctg caggttaatt aagaacatgt gagcaaaagg ccagcaaaag    3540
gccaggaacc gtaaaaaggc cgcgttgctg gcgtttttcc ataggctccg ccccctgac     3600 gagcatcaca aaaatcgacg ctcaagtcag aggtggcgaa acccgacagg actataaaga    3660
taccaggcgt ttccccctgg aagctccctc gtgcgctctc ctgttccgac cctgccgctt    3720
accggatacc tgtccgcctt tctcccttcg ggaagcgtgg cgctttctca tagctcacgc    3780
tgtaggtatc tcagttcggt gtaggtcgtt cgctccaagc tgggctgtgt gcacgaaccc    3840
cccgttcagc ccgaccgctg cgccttatcc ggtaactatc gtcttgagtc aacccggta    3900 agacacgact tatcgccact ggcagcagcc actggtaaca ggattagcag agcgaggtat    3960
gtaggcggtg ctacagagtt cttgaagtgg tggcctaact acggctacac tagaagaaca    4020
gtatttggta tctgcgctct gctgaagcca gttaccttcg aaaaagagt tggtagctct     4080 tgatccggca aacaaaccac cgctggtagc ggtggttttt ttgtttgcaa gcagcagatt    4140
acgcgcagaa aaaaggatc tcaagaagat cctttgatct tttctacggg gtctgacgct     4200
cagtggaacg aaaactcacg ttaagggatt ttggtcatgg ctagttaatt aacatttaaa    4260
tcagcggccg caataaaata tctttatttt cattacatct gtgtgttggt ttttgtgtg    4320 aatcgtaact aacatacgct ctccatcaaa acaaaacgaa acaaaacaaa ctagcaaaat    4380
aggctgtccc cagtgcaagt gcaggtgcca gaacatttct ctatcgaa              4428
```

<210> SEQ ID NO 103
<211> LENGTH: 4425
<212> TYPE: DNA
<213> ORGANISM: Artificial Sequence
<220> FEATURE:
<223> OTHER INFORMATION: pCXCL13-IgG4Fc

<400> SEQUENCE: 103

```
ggatctgcga tcgctccggt gcccgtcagt gggcagagcg cacatcgccc acagtccccg    60
agaagttggg gggaggggtc ggcaattgaa cgggtgccta gagaaggtgg cgcggggtaa    120
actgggaaag tgatgtcgtg tactggctcc gcctttttcc cgagggtggg ggagaaccgt    180
atataagtgc agtagtcgcc gtgaacgttc tttttcgcaa cgggtttgcc gccagaacac    240
agctgaagct cgaggggct cgcatctctc cttcacgcgc ccgccgccct aacctgaggcc    300 gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cggttctgga ggtctattac acaagcttga    660
ggtgtagatg tgtccaagag agctcagtct ttatccctag acgcttcatt gatcgaattc    720
aaatcttgcc ccgtgggaat ggttgtccaa gaaagaaat catagtctgg aagaagaaca    780
agtcaattgt gtgtgtggac cctcaagctg aatggataca aagaatgatg gaagtattga    840 gaaaagaag ttcttcaact ctaccagttc cagtgtttaa gagaaagatt cccccccccat    900 gcccatcatg cccagcacct gagttcctgg ggggaccatc agtcttcctg ttcccccccaa    960
```

```
aacccaagga cactctcatg atctcccgga cccctgaggt cacgtgcgtg gtggtggacg    1020
tgagccagga agaccccgag gtccagttca actggtacgt ggatggcgtg gaggtgcata    1080
atgccaagac aaagccgcgg gaggagcagt tcaacagcac gtaccgtgtg gtcagcgtcc    1140
tcaccgtcct gcaccaggac tggctgaacg gcaaggagta caagtgcaag gtctccaaca    1200
aaggcctccc gtcctccatc gagaaaacca tctccaaagc caaagggcag ccccgagagc    1260
cacaggtgta caccctgccc ccatcccagg aggagatgac caagaaccag gtcagcctga    1320
cctgcctggt caaaggcttc taccccagcg acatcgccgt ggagtgggag agcaatgggc    1380
agccggagaa caactacaag accacgcctc ccgtgctgga ctccgacggc tccttcttcc    1440
tctacagcag gctaaccgtg gacaagagca ggtggcagga ggggaatgtc ttctcatgct    1500
ccgtgatgca tgaggctctg cacaaccact acacacagaa gagcctctcc ctgtctccgg    1560
gtaaatgagt gctagctggc cagacatgat aagatacatt gatgagtttg gacaaaccac    1620
aactagaatg cagtgaaaaa aatgctttat ttgtgaaatt tgtgatgcta ttgctttatt    1680
tgtaaccatt ataagctgca ataaacaagt taacaacaac aattgcattc attttatgtt    1740
tcaggttcag ggggaggtgt gggaggtttt ttaaagcaag taaaacctct acaaatgtgg    1800
tatggaatta attctaaaat acagcatagc aaaactttaa cctccaaatc aagcctctac    1860
ttgaatcctt ttctgaggga tgaataaggc ataggcatca ggggctgttg ccaatgtgca    1920
ttagctgttt gcagcctcac cttctttcat ggagtttaag atatagtgta ttttcccaag    1980
gtttgaacta gctcttcatt tctttatgtt ttaaatgcac tgacctccca cattcccttt    2040
ttagtaaaat attcagaaat aatttaaata catcattgca atgaaaataa atgtttttta    2100
ttaggcagaa tccagatgct caaggccctt cataatatcc cccagtttag tagttggact    2160
tagggaacaa aggaaccttt aatagaaatt ggacagcaag aaagcgagct tctagcttat    2220
cctcagtcct gctcctctgc cacaaagtgc acgcagttgc cggccgggtc gcgcagggcg    2280
aactcccgcc cccacggctg ctcgccgatc tcggtcatgg ccggcccgga ggcgtcccgg    2340
aagttcgtgg acacgacctc cgaccactcg gcgtacagct cgtccaggcc gcgcacccac    2400
acccaggcca gggtgttgtc cggcaccacc tggtcctgga ccgcgctgat gaacagggtc    2460
acgtcgtccc ggaccacacc ggcgaagtcg tcctccacga agtcccggga gaacccgagc    2520
cggtcggtcc agaactcgac cgctccggcg acgtcgcgcg cggtgagcac cggaacggca    2580
ctggtcaact tggccatgat ggctcctcct gtcaggagag gaaagagaag aaggttagta    2640
caattgctat agtgagttgt attatactat gcagatatac tatgccaatg attaattgtc    2700
aaactagggc tgcagggttc atagtgccac ttttcctgca ctgccccatc tcctgcccac    2760
cctttcccag gcatagacag tcagtgactt accaaactca caggagggag aaggcagaag    2820
cttgagacag acccgcggga ccgccgaact gcgagggac gtggctaggg cggcttcttt    2880
tatggtgcgc cggccctcgg aggcaggcg ctcggggagg cctagcggcc aatctgcggt     2940
ggcaggaggc ggggccgaag gccgtgcctg accaatccgg agcacatagg agtctcagcc    3000
ccccgcccca aagcaagggg aagtcacgcg cctgtagcgc cagcgtgttg tgaaatgggg    3060
gcttgggggg gttgggcc tgactagtca aaacaaactc ccattgacgt caatggggtg    3120
gagacttgga aatccccgtg agtcaaaccg ctatccacgc ccattgatgt actgccaaaa    3180
ccgcatcatc atggtaatag cgatgactaa tacgtagatg tactgccaag taggaaagtc    3240
ccataaggtc atgtactggg cataatgcca ggcgggccat ttaccgtcat tgacgtcaat    3300
```

| | |
|---|---|
| aggggggcgta cttggcatat gatacacttg atgtactgcc aagtgggcag tttaccgtaa | 3360 |
| atactccacc cattgacgtc aatggaaagt ccctattggc gttactatgg aacatacgt | 3420 |
| cattattgac gtcaatgggc gggggtcgtt gggcggtcag ccaggcgggc catttaccgt | 3480 |
| aagttatgta acgcctgcag gttaattaag aacatgtgag caaaaggcca gcaaaaggcc | 3540 |
| aggaaccgta aaaaggccgc gttgctggcg ttttttccata ggctccgccc ccctgacgag | 3600 |
| catcacaaaa atcgacgctc aagtcagagg tggcgaaacc cgacaggact ataaagatac | 3660 |
| caggcgtttc cccctggaag ctccctcgtg cgctctcctg ttccgaccct gccgcttacc | 3720 |
| ggatacctgt ccgcctttct cccttcggga agcgtggcgc tttctcatag ctcacgctgt | 3780 |
| aggtatctca gttcggtgta ggtcgttcgc tccaagctgg gctgtgtgca cgaaccccc | 3840 |
| gttcagcccg accgctgcgc cttatccggt aactatcgtc ttgagtccaa cccgtaaga | 3900 |
| cacgacttat cgccactggc agcagccact ggtaacagga ttagcagagc gaggtatgta | 3960 |
| ggcggtgcta cagagttctt gaagtggtgg cctaactacg gctacactag aagaacagta | 4020 |
| tttggtatct gcgctctgct gaagccagtt accttcggaa aaagagttgg tagctcttga | 4080 |
| tccggcaaac aaaccaccgc tggtagcggt ggtttttttg tttgcaagca gcagattacg | 4140 |
| cgcagaaaaa aaggatctca agaagatcct ttgatctttt ctacggggtc tgacgctcag | 4200 |
| tggaacgaaa actcacgtta agggattttg gtcatggcta gttaattaac atttaaatca | 4260 |
| gcggccgcaa taaatatct ttattttcat tacatctgtg tgttggtttt ttgtgtgaat | 4320 |
| cgtaactaac atacgctctc catcaaaaca aaacgaaaca aaacaaacta gcaaatagg | 4380 |
| ctgtccccag tgcaagtgca ggtgccagaa catttctcta tcgaa | 4425 |

<210> SEQ ID NO 104
<211> LENGTH: 4419
<212> TYPE: DNA
<213> ORGANISM: Artificial Sequence
<220> FEATURE:
<223> OTHER INFORMATION: pCXCL13(3-87)-IgG4Fc

<400> SEQUENCE: 104

| | |
|---|---|
| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gcctttttcc cgagggtggg ggagaaccgt | 180 |
| atataagtgc agtagtcgcc gtgaacgttc tttttcgcaa cgggtttgcc gccagaacac | 240 |
| agctgaagct tcgaggggct cgcatctctc cttcacgcgc ccgccgccct aacctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg tgaccggcgc | 540 |
| ctacctgaga tcaccggcga aggagggcca ccatgtacag gatgcaactc ctgtcttgca | 600 |
| ttgcactaag tcttgcactt gtcacgaatt cggaggtcta ttacacaagc ttgaggtgta | 660 |
| gatgtgtcca agagagctca gtcttatcc ctagacgctt cattgatcga attcaaatct | 720 |
| tgccccgtgg gaatggttgt ccaagaaaag aaatcatagt ctggaagaag aacaagtcaa | 780 |
| ttgtgtgtgt ggaccctcaa gctgaatgga tacaaagaat gatggaagta ttgagaaaaa | 840 |
| gaagttcttc aactctacca gttccagtgt ttaagagaaa gattcccccc ccatgccat | 900 |
| catgcccagc acctgagttc ctggggggac catcagtctt cctgttcccc ccaaaaccca | 960 |

-continued

```
aggacactct catgatctcc cggacccctg aggtcacgtg cgtggtggtg gacgtgagcc   1020
aggaagaccc cgaggtccag ttcaactggt acgtggatgg cgtggaggtg cataatgcca   1080
agacaaagcc gcgggaggag cagttcaaca gcacgtaccg tgtggtcagc gtcctcaccg   1140
tcctgcacca ggactggctg aacggcaagg agtacaagtg caaggtctcc aacaaaggcc   1200
tcccgtcctc catcgagaaa accatctcca aagccaaagg gcagccccga gagccacagg   1260
tgtacaccct gccccatcc caggaggaga tgaccaagaa ccaggtcagc ctgacctgcc   1320
tggtcaaagg cttctacccc agcgacatcg ccgtggagtg ggagagcaat gggcagccgg   1380
agaacaacta caagaccacg cctcccgtgc tggactccga cggctccttc ttcctctaca   1440
gcaggctaac cgtggacaag agcaggtggc aggaggggaa tgtcttctca tgctccgtga   1500 tgcatgagc tctgcacaac cactacacac agaagagcct ctccctgtct ccgggtaaat   1560
gagtgctagc tggccagaca tgataagata cattgatgag tttggacaaa ccacaactag   1620
aatgcagtga aaaaaatgct ttatttgtga aatttgtgat gctattgctt tatttgtaac   1680
cattataagc tgcaataaac aagttaacaa caacaattgc attcatttta tgtttcaggt   1740
tcagggggag gtgtgggagg ttttttaaag caagtaaaac ctctacaaat gtggtatgga   1800
attaattcta aaatacagca tagcaaaact ttaacctcca aatcaagcct ctacttgaat   1860
ccttttctga gggatgaata aggcataggc atcaggggct gttgccaatg tgcattagct   1920
gtttgcagcc tcaccttctt tcatggagtt taagatatag tgtattttcc caaggtttga   1980
actagctctt catttctta tgttttaaat gcactgacct cccacattcc cttttagta   2040 aaatattcag aaataattta aatacatcat tgcaatgaaa ataaatgttt tttattaggc   2100
agaatccaga tgctcaaggc ccttcataat atccccagt ttagtagttg gacttaggga   2160
acaaaggaac ctttaataga aattggacag caagaaagcg agcttctagc ttatcctcag   2220
tcctgctcct ctgccacaaa gtgcacgcag ttgccggccg ggtcgcgcag ggcgaactcc   2280
cgcccccacg gctgctcgcc gatctcggtc atggccggcc cggaggcgtc ccggaagttc   2340
gtggacacga cctccgacca ctcggcgtac agctcgtcca ggccgcgcac ccacacccag   2400
gccagggtgt tgtccggcac cacctggtcc tggaccgcgc tgatgaacag ggtcacgtcg   2460
tcccggacca caccggcgaa gtcgtcctcc acgaagtccc gggagaaccc gagccggtcg   2520
gtccagaact cgaccgctcc ggcgacgtcg cgcgcggtga gcaccggaac ggcactggtc   2580
aacttggcca tgatggctcc tcctgtcagg agaggaaaga gaagaaggtt agtacaattg   2640
ctatagtgag ttgtattata ctatgcagat atactatgcc aatgattaat tgtcaaacta   2700
gggctgcagg gttcatagtg ccactttcc tgcactgccc catctcctgc ccacccttc   2760 ccaggcatag acagtcagtg acttaccaaa ctcacaggag ggagaaggca gaagcttgag   2820
acagacccgc gggaccgccg aactgcgagg ggacgtggct agggcggctt cttttatggt   2880
gcgccggccc tcgaggcag ggcgctcggg gaggcctagc ggccaatctg cggtggcagg   2940
aggcggggcc gaaggccgtg cctgaccaat ccggagcaca taggagtctc agccccccgc   3000
cccaaagcaa ggggaagtca cgcgcctgta gcgccagcgt tttgtgaaat gggggcttgg   3060
gggggttggg gccctgacta gtcaaaacaa actcccattg acgtcaatgg ggtggagact   3120
tggaaatccc cgtgagtcaa accgctatcc acgcccattg atgtactgcc aaaaccgcat   3180
catcatggta atagcgatga ctaatacgta gatgtactgc caagtaggaa agtcccataa   3240
ggtcatgtac tgggcataat gccaggcggg ccatttaccg tcattgacgt caatagggggg   3300
```

```
cgtacttggc atatgataca cttgatgtac tgccaagtgg gcagtttacc gtaaatactc    3360
cacccattga cgtcaatgga aagtccctat tggcgttact atgggaacat acgtcattat    3420
tgacgtcaat gggcgggggt cgttgggcgg tcagccaggc gggccattta ccgtaagtta    3480
tgtaacgcct gcaggttaat taagaacatg tgagcaaaag gccagcaaaa ggccaggaac    3540
cgtaaaaagg ccgcgttgct ggcgtttttc cataggctcc gcccccctga cgagcatcac    3600
aaaaatcgac gctcaagtca gaggtggcga acccgacag gactataaag ataccaggcg    3660
tttccccctg gaagctccct cgtgcgctct cctgttccga ccctgccgct taccggatac    3720
ctgtccgcct ttctcccttc gggaagcgtg gcgctttctc atagctcacg ctgtaggtat    3780
ctcagttcgg tgtaggtcgt tcgctccaag ctgggctgtg tgcacgaacc ccccgttcag    3840
cccgaccgct gcgccttatc cggtaactat cgtcttgagt ccaacccggt aagacacgac    3900
ttatcgccac tggcagcagc cactggtaac aggattagca gagcgaggta tgtaggcggt    3960
gctacagagt tcttgaagtg gtggcctaac tacggctaca ctagaagaac agtatttggt    4020
atctgcgctc tgctgaagcc agttaccttc ggaaaaagag ttggtagctc ttgatccggc    4080
aaacaaacca ccgctggtag cggtggtttt tttgtttgca agcagcagat tacgcgcaga    4140 aaaaaggat ctcaagaaga tcctttgatc ttttctacgg ggtctgacgc tcagtggaac    4200
gaaaactcac gttaagggat tttggtcatg ctagttaat taacatttaa atcagcggcc    4260
gcaataaaat atctttattt tcattacatc tgtgtgttgg ttttttgtgt gaatcgtaac    4320
taacatacgc tctccatcaa acaaaacga acaaaacaa actagcaaaa taggctgtcc    4380
ccagtgcaag tgcaggtgcc agaacatttc tctatcgaa                          4419
```

<210> SEQ ID NO 105  
<211> LENGTH: 4419  
<212> TYPE: DNA  
<213> ORGANISM: Artificial Sequence  
<220> FEATURE:  
<223> OTHER INFORMATION: pCXCL13(3-87K/H-A)-IgG4Fc

<400> SEQUENCE: 105

```
ggatctgcga tcgctccggt gcccgtcagt gggcagagcg cacatcgccc acagtccccg     60
agaagttggg gggaggggtc ggcaattgaa cgggtgccta gagaaggtgg cgcggggtaa    120
actgggaaag tgatgtcgtg tactggctcc gccttttttcc cgagggtggg ggagaaccgt    180
atataagtgc agtagtcgcc gtgaacgttc ttttttcgcaa cgggtttgcc gccagaacac    240
agctgaagct cgagggggct cgcatctctc cttcacgcgc ccgccgccct aacctgaggcc    300 gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaccggcga aggagggcca ccatgtacag gatgcaactc ctgtcttgca    600
ttgcactaag tcttgcactt gtcacgaatt cggaggtcta ttacacaagc ttgaggtgta    660
gatgtgtcca agagagctca gtctttatcc ctagacgctt cattgatgcc attcaaatct    720
tgccccgtgg gaatggttgt ccaagaaaag aaatcatagt ctgggctgcg aacgcttcaa    780
ttgtgtgtgt ggaccctcaa gctgaatgga tacaagccat gatggaagta ttggctgcgg    840
ctagttcttc aactctacca gttccagtgt ttgccgctgc gattcccccc ccatgcccat    900
catgcccagc acctgagttc ctggggggac catcagtctt cctgttcccc ccaaaaccca    960
```

-continued

```
aggacactct catgatctcc cggacccctg aggtcacgtg cgtggtggtg gacgtgagcc    1020
aggaagaccc cgaggtccag ttcaactggt acgtggatgg cgtggaggtg cataatgcca    1080
agacaaagcc gcgggaggag cagttcaaca gcacgtaccg tgtggtcagc gtcctcaccg    1140
tcctgcacca ggactggctg aacggcaagg agtacaagtg caaggtctcc aacaaaggcc    1200
tcccgtcctc catcgagaaa accatctcca aagccaaagg gcagccccga gagccacagg    1260
tgtacaccct gcccccatcc caggaggaga tgaccaagaa ccaggtcagc ctgacctgcc    1320
tggtcaaagg cttctacccc agcgacatcg ccgtggagtg ggagagcaat gggcagccgg    1380
agaacaacta caagaccacg cctcccgtgc tggactccga cggctccttc ttcctctaca    1440
gcaggctaac cgtggacaag agcaggtggc aggaggggaa tgtcttctca tgctccgtga    1500
tgcatgaggc tctgcacaac cactacacac agaagagcct ctccctgtct ccgggtaaat    1560
gagtgctagc tggccagaca tgataagata cattgatgag tttggacaaa ccacaactag    1620
aatgcagtga aaaaaatgct ttatttgtga aatttgtgat gctattgctt tatttgtaac    1680
cattataagc tgcaataaac aagttaacaa caacaattgc attcatttta tgtttcaggt    1740
tcagggggag gtgtgggagg ttttttaaag caagtaaaac ctctacaaat gtggtatgga    1800
attaattcta aaatacagca tagcaaaact ttaacctcca aatcaagcct ctacttgaat    1860
ccttttctga gggatgaata aggcataggc atcaggggct gttgccaatg tgcattagct    1920
gtttgcagcc tcaccttctt tcatggagtt taagatatag tgtattttcc caaggtttga    1980
actagctctt catttcttta tgttttaaat gcactgacct cccacattcc cttttttagta    2040 aaatattcag aaataattta aatacatcat tgcaatgaaa ataaatgttt tttattaggc    2100
agaatccaga tgctcaaggc ccttcataat atccccagt ttagtagttg gacttaggga    2160
acaaaggaac ctttaataga aattggacag caagaaagcg agcttctagc ttatcctcag    2220
tcctgctcct ctgccacaaa gtgcacgcag ttgccggccg ggtcgcgcag ggcgaactcc    2280
cgcccccacg gctgctcgcc gatctcggtc atggccggcc cggaggcgtc ccggaagttc    2340
gtggacacga cctccgacca ctcggcgtac agctcgtcca ggccgcgcac ccacacccag    2400
gccagggtgt tgtccggcac cacctggtcc tggaccgcgc tgatgaacag ggtcacgtcg    2460
tcccggacca caccggcgaa gtcgtcctcc acgaagtccc gggagaaccc gagccggtcg    2520
gtccagaact cgaccgctcc ggcgacgtcg cgcgcggtga gcaccggaac ggcactggtc    2580
aacttggcca tgatggctcc tcctgtcagg agaggaaaga gaagaaggtt agtacaattg    2640
ctatagtgag ttgtattata ctatgcagat atactatgcc aatgattaat tgtcaaacta    2700
gggctgcagg gttcatagtg ccacttttcc tgcactgccc catctcctgc ccacccttttc    2760 ccaggcatag acagtcagtg acttaccaaa ctcacaggag ggagaaggca gaagcttgag    2820
acagacccgc gggaccgccg aactgcgagg ggacgtggct agggcggctt cttttatggt    2880
gcgccggccc tcgaggcag ggcgctcggg gaggcctagc ggccaatctg cggtggcagg    2940
aggcggggcc gaaggccgtg cctgaccaat ccggagcaca taggagtctc agccccccgc    3000
cccaaagcaa ggggaagtca cgcgcctgta gcgccagcgt gttgtgaaat ggggcttgg    3060 gggggttggg gccctgacta gtcaaaacaa actcccattg acgtcaatgg ggtggagact    3120
tggaaatccc cgtgagtcaa accgctatcc acgcccattg atgtactgcc aaaaccgcat    3180
catcatggta atagcgatga ctaatacgta gatgtactgc caagtaggaa agtcccataa    3240
ggtcatgtac tgggcataat gccaggcggg ccatttaccg tcattgacgt caataggggg    3300
```

```
cgtacttggc atatgataca cttgatgtac tgccaagtgg gcagtttacc gtaaatactc    3360
cacccattga cgtcaatgga aagtccctat tggcgttact atgggaacat acgtcattat    3420
tgacgtcaat gggcgggggt cgttgggcgg tcagccaggc gggccattta ccgtaagtta    3480
tgtaacgcct gcaggttaat taagaacatg tgagcaaaag gccagcaaaa ggccaggaac    3540
cgtaaaaagg ccgcgttgct ggcgtttttc cataggctcc gcccccctga cgagcatcac    3600
aaaaatcgac gctcaagtca gaggtggcga acccgacag gactataaag ataccaggcg    3660
tttccccctg gaagctccct cgtgcgctct cctgttccga ccctgccgct taccggatac    3720
ctgtccgcct ttctcccttc gggaagcgtg gcgctttctc atagctcacg ctgtaggtat    3780
ctcagttcgg tgtaggtcgt tcgctccaag ctgggctgtg tgcacgaacc ccccgttcag    3840
cccgaccgct gcgccttatc cggtaactat cgtcttgagt ccaacccggt aagacacgac    3900
ttatcgccac tggcagcagc cactggtaac aggattagca gagcgaggta tgtaggcggt    3960
gctacagagt tcttgaagtg gtggcctaac tacggctaca ctagaagaac agtatttggt    4020
atctgcgctc tgctgaagcc agttaccttc ggaaaaagag ttggtagctc ttgatccggc    4080
aaacaaacca ccgctggtag cggtggtttt tttgtttgca agcagcagat tacgcgcaga    4140 aaaaaggat ctcaagaaga tcctttgatc ttttctacgg ggtctgacgc tcagtggaac    4200
gaaaactcac gttaagggat tttggtcatg gctagttaat taacatttaa atcagcggcc    4260
gcaataaaat atctttattt tcattacatc tgtgtgttgg ttttttgtgt gaatcgtaac    4320
taacatacgc tctccatcaa aacaaaacga aacaaaacaa actagcaaaa taggctgtcc    4380
ccagtgcaag tgcaggtgcc agaacatttc tctatcgaa                          4419
```

<210> SEQ ID NO 106
<211> LENGTH: 20
<212> TYPE: PRT
<213> ORGANISM: Artificial Sequence
<220> FEATURE:
<223> OTHER INFORMATION: IL-2 Secretion Signal

<400> SEQUENCE: 106

```
Met Tyr Arg Met Gln Leu Leu Ser Cys Ile Ala Leu Ser Leu Ala Leu
1               5                   10                  15

Val Thr Asn Ser
            20
```

US 9,493,531 B2

CHEMOKINE-IMMUNOGLOBULIN FUSION POLYPEPTIDES, COMPOSITIONS, METHOD OF MAKING AND USE THEREOF

This application is a continuation of U.S. patent application Ser. No. 14/612,884, filed Feb. 3, 2015, which is a continuation-in-part of U.S. patent application Ser. No. 13/962,401, filed on Aug. 8, 2013, now U.S. Pat. No. 8,987,210, which is a continuation of U.S. patent application Ser. No. 13/962,110, filed Aug. 8, 2013, now U.S. Pat. No. 8,796,422, which is a continuation-in-part application of U.S. patent application Ser. No. 13/480,526, filed May 25, 2012, now U.S. Pat. No. 8,541,564, which claims priority of U.S. Provisional Patent Application No. 61/492,260, filed on Jun. 1, 2011. The entirety of the aforementioned applications is incorporated herein by reference.

FIELD

The present application generally relates to compositions that can be used for treating chemokine receptor-mediated disorders and modulating inflammation, inflammatory cell motility, cancer cell motility, or cancer cell survival.

BACKGROUND

Chemokines are chemotactic cytokines, of molecular weight 6-15 kDa, that are released by a wide variety of cells to attract and activate, among other cell types, macrophages, T and B lymphocytes, eosinophils, basophils and neutrophils. There are four classes of chemokines, CXC, CC, C, and CX3C, depending on whether the first two cysteines in the amino acid sequence are separated by a single amino acid (CXC) or are adjacent (CC). Unlike other chemokines, C chemokines have only two cysteines; one N-terminal and one downstream cysteine. The only CX3C chemokine, CX3CL1, has three amino acids between two N-terminal cysteines. The CXC chemokines, such as interleukin-8 (IL-8/CXCL8), neutrophil-activating protein-2 (NAP-2/CXCL7) and melanoma growth stimulatory activity protein (MGSA/CXCL1) are chemotactic primarily for neutrophils and T lymphocytes, whereas the CC chemokines, such as RANTES/CCL5, MIP-1α/CCL3, MIP-1β/CCL4, the monocyte chemotactic proteins (MCP-1/CCL2, MCP-2/CCL8, MCP-3/CCL7, MCP-4/CCL13, and MCP-5/CCL12) and the eotaxins (-1/CCL11 and -2/CCL24) are chemotactic for, among other cell types, macrophages, T lymphocytes, eosinophils, dendritic cells, and basophils. There also exist the chemokines lymphotactin-1/XCL1, lymphotactin-2/XCL2 (both C chemokines), and fractalkine/CX3CL1 (a CX3C chemokine) that do not fall into either of the major chemokine subfamilies, CXC and CC.

Chemokines bind to specific cell-surface receptors belonging to the family of G-protein-coupled seven-transmembrane-domain proteins, which are termed "chemokine receptors." On binding to their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration.

Chemokine receptors have been implicated as being important mediators of inflammatory, infectious, and immunoregulatory disorders and diseases, including cancer, asthma and allergic diseases, as well as autoimmune pathologies such as rheumatoid arthritis and atherosclerosis. For example, the chemokine receptor CCR3 plays a pivotal role in attracting eosinophils to sites of allergic inflammation and in subsequently activating these cells. The chemokine ligands for CCR3 induce a rapid increase in intracellular calcium concentration, increased expression of cellular adhesion molecules, cellular degranulation, and the promotion of eosinophil migration. Another chemokine receptor, CCR2, contributes to cancer progression and can induce tumor cell proliferation or chemotaxis. Accordingly, agents which modulate chemokine receptors would be useful in such disorders and diseases.

Chemokines have also been implicated in the pathogenesis of cell proliferative disorders, including for example induction of tumor angiogenesis and growth. Many tumor cells have also been shown to express chemokine receptors, such as CXCR1, CXCR2, CXCR3, CXCR4, CXCR5, CXCR6, CXCR7, CX3CL1, CCR2, CCR5, and CCR9, and thus tumor cells may also stimulate their own growth, migration, and/or invasion when responding to secreted chemokines.

Chemokines are critical for leukocyte recruitment to injured tissues and play an important role in the wound healing process. Impaired wound healing in diabetic patients is accompanied by decreased early inflammatory cell infiltration, but persistence of neutrophils and macrophages leading to chronic, nonhealing wounds. Chemokines may have both direct and inflammatory-mediated effects on many different aspects of diabetic wound healing, including: impairments in growth factor expression, angiogenesis, extracellular matrix formation, and reepithelialization. Certain chemokine receptor expression in wounds may accelerate healing, and be beneficial in the context of surgery, chronic ulcers, and other conditions.

Chemokine receptors therefore represent promising targets for the development of novel anti-inflammatory and anti-tumor as well as angiostatic, angiogenic, and wound healing agents. Thus, there remains a need for compositions that are capable of modulating activity of chemokine receptors.

SUMMARY

One aspect of the present application relates to an isolated chemokine-immunoglobulin fusion polypeptide having a chemokine moiety and an immunoglobulin moiety. In some embodiments, the chemokine moiety comprises a chemokine selected from the group consisting of human CCL1, CCL2, CCL3, CCL4, CCL4L1, CCL5, CCL7, CCL8, CCL11, CCL13, CCL14-1, CCL14-2, CCL15, CCL16, CCL17, CCL 18, CCL19, CCL20-1, CCL20-2, CCL21, CCL22, CCL23-1, CCL23-1, CCL24, CCL25-1, CCL25-2, CCL25-3, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL16, XCL1, XCL2, CX3CL1 and functional variants thereof, and the immunoglobulin moiety comprises a peptide selected from the group consisting of the constant region of human Ig G1, the constant region of human Ig G2, the constant region of human Ig G3, the constant region of human Ig G4, and functional variants thereof. In one embodiment, the isolated chemokine-immunoglobulin fusion polypeptide is a pegylated chemokine-immunoglobulin fusion polypeptide.

In one particular embodiment, the chemokine-immunoglobulin fusion polypeptide is selected from the group consisting of CCL2-IgG1Fc, CCL2(5-76)-IgG1Fc, CCL2(5-76K/H→A)-IgG1Fc, CCL2-IgG4Fc, CCL2(5-76)-IgG4Fc, CCL2(5-76K/H→A)-IgG4Fc, CCL7-IgG1Fc, CCL7(5-76)-IgG1Fc, CCL7(5-76K/H→A)-IgG1Fc, CCL7-IgG4Fc, CCL7(5-76)-IgG4Fc, CCL7(5-76K/H→A)-IgG4Fc, CCL8-IgG1Fc, CCL8(5-76)-IgG1Fc, CCL8(5-76K/H/R→A)-IgG1Fc, CCL8-IgG4Fc, CCL8(5-76)-IgG4Fc, CCL8(5-76K/H/R→A)-IgG4Fc, CCL13-IgG1Fc, CCL13(5-75)-IgG1Fc, CCL13(5-75K/H→A)-IgG1Fc, CCL13-IgG4Fc, CCL13(5-75)-IgG4Fc, CCL13(5-75K/H→A)-IgG4Fc, CCL25-IgG1Fc, CCL25(4-127)-IgG1Fc, CCL25(4-127K/H/R→A)-IgG1Fc, CCL25-IgG4Fc, CCL25(4-127)-IgG4Fc, CCL25(4-127K/H/R→A)-IgG4Fc, CXCL11-IgG1Fc, CXCL11(4-73)-IgG1Fc, CXCL11(4-73K/R→A)-IgG1Fc, CXCL11-IgG4Fc, CXCL11(4-73)-IgG4Fc, CXCL11(4-73K/R→A)-IgG4Fc, CXCL12α-IgG1Fc, CXCL12α(3-67)-IgG1Fc, CXCL12α(3-67K/R→A)-IgG1Fc, CXCL12α-IgG4Fc, CXCL12α(3-67)-IgG4Fc, CXCL12α(3-67K/R→A)-IgG4Fc, CXCL13-IgG1Fc, CXCL13(3-87)-IgG1Fc, CXCL13(3-87K/R→A)-IgG1Fc, CXCL13-IgG4Fc, CXCL13(3-87)-IgG4Fc, and CXCL13(3-87K/R→A)-IgG4Fc.

Another aspect of the present application is directed to an isolated polynucleotide encoding a chemokine-immunoglobulin fusion polypeptide having a chemokine moiety and an immunoglobulin moiety, wherein the chemokine moiety comprises a chemokine selected from the group consisting of human CCL1, CCL2, CCL3, CCL4, CCL5, CCL7, CCL8, CCL11, CCL13, CCL14, CCL15, CCL16, CCL17, CCL19, CCL21, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, XCL1, XCL2, CX3CL1 and functional variants thereof and wherein the immunoglobulin moiety comprises a peptide selected from the group consisting of the constant regions of human IgG1 (hIgG1Fc), the constant regions of human IgG2 (hIgG2Fc), the constant regions of human IgG3 (hIgG3Fc), the constant regions of human IgG4 (hIgG4Fc), and functional variants thereof.

In a particular embodiment, the isolated polynucleotide encoding a chemokine-immunoglobulin fusion polypeptide is selected from the group consisting of CCL2-IgG1Fc, CCL2(5-76)-IgG1Fc, CCL2(5-76K/H→A)-IgG1Fc, CCL2-IgG2Fc, CCL2(5-76)-IgG2Fc, CCL2(5-76K/H→A)-IgG2Fc, CCL2-IgG3Fc, CCL2(5-76)-IgG3Fc, CCL2(5-76K/H→A)-IgG3Fc, CCL2-IgG4Fc, CCL2(5-76)-IgG4Fc, CCL2(5-76K/H→A)-IgG4Fc, CCL7-IgG1Fc, CCL7(5-76)-IgG1Fc, CCL7(5-76K/H→A)-IgG1Fc, CCL7-IgG2Fc, CCL7(5-76)-IgG2Fc, CCL7(5-76K/H→A)-IgG2Fc, CCL7-IgG3Fc, CCL7(5-76)-IgG3Fc, CCL7(5-76K/H→A)-IgG3Fc, CCL7-IgG4Fc, CCL7(5-76)-IgG4Fc, CCL7(5-76K/H→A)-IgG4Fc, CCL8-IgG1Fc, CCL8(5-76)-IgG1Fc, CCL8(5-76K/H/R→A)-IgG1Fc, CCL8-IgG1Fc, CCL8(5-76)-IgG1Fc, CCL8(5-76K/H/R→A)-IgG1Fc, CCL8-IgG2Fc, CCL8(5-76)-IgG2Fc, CCL8(5-76K/H/R→A)-IgG2Fc, CCL8-IgG3Fc, CCL8(5-76)-IgG3Fc, CCL8(5-76K/H/R→A)-IgG3Fc, CCL8-IgG4Fc, CCL8(5-76)-IgG4Fc, CCL8(5-76K/H/R→A)-IgG4Fc, CCL13-IgG1Fc, CCL13(5-75)-IgG1Fc, CCL13(5-75K/H→A)-IgG1Fc, CCL13-IgG2Fc, CCL13(5-75)-IgG2Fc, CCL13(5-75K/H→A)-IgG2Fc, CCL13-IgG3Fc, CCL13(5-75)-IgG3Fc, CCL13(5-75K/H→A)-IgG3Fc, CCL13-IgG4Fc, CCL13(5-75)-IgG4Fc, CCL13(5-75K/H→A)-IgG4Fc, CCL25-IgG1Fc, CCL25(4-127)-IgG1Fc, CCL25(4-127K/H/R→A)-IgG1Fc, CCL25-IgG2Fc, CCL25(4-127)-IgG2Fc, CCL25(4-127K/H/R→A)-IgG2Fc, CCL25-IgG3Fc, CCL25(4-127)-IgG3Fc, CCL25(4-127K/H/R→A)-IgG3Fc, CCL25-IgG4Fc, CCL25(4-127)-IgG4Fc, CCL25(4-127K/H/R→A)-IgG4Fc, CXCL11-IgG1Fc, CXCL11(4-73)-IgG1Fc, CXCL11(4-73K/R→A)-IgG1Fc, CXCL11-IgG2Fc, CXCL11(4-73)-IgG2Fc, CXCL11(4-73K/R→A)-IgG2Fc, CXCL11-IgG3Fc, CXCL11(4-73)-IgG3Fc, CXCL11(4-73K/R→A)-IgG3Fc, CXCL11-IgG4Fc, CXCL11(4-73)-IgG4Fc, CXCL11(4-73K/R→A)-IgG4Fc, CXCL12α-IgG1Fc, CXCL12α(3-67)-IgG1Fc, CXCL12α(3-67K/R→A)-IgG1Fc, CXCL12α-IgG2Fc, CXCL12α(3-67)-IgG2Fc, CXCL12α(3-67K/R→A)-IgG2Fc, CXCL12α-IgG3Fc, CXCL12α(3-67)-IgG3Fc, CXCL12α(3-67K/R→A)-IgG3Fc, CXCL12α-IgG4Fc, CXCL12α(3-67)-IgG4Fc, CXCL12α(3-67K/R→A)-IgG4Fc, CXCL13-IgG1Fc, CXCL13(3-87)-IgG1Fc, CXCL13(3-87K/R→A)-IgG1Fc, CXCL13-IgG2Fc, CXCL13(3-87)-IgG2Fc, CXCL13(3-87K/R→A)-IgG2Fc, CXCL13-IgG3Fc, CXCL13(3-87)-IgG3Fc, CXCL13(3-87K/R→A)-IgG3Fc, CXCL13-IgG4Fc, CXCL13(3-87)-IgG4Fc, and CXCL13(3-87K/R→A)-IgG4Fc.

A further aspect of the present application is directed to a pharmaceutical composition comprising (1) a chemokine-immunoglobulin fusion polypeptide of the present application or an expression vector encoding a chemokine-immunoglobulin fusion polypeptide of the present application, and (2) a pharmaceutically acceptable carrier.

A further aspect of the present application is directed to a method for treating a chemokine receptor-mediated disorder in a subject, comprising administering to said subject an effective amount of the pharmaceutical composition of the present application.

Another aspect of the present application relates to a method for modulating inflammation in a subject, comprising administering to said subject an effective amount of the pharmaceutical composition of the present application.

Another aspect of the present application relates to a method for treating a chemokine receptor-mediated disorder in a subject, comprising administering to said subject an effective amount of a pegylated chemokine, wherein the chemokine is selected from the group consisting of human CCL1, CCL2, CCL3, CCL4, CCL5, CCL7, CCL8, CCL11, CCL13, CCL14, CCL15, CCL16, CCL17, CCL19, CCL21, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, XCL1, XCL2, CX3CL1 and functional variants thereof.

In a further embodiment, the pegylated chemokine is selected from the group consisting of CCL2-PEG, var-CCL2-PEG, CCL7-PEG, var-CCL7-PEG, CCL8-PEG, var-CCL8-PEG, CCL13-PEG, var-CCL13-PEG, CCL25-PEG, var-CCL25-PEG, CXCL11-PEG, var-CXCL11-PEG, CXCL13-PEG, var-CXCL13-PEG, CXCL16-PEG, and var-CXCL16-PEG.

BRIEF DESCRIPTION OF THE DRAWINGS

FIG. 1A depicts the expression vector pCCL2.hIgG1Fc. The Fc region comprises the CH2 and CH3 domains of the IgG heavy chain and the hinge region. The hinge serves as a flexible spacer between the two parts of the Fc-fusion protein, allowing each part of the molecule to function independently. hEF1-HTLV prom is a composite promoter comprising the Elongation Factor-1α (EF-1α) core promoter 1 and the R segment and part of the U5 sequence (R-U5') of the Human T-Cell Leukemia Virus (HTLV) Type 1 Long Terminal Repeat2. The EF-1α promoter exhibits a strong activity and yields long lasting expression of a transgene in vivo. The R-U5' has been coupled to the EF-1α core promoter to enhance stability of RNA. MCS: The multiple cloning site. SV40 pAn: the Simian Virus 40 late polyadenylation signal. ori: a minimal *E. coli* origin of replication. CMV enh/hFerL prom: This composite promoter combines the human cytomegalovirus immediate-early gene 1 enhancer and the core promoter of the human ferritin light chain gene. This ubiquitous promoter drives the expression of the Zeocin™-resistance gene in mammalian cells. EM2KC is a bacterial promoter that enables the constitutive expression of the antibiotic resistance gene in *E. coli*. EM2KC is located within an intron and is spliced out in mammalian cells. Zeo: Resistance to Zeocin™ is conferred by the Sh ble gene from *Streptoalloteichus hindustanus* The same resistance gene confers selection in both mammalian cells and *E. coli*. βGlo pAn: The human beta-globin 3'UTR and polyadenylation sequence allows efficient arrest of the transgene transcription4

FIG. 1B depicts the expression vector pCCL2(5-76).hIgG1Fc.

FIG. 1C shows the nucleotide sequence of the expression vector pCCL2.hIgG1Fc.

FIG. 1D shows the nucleotide sequence of the expression vector pCCL2(5-76).hIgG1Fc.

FIG. 1E shows the nucleotide sequence of the expression vector pCCL2(5-76).hIgG1Fc with alanine substitutions for removal of GAG binding sites—lys and his.

Figure 2D:
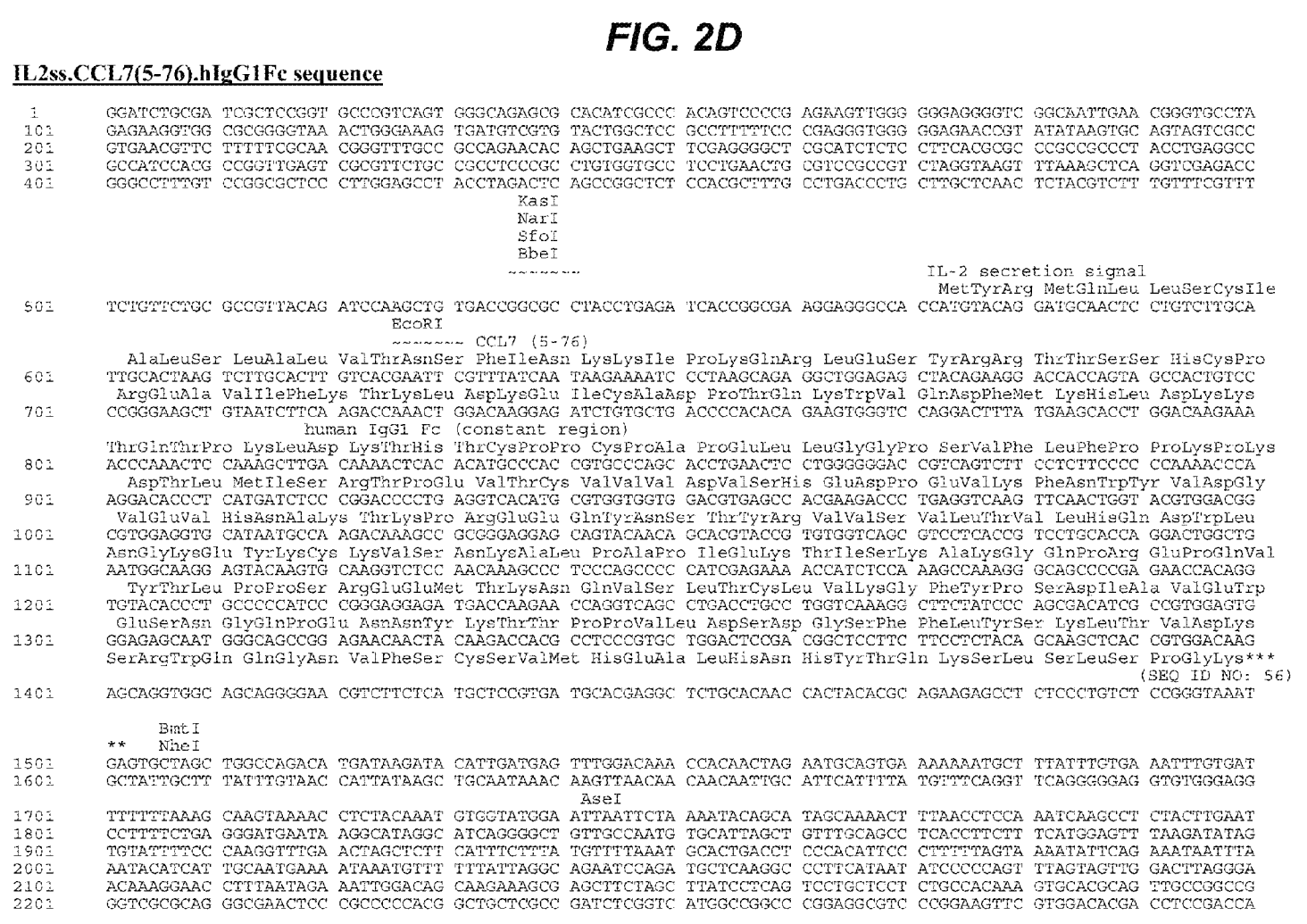

FIG. 2C shows the nucleotide sequence of the expression vector pCCL7.hIgG1Fc.

FIG. 2D shows the nucleotide sequence of the expression vector pCCL7(5-76).hIgG1Fc.

FIG. 2E shows the nucleotide sequence of the expression vector pCCL7(5-76).hIgG1Fc with alanine substitutions for removal of GAG binding sites—lys and his.

FIG. 3A depicts the expression vector pCCL8.hIgG1Fc.

FIG. 3B depicts the expression vector pCCL8(5-76).hIgG1Fc.

FIG. 3C shows the nucleotide sequence of the expression vector pCCL8.hIgG1Fc.

FIG. 3D shows the nucleotide sequence of the expression vector pCCL8(5-76).hIgG1Fc.

FIG. 3E shows the nucleotide sequence of the expression vector pCCL8(5-76).hIgG1Fc with alanine substitution

Figure 4D:
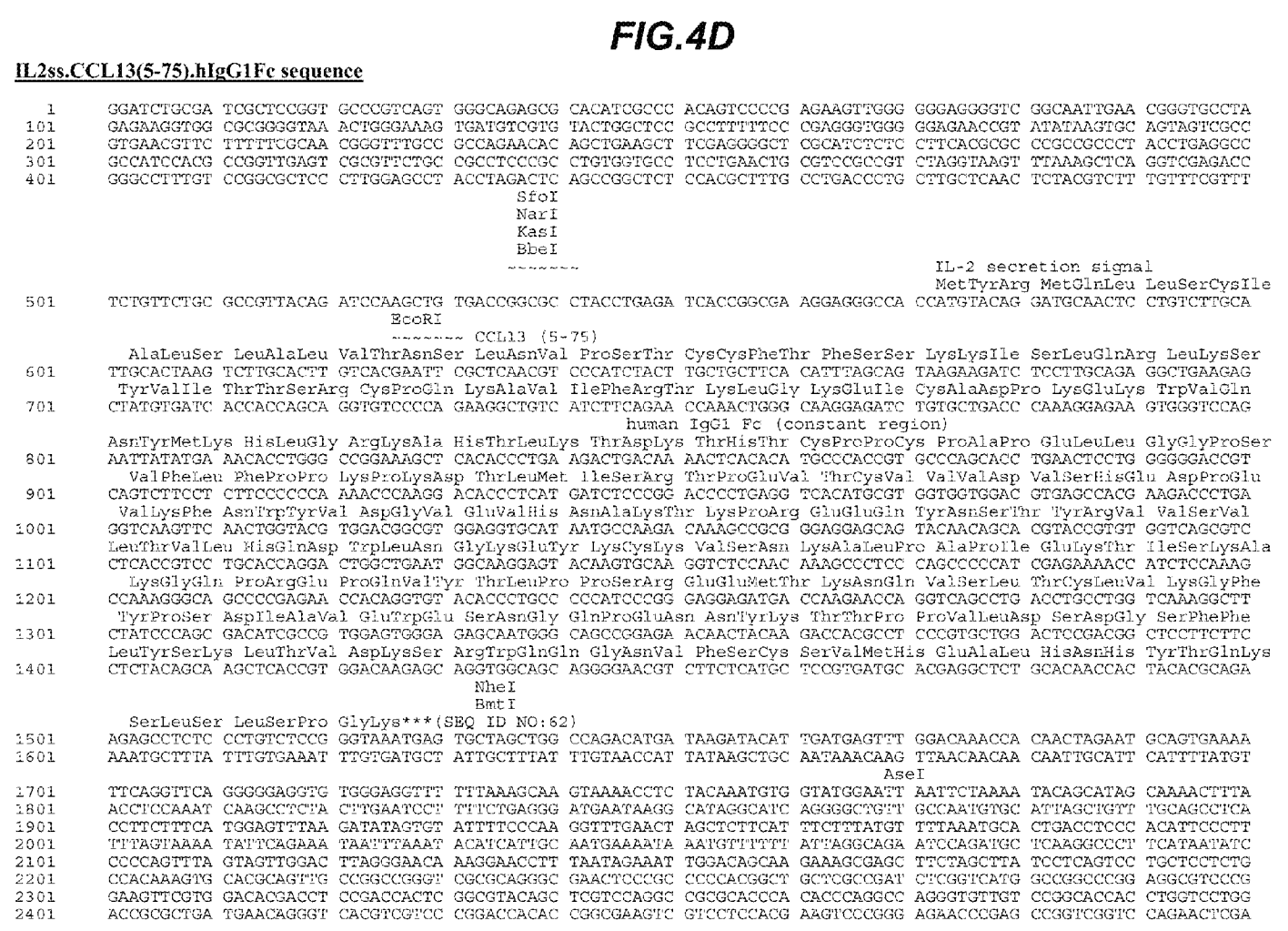

FIG. 4C shows the nucleotide sequence of the expression vector pCCL13.hIgG1Fc.

FIG. 4D shows the nucleotide sequence of the expression vector pCCL13(5-75).hIgG1Fc.

FIG. 4E shows the nucleotide sequence of the expression vector pCCL13(5-76).hIgG1Fc with alanine substitutions for removal of GAG binding sites—lys and his.

Figure 5D:
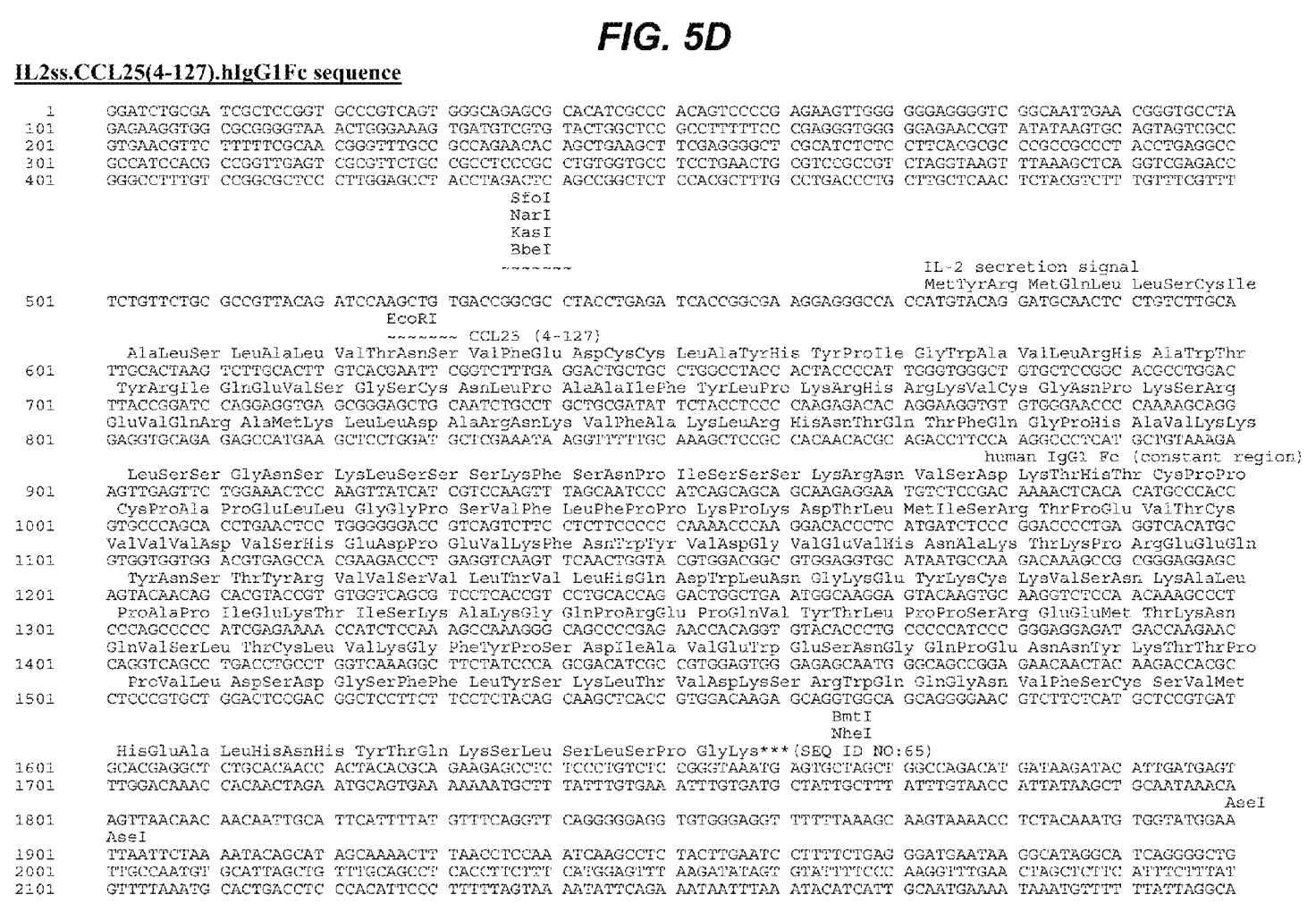

FIG. 5C shows the nucleotide sequence of the expression vector pCCL25.hIgG1Fc.

FIG. 5D shows the nucleotide sequence of the expression vector pCCL25(4-127).hIgG1Fc.

FIG. 5E shows the nucleotide sequence of the expression vector pCCL25(4-127).hIgG1Fc with alanine substitutions for removal of GAG binding sites—lys and his.

FIG. 6C shows the nucleotide sequence of the expression vector pCXCL11.hIgG1Fc.

FIG. 6D shows the nucleotide sequence of the expression vector pCXCL11(4-73).hIgG1Fc.

FIG. 6E shows the nucleotide sequence of the expression vector pCXCL11(4-127).hIgG1Fc with alanine substitutions for removal of GAG binding sites—lys and his.

FIG. 7C shows the nucleotide sequence of the expression vector pCXCL11.hIgG4Fc.

FIG. 7D shows the nucleotide sequence of the expression vector pCXCL11(4-73).hIgG4Fc.

FIG. 7E shows the nucleotide sequence of the expression vector pCXCL11(4-127).hIgG4Fc with alanine substitutions for removal of GAG binding sites—lys and his.

Figure 8E:
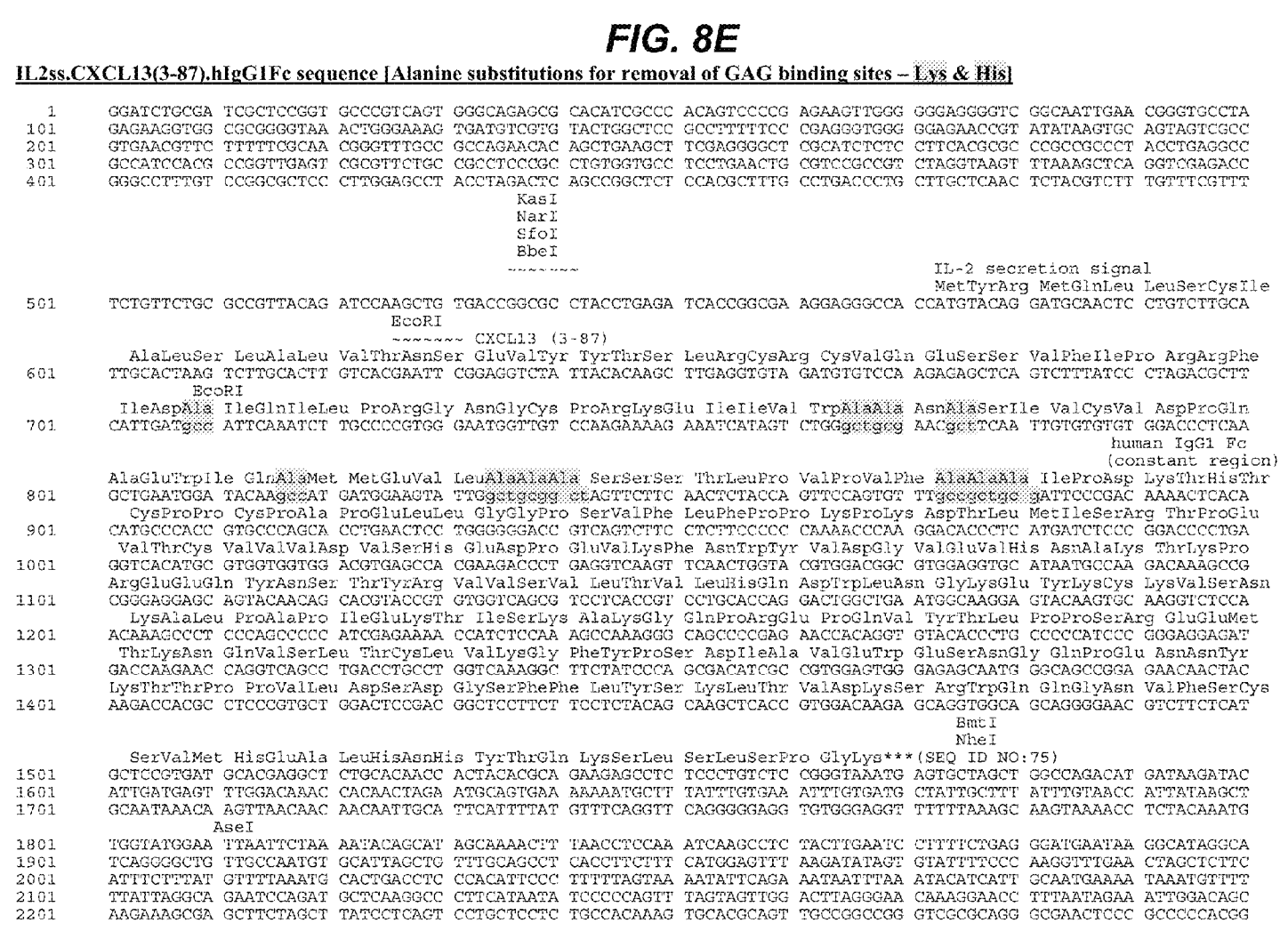

FIG. 8A depicts the expression vector pCXCL13.hIgG1Fc.

FIG. 8B depicts the expression vector pCXCL13(3-87).hIgG1Fc.

FIG. 8C shows the nucleotide sequence of the expression vector pCXCL13.hIgG1Fc.

FIG. 8D shows the nucleotide sequence of the expression vector pCXCL13(4-73).hIgG1Fc.

FIG. 8E shows the nucleotide sequence of the expression vector pCXCL13(4-127).hIgG1Fc with alanine substitutions for removal of GAG binding sites—lys and his.

FIG. 9A depicts the expression vector pCXCL13.hIgG4Fc.

FIG. 9B depicts the expression vector pCXCL13(3-87).hIgG4Fc.

FIG. 9C shows the nucleotide sequence of the expression vector pCXCL13.hIgG4Fc.

FIG. 9D shows the nucleotide sequence of the expression vector pCXCL13(3-87).hIgG4Fc.

FIG. 9E shows the nucleotide sequence of the expression vector pCXCL11(4-127).hIgG4Fc with alanine substitutions for removal of GAG binding sites—lys and his.

FIG. 12 shows the amino acid sequences of the chemokines and human IgG Fc fragments listed in Table 1.

DETAILED DESCRIPTION

Figure 2A:
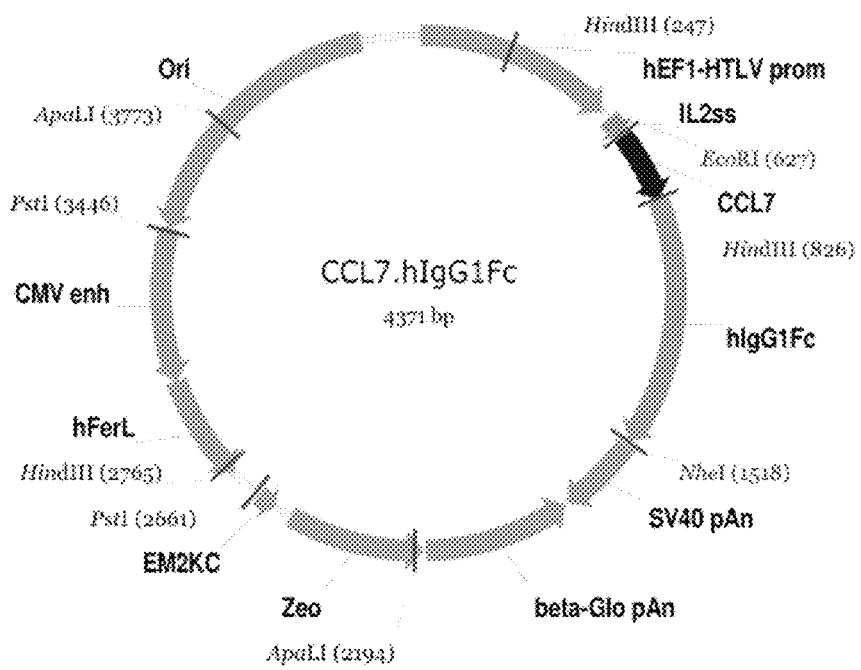
FIG. 2A depicts the expression vector pCCL7.hIgG1Fc.
Figure 2B:
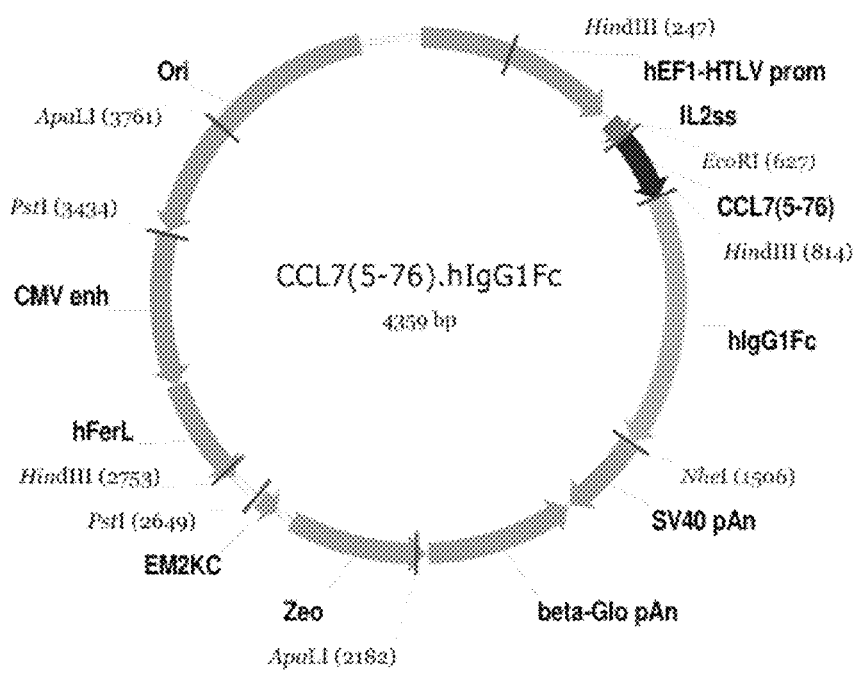
FIG. 2B depicts the expression vector pCCL7(5-76).hIgG1Fc.
Figure 4A:
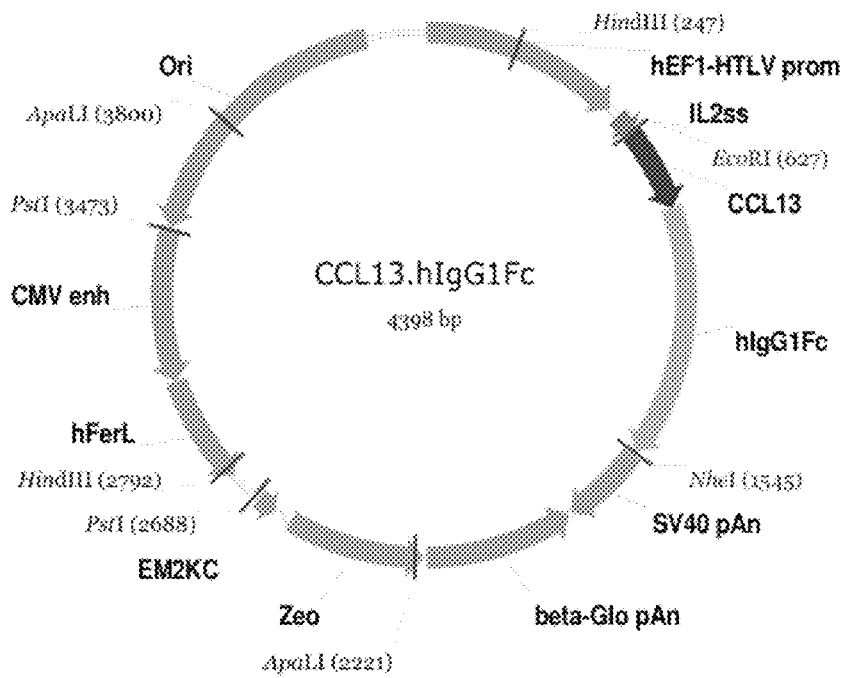
FIG. 4A depicts the expression vector pCCL13.hIgG1Fc.
Figure 4B:
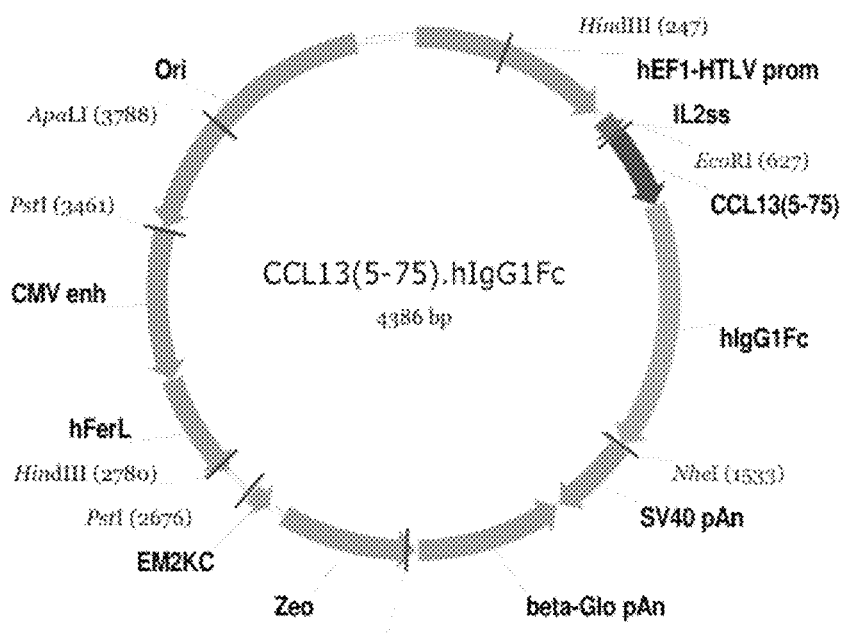
FIG. 4B depicts the expression vector pCCL13(5-75).hIgG1Fc.
Figure 5A:
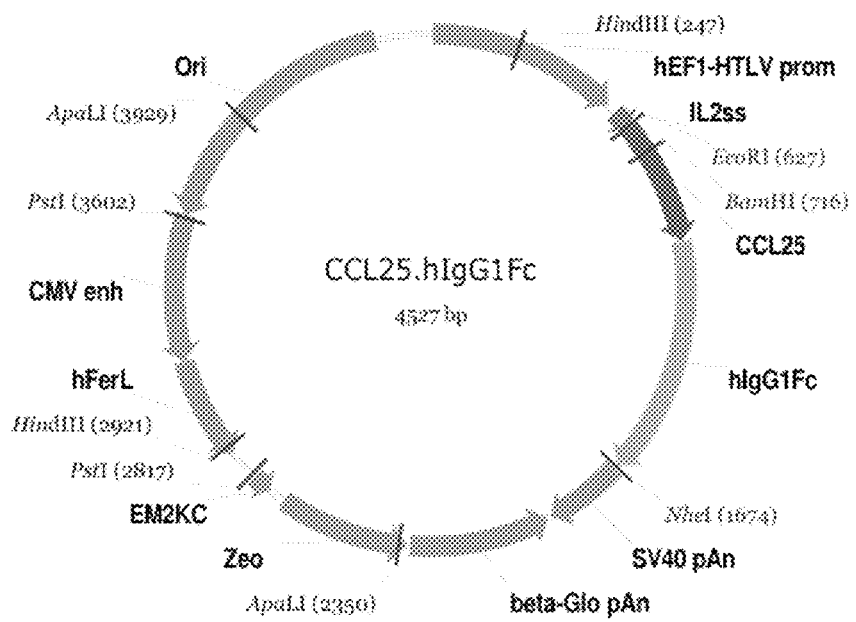
FIG. 5A depicts the expression vector pCCL25.hIgG1Fc.
Figure 5B:
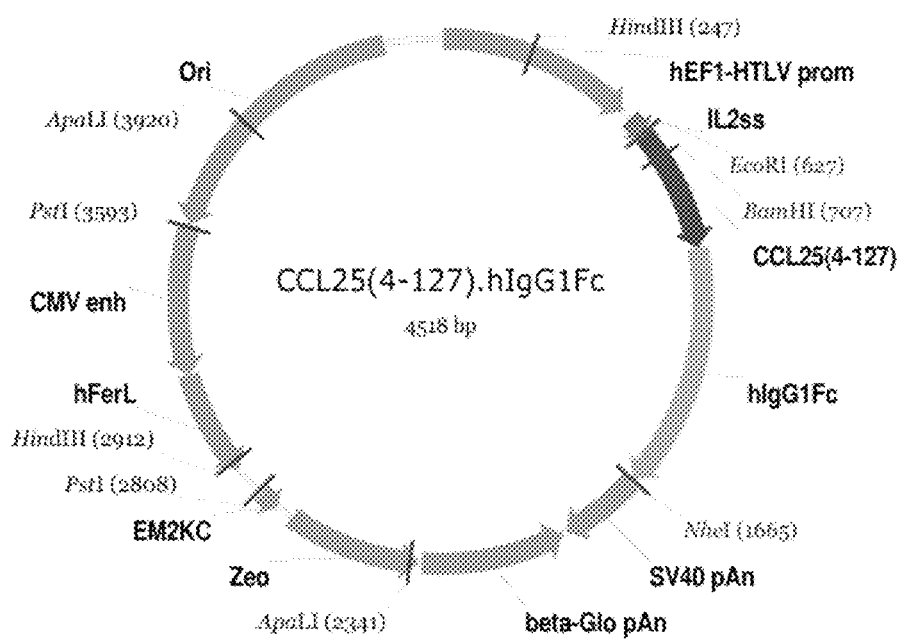
FIG. 5B depicts the expression vector pCCL25(4-127).hIgG1Fc.
Figure 6A:
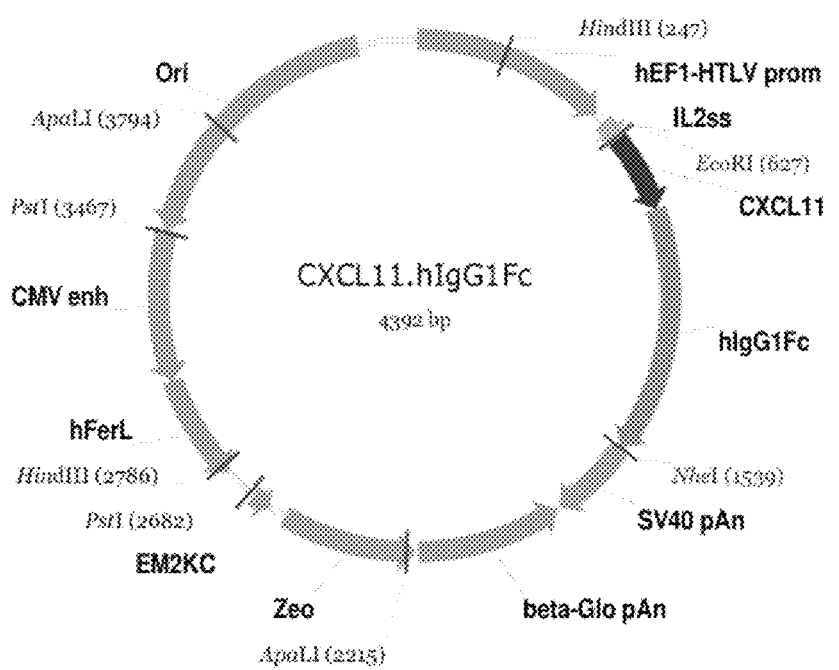
FIG. 6A depicts the expression vector pCXCL11.hIgG1Fc.
Figure 6B:
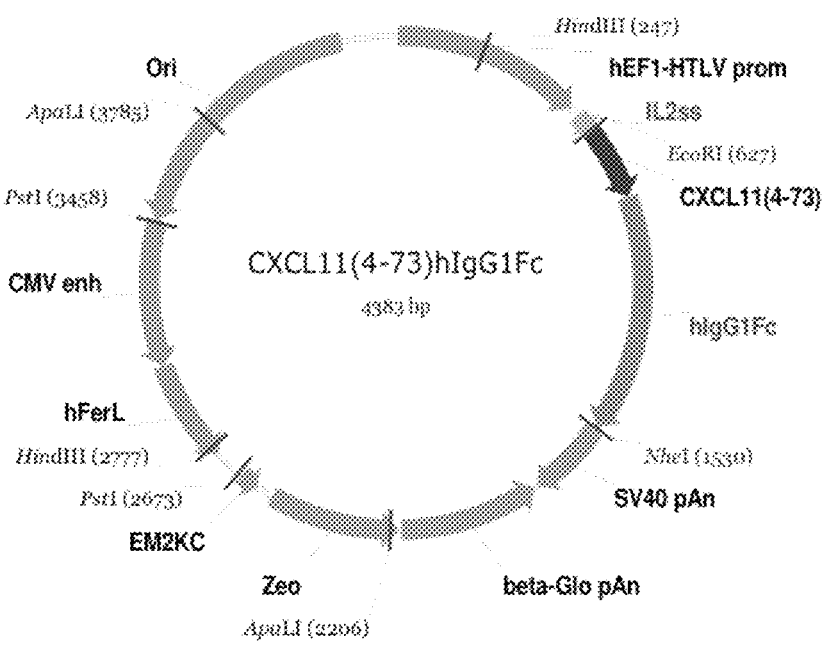
FIG. 6B depicts the expression vector pCXCL11(4-73).hIgG1Fc.
Figure 7A:
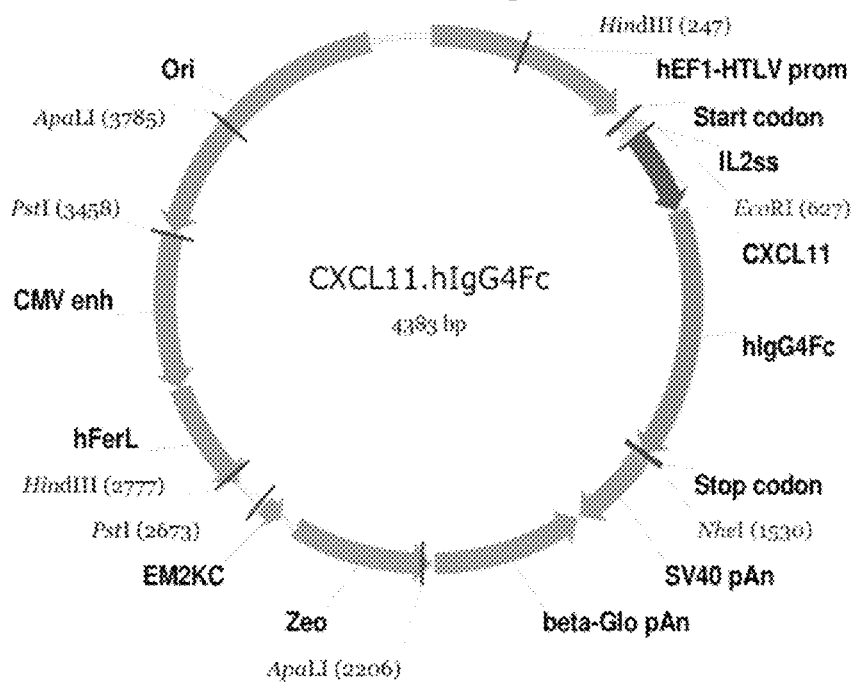
FIG. 7A depicts the expression vector pCXCL11.hIgG4Fc.
Figure 7B:
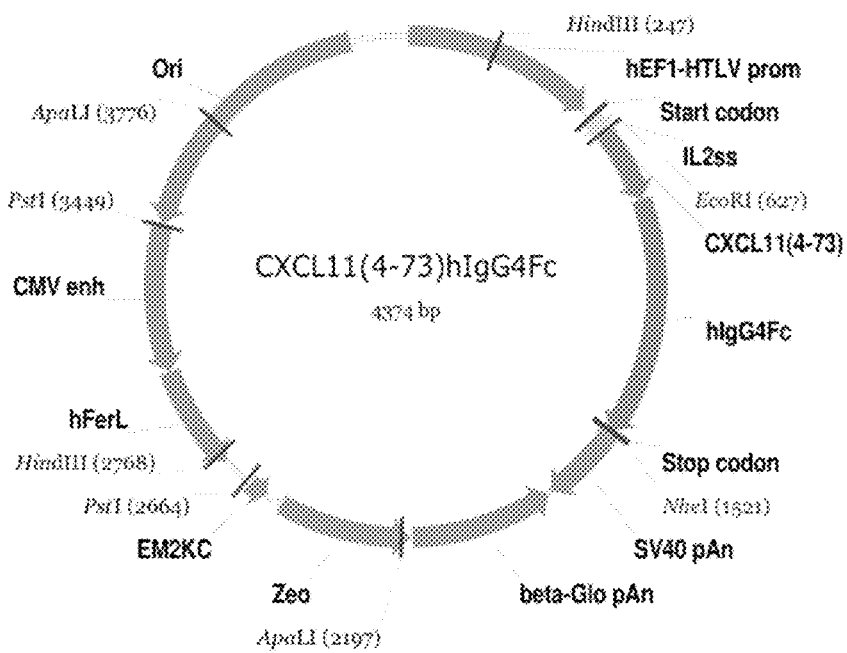
FIG. 7B depicts the expression vector pCXCL11(4-73).hIgG4Fc.
Figure 10A:
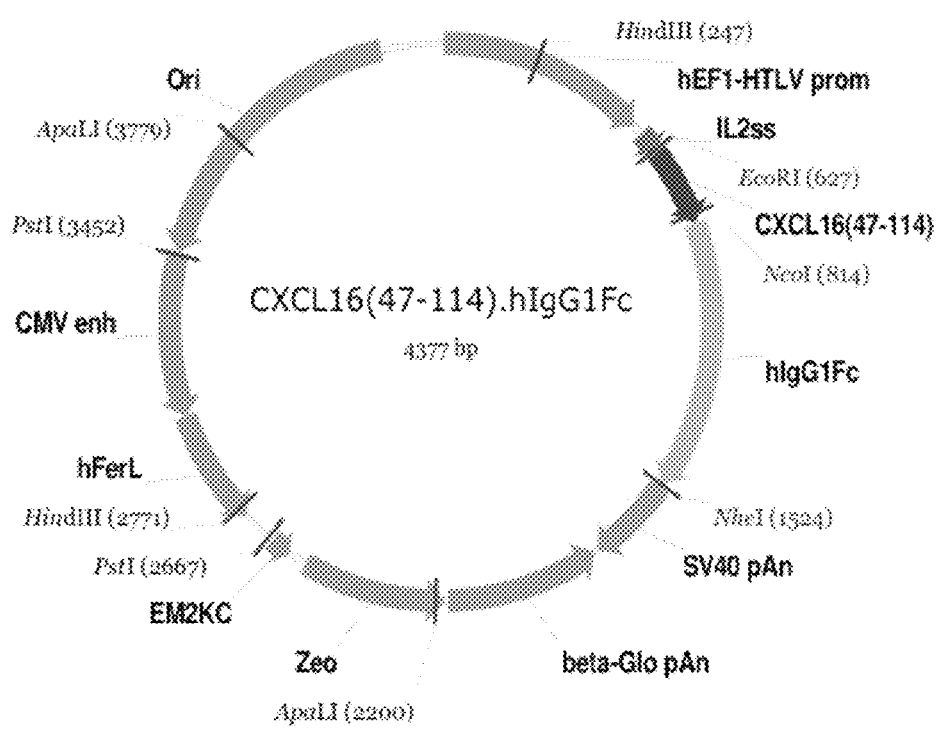
FIG. 10A depicts the expression vector pCXCL16(47-114).hIgG1Fc.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the widest possible scope consistent with the principles and features disclosed herein.

Unless otherwise defined, scientific and technical terms used in connection with the present invention shall have the meanings that are commonly understood by those of ordinary skill in the art. Although any methods, devices, and materials similar or equivalent to those described herein can be used in the practice or testing of the presently disclosed subject matter, representative methods, devices, and materials are now described. Further, unless otherwise required by context, singular terms shall include pluralities and plural terms shall include the singular.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

The present application generally relates to compositions and methods for treating chemokine receptor-mediated disorders and modulating inflammation. Particularly, the present application relates to chemokine-immunoglobulin fusion polypeptides, chemokine-polymer conjugates, and uses thereof to modulate immunity, cancer progression, and inflammation as well as treat chemokine receptor-mediated disorders, including tissue regeneration, wound repair, stem cell homeostasis, cell proliferative disorders, and inflammatory.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The terms "treat," "treating" or "treatment" as used herein, refers to a method of alleviating or abrogating a disorder and/or its attendant symptoms. The terms "prevent", "preventing" or "prevention," as used herein, refer to a method of barring a subject from acquiring a disorder and/or its attendant symptoms. In certain embodiments, the terms "prevent," "preventing" or "prevention" refer to a method of reducing the risk of acquiring a disorder and/or its attendant symptoms.

In a pharmacological sense, in the context of the present invention, an "effective amount" of a composition refers to an amount effective in the prevention or treatment of a disorder for the treatment of which the composition is effective. A "disorder" is any condition that would benefit from treatment with the composition.

"Mammal" for purposes of treatment refers to any animal classified as a mammal, including humans, non-human primates, domestic and farm animals, and zoo, sports, or pet animals, such as dogs, horses, cats, cows, etc. Preferably, the mammal is human.

The term "inhibits" is a relative term, an agent inhibits a response or condition if the response or condition is quantitatively diminished following administration of the agent, or if it is diminished following administration of the agent, as compared to a reference agent. Similarly, the term "prevents" does not necessarily mean that an agent completely eliminates the response or condition, so long as at least one characteristic of the response or condition is eliminated. Thus, a composition that reduces or prevents an infection or a response, such as a pathological response, can, but does not necessarily completely eliminate such an infection or response, so long as the infection or response is measurably diminished, for example, by at least about 50%, such as by at least about 70%, or about 80%, or even by about 90% of (that is to 10% or less than) the infection or response in the absence of the agent, or in comparison to a reference agent.

Chemokine-Immunoglobulin Fusion Polypeptides

Chemokines have been demonstrated to mediate a number of cellular functions involving motility, invasion, adherence, proliferation, and survival. At the appropriate levels and expression, these chemotactic cytokines promote proper wound healing, neovascularization or immunity. If inappropriately expressed, these factors can dictate chronic diseases like keloid formation, angiogenesis, metastasis/drug resistance of cancer cells, autoimmunity, graft rejection, inflammation (e.g., arthritis, ulcerative colitis, Crohn's disease, multiple sclerosis, COPD, etc.), diabetes. Both beneficial and deleterious functions are mediated by binding and activation of chemokine receptors, which are class A, G protein coupled receptors.

A number of small molecule antagonists have been constructed to block the action of these receptors. Remarkably, many of these compounds have high affinities (5-50 nM) and specificities for their target. However, these inhibitors have two major limitations: (i) hydrophobicity and possible liver retention/toxicity and (ii) relative short serum-half life or bioavailability (<6 hours).

The present application provides isolated chemokine-immunoglobulin fusion polypeptides for clinical use. The fusion polypeptides comprise a wild-type human chemokine or a variant thereof fused to the constant region (i.e., CH2 and CH3) of a human immunoglobulin (Ig) G or a variant thereof. The chemokine-immunoglobulin fusion polypeptide can bind with specificity to one or more particular chemokine receptors and thereby modulate one or more biological activities (e.g., receptor activation) of the receptor(s).

One aspect of the present invention relates to an isolated chemokine-immunoglobulin fusion polypeptide having a chemokine moiety and an immunoglobulin moiety. In some embodiments, the chemokine moiety comprises a chemokine selected from the group consisting of human CCL1, CCL2, CCL3, CCL4, CCL4L1, CCL5, CCL7, CCL8, CCL11, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL16, XCL1, XCL2, CX3CL1 and functional variants thereof. In some embodiments, the chemokine moiety comprises CCL2 and functional variants thereof. In other embodiments, the chemokine moiety comprises CCL25 and functional variants thereof. In other embodiments, the chemokine moiety comprises CXCL12 and functional variants thereof. In other embodiments, the chemokine moiety comprises CXCL13 and functional variants thereof. In other embodiments, the chemokine moiety comprises CXCL16 and functional variants thereof. As used herein, each chemokine noted above refers to all isoforms of the chemokine. The immunoglobulin moiety comprises a human immunoglobulin fragment, such as a constant region of a human immunoglobulin, a Fc fragment of a human immunoglobulin, or a functional variant thereof. In certain embodiments, human immunoglobulin fragment is selected from the group consisting of the constant region (Fc) of human IgG1 (IgG1Fc), the constant region of human IgG2 (IgG2Fc), the constant region of human IgG3 (IgG3Fc), the constant region of human IgG4 (IgG4Fc), and functional variants thereof. The complete amino acid sequences of the above-described chemokines and the Fc regions of human IgG1, IgG2, IgG3 and IgG4 are listed in Table 1 below and shown in FIG. 12.

TABLE 1

| Chemokine/Receptor | Protein Accession No. | SEQ ID NO: |
|---|---|---|
| CCL1 | NP_002972 | 1 |
| CCL2 | NP_002973 | 2 |
| CCL3 | NP_002974 | 3 |
| CCL4 | NP_002975 | 4 |
| CCL4L1 | NP_001001435 | 5 |
| CCL5 | NP_002976 | 6 |
| CCL7 | NP_006264 | 7 |
| CCL8 | NP_005614 | 8 |
| CCL11 | CAG33702 | 9 |
| CCL13 | NP_005399 | 10 |
| CCL14-1 | NP_116739 | 11 |
| CCL14-2 | NP_116738 | 12 |
| CCL15 | NP_116741 | 13 |
| CCL16 | NP_004581 | 14 |
| CCL17 | NP_002978 | 15 |
| CCL18 | NP_002979 | 16 |
| CCL19 | NP_006265 | 17 |
| CCL20-1 | NP_004582 | 18 |
| CCL20-2 | NP_001123518 | 19 |
| CCL21 | NP_002980 | 20 |
| CCL22 | NP_002981 | 21 |
| CCL23-1 | NP_665905 | 22 |
| CCL23-2 | NP_005055 | 23 |
| CCL24 | NP_002982 | 24 |
| CCL25-1 | NP_005615 | 25 |
| CCL25-2 | NP_683686 | 26 |
| CCL25-3 | EAW68951 | 27 |
| CCL26 | NP_006063 | 28 |
| CCL27 | NP_006655 | 29 |
| CCL28 | NP_683513 | 30 |
| CXCL1 | NP_001502 | 31 |
| CXCL2 | NP_002080 | 32 |
| CXCL3 | NP_002081 | 33 |
| CXCL4 | NP_002610 | 34 |
| CXCL5 | NP_002985 | 35 |
| CXCL6 | NP_002984 | 36 |
| CXCL7 | NP_002695 | 37 |
| CXCL8 | NP_000575 | 38 |
| CXCL9 | NP_002407 | 39 |
| CXCL10 | NP_001556 | 40 |
| CXCL11 | NP_005400 | 41 |
| CXCL12 | NP_000600 | 42 |
| CXCL13 | NP_006410 | 43 |
| CXCL16 | NP_071342 | 44 |
| XCL1 | AAH69817 | 45 |
| XCL2 | NP_003166 | 46 |
| CX3CL1 | NP_002987 | 47 |
| IgG1Fc | CBX54381.1 | 48 |
| IgG2Fc | CBX54382.1 | 49 |
| IgG3Fc | CBX54383.1 | 50 |
| IgG4Fc | CBX54384.1 | 51 |

Without wishing to be bound by any particular theory of operation, the immunoglobulin region can increase serum-half life or bioavailability of the fusion polypeptide and the precise polypeptide sequences of the Fc portion can be selected to maximize serum-half life and/or bioavailability. In addition, Fc regions from different IgG subclasses (e.g., IgG1, IgG2, IgG3, and IgG4) exhibit different immunological activities, and therefore the IgG Fc region can be selected based on a desired immunological activity. For example, the Fc region of IgG1 can activate complement, while the Fc region of IgG4 has reduced complement activity.

Thus, a particular Fc region can be selected for a particular application based on the desired immunological activities manifested by each region. In some particular embodiments, the Fc region can be the Fc region of human IgG1, IgG2, IgG3 or IgG4. As such, the chemokine-immunoglobulin fusion polypeptide find utility in enhancing immunity, suppressing autoimmunity, suppressing inflammation, and/or inhibiting growth/metastasis of proliferative disorder cells. The present application further provides isolated polynucleotide which encode the chemokine-immunoglobulin fusion polypeptide disclosed herein and expression vectors capable of expressing the chemokine-immunoglobulin fusion polypeptide in vivo.

The term "isolated", when applied to a protein or polynucleotide, denotes that the protein or polynucleotide is essentially free of other cellular components with which it is associated in the natural state. It can be in a homogeneous state although it can be in either a dry or aqueous solution. Homogeneity and whether a molecule is isolated can be determined using analytical chemistry techniques such as polyacrylamide gel electrophoresis or high performance liquid chromatography. A protein that is the predominant species present in a preparation is substantially isolated. The term "isolated" denotes that a protein or polynucleotide gives rise to essentially one band in an electrophoretic gel. Particularly, it means that the protein or polynucleotide is in some embodiments at least about 50% pure, in some embodiments at least about 85% pure, and in some embodiments at least about 99% pure.

The term "polynucleotide" refers to deoxyribonucleotides or ribonucleotides and polymers thereof in either single- or double-stranded form. Unless specifically limited, the terms encompass nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues. The term "polynucleotide" or "polynucleotide sequence" can also be used interchangeably with gene, open reading frame (ORF), cDNA, and mRNA encoded by a gene.

The terms "polypeptide", "protein", and "peptide", which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide" and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

The chemokine portion of the chemokine-immunoglobulin fusion polypeptide can be selected based on the chemokine receptor or receptors to which it exhibits binding specificity. This provides for the selective targeting of the chemokine-immunoglobulin fusion polypeptide to one or more specific chemokine receptors to thereby modulate activation and subsequent biological activities of the receptor(s). Table 1 (adapted from Allen et al. (2007) Annu. Rev. Immunol. 25:787-820) provides an exemplary list of receptors that can be targeted by one or more chemokines, which can be incorporated into the chemokine-immunoglobulin fusion polypeptide of the presently-disclosed subject matter.

As disclosed in Table 2, certain chemokines can specifically bind more than one chemokine receptor. For example, CXCL11 can bind with specificity to chemokine receptors CXCR3-A, CXCR3-B, CXCR7, and DARC/Duffy. As such, if it is desirable to target more than one chemokine receptor, a particular chemokine, such as CXC11, can be selected for incorporation into the chemokine-immunoglobulin fusion polypeptide of the presently-disclosed subject matter. In some embodiments of the presently disclosed subject matter, the chemokine-immunoglobulin fusion polypeptide can comprise of a chemokine portion selected from the group consisting of CCL2, CCL7, CCL8, CCL13, CCL25, CXCL11, CXCL13, and mutations thereof. "Mutations" of the polypeptides include variants and fragments of the reference polypeptides.

TABLE 2

Chemokine receptors and their ligands

| Receptor | Ligands |
| --- | --- |
| CCR1 | CCL3, CCL5, CCL7, CCL13, CCL14, CCL15, CCL16, CCL23 |
| CCR2 | CCL2, CCL7, CCL8, CCL13, CCL16 |
| CCR3 | CCL5, CCL7, CCL8, CCL11, CCL13, CCL15, CCL16, CCL24, CCL26, CCL28 |
| CCR4 | CCL17, CCL22 |
| CCR5 | CCL3, CCL4, CCL5, CCL8, CCL11, CCL14, CCL16 |
| CCR6 | CCL20 |
| CCR7 | CCL19, CCL21 |
| CCR8 | CCL1 |
| CCR9 | CCL25 |
| CCR10 | CCL27, CCL28 |
| CXCR1 | CXCL6, CXCL7, CXCL8 |
| CXCR2 | CXCL1, CXCL2, CXCL3, CXCL5, CXCL6, CXCL7, CXCL8 |
| CXCR3-A | CXCL9, CXCL10, CXCL11, CCL11 |
| CXCR3-B | CXCL4, CXCL9, CXCL10, CXCL11, CCL11 |
| CXCR4 | CXCL12 |
| CXCR5 | CXCL13 |
| CXCR6 | CXCL16 |
| CXCR7 | CXCL12, CXCL11 |
| XCR1 | XCL1, XCL2 |
| CX$_3$CR1 | CX$_3$CL1 |
| CCX-CKR | CCL19, CCL21, CCL25 |
| D6 | CCL2, CCL3L1, CCL4, CCL5, CCL7, CCL8, CCL11, CCL13, CCL14, CCL17, CCL22 |
| DARC/Duffy | CCL2, CCL7, CCL8, CCL11, CCL13, CCL14, CCL16, CCL17, CXCL1, CXCL5, CXCL6, CXCL7, CXCL8, CXCL9, CXCL11, CXCL13 |

The term "functional variant" refers to protein or polypeptide that is different from the reference protein or polypeptide by one or more amino acids, e.g., one or more amino acid substitutions, but substantially maintains the biological function of the reference protein or polypeptide. As used herein, a functional variant of a chemokine is a variant that maintains the receptor binding function of the original chemokine and a functional variant of the Fc region of IgG is a variant that maintains the immunologivla activities of the original Fc region.

A functional variant of a polypeptide may be a fragment of the original polypeptide. The term "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both. Fragments typically are at least 3, 5, 6, 8 or 10 amino acids long, at least 14 amino acids long, at least 20, 30, 40 or 50 amino acids long, at least 75 amino acids long, or at least 100, 150, 200, or more amino acids long.

The term "functional variant" further includes conservatively substituted variants. The term "conservatively substituted variant" refers to a peptide comprising an amino acid residue sequence that differs from a reference peptide by one or more conservative amino acid substitution, and maintains some or all of the activity of the reference peptide as described herein. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another, such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. The phrase "conservatively substituted variant" also includes peptides wherein a residue is replaced with a chemically derivatized residue, provided that the resulting peptide maintains some or all of the activity of the reference peptide as described herein. In some embodiments, the functional variant of a peptide shares a sequence identity of 70%, 75%, 80%, 85%, 90%, 91%, 92%, 93%, 94%, 95%, 96%, 97%, 98% or 99% with the reference peptide. For example, a functional variant of a chemokine may shares a sequence identity of 70%, 75%, 80%, 85%, 90%, 91%, 92%, 93%, 94%, 95%, 96%, 97%, 98% and 99% with the reference chemokine; a functional variant of an immunoglobin Fc fragment may shares a sequence identity of 70%, 75%, 80%, 85%, 90%, 91%, 92%, 93%, 94%, 95%, 96%, 97%, 98% and 99% with the reference immunoglobin Fc fragment; and a functional variant of a chemokine-immunoglobin fusion protein may shares a sequence identity of 70%, 75%, 80%, 85%, 90%, 91%, 92%, 93%, 94%, 95%, 96%, 97%, 98% and 99% with the reference chemokine-immunoglobin fusion protein.

The term "sequence identity," as used herein, means that two peptide sequences are identical (i.e., on an amino acid-by-amino acid basis) over the window of comparison. The term "percentage of sequence identity" is calculated by comparing two optimally aligned sequences over the window of comparison, determining the number of positions at which the identical amino acid residue occurs in both sequences to yield the number of matched positions, dividing the number of matched positions by the total number of positions in the window of comparison (i.e., the window size), and multiplying the result by 100 to yield the percentage of sequence identity. The reference sequence may be a subset of a larger sequence, for example, as a segment of the full-length sequences of the compositions claimed in the present invention.

In some particular embodiments, the chemokine-immunoglobulin fusion polypeptides disclosed herein include functional variants to the chemokine portion that introduce amino acid substitutions to eliminate glycosaminoglycan (e.g., heparin, laminin, GAG)-binding, which can thereby increase the serum half-life of the polypeptide. For example, in some embodiments one or more alanines can be substituted for lysines, arginines and/or histidines within GAG binding sites of the chemokine portions.

Specific chemokine-immunoglobulin fusion polypeptides disclosed herein that include a chemokine variant having one or more mutations in the chemokine sequence are named accordingly to indicate the particular mutation. For example "var-" before the chemokine name (e.g., var-CCL2) is indicative of a functional variant having an engineered mutation to the chemokine portion that results in a polypeptide sequence that differs from the reference chemokine sequence (e.g., CCL2). A fragment mutation resulting from a truncation is notated be the sequence remaining after truncation. For example, a truncation of the N-terminal 4 amino acids of the 76 amino acid CCL2 chemokine would be notated as "var-CCL2" or "CCL2(5-76)". A variant mutation resulting from one or more amino acid substitutions would be notated as a parenthetical after the chemokine name in the form "X#Y" or "X→Y", wherein the amino acid X (in standard one letter amino acid code, as is known in the art) in the reference polypeptide is substituted with the amino acid Y either at a particular residue (#) or throughout the polypeptide, or a particular region of the polypeptide (X→Y), such as for example a GAG-binding region of the chemokine polypeptide. In some embodiments, a mutation can include both a variant and a fragment of the reference chemokine polypeptide. These mutants are indicated in the named polypeptide in succession in a parenthetical following the chemokine name. For example, "CCL2(5-76K/H→A)" indicates a chemokine-immunoglobulin fusion polypeptide including in the chemokine portion a mutant CCL2 polypeptide that has been truncated at the N-terminus to remove residues 1-4 and also mutated to substitute alanines (A) for lysines (K) and histidines (H) within the sequence. In some embodiments, a chemokine variant (e.g., var-CXCL13) shares a sequence identity of 70%, 75%, 80%, 85%, 90%, 91%, 92%, 93%, 94%, 95%, 96%, 97%, 98% and 99% with the reference chemokine (i.e., CXCL13). Finally, in reference to nomenclature, the chemokine-immunoglobulin fusion polypeptides disclosed herein are named according to the chemokine portion (A) and the immunoglobulin portion (B) fused together (i.e. A-B). Thus, for example, CCL2-IgG1Fc refers to a chemokine-immunoglobulin fusion polypeptide comprising a wild-type CCL2 chemokine portion fused with an Fc constant region of an IgG class 1 immunoglobulin.

In some embodiments, the present application provides a human chemokine polypeptide fused to a human immunoglobulin polypeptide. In some embodiments, the present application provides the following novel isolated chemokine-immunoglobulin fusion polypeptides: CCL2-IgG1Fc, var-CCL2-IgG1Fc, CCL2-IgG2Fc, var-CCL2-IgG2Fc, CCL2-IgG3Fc, var-CCL2-IgG3Fc, CCL2-IgG4Fc, var-CCL2-IgG4Fc, CCL7-IgG1Fc, var-CCL7-IgG1Fc, CCL7-IgG2Fc, var-CCL7-IgG2Fc, CCL7-IgG3Fc, var-CCL7-IgG3Fc, CCL7-IgG4Fc, var-CCL7-IgG4Fc, CCL8-IgG1Fc, var-CCL8-IgG1Fc, CCL8-IgG2Fc, var-CCL8-IgG2Fc, CCL8-IgG3Fc, var-CCL8-IgG3Fc, CCL8-IgG4Fc, var-CCL8-IgG4Fc, CCL13-IgG1Fc, var-CCL13-IgG1Fc, CCL13-IgG2Fc, var-CCL13-IgG2Fc, CCL13-IgG3Fc, var-CCL13-IgG3Fc, CCL13-IgG4Fc, var-CCL13-IgG4Fc, CCL25-IgG1Fc, var-CCL25-IgG1Fc, CCL25-IgG2Fc, var-CCL25-IgG2Fc, CCL25-IgG3Fc, var-CCL25-IgG3Fc, CCL25-IgG4Fc, var-CCL25-IgG4Fc, CXCL11-IgG1Fc, var-CXCL11-IgG1Fc, CXCL11-IgG2Fc, var-CXCL11-IgG2Fc, CXCL11-IgG3Fc, var-CXCL11-IgG3Fc, CXCL11-IgG4Fc, var-CXCL11-IgG4Fc, CXCL13-IgG1Fc, var-CXCL13-IgG1Fc, CXCL13-IgG2Fc, var-CXCL13-IgG2Fc, CXCL13-IgG3Fc, var-CXCL13-IgG3Fc, CXCL13-IgG4Fc, and var-CXCL13-IgG4Fc.

In particular embodiments, the present application provides the following novel isolated chemokine-immunoglobulin fusion polypeptides: CCL2-IgG1Fc (SEQ ID NO:52), CCL2(5-76)-IgG1Fc (SEQ ID NO:53), CCL2(5-76K/H→A)-IgG1Fc (SEQ ID NO:54), CCL7-IgG1Fc (SEQ ID NO:55), CCL7(5-76)-IgG1Fc (SEQ ID NO:56), CCL7(5-76K/H→A)-IgG1Fc (SEQ ID NO:57), CCL8-IgG1Fc (SEQ ID NO:58), CCL8(5-76)-IgG1Fc (SEQ ID NO:59), CCL8(5-76K/H→A)-IgG1Fc (SEQ ID NO:60), CCL13-IgG1Fc (SEQ ID NO:61), CCL13(5-75)-IgG1Fc (SEQ ID NO:62), CCL13(5-75K/H→A)-IgG1Fc (SEQ ID NO:63), CCL25-IgG1Fc (SEQ ID NO:64), CCL25(4-127)-IgG1Fc (SEQ ID NO:65), CCL25(4-127K/H→A)-IgG1Fc (SEQ ID NO:66), CXCL11-IgG1Fc (SEQ ID NO:67), CXCL11(4-73)-IgG1Fc (SEQ ID NO:68), CXCL11(4-73K/H→A)-IgG1Fc (SEQ ID NO:69), CXCL11-IgG4Fc (SEQ ID NO:70), CXCL11(4-73)-IgG4Fc (SEQ ID NO:71), CXCL11(4-73K/H→A)-IgG4Fc (SEQ ID NO:72), CXCL13-IgG1Fc (SEQ ID NO:73), CXCL13(3-87)-IgG1Fc (SEQ ID NO:74), CXCL13(3-87K/H→A)-IgG1Fc (SEQ ID NO:75), CXCL13-IgG4Fc (SEQ ID NO:76), CXCL13(3-87)-IgG4Fc (SEQ ID NO:77), and CXCL13(3-87K/H→A)-IgG4Fc (SEQ ID NO:78).

The novel chemokine-immunoglobulin fusion polypeptides disclosed herein can be produced using any of a variety of peptide production techniques generally known in the art. For example, recombinant genetic techniques can be utilized to produce the fusion polypeptides disclosed herein. As such, in some embodiments, an isolated nucleic acid molecule which encodes a chemokine-immunoglobulin fusion polypeptide selected from the group consisting of CCL2-IgG1Fc, var-CCL2-IgG1Fc, CCL2-IgG2Fc, var-CCL2-IgG2Fc, CCL2-IgG3Fc, var-CCL2-IgG3Fc, CCL2-IgG4Fc, var-CCL2-IgG4Fc, CCL7-IgG1Fc, var-CCL7-IgG1Fc, CCL7-IgG2Fc, var-CCL7-IgG2Fc, CCL7-IgG3Fc, var-CCL7-IgG3Fc, CCL7-IgG4Fc, var-CCL7-IgG4Fc, CCL8-IgG1Fc, var-CCL8-IgG1Fc, CCL8-IgG2Fc, var-CCL8-IgG2Fc, CCL8-IgG3Fc, var-CCL8-IgG3Fc, CCL8-IgG4Fc, var-CCL8-IgG4Fc, CCL13-IgG1Fc, var-CCL13-IgG1Fc, CCL13-IgG2Fc, var-CCL13-IgG2Fc, CCL13-IgG3Fc, var-CCL13-IgG3Fc, CCL13-IgG4Fc, var-CCL13-IgG4Fc, CCL25-IgG1Fc, var-CCL25-IgG1Fc, CCL25-IgG2Fc, var-CCL25-IgG2Fc, CCL25-IgG3Fc, var-CCL25-IgG3Fc, CCL25-IgG4Fc, var-CCL25-IgG4Fc, CXCL11-IgG1Fc, var-CXCL11-IgG1Fc, CXCL11-IgG2Fc, var-CXCL11-IgG2Fc, CXCL11-IgG3Fc, var-CXCL11-IgG3Fc, CXCL11-IgG4Fc, var-CXCL11-IgG4Fc, CXCL13-IgG1Fc, var-CXCL13-IgG1Fc, CXCL13-IgG2Fc, var-CXCL13-IgG2Fc, CXCL13-IgG3Fc, var-CXCL13-IgG3Fc, CXCL13-IgG4Fc, and var-CXCL13-IgG4Fc is provided.

In particular embodiments, the isolated nucleic acid molecule encodes a chemokine-immunoglobulin fusion polypeptide selected from the group consisting of CCL2-IgG1Fc, CCL2(5-76)-IgG1Fc, CCL2(5-76K/H→A)-IgG1Fc, CCL2-IgG2Fc, CCL2(5-76)-IgG2Fc, CCL2(5-76K/H→A)-IgG2Fc, CCL2-IgG3Fc, CCL2(5-76)-IgG3Fc, CCL2(5-76K/H→A)-IgG3Fc, CCL2-IgG4Fc, CCL2(5-76)-IgG4Fc, CCL2(5-76K/H→A)-IgG4Fc, CCL7-IgG1Fc, CCL7(5-76)-IgG1Fc, CCL7(5-76K/H→A)-IgG1Fc, CCL7-IgG2Fc, CCL7(5-76)-IgG2Fc, CCL7(5-76K/H→A)-IgG2Fc, CCL7-IgG3Fc, CCL7(5-76)-IgG3Fc, CCL7(5-76K/H→A)-IgG3Fc, CCL7-IgG4Fc, CCL7(5-76)-IgG4Fc, CCL7(5-76K/H→A)-IgG4Fc, CCL8-IgG1Fc, CCL8(5-76)-IgG1Fc, CCL8(5-76K/H→A)-IgG1Fc, CCL8-IgG2Fc, CCL8(5-76)-IgG2Fc, CCL8(5-76K/H→A)-IgG2Fc, CCL8-IgG3Fc, CCL8(5-76)-IgG3Fc, CCL8(5-76K/H→A)-IgG3Fc, CCL8-IgG4Fc, CCL8(5-76)-IgG4Fc, CCL8(5-76K/H→A)-IgG4Fc, CCL13-IgG1Fc, CCL13(5-75)-IgG1Fc, CCL13(5-75K/H→A)-IgG1Fc, CCL13-IgG2Fc, CCL13(5-75)-IgG2Fc, CCL13(5-75K/H→A)-IgG2Fc, CCL13-IgG3Fc, CCL13(5-75)-IgG3Fc, CCL13(5-75K/

H→A)-IgG3Fc, CCL13-IgG4Fc, CCL13(5-75)-IgG4Fc, CCL13(5-75K/H→A)-IgG4Fc, CCL25-IgG1Fc, CCL25(4-127)-IgG1Fc, CCL25(4-127K/H→A)-IgG1Fc, CCL25-IgG2Fc, CCL25(4-127)-IgG2Fc, CCL25(4-127K/H→A)-IgG2Fc, CCL25-IgG3Fc, CCL25(4-127)-IgG3Fc, CCL25(4-127K/H→A)-IgG3Fc, CCL25-IgG4Fc, CCL25(4-127)-IgG4Fc, CCL25(4-127K/H→A)-IgG4Fc, CXCL11-IgG1Fc, CXCL11(4-73)-IgG1Fc, CXCL11(4-73K/H→A)-IgG1Fc, CXCL11-IgG2Fc, CXCL11(4-73)-IgG2Fc, CXCL11(4-73K/H→A)-IgG2Fc, CXCL11-IgG3Fc, CXCL11(4-73)-IgG3Fc, CXCL11(4-73K/H→A)-IgG3Fc, CXCL11-IgG4Fc, CXCL11(4-73)-IgG4Fc, CXCL11(4-73K/H→A)-IgG4Fc, CXCL13-IgG1Fc, CXCL13(3-87)-IgG1Fc, CXCL13(3-87K/H→A)-IgG1Fc, CXCL13-IgG2Fc, CXCL13(3-87)-IgG2Fc, CXCL13(3-87K/H→A)-IgG2Fc, CXCL13-IgG3Fc, CXCL13(3-87)-IgG3Fc, CXCL13(3-87K/H→A)-IgG3Fc, CXCL13-IgG4Fc, CXCL13(3-87)-IgG4Fc, and CXCL13(3-87K/H→A)-IgG4Fc. Recombinant cloning techniques may also be used to construct the heterologous gene sequences that encode for the fusion polypeptide gene product, as is known in the art.

Expression Vectors

Recombinant expression vectors comprising nucleic acid molecules which encode the polypeptides disclosed herein are also provided. Particularly useful vectors are contemplated to be those vectors in which the coding portion of the DNA segment is positioned under the control of a promoter. The promoter may be in the form of the promoter which is naturally associated with the chemokine or immunoglobulin gene, e.g., in mammalian tissues, as may be obtained by isolating the 5' non-coding sequences located upstream of the coding segment or exon, for example, using recombinant cloning and/or PCR technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a chemokine or immunoglobulin gene in its natural environment. Such promoters may include promoters isolated from plant, insect, bacterial, viral, eukaryotic, fish, avian or mammalian cells. Naturally, it will be important to employ a promoter that effectively directs the expression of the DNA segment in the cell type chosen for expression. The use of promoter and cell type combinations for protein expression is generally known to those of skill in the art of molecular biology. The promoters employed may be constitutive, or inducible, and can be used under the appropriate conditions to direct high level expression of the introduced DNA segment, such as is advantageous in the large-scale production of recombinant proteins or peptides.

Expression vectors generally contain sequences for transcriptional termination, and may additionally contain one or more elements positively affecting mRNA stability. An expression vector may further include an internal ribosome entry site (IRES) between adjacent protein coding regions to facilitate expression two or more proteins from a common mRNA in an infected or transfected cell. Additionally, the expression vectors may further include nucleic acid sequence encoding a marker product. This marker product may be used to determine if the gene has been delivered to the cell and is being expressed. Preferred marker genes are the *E. coli* lacZ gene, which encodes β-galactosidase, and green fluorescent protein (GFP).

In some embodiments, the expression vectors of the present application are plasmid expression vectors that are capable of expressing the chemokine-immunoglobulin fusion polypeptides of the present application in an in vitro setting. The expressed fusion polypeptide is then isolated and purified using methods well known to a person skilled in the art.

In other embodiments, the expression vectors of the present application are plasmid expression vectors that are capable of expressing the chemokine-immunoglobulin fusion polypeptides of the present application in an in vivo setting. These expression vectors may be introduced into a subject using delivery systems such as liposomes, including cationic liposomes (e.g., DOTMA, DOPE, DC-cholesterol) and anionic liposomes, microcapsules, nanoparticles and electroporation. In some embodiments, the expression vectors are targeted to a particular cell type via antibodies, receptors, or receptor ligands. Vehicles such as "stealth" and other antibody conjugated liposomes (including lipid mediated drug targeting to cells of interest), receptor mediated targeting of DNA through cell specific ligands or viral vectors targeting e.g., lymphoid, epithelial or endothelial cells. In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor level regulation. Many receptors follow more than one intracellular pathway, depending on the cell type, receptor concentration, type of ligand, ligand valency, and ligand concentration.

In yet other embodiments, the expression vectors of the present application are virus-based expression vectors that are capable of expressing the chemokine-immunoglobulin fusion polypeptides of the present application in an in vivo setting. Exemplary viral vectors may include or be derived from adenovirus, adeno-associated virus, herpesvirus, vaccinia virus, poliovirus, poxvirus, HIV virus, lentivirus, retrovirus, Sindbis and other RNA viruses, and the like. Also preferred are any viral families which share the properties of these viruses which make them suitable for use as vectors. Retroviruses include Murine Moloney Leukemia virus (MMLV), HIV and other lentivirus vectors. Adenovirus vectors are relatively stable and easy to work with, have high titers, and can be delivered in aerosol formulation, and can transfect non-dividing cells. Poxviral vectors are large and have several sites for inserting genes, they are thermostable and can be stored at room temperature. Viral delivery systems typically utilize viral vectors having one or more genes removed and with and an exogenous gene and/or gene/promotor cassette being inserted into the viral genome in place of the removed viral DNA. The necessary functions of the removed gene(s) may be supplied by cell lines which have been engineered to express the gene products of the early genes in trans.

In other embodiments, the expression vectors are phage DNA, yeast plasmids or baculovirus.

Exemplary expression vector constructs comprising polynucleotides which encode chemokine-immunoglobulin fusion polypeptides disclosed herein are shown in FIGS. 1-10. These expression vectors include pCCL2-IgG1Fc (SEQ ID NO:79), pCCL2(5-76)-IgG1Fc (SEQ ID NO:80), pCCL2(5-76K/H→A)-IgG1Fc (SEQ ID NO:81), pCCL7-IgG1Fc (SEQ ID NO:82), pCCL7(5-76)-IgG1Fc (SEQ ID NO:83), pCCL7(5-76K/H→A)-IgG1Fc (SEQ ID NO:84), pCCL8-IgG1Fc (SEQ ID NO:85), pCCL8(5-76)-IgG1Fc (SEQ ID NO:86), pCCL8(5-76K/H→A)-IgG1Fc (SEQ ID NO:87), pCCL13-IgG1Fc (SEQ ID NO:88), pCCL13(5-75)-IgG1Fc (SEQ ID NO:89), pCCL13(5-75K/H→A)-IgG1Fc (SEQ ID NO:90), pCCL25-IgG1Fc (SEQ ID NO:91), pCCL25(4-127)-IgG1Fc (SEQ ID NO:92), pCCL25(4-127K/H→A)-IgG1Fc (SEQ ID NO:93), pCXCL11-IgG1Fc (SEQ ID NO:94), pCXCL11(4-73)-IgG1Fc (SEQ ID NO:95), pCXCL11(4-73K/H→A)-IgG1Fc (SEQ ID NO:96), pCXCL11-IgG4Fc (SEQ ID NO:97), pCXCL11(4-73)-IgG4Fc (SEQ ID NO:98), pCXCL11(4-73K/H→A)-IgG4Fc (SEQ ID NO:99), pCXCL13-IgG1Fc (SEQ ID NO:100), pCXCL13(3-87)-IgG1Fc (SEQ ID NO:101), pCXCL13(3-87K/H→A)-IgG1Fc (SEQ ID NO:102), pCXCL13-IgG4Fc (SEQ ID NO:103), pCXCL13(3-87)-IgG4Fc (SEQ ID NO:104), and CXCL13(3-87K/H→A)-IgG4Fc (SEQ ID NO:105). It is understood that additional combinations of vectors and genes than those specifically disclosed above are contemplated by the presently-disclosed subject matter, as would be understood by one of ordinary skill in the art.

Protein Conjugates

In some embodiments, the chemokine-immunoglobulin fusion polypeptides of the present application, as well as certain chemokines and variants thereof, are conjugated to a non-protein polymer to form protein-polymer conjugates. Unless specifically indicated to the contrary, the term "non-protein polymer" is defined as a molecule formed by covalent linkage of two or more monomers, wherein none of the monomers is contained in the group consisting of alanine (Ala), cysteine (Cys), aspartic acid (Asp), glutamic acid (Glu), phenylalanine (Phe), glycine (Gly), histidine (His), isoleucine (Ile), lysine (Lys), leucine (Leu), methionine (Met), asparagine (Asn), proline (Pro), glutamine (GM), arginine (Arg), serine (Ser), threonine (Thr), valine (Val), tryptophan (Trp), and tyrosine (Tyr) residues. Serum soluble non-protein polymers, such as polyethylene glycol, and tissue or fat soluble polymers, such as polycaprolactone, can be used for delivery, release, and/or retention of polypeptides. In some embodiments, the protein-polymer conjugate is a pegylated chemokine-immunoglobulin fusion polypeptide, chemokine or a variant thereof.

In one aspect, the present application encompass a conjugate having any molar ratio of polymer to chemokine or fragment thereof that endows the conjugate with an apparent size in the desired range as taught herein. The apparent size of the conjugate will depend in part upon the size and shape of the polymer used, the size and shape of the chemokine or fragment thereof used, the number of polymer molecules attached to the chemokine or fragment thereof, and the location of such attachment site(s) on the chemokine or fragment thereof. These parameters can easily be identified and maximized to obtain the conjugate with the desired apparent size for any type of chemokine or fragment thereof, polymer and linkage system.

In some embodiments, the protein-polymer conjugate of the present application has an effective size of at least about 500,000 D, or at least about 800,000 D, or at least about 900,000 D, or at least about 1,000,000 D, or at least about 1,200,000 D, or at least about 1,400,000 D, or at least about 1,500,000 D, or at least about 1,800,000 D, or at least about 2,000,000 D, or at least about 2,500,000 D. In one embodiment, the polymer is PEG.

In other embodiments, the protein-polymer conjugate of the present application has an effective size of at or about 500,000 D to at or about 10,000,000 D, or an effective size of at or about 500,000 D to at or about 8,000,000 D, or an effective size of at or about 500,000 D to at or about 5,000,000 D, or an effective size of at or about 500,000 D to at or about 4,000,000 D, or an effective size of at or about 500,000 D to at or about 3,000,000 D, or an effective size of at or about 500,000 D to at or about 2,500,000 D, or an effective size of at or about 500,000 D to at or about 2,000,000 D, or an effective size of at or about 500,000 D to at or about 1,800,000 D, or an effective size of at or about 500,000 D to at or about 1,600,000 D, or an effective size of at or about 500,000 D to at or about 1,500,000 D, or an effective size of at or about 500,000 D to at or about 1,000,000 D. In one embodiment, the polymer is PEG.

In a further embodiment, the protein-polymer conjugate has an effective size that is at least about 8 fold greater, or at least about 10 fold greater, or at least about 12 fold greater, or at least about 15 fold greater, or at least about 18 fold greater, or at least about 20 fold greater, or at least about 25 fold greater, or at least about 28 fold greater, or at least about 30 fold greater, or at least about 40 fold greater, than the effective size of the unconjugated chemokine-immunoglobulin fusion polypeptide, chemokine or variant thereof. In one embodiment, the polymer is PEG.

In another embodiment, the protein-polymer conjugate has an effective size that is about 8 fold to about 100 fold greater, or is about 8 fold to about 80 fold greater, or is about 8 fold to about 50 fold greater, or is about 8 fold to about 40 fold greater, or is about 8 fold to about 30 fold greater, or is about 8 fold to about 28 fold greater, or is about 8 fold to about 25 fold greater, or is about 8 fold to about 20 fold greater, or is about 8 fold to about 18 fold greater, or is about 8 fold to about 15 fold greater, than the effective size of the unconjugated chemokine-immunoglobulin fusion polypeptide, chemokine or variant thereof. In one embodiment, the polymer is PEG.

In another embodiment, the protein-polymer conjugate has an effective size that is about 25 fold to about 100 fold greater, or is about 25 fold to about 80 fold greater, or is about 25 fold to about 50 fold greater, or is about 25 fold to about 40 fold greater, or is about 25 fold to about 30 fold greater, or is about 25 fold to about 28 fold greater, than the effective size of the unconjugated chemokine-immunoglobulin fusion polypeptide, chemokine or variant thereof. In one embodiment, the polymer is PEG.

In another embodiment, the protein-polymer conjugate has a polymer-to-protein molar ratio of no more than about 10:1, or no more than about 5:1, or no more than about 4:1, or no more than about 3:1, or no more than about 2:1, or no more than 1:1. In one embodiment, the polymer is PEG.

In still another embodiment, the protein-polymer conjugate is a chemokine-immunoglobulin fusion polypeptide, chemokine or variant thereof covalently attached to at least one polymer having an actual MW of at least about 20,000 D. In one embodiment, the polymer is PEG.

In a further embodiment, the conjugate is a chemokine-immunoglobulin fusion polypeptide, chemokine or variant thereof covalently attached to at least one polymer having an actual MW of at least about 30,000 D. In one embodiment, the polymer is PEG.

In yet another embodiment, the conjugate is a chemokine-immunoglobulin fusion polypeptide, chemokine or variant thereof covalently attached to at least one polymer having an actual MW of at least about 40,000 D. In one embodiment, the polymer is PEG.

In another embodiment, the conjugate is a chemokine-immunoglobulin fusion polypeptide, chemokine or variant thereof covalently attached to at least one polymer having an actual MW that is at or about 20,000 D to at or about 300,000 D, or is at or about 30,000 D to at or about 300,000 D, or is at or about 40,000 D to at or about 300,000 D. In one embodiment, the polymer is PEG.

The conjugates of the present application can be made using any suitable technique now known or hereafter developed for derivatizing chemokines or fragments thereof with polymers. It will be appreciated that the invention is not limited to conjugates utilizing any particular type of linkage between a chemokine or fragment thereof and a polymer.

The conjugates of the present application include species wherein a polymer is covalently attached to a non-specific site or non-specific sites on a chemokine-immunoglobulin fusion polypeptide, a chemokine or a variant thereof (i.e. the polymer attachment is not targeted to a particular region or a particular amino acid residue in the unconjugated chemokine or fragment thereof). In such embodiments, the coupling chemistry can, for example, utilize the free epsilon amino groups of lysine residues in the unconjugated antibody as attachment sites for the polymer, wherein such lysine residue amino groups are randomly derivatized with polymer.

Figure 11:
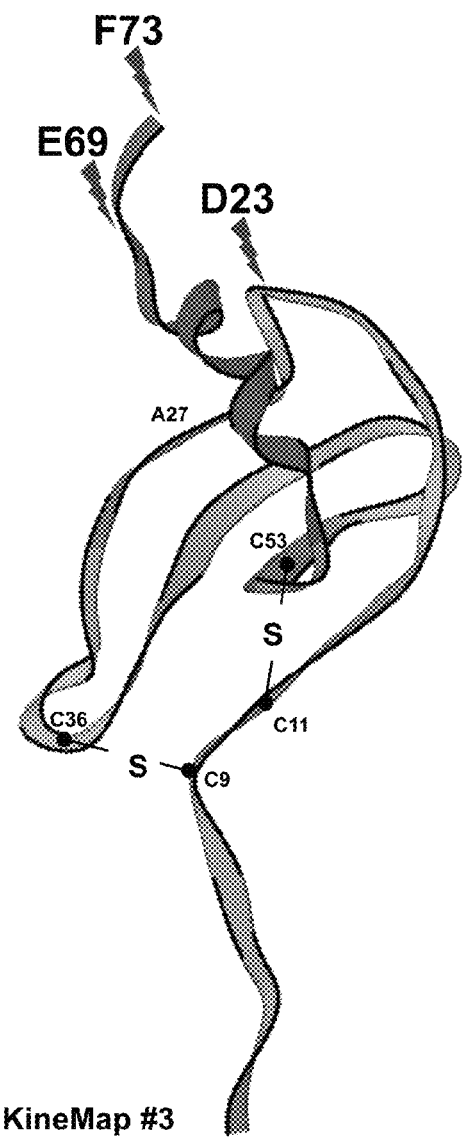
FIG. 11 depicts a cartoon of the structure of CXCL11 indication potential pegylation sites.

In addition, the conjugates of the invention include species wherein a polymer is covalently attached to a specific site or specific sites on the unconjugated chemokine or fragment thereof (i.e. a polymer attachment is targeted to a particular region or a particular amino acid residue or residues in the unconjugated chemokine or fragment thereof). FIG. 11 depicts a cartoon of the structure of CXCL11 indication potential pegylation sites. In such embodiments, the coupling chemistry can, for example, utilize the free sulfhydryl group of a cysteine residue not in a disulfide bridge in the unconjugated chemokine or fragment thereof. In one embodiment, one or more cysteine residue(s) is (are) engineered into a selected site or sites in the unconjugated chemokine or fragment thereof for the purpose of providing a specific attachment site or sites for polymer. The polymer can be activated with any functional group that is capable of reacting specifically with the free sulfhydryl or thiol group(s) on the unconjugated antibody, such as maleimide, sulfhydryl, thiol, triflate, tesylate, aziridine, exirane, and 5-pyridyl functional groups. The polymer can be coupled to the unconjugated chemokine or fragment thereof using any protocol suitable for the chemistry of the coupling system selected.

In another embodiment, polymer attachment is targeted to the receptor binding site of the unconjugated chemokine or fragment thereof. In another embodiment, polymer attachment is targeted to a site on the chemokine or fragment thereof away from the receptor binding site of the unconjugated chemokine or fragment thereof.

In certain embodiments, the protein portion of the protein-polymer conjugate is selected from the group consisting of human CCL1, CCL2, CCL3, CCL4, CCL4L1, CCL5, CCL7, CCL8, CCL11, CCL13, CCL14, CCL15, CCL16, CCL17, CCL 18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL16, XCL1, XCL2, CX3CL1 and functional variants thereof and the polymer portion of the protein-polymer conjugate is PEG. Figure. 11 depicts a cartoon of the structure of CXCL11 indication potential pegylation sites.

In other embodiments, the protein portion of the protein-polymer conjugate is a chemokine-immunoglobulin fusion polypeptide wherein the chemokine moiety is selected from the group consisting of a human CCL1, CCL2, CCL3, CCL4, CCL4L1, CCL5, CCL7, CCL8, CCL11, CCL13, CCL14, CCL15, CCL16, CCL17, CCL 18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL16, XCL1, XCL2, CX3CL1 and functional variants thereof and the immunoglobulin moiety is selected from the group consisting of the Fc region of human IgG1, the Fc region of human IgG2, the Fc region of human IgG3, the Fc region of human IgG4 and variants thereof.

In some embodiments, the protein-polymer conjugate is a serum labile polypeptide selected from the group consisting of CCL2-PEG, var-CCL2-PEG, CCL7-PEG, var-CCL7-PEG, CCL8-PEG, var-CCL8-PEG, CCL13-PEG, var-CCL13-PEG, CCL25-PEG, var-CCL25-PEG, CXCL11-PEG, var-CXCL11-PEG, CXCL13-PEG, var-CXCL13-PEG, CXCL16-PEG, and var-CXCL16-PEG.

In particular embodiments, the protein-polymer conjugate is a serum labile polypeptide selected from the group consisting of CCL2-PEG, CCL2(5-76)-PEG, CCL2(5-76K/H→A)-PEG, CCL7-PEG, CCL7(5-76)-PEG, CCL7(5-76K/H→A)-PEG, CCL8-PEG, CCL8(5-76)-PEG, CCL8(5-76K/H→A)-PEG, CCL13-PEG, CCL13(5-75)-PEG, CCL13(5-75K/H→A)-PEG, CCL25-PEG, CCL25(4-127)-PEG, CCL25(4-127K/H→A)-PEG, CXCL11-PEG, CXCL11(4-73)-PEG, CXCL11(4-73K/H→A)-PEG, CXCL11-IgG4Fc, CXCL11(4-73)-IgG4Fc, CXCL11(4-73K/H→A)-IgG4Fc, CXCL13-PEG, CXCL13(3-87)-PEG, CXCL13(3-87K/H→A)-PEG, CXCL16-PEG, CXCL16(3-87)-PEG, and CXCL16(3-87K/H→A)-PEG.

It is believed that the serum half-life, MRT and/or serum clearance rate of any chemokine or fragment thereof can be greatly improved by derivatizing the chemokine or fragment thereof with polymer as taught herein. In a preferred embodiment, the conjugate contains a chemokine or fragment thereof selected from the group consisting of CCL2, CCL7, CCL8, CCL13, CCL25, CXCL11, CXCL12α, CXCL13, and mutations, variants and fragments thereof.

Methods of Producing Chemokine-Immunoglobulin Fusion Polypeptides

The chemokine-immunoglobulin fusion polypeptides or variants thereof may be produced using methods well known in the art. In certain embodiments, the chemokine-immunoglobulin fusion polypeptide or variants thereof are produced by chemical synthesis. Briefly, a chemokine-immunoglobulin fusion polypeptide may be synthesized by coupling the carboxyl group or C-terminus of one amino acid to the amino group or N-terminus of another. Due to the possibility of unintended reactions, protecting groups are usually necessary. Chemical peptide synthesis starts at the C-terminal end of the peptide and ends at the N-terminus. This is the opposite of protein biosynthesis, which starts at the N-terminal end.

In some embodiments, the chemokine-immunoglobulin fusion polypeptide may be synthesized using traditional liquid- or solid-phase synthesis. Fmoc and t-Boc solid phase peptide synthesis (SPPS) can be employed to grow the peptides from carboxy to amino-terminus. In certain embodiments, the last "amino acid" added to the reaction is pegylated. This last amino acid is often referred to as a carboxyl-PEG-amine, carboxyl-PEO-amine, or amine-PEG-acid, whereby the amine is blocked to protect against reaction and the acid is free to react with the amine group from the previously added amino acid in the reaction.

In other embodiments, the chemokine-immunoglobulin fusion polypeptides or variants thereof are produced using recombinant DNA technologies. Procedures for the expression and purification of recombinant proteins are well established.

In certain embodiments, the chemokine-immunoglobulin fusion polypeptides are expressed using the expression vectors such as bacterial plasmids; phage DNA; baculovirus; yeast plasmids; vectors derived from combinations of plasmids and phage DNA, and viral vectors such as vaccinia, adenovirus, fowl pox virus, pseudorabies, adenovirus, adeno-associated virus, retroviruses and many others viruses.

Expression vectors carrying the chemokine-immunoglobulin fusion polypeptides can be introduced into host cells by any of a variety of well-known procedures, such as electroporation, liposome mediated transfection, calcium phosphate precipitation, infection, transfection and the like, depending on the selection of vectors and host cells.

Host cells that contain expression vectors of chemokine-immunoglobulin fusion polypeptides are, thus, also a feature of this disclosure. Favorable host cells include prokaryotic (i.e., bacterial) host cells, such as E. coli, as well as numerous eukaryotic host cells, including fungal (e.g., yeast, such as Saccharomyces cerevisiae and Picchia pastoris) cells, insect cells, plant cells, and mammalian cells (such as CHO cells). Examples of appropriate expression hosts include: bacterial cells, such as E. coli, Streptomyces, and Salmonella typhimurium; fungal cells, such as Saccharomyces cerevisiae, Pichia pastoris, and Neurospora crassa; insect cells such as Drosophila and Spodoptera frugiperda; mammalian cells such as 3T3, COS, CHO, BHK, HEK 293 or Bowes melanoma; plant cells, including algae cells, etc.

The host cells can be cultured in conventional nutrient media modified as appropriate for activating promoters, selecting transformants, or amplifying the inserted polynucleotide sequences. The culture conditions, such as temperature, pH and the like, are typically those previously used with the host cell selected for expression, and will be apparent to those skilled in the art and in the references cited herein. The chemokine-immunoglobulin fusion polypeptides can also be produced in non-animal cells such as plants, yeast, fungi, bacteria and the like. In bacterial systems, a number of expression vectors can be selected depending upon the use intended for the expressed product. For example, when large quantities of a polypeptide or fragments thereof are needed for the production of antibodies, vectors which direct high level expression of fusion polypeptides that are readily purified are favorably employed. Such vectors include, but are not limited to, multifunctional E. coli cloning and expression vectors such as BLUESCRIPT (Stratagene), in which the coding sequence of interest, e.g., a polynucleotide of the invention as described above, can be ligated into the vector in-frame with sequences for the amino-terminal translation initiating Methionine and the subsequent 7 residues of beta-galactosidase producing a catalytically active beta galactosidase fusion polypeptide; pIN vectors (Van Heeke & Schuster (1989) J Biol Chem 264:5503-5509); pET vectors (Novagen, Madison Wis.), in which the amino-terminal methionine is ligated in frame with a histidine tag; and the like.

Similarly, in yeast, such as Saccharomyces cerevisiae, a number of vectors containing constitutive or inducible promoters such as alpha factor, alcohol oxidase and PGH can be used for production of the desired expression products. In mammalian host cells, a number expression systems, including both plasmids and viral-based systems, can be utilized.

For long-term, high-yield production of the chemokine-immunoglobulin fusion polypeptides, stable expression systems are typically used. For example, polynucleotides encoding a the chemokine-immunoglobulin fusion polypeptide are introduced into the host cell using expression vectors which contain viral origins of replication or endogenous expression elements and a selectable marker gene. Following the introduction of the vector, cells are allowed to grow for 1-2 days in an enriched media before they are switched to selective media. The purpose of the selectable marker is to confer resistance to selection, and its presence allows growth and recovery of cells, which successfully express the introduced sequences. For example, resistant groups or colonies of stably transformed cells can be proliferated using tissue culture techniques appropriate to the cell type. Host cells transformed with a nucleic acid encoding a c the chemokine-immunoglobulin fusion polypeptide are optionally cultured under conditions suitable for the expression and recovery of the encoded protein from cell culture.

Following transduction of a suitable host cell line and growth of the host cells to an appropriate cell density, the selected promoter is induced by appropriate means (e.g., temperature shift or chemical induction) and cells are cultured for an additional period. The secreted polypeptide product is then recovered from the culture medium. Alternatively, cells can be harvested by centrifugation, disrupted by physical or chemical means, and the resulting crude extract retained for further purification. Eukaryotic or microbial cells employed in expression of proteins can be disrupted by any convenient method, including freeze-thaw cycling, sonication, mechanical disruption, or use of cell lysing agents, or other methods, which are well know to those skilled in the art.

Expressed the chemokine-immunoglobulin fusion polypeptides can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems noted herein), hydroxylapatite chromatography, and lectin chromatography. Protein refolding steps can be used, as desired, in completing configuration of the mature protein. Finally, high performance liquid chromatography (HPLC) can be employed in the final purification steps. In addition to the references noted above, a variety of purification methods are well known in the art.

In another example, a polynucleotide sequence that encodes the chemokine-immunoglobulin fusion polypeptide is introduced into insect cells using a Baculovirus Expression Vector System (BEVS). Recombinant baculovirus capable of infecting insect cells can be generated using commercially available vectors, kits and/or systems, such as the BD BaculoGold system from BD BioScience. Briefly, the polynucleotide sequence encoding the chemokine-immunoglobulin fusion polypeptide is inserted into the pAcSG2 transfer vector. Then, host cells SF9 (Spodoptera frugiperda) are co-transfected by pAcSG2-chimer plasmid and BD BaculoGold, containing the linearized genomic DNA of the baculovirus Autographa californica nuclear polyhedrosis virus (AcNPV). Following transfection, homologous recombination occurs between the pACSG2 plasmid and the Baculovirus genome to generate the recombinant virus. In one example, the chemokine-immunoglobulin fusion polypeptide is expressed under the regulatory control of the polyhedrin promoter (pH). Similar transfer vectors can be produced using other promoters, such as the basic (Ba) and p10 promoters. Similarly, alternative insect cells can be employed, such as SF21, which is closely related to the Sf9, and the High Five (Hi5) cell line derived from a cabbage looper, *Trichoplusia ni*. Following transfection and induction of expression (according to the selected promoter and/or enhancers or other regulatory elements), the expressed the chemokine-immunoglobulin fusion polypeptides are recovered (e.g., purified or enriched) and renatured to ensure folding into a biologically active conformation.

In yet other embodiments, the chemokine-immunoglobulin fusion polypeptides are expressed in vivo by a plasmid vector or a viral vector.

Treatment Methods

The present application further provides methods of using the chemokine-immunoglobulin fusion polypeptides disclosed herein to modulate inflammation and/or treat chemokine receptor-mediated disorders. In some embodiments, a method for treating a chemokine receptor-mediated disorder in a subject is provided. In some embodiments, the method comprises administering an effective amount of a chemokine-immunoglobulin fusion polypeptide disclosed herein to a subject in need thereof.

As used herein, the terms "treatment" or "treating" relate to any treatment of a chemokine receptor-mediated disorder, including but not limited to prophylactic treatment and therapeutic treatment. As such, the terms "treatment" or "treating" include, but are not limited to: preventing a chemokine receptor-mediated disorder or the development of a chemokine receptor-mediated disorder; inhibiting the progression of a chemokine receptor-mediated disorder; arresting or preventing the development of a chemokine receptor-mediated disorder; reducing the severity of a chemokine receptor-mediated disorder; ameliorating or relieving symptoms associated with a chemokine receptor-mediated disorder; and causing a regression of the chemokine receptor-mediated disorder or one or more of the symptoms associated with the chemokine receptor-mediated disorder.

The embodiments of the therapeutic compounds exhibit activity in the treatment of chemokine receptor-mediated disorders and inflammation, when administered in effective amounts. An effective amount of a composition disclosed herein is a nontoxic, but sufficient amount of the composition, such that the desired prophylactic or therapeutic effect is produced. The exact amount of the composition that is required will vary from subject to subject, depending on the species, age, condition of the animal, severity of the inflammation or chemokine receptor-mediated disorder in the animal, the particular carrier or adjuvant being used, its mode of administration, and the like. Accordingly, the effective amount of any particular therapeutic composition disclosed herein will vary based on the particular circumstances, and an appropriate effective amount can be determined in each case of application by one of ordinary skill in the art using only routine experimentation. The compositions disclosed herein can be administered in amounts ranging from about 0.1 µg to about 100 mg per kilogram of body weight. For example, the dosage regimen could be from about 1 µg to about 10 mg per kilogram of body weight, and such dosage units could be employed so that a total of from about 7 µg to about 700 mg of the composition is administered to a subject of about 70 kg of body weight.

A dosage regimen can be adjusted to provide an optimum therapeutic response and can be administered daily, biweekly, weekly, bimonthly, monthly, or at other appropriate time intervals. For example, compositions disclosed herein can be administered from once a day to once a week in dosages of about 5-250 mg per administration. For another example, several divided doses can be administered daily or the dose can be proportionally reduced as indicated by the exigencies of the therapeutic situation. One practical advantage is that the compound can be administered in a convenient manner such as intravenously, intratumorally, subcutaneously, transdermally, intraperitoneally or orally.

In some embodiments, the active composition is administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. The form should be sterile and fluid to the extent that easy syringability exists. It should be stable under the conditions of manufacture and storage and should be preserved against the contaminating action of microorganisms, such as bacteria and fungi. The pharmaceutical carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thimerosal, and the like. In many cases, the inclusion of isotonic agents can be desirable, for example, sugars or sodium chloride. Prolonged absorption of the injectable compositions can be brought about by the use in the compositions of agents, delaying absorption, for example, aluminum monostearate and gelatin.

Sterile injectable solutions can be prepared by incorporating the composition in the required amount in the appropriate solvent with various of the other ingredients enumerated above, followed by filtered sterilization. Generally, dispersions can be prepared by incorporating the various sterilized active ingredient into a sterile vehicle containing the basic dispersion medium and the required other ingredients from those enumerated above. In the case of sterile powders for the preparation of sterile injectable solutions, methods of preparation include vacuum drying and freeze drying techniques, which yield a powder of the active ingredient plus any additional desired ingredient from previously sterile filtered solution thereof.

As used herein, "pharmaceutically acceptable carrier" and "pharmaceutical carrier" are used interchangeably and include solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

Parenteral compositions may be formulated in dosage-unit form for ease of administration and uniformity of dosage. Dosage-unit form, as used herein, refers to physically discrete units suited as unitary dosages for the subjects to be treated, each unit containing a predetermined quantity of active material calculated to produce the desired therapeutic effect in association with the required pharmaceutical carrier. The specification for the dosage-unit forms of the present application can be chosen based upon: (a) the unique characteristics of the active material and the particular therapeutic effect to be achieved, and (b) the limitations inherent in the art of compounding such an active material for the treatment of conditions in living subjects having a condition in which bodily health is impaired as described herein.

The active ingredient can be compounded for convenient and effective administration in effective amounts with a suitable pharmaceutically acceptable carrier in dosage unit form as described herein. A unit dosage form can, for example, contain the principle active compound in amounts ranging from, for example, about 0.1 to about 1000 mg or, for another example, from about 5 to about 500 mg. Expressed in proportions, the compound is generally present in from about 1 to about 100 mg/ml of carrier. In the case of compositions containing supplementary active ingredients, the dosages can be determined by reference to the usual dose and manner of administration of the ingredients.

Further, with respect to the therapeutic methods of the presently disclosed subject matter, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided in accordance with the presently disclosed subject matter.

As such, the presently application provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos.

Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

In some embodiments of the presently-disclosed subject matter, the chemokine receptor-mediated disorder treated is a cell proliferative disorder, such as tumor or cancer. The present application provides chemokine-immunoglobulin fusion polypeptides that can target specific chemokine receptors expressed on cells of proliferative disorders disclosed herein. Cancer cells express functionally active chemokine receptors that may support adhesion, invasion, and cell survival. Chemokine receptor signaling and aggregation following binding of chemokines is coupled to integrin clustering, which enhances cell survival and firm cell adhesion. Without wishing to be bound by theory, the novel chemokine-immunoglobulin fusion polypeptides disclosed herein can bind chemokine receptors on these diseased cells and inhibit cellular events, including cell survival, migration, invasion, adhesion, or combinations thereof, and thereby treat the cell proliferative disorder. Table 3 lists various cancers and associations of the listed cancers with particular chemokines and chemokine receptors.

TABLE 3

Chemokine, Chemokine Receptor and Cancer Association (dependent of stage of disease)

| Cancer | Chemokine | Chemokine Receptor |
| --- | --- | --- |
| Carcinoma | CCL1, CCL4, CCL17, CCL19, CCL21, CCL22, CCL25, CXCL1, CXCL2, CXCL5, CXCL8, CXCL11, CXCL12, CXCL13, CXCL16 | CCR7, CCR8, CCR9, CXCR1, CXCR2, CXCR3, CXCR4, CXCR5, CXCR6, CXCR7, CX3CR1 |
| Leukemia | CCL1, CCL4, CCL17, CCL19, CCL21, CCL22, CCL25, CXCL12 | CCR7, CCR8, CCR9, CXCR4 |
| Lymphoma | CXCL12, CXCL13 | CXCR4, CXCR5 |
| Melanoma | CCL25, CCL27, CXCL1, CXCL2, CXCL3, CXCL5, CXCL6, CXCL7, CXCL8, CXCL12, CXCL13, CXCL16 CX3CL1 | CCR9, CCR10, CXCR1, CXCR2, CXCR4, CXCR5, CXCR6, CX3CR1 |
| Sarcoma | CCL1, CCL3, CCL4, CCL5, CCL7, CCL8, CCL11, CCL13, CCL17, CCL19, CCL22, CCL24, CXCL12, CX3CL1 | CCR3, CCR5, CCR8 CXCR4 CX3CR1, CCXCKR |

"Cell proliferative disorder" refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is neoplasm or tumor, which is an abnormal growth of tissue. "Cancer" refers to any of various malignant neoplasms characterized by the proliferation of cells that have the capability to invade surrounding tissue and/or metastasize to new colonization sites, and includes leukemia, lymphoma, carcinoma, melanoma, sarcoma, germ cell tumor and blastoma. Examples of cancers are cancer of the brain, bladder, breast, cervix, colon, head and neck, kidney, lung, non-small cell lung, mesothelioma, ovary, prostate, stomach and uterus, leukemia, and medulloblastoma.

By "leukemia" is meant broadly progressive, malignant diseases of the blood-forming organs and is generally characterized by a distorted proliferation and development of leukocytes and their precursors in the blood and bone marrow. Leukemia diseases include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "sarcoma" generally refers to a tumor which is made up of a substance like the embryonic connective tissue and is generally composed of closely packed cells embedded in a fibrillar or homogeneous substance. Sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphomas (e.g., Non-Hodgkin Lymphoma), immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

Additional cancers include, for example, Hodgkin's Disease, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, pre-malignant skin lesions, testicular cancer, thyroid cancer, neuroblastoma, esophageal cancer, genitourinary tract cancer, malignant hypercalcemia, cervical cancer, endometrial cancer, and adrenal cortical cancer.

In some embodiments, a chemokine-immunoglobulin fusion polypeptide of the present application is used for the treatment of cancer. The chemokine-immunoglobulin fusion polypeptide comprises a chemokine moiety selected from the group consisting of CCL1, CCL2, CCL3, CCL4, CCL4L1, CCL5, CCL7, CCL8, CCL11, CCL13, CCL14, CCL15, CCL16, CCL17, CCL 18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL16, XCL1, XCL2, CX3CL1 and functional variants thereof, and an immunoglobulin moiety selected from the group consisting of the constant region of human IgG1 and functional variants thereof.

In other embodiments, the chemokine receptor-mediated disorder treated is an inflammatory disorder. Without wishing to be bound by theory, the novel chemokine-immunoglobulin fusion polypeptides disclosed herein can bind chemokine receptors on these cells and inhibit cellular events that can result in inflammation and inflammatory disorders. Table 4 lists various exemplary inflammatory disorders and associations of the listed disorders with particular chemokines and chemokine receptors. Targeting of the listed chemokine receptors with chemokine-immunoglobulin fusion polypeptides disclosed herein that act as specific ligands of the receptors can be useful for treating the listed inflammatory disorders.

In some embodiments, a chemokine-immunoglobulin fusion polypeptide of the present application is used for the treatment of an inflammatory disorder. The chemokine-immunoglobulin fusion polypeptide comprises a chemokine moiety selected from the group consisting of CCL1, CCL2, CCL3, CCL4, CCL4L1, CCL5, CCL7, CCL8, CCL11, CCL13, CCL14, CCL15, CCL16, CCL17, CCL 18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL16, XCL1, XCL2, CX3CL1 and functional variants thereof, and an immunoglobulin moiety selected from the group consisting of the constant region of human IgG4 and functional variants thereof.

part, or exacerbated, by inflammation, which is generally characterized by increased blood flow, edema, activation of immune cells (e.g., proliferation, cytokine production, or enhanced phagocytosis), heat, redness, swelling, pain and/or loss of function in the affected tissue or organ. The cause of inflammation can be due to physical damage, chemical substances, micro-organisms, tissue necrosis, cell proliferative disorders, or other agents Inflammatory disorders include acute inflammatory disorders, chronic inflammatory disorders, and recurrent inflammatory disorders. Acute inflammatory disorders are generally of relatively short duration, and last for from about a few minutes to about one to two days, although they can last several weeks. Characteristics of acute inflammatory disorders include increased blood flow, exudation of fluid

TABLE 4

Chemokine, Chemokine Receptor and Inflammatory Disorder Association (dependent of stage of disease)

| Inflammatory Disorder | Chemokine | Chemokine Receptor |
| --- | --- | --- |
| Allergies (Skin, Food & Respiratory) | CCL1, CCL2, CCL5, CCL7, CCL8, CCL11, CCL13, CCL17, CCL22, CCL24, CCL25, CCL26 | CCR3, CCR4, CCR8, CCR9 |
| Asthma | CCL3, CCL4, CCL5, CCL7, CCL8, CCL11, CCL15, CCL17, CCL22, CCL24, CCL26 | CCR3, CCR4, CCR5 |
| Septic Shock, Anaphylaxis | CXCL1, CXCL2, CXCL3, CXCL5, CXCL6, CXCL7, CXCL8, CXCL9, CXCL10, CXCL11, CCL5 | CXCR1, CXCR2, CXCR3 |
| Arthritis (septic, rheumatoid, psoriatic) | CXCL9, CXCL10, CXCL11, CXCL12, CXCL13 | CXCR3, CXCR4, CXCR5 |
|  | CCL20 | CCR6 |
|  | XCL1 | XCR1 |
|  | CX3CL1 | CX3CR1 |
| Osteoarthritis | CXCL1, CXCL2, CXCL3, CXCL5, CXCL6, CXCL7, CXCL8, CXCL12, CXCL13 | CXCR1, CXCR2 |
|  | CCL2, CCL3, CCL4, CCL7, CCL8, CCL13, CCL5, CCL18 | CCR2, CCR5 |
| Atherosclerosis | CXCL1, CXCL2, CXCL3, CXCL4, CXCL5, CXCL8 | CXCR1, CXCR2 |
|  | CCL2, CCL3, CCL4, CCL8, CCL12, CCL13, CCL17, CCL22 | CCR2, CCR8 |
|  | CX3CL1 | CX3CR1 |
| Dermatitis & Delayed-Typed Hypersensitivity | CXCL9, CXCL10, CXCL11 | CXCR3 |
|  | CCL2, CCL3, CCL4, CCL5, CCL17, CCL20, CCL22, CCL27 | CCR4, CCR5, CCR6, CCR10 |
| Diabetes | CXCL9, CXCL10, CXCL11 | CXCR3 |
|  | CCL2, CCL9 | CCR2, CCR4 |
|  | CX3CL1 | CX3CR1 |
| Graft rejection | CXCL9, CXCL10, CXCL11 | CXCR3 |
|  | CCL3, CCL4, CCL5 | CCR5 |
|  | XCL1, XCL2 | XCR1 |
| Inflammatory Bowel Disorders | CXCL9, CXCL10, CXCL11 | CXCR3 |
|  | CCL3, CCL4, CCL5, CCL25 | CCR5 |
| Interstitial Cystitis | CXCL9, CXCL10, CXCL11 | CXCR3 |
|  | CCL3, CCL4, CCL5 | CCR5 |
| Multiple Sclerosis | CXCL9, CXCL10, CXCL11 | CXCR3 |
|  | CCL3, CCL4, CCL5, CCL7, CCL14, CCL15, CCL23 | CCR1, CCR5 |
| Myasthemia gravis, Grave's disease, & Hashimoto thyroiditis | CXCL9, CXCL10, CXCL11 | CXCR3 |
|  | CCL3, CCL4, CCL5 | CCR5 |
|  | XCL1, XCL2 | XCR1 |
| Nephritis & Systemic Lupus Erthematosus | CXCL9, CXCL10, CXCL11, CXCL13 | CXCR3, CXCR5 |
|  | CCL2, CCL3, CCL4, CCL5, CCL8, CCL12, CCL13 | CCR2, CCR4 |
|  | CX3CL1 | CX3CR1 |
| Pneumonitis, Chronic Obstructive Pulmonary Disease, & Chronic Bronchitis | CXCL1, CXCL2, CXCL3, CXCL5, CXCL7, CXCL8 | CXCR2, CXCR3 |
|  | CCL3, CCL5, CCL7, CCL8, CCL11, CCL13, CCL24, CCL26 | CCR3 |

As used herein, the term "inflammatory disorder" includes diseases or disorders which are caused, at least in part, or exacerbated, by inflammation, which is generally and plasma proteins (edema) and emigration of leukocytes, such as neutrophils. Chronic inflammatory disorders, generally, are of longer duration, e.g., weeks to months to years or longer, and are associated histologically with the presence of lymphocytes and macrophages and with proliferation of blood vessels and connective tissue. Recurrent inflammatory disorders include disorders which recur after a period of time or which have periodic episodes. Some inflammatory disorders fall within one or more categories. Exemplary inflammatory disorders include, but are not limited to, inflammatory disorders of the central or peripheral nervous system (e.g., abscess, AIDS related infections, Alzheimer's disease, chronic fatigue syndrome, congenital infections, encephalitis, ischemia, meningitis, multiple sclerosis, traumatic brain injury, etc.); inflammatory disorders of the urogenital system (e.g., endometriosis, glomerulosclerosis, infections of the vagina and cervix, intra-amniotic infection, pelvic inflammatory disease, renal inflammation/nephritis, sexually transmitted diseases, urethritis, urinary tract infections, yeast infection, etc.); inflammatory disorders of the digestive system (e.g., colon cancer, hepatitis, inflammatory bowel disease, interstitial cystitis, irritable bowel syndrome, ulcers, etc.); inflammatory disorders of the respiratory system (e.g., chronic lung disease, asthma, tuberculosis, pneumonia, etc.); inflammatory disorders of the skin, integument and musculoskeletal system (e.g., Behçet's disease, Crohn's disease, dermatitis, gingivitis, gout, myalgias, osteoarthritis, periodontitis, psoriasis, rheumatoid arthritis, spondyloarthropathies, skin sunburn, etc.); inflammatory disorders of the cardiovascular system (e.g., atherosclerosis, pericarditis, endocarditis, Kawasaki's disease, myocarditis, rheumatic fever, vasculitis); autoimmune disorders; cat scratch disease; infections of the eye; Lyme disease; lymphadenopathy; lymphatic inflammation; radiation-induced inflammation; sarcoidosis; Sjogren's syndrome; systemic lupus erythematosus and related disorders; and inflammatory disorders resulting from infections by microorganisms and inflammatory molecules. As used herein, the term "microorganism" refers to any species or type of microorganism, including but not limited to, bacteria, viruses, archaea, fungi, protozoans, mycoplasma, prions, and parasitic organisms. The term microorganism encompasses both those organisms that are in and of themselves pathogenic to another organism (e.g., animals, including humans, and plants) and those organisms that produce agents that are pathogenic to another organism, while the organism itself is not directly pathogenic or infective to the other organism. As noted, an inflammatory disorder is often caused, at least in part, or exacerbated by, inflammation, which may be characterized by symptoms and/or manifestations of the inflammatory disorder which may include, but are not limited to, increased blood flow, edema, activation of immune cells (e.g., proliferation, cytokine production, or enhanced phagocytosis), heat, redness, swelling, pain and loss of function in the affected tissue and organ. As such, the present application further provides methods of modulating inflammation. The term "modulating inflammation" refers to either inducement of inflammation or alleviating inflammation where inflammation is pathological, as occurs in inflammatory disorders. The term "alleviating" as used herein refers to preventing the symptoms and/or manifestations of inflammation or the development of the symptoms and/or manifestations of inflammation; inhibiting the progression of the symptoms and/or manifestations of inflammation; arresting or preventing the development of the symptoms and/or manifestations of inflammation; reducing the severity of symptoms and/or manifestations inflammation; ameliorating or relieving the symptoms and/or manifestations associated with inflammation; and/or causing a regression of the symptoms and/or manifestations of inflammation. The present invention is further illustrated by the following examples that should not be construed as limiting. The following examples may include compilations of data that are representative of data gathered at various times during the course of development and experimentation related to the present subject matter.

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1

Generation of Plasmid Expression Vectors

Expression vectors capable of expressing a chemokine-immunoglobulin fusion polypeptide are generated from pFUSE-hIgG1-Fc1, pFUSE-hIgG2-Fc1, pFUSE-hIgG3-Fc1 and pFUSE-hIgG4-Fc1 vectors from InvivoGen (San Diego, Calif.) using standard molecular biology procedures. Examples of the expression vectors are shown in FIGS. 1-10.

Example 2

Expression of Chemokine Receptors in Breast Cancer Cell Lines

Experiments are conducted to compare expression levels of CXCR7 and CXCR3 in breast cancer tissue of various stages, in non-neoplastic breast tissue. Non-neoplastic breast tissue does not express detectable levels of CXCR7. CXCR7 expression is significantly higher in tissues with advanced breast cancer, comparing to non-neoplastic breast tissue. CXCR7 and CXCR3 mRNAs are also elevated in breast cancer cell lines (MDA-MB-231), compared to normal breast cells (MCF-10A).

Example 3 var-CXCL11-IgG Fusion Polypeptide Inhibits CXCR7 and CXCR3 Activation in Breast Cancer Cells Using Amnis ImageStream analysis, we found that CXCL11 stimulates CXCR3 and CXCR7 aggregation and rapid desensitization, that CXCL12 modulates modest CXCR7 clustering, and that adrenomedullin (AM) stimulates CXCR3 and CXCR7 clustering. CXCL11-IgG fusion polypeptide abrogates CXCR3 and CXCR7, but not CXCR4, clustering and desensitization by CXCL11, CXCL12 and AM.

The above description is for the purpose of teaching the person of ordinary skill in the art how to practice the present invention, and is not intended to detail all those obvious modifications and variations of it that will become apparent to the skilled worker upon reading the description. It is intended, however, that all such obvious modifications and variations be included within the scope of the present invention, which is defined by the following embodiments. The embodiments are intended to cover the components and steps in any sequence that is effective to meet the objectives there intended, unless the context specifically indicates the contrary. All the references cited in the specification are herein incorporated by reference in their entirely.

What is claimed is:

1. An isolated chemokine-immunoglobulin fusion polypeptide, comprising
   a chemokine moiety of human CCL18; and
   an immunoglobulin moiety selected from the group consisting of the constant region of human IgG2 (IgG2Fc), the constant region of human IgG3 (IgG3Fc), the constant region of human IgG4 (IgG4Fc).

2. The isolated chemokine-immunoglobulin fusion polypeptide of claim 1, wherein said fusion polypeptide is a pegylated fusion polypeptide.

3. The isolated chemokine-immunoglobulin fusion polypeptide of claim 2, wherein said pegylated fusion polypeptide has a molecular weight of at least about 500,000 dalton.

4. The isolated chemokine-immunoglobulin fusion polypeptide of claim 2, wherein said pegylated fusion polypeptide has a PEG-to-fusion polypeptide molar ratio of no more than about 10:1.

5. The isolated chemokine-immunoglobulin fusion polypeptide of claim 2, wherein said pegylated fusion polypeptide has a PEG-to-fusion polypeptide molar ratio of no more than about 2:1.

6. An isolated polynucleotide, encoding the chemokine-immunoglobulin fusion polypeptide of claim 1.

7. An expression vector, comprising:
   a regulatory element; and
   a polynucleotide operably linked to said regulatory element,
   wherein said polynucleotide encodes the chemokine-immunoglobulin fusion polypeptide of claim 1.

8. The expression vector of claim 7, wherein said vector is a plasmid-based expression vector or a virus-based expression vector.

9. A pharmaceutical composition, comprising:
   the chemokine-immunoglobulin fusion polypeptide of claim 1; and
   a pharmaceutically acceptable carrier.

10. A pharmaceutical composition, comprising:
the expression vector of claim 7; and
a pharmaceutically acceptable carrier.

11. A method for treating a chemokine receptor-mediated disorder in a subject, wherein said chemokine receptor-mediated disorder is breast cancer, comprising: administering to said subject an effective amount of the pharmaceutical composition of claim 9.

* * * * *